United States Patent
Zhang et al.

(10) Patent No.: US 11,014,964 B2
(45) Date of Patent: May 25, 2021

(54) PEPTIDE AMIDE COMPOUND AND PREPARATION METHOD AND MEDICAL USE THEREOF

(71) Applicant: Sichuan Haisco Pharmaceutical Co., Ltd., Sichuan (CN)

(72) Inventors: Chen Zhang, Sichuan Province (CN); Anbang Huang, Sichuan Province (CN); Fei Ye, Sichuan Province (CN); Longbin Huang, Sichuan Province (CN); Zhenggang Huang, Sichuan Province (CN); Jianmin Wang, Sichuan Province (CN); Yonggang Wei, Sichuan Province (CN); Pangke Yan, Sichuan Province (CN); Wei Zheng, Sichuan Province (CN)

(73) Assignee: Sichuan Haisco Pharmaceutical Co., Ltd., Sichuan (CN)

( * ) Notice: Subject to any disclaimer, the term of this patent is extended or adjusted under 35 U.S.C. 154(b) by 0 days.

(21) Appl. No.: 16/632,228

(22) PCT Filed: Jul. 19, 2018

(86) PCT No.: PCT/CN2018/096271
§ 371 (c)(1),
(2) Date: Jan. 17, 2020

(87) PCT Pub. No.: WO2019/015644
PCT Pub. Date: Jan. 24, 2019

(65) Prior Publication Data
US 2020/0172573 A1    Jun. 4, 2020

(30) Foreign Application Priority Data

Jul. 21, 2017  (CN) .......................... 201710598408.7
Jan. 11, 2018  (CN) .......................... 201810014939.1

(51) Int. Cl.
*A61K 38/00* (2006.01)
*C07K 5/117* (2006.01)

(52) U.S. Cl.
CPC ............ *C07K 5/1024* (2013.01); *A61K 38/00* (2013.01)

(58) Field of Classification Search
CPC .... A61K 38/00; A61K 38/07; A61K 2121/00; A61K 2123/00; C07K 5/1024; A61P 25/04
USPC .... 424/1.11, 1.65, 1.69, 9.1, 9.2; 514/1, 1.1, 514/19.2, 19.3, 19.4, 19.5, 19.6; 530/300
See application file for complete search history.

(56) References Cited

U.S. PATENT DOCUMENTS

| | | | |
|---|---|---|---|
| 5,965,701 A | 10/1999 | Junien et al. | |
| 7,402,564 B1 | 7/2008 | Schteingart et al. | |
| 7,842,662 B2 | 11/2010 | Schteingart et al. | |
| 10,550,150 B2 | 2/2020 | Desai et al. | |
| 2010/0029575 A1 | 2/2010 | Junien et al. | |
| 2010/0075910 A1 | 3/2010 | Schteingart et al. | |
| 2011/0212882 A1 | 9/2011 | Schteingart et al. | |
| 2019/0241610 A1 | 8/2019 | Schteingart et al. | |

FOREIGN PATENT DOCUMENTS

| | | |
|---|---|---|
| WO | WO-99/32510 A1 | 7/1999 |
| WO | WO-2008/057608 | 5/2008 |
| WO | WO-2016/181408 A2 | 11/2016 |

OTHER PUBLICATIONS

Bileviciute-Ljungar, I., et al., Anti-inflammatory effects of contralateral administration of the κ-opioid agonist U-50,448H in rats with unilaterally induced adjuvant arthritis, Rheumatology (2006, 45, 295-302).
Jolivalt, C.G., et al., Dynorphin A, kappa opioid receptors and the antinociceptive efficacy of asimadoline in streptzotocin-induced diabetic rats, Diabetologia (2006, 49 (11),2775-2785).
Kaushik, S. et al., Neuroprotection in Glaucoma, J. Postgraduate Medicine (2003, 49 (1) ,90-95).
Lembo, A., Peripheral Opioids for Functional GI Disease: A Reappraisal, Diges.Dis. (2006, 24,91-98).
Potter, D.E., et al., Bremazocine Increases C-Type Natriuretic Peptide Levels in Aqueous Humor and Enhances Outflow Facility, J.Pharmacol.Exp.Ther (2004, 309,548-553).
Wikstrom, B., et al, κ-Opioid System in Uremic Pruritus: Multicenter, Randomized, Double-Blind, Placebo-Controlled Clinical Studies, J. Am. Soc.Nephrol (2005, 16,3742-3747).

(Continued)

*Primary Examiner* — D. L. Jones
(74) *Attorney, Agent, or Firm* — Foley & Lardner LLP

(57) ABSTRACT

The invention provides a peptide amide compound represented by the general general formula (I), a preparation method thereof, and a medical application thereof. The compound has a novel structure, better biological activity, and better analgesic effect.

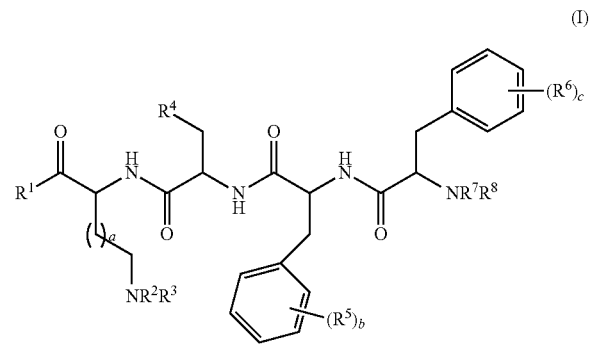

13 Claims, No Drawings

(56) References Cited

OTHER PUBLICATIONS

Woolf, C.J., et al., Preemptive Analgesia-Treating Postoperative Pain by Preventing the Establishment of Cetral Sensitization, Anesthesia and Analgesia (1993, 77,362-379).

Wu, S. et al., Cardioprotection of Preconditioning by Metabolic Inhibition in the Rat Ventricular Myocyte: Involvement of κ-Opioid Receptor, Circulation Res (1999, 84,1388-1395).

English translation of international search report regarding Application No. PCT/CN2018/096271, dated Oct. 8, 2018, 5 pps.

Examination Report regarding Australian Appl. No. 2018-303080 dated Jul. 6, 2020, 3 pps.

Office Action and Search Report received regarding Taiwan Application No. 107124926 dated May 26, 2020, 4 pps.

PEPTIDE AMIDE COMPOUND AND PREPARATION METHOD AND MEDICAL USE THEREOF

CROSS-REFERENCE TO RELATED APPLICATIONS

This application is a National Stage Application of PCT/CN2018/096271, filed Jul. 19, 2018, which claims the benefit of and priority to Chinese Patent Application Nos. CN 201710598408.7, filed Jul. 21, 2017 and CN 201810014939.1, filed Nov. 1, 2018, the entire contents of which are incorporated herein by reference.

TECHNICAL FIELD

The present invention relates to a peptide amide compound having an analgesic effect, a preparation method thereof and use in medicine.

BACKGROUND

Opioid drugs have been used for the treatment of pain for thousands of years and play a physiological role primarily by binding to the known three classical opioid receptors μ, δ and κ. These three receptors are members of the G-protein coupled receptor family, mainly distributed in the central nervous system, and also in many peripheral tissues. One of the most classic drugs is morphine, which exerts an analgesic effect mainly through the action of μ opioid receptors.

In addition, commonly used clinical analgesics include other μ opioid receptor drugs, such as traditional opioids represented by dihydromorphinone and fentanyl.

However, μ opioid receptor drugs produce a variety of side effects after long-term use, such as tolerance, dependence and respiratory depression, and effects on gastrointestinal motility, which not only increases the cost of treatment, but also affects the cycle for patient to recover. Some non-opioid injections, such as acetaminophen and NSAIDs (Non-steroidal anti-inflammatory drugs), have limited use and dosage due to their poor analgesic effect. In addition, they have certain side effects, such as acetaminophen increases liver toxicity, and NSAIDs (non-steroidal anti-inflammatory drugs) cause various gastrointestinal diseases.

With the increasing pressure of life and work in modern society and the arrival of the elderly society, and in view of the critical role of the opioid receptors for the treatment of different types of pain, the search for new opioids with high analgesic activity and low toxic side effects has important scientific and social significance.

Studies have found that by using K opioid receptor agonists, K opioid receptors can be used as targets for intervention to treat pain and prevent a wide variety of diseases and conditions. For example, in 1993, Woold et al. described the use of κ opioid receptor agonists for the treatment of pain sensitization (Anasthesia and Analgesia, 1993, 77, 362-379); in 1999, Wu et al. proposed κ opioid receptor agonists as targets for the prevention and treatment of cardiovascular diseases (Circulation Res 1999, 84, 1388-1395); in 2003, Kaushik et al. described the neuroprotective effects of κ opioid receptor agonists (J. Postgraduate Medicine 2003, 49 (1), 90-95); in 2004, Potter et al. described the use of κ opioid receptor agonists in ocular disorders and ocular pain (Pharmacol. Exp. Ther 2004, 209, 548-553); in 2005, Wikstrom et al. described the use of κ agonists in the treatment of uremia and opium-induced pruritus (J. Am. Soc. Nephrol 2005, 16, 3742-3747.); in 2006, Bileviciute-Ljungar et al. evaluated the properties of κ opioid receptor agonists for inflammatory diseases such as osteoarthritis and rheumatoid arthritis (Rheumatology 2006, 45, 295-302); in 2006, Lembo evaluated the use of κ opioid receptor agonists in gastrointestinal diseases (Diges. Dis. 2006,24, 91-98); in 2006, Jolivalt et al. described the role of the κ opioid receptor agonist acimadrine in rodent diabetic neuropathy (Diabetologia 2006, 49 (11), 2775-2785); in 2008, Schteingart, Claudio, D et al. from Cara Therapeutics Co., Ltd. evaluated the effects of κ opioid receptor agonists on visceral pain, pH-sensitive nociceptor activation-related pain, and capsaicin-induced eye pain in WO2008057608A2.

SUMMARY

The object of the present invention is to provide a κ opioid receptor agonist which has novel structure, better biological activity and better analgesic effect, and a preparation method thereof and use in medicine.

The present invention provides a compound of the general formula (I) or a stereoisomer, hydrate, metabolite, solvate, pharmaceutically acceptable salt or cocrystal thereof:

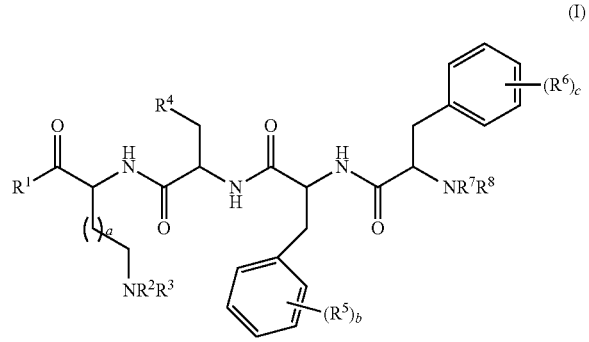

wherein
$R^1$ is selected from

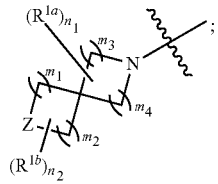

each of $m_1$, and $m_2$ is independently selected from 1, 2, 3 or 4;
each of $m_3$, and $m_4$ is independently selected from 0, 1, 2, 3 or 4; with the condition that $m_3$ and $m_4$ cannot be 0 at the same time;
each of $n_1$, and $n_2$ is independently selected from 0, 1, 2, 3 or 4;
Z is selected from $CR^{z1}R^{z2}$ or $NR^{z3}$;
each of $R^{z1}$, and $R^{z2}$ is independently selected from H, F, Cl, Br, I, OH, $CF_3$, nitro, $C_{1-6}$ alkyl, $C_{1-6}$ alkoxy, $C_{2-6}$ alkenyl, $C_{2-6}$ alkynyl, —C(=O)—$C_{1-6}$ alkyl, —$(CH_2)_q$—C(=O)O—$C_{1-6}$ alkyl, —$(CH_2)_q$—$NR^{1e}R^{1f}$, —$(CH_2)_q$—COOH, —$(CH_2)_q$—$CONH_2$, $C_{3-8}$ carbocyclic group or 3 to 8 membered heterocyclic group. The alkyl, alkoxy, alkenyl, alkynyl, carbocyclic or heterocyclic group is optionally further substituted with 0 to 5 substituent(s) selected from the group consisting of F, Cl, Br, I, OH, CF$_3$, =O, carboxyl, nitro, cyano, amino, C$_{1-6}$ alkyl, C$_{1-6}$ alkoxy, C$_{2-6}$ alkenyl, C$_{2-6}$ alkynyl, C$_{3-8}$ carbocyclic group or 3 to 8 membered heterocyclic group. The heterocyclic group contains 1 to 3 heteroatom(s) optionally selected from N, O or S, and when the heteroatom is selected from S, it is optionally in form of S, S=O or S(=O)$_2$;

each of R$^{1e}$, R$^{1f}$ is independently selected from H, C$_{1-6}$ alkyl, —C(=O)O—C$_{1-6}$ alkyl, —C(=O)O—(CH$_2$)$_q$—C$_{3-8}$ carbocyclic group or —C(=O)O—(CH$_2$)$_q$— 3 to 8 membered heterocyclic group. The alkyl, carbocyclic or heterocyclic group is optionally further substituted with 0 to 5 substituent(s) selected from the group consisting of F, Cl, Br, I, OH, CF$_3$, cyano, nitro, C$_{1-6}$ alkyl, C$_{1-6}$ alkoxy, C$_{2-6}$ alkenyl, C$_{2-6}$ alkynyl, C$_{3-8}$ carbocyclic group or 3 to 8 membered heterocyclic group. The heterocyclic group contains 1 to 3 heteroatom(s) selected from N, O or S;

alternatively, R$^{z1}$ and R$^{z2}$ form a 3 to 10 membered nitrogen-containing heterocyclic ring with the carbon atom to which they are attached. The ring is optionally further substituted with substituent(s) selected from the group consisting of F, Cl, Br, I, OH, CF$_3$, cyano, nitro, =O, C$_{1-6}$ alkyl, C$_{1-6}$ alkoxy, C$_{2-6}$ alkenyl, C$_{2-6}$ alkynyl, C$_{3-8}$ carbocyclic group or 3 to 8 membered heterocyclic group;

each of R$^{1a}$, R$^{1b}$ is independently selected from F, CF$_3$, C$_{1-6}$ alkyl, C$_{2-6}$ alkenyl, C$_{2-6}$ alkynyl or 3 to 8 membered heterocyclic group. The alkyl, alkenyl, alkynyl or heterocyclic group is optionally further substituted with 0 to 5 substituent(s) selected from the group consisting of F, Cl, Br, I, OH, CF$_3$, nitro, cyano, C$_{1-6}$ alkyl, C$_{1-6}$ alkoxy, C$_{2-6}$ alkenyl, C$_{2-6}$ alkynyl, C$_{3-8}$ carbocyclic group or 3 to 8 membered heterocyclic group. The heterocyclic group contains 1 to 3 heteroatom(s) optionally selected from N, O or S; R$^{z3}$ is independently selected from H, —C(=O)—C$_{1-6}$ alkyl, —C(=O)O—C$_{1-6}$ alkyl, —C(=O)—C$_{3-8}$ carbocyclic group, —C(=O)O—C$_{3-8}$ carbocyclic group, —C(=O)O— (3 to 8 membered heterocyclic group), —S(=O)$_p$—C$_{1-6}$ alkyl, —S(=O)$_p$—C$_{3-8}$ carbocyclic group, —S(=O)$_p$— (3 to 8 membered heterocyclic group), —C(=O) NR$^{1g}$R$^{1h}$, —S(=O)$_p$—NR$^{1i}$R$^{1j}$ or 3 to 8 membered heterocyclic group.

The alkyl, carbocyclic or heterocyclic group is optionally further substituted with 0 to 5 substituent(s) selected from the group consisting of F, Cl, Br, I, OH, CF$_3$, nitro, cyano, amino, C$_{1-6}$ alkyl, C$_{1-6}$ alkoxy, C$_{2-6}$ alkenyl, C$_{2-6}$ alkynyl, C$_{3-8}$ carbocyclic group or 3 to 8 membered heterocyclic group. The heterocyclic group contains 1 to 3 heteroatom(s) optionally selected from N, O or S;

each of R$^{1g}$, R$^{1h}$, R$^{1i}$, R$^{1j}$ is independently selected from H or C$_{1-6}$ alkyl;

alternatively, R$^{1g}$, R$^{1h}$ form a 3 to 10 membered heterocyclic ring with the nitrogen atom to which they are attached. The ring is optionally further substituted with substituent(s) selected from the group consisting of F, Cl, Br, I, OH, CF$_3$, cyano, nitro, C$_{1-6}$ alkyl, C$_{1-6}$ alkoxy, C$_{2-6}$ alkenyl, C$_{2-6}$ alkynyl or —S(=O)$_p$—C$_{1-6}$ alkyl. The heterocyclic group contains 1 to 3 heteroatom(s) selected from N, O or S;

q is selected from 0, 1, 2, 3 or 4;
p is selected from 0, 1 or 2;
a is selected from 0, 1, 2 or 3;
R$^4$ is independently selected from H, C$_{1-6}$ alkyl, C$_{2-6}$ alkenyl, C$_{2-6}$ alkynyl or —(CH$_2$)$_q$—C$_{3-8}$ carbocyclic group. The alkyl, alkenyl, alkynyl or carbocyclic group is optionally further substituted with 0 to 5 substituent(s) selected from the group consisting of F, Cl, Br, I, OH, CN, CF$_3$, NO$_2$, C$_{1-6}$ alkyl, C$_{1-6}$ alkoxy, C$_{2-6}$ alkenyl, C$_{2-6}$ alkynyl, C$_{3-8}$ carbocyclic group or 3 to 8 membered heterocyclic group. The heterocyclic group contains 1 to 3 heteroatom(s) selected from N, O or S;

each of R$^2$, R$^3$, R$^7$, R$^8$ is independently selected from H, C$_{1-6}$ alkyl, —C(=O)O—C$_{1-4}$ alkyl, —C(=O)O—(CH$_2$)$_q$—C$_{3-8}$ carbocyclic group, —C(=O)O—(CH$_2$)$_{q-3}$ to 8 membered heterocyclic group or

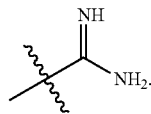 [SMILES: *C(=N)N]

The alkyl, carbocyclic or heterocyclic group is optionally further substituted with 0 to 5 substituent(s) selected from the group consisting of F, Cl, Br, I, OH, CF$_3$, nitro, cyano, C$_{1-6}$ alkyl, C$_{1-6}$ alkoxy, C$_{2-6}$ alkenyl, C$_{2-6}$ alkynyl, C$_{3-8}$ carbocyclic group or 3 to 8 membered heterocyclic group. The heterocyclic group contains 1 to 3 heteroatom(s) optionally selected from N, O or S;

b is selected from 0, 1, 2, 3, 4 or 5;
c is selected from 0, 1, 2, 3, 4 or 5;
Each of R$^5$, R$^6$ is each independently selected from F, Cl, Br, I, CF$_3$, cyano, nitro, C$_{1-4}$ alkyl, —OR$^{5a}$, —C(O)OR$^{5b}$, —SR$^{5c}$, —S(O)R$^{5d}$, —S(O)$_2$R$^{5e}$ or —NR$^{5f}$R$^{5g}$;

each of R$^{5a}$, R$^{5b}$, R$^{5c}$, R$^{5d}$, R$^{5e}$, R$^{5f}$ and R$^{5g}$ is independently selected from H or C$_{1-4}$ alkyl;

alternatively, R$^{5f}$, R$^{5g}$ form a 5 to 6 membered heterocyclic ring with the nitrogen atom to which they are attached. The heterocyclic group contains 1 to 3 heteroatom(s) optionally selected from N, O or S.

In a preferred embodiment of the invention, a compound of the general formula (I) or a stereoisomer, hydrate, metabolite, solvate, pharmaceutically acceptable salt or cocrystal thereof, wherein:

R$^1$ is selected from

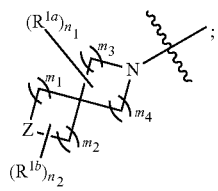

each of m$_1$, m$_2$, m$_3$, m$_4$ is independently selected from 1 or 2;

each of n$_1$, n$_2$ is independently selected from 0, 1 or 2;
Z is selected from CR$^{z1}$R$^{z2}$ or NR$^{z3}$;
each of R$^{z1}$, R$^{z2}$ is independently selected from H, F, Cl, Br, I, OH, CF$_3$, nitro, C$_{1-4}$ alkyl, C$_{1-4}$ alkoxy, C$_{2-4}$ alkenyl, C$_{2-4}$ alkynyl, —C(=O)—C$_{1-4}$ alkyl, —(CH$_2$)$_q$—C(=O) O—C$_{1-4}$ alkyl, —(CH$_2$)$_q$—NR$^{1e}$R$^{1f}$, —(CH$_2$)$_q$—COOH, —(CH$_2$)$_q$—CONH$_2$, C$_{3-6}$ carbocyclic group or a 3 to 6 membered heterocyclic group, preferably H, C$_{1-4}$ alkyl, —(CH$_2$)$_q$—C(=O)O—C$_{1-4}$ alkyl, —(CH$_2$)$_q$—NR$^{1e}$R$^{1f}$, —(CH$_2$)$_q$—COOH, —(CH$_2$)$_q$—CONH$_2$, C$_{3-6}$ carbocyclic group or a 3 to 6 membered heterocyclic group. The alkyl, alkoxy, alkenyl, alkynyl, carbocyclic or heterocyclic group is optionally further substituted with 0 to 3 substituent(s) selected from the group consisting of F, Cl, Br, I, OH, CF$_3$, nitro, =O, carboxyl, cyano, amino, C$_{1-4}$ alkyl, C$_{1-4}$ alkoxy, C$_{2-4}$ alkenyl, C$_{2-4}$ alkynyl, C$_{3-6}$ carbocyclic group or a 3 to 6 membered heterocyclic group. The heterocyclic group contains 1 to 3 heteroatom(s) optionally selected from N, O or S. The heterocyclic group contains 1 to 3 heteroatom(s) optionally selected from N, O or S, and when the heteroatom is selected from S, it is optionally in form of S, S=O or S(=O)$_2$;

each of $R^{1e}$, $R^{1f}$ is independently selected from H, $C_{1-4}$ alkyl, —C(=O)O—$C_{1-4}$ alkyl, —C(=O)O—(CH$_2$)$_q$—$C_{3-6}$ carbocyclic group or —C(=O)O—(CH$_2$)$_{q-3}$ to 6 membered heterocyclic group, preferably H, $C_{1-4}$ alkyl, —C(=O)O—$C_{1-4}$ alkyl or —C(=O)O—(CH$_2$)$_q$—$C_{3-6}$ carbocyclic group.

The alkyl, carbocyclic or heterocyclic group is optionally further substituted with 0 to 3 substituent(s) selected from the group consisting of F, Cl, Br, I, OH, CF$_3$, cyano, nitro, $C_{1-4}$ alkyl, $C_{1-4}$ alkoxy, $C_{2-4}$ alkenyl, $C_{2-4}$ alkynyl, $C_{3-6}$ carbocyclic group or a 3 to 6 membered heterocyclic group. The heterocyclic group contains 1 to 3 heteroatom(s) selected from N, O or S;

alternatively, $R^{z1}$ and $R^{z2}$ form a 3 to 10 membered nitrogen-containing heterocyclic ring, preferably form a 4 to 6 membered nitrogen-containing heterocyclic ring, with the carbon atom to which they are attached. The ring is optionally further substituted with substituent(s) selected from the group consisting of F, Cl, Br, I, OH, CF$_3$, cyano, nitro, =O, $C_{1-4}$ alkyl, $C_{1-4}$ alkoxy, $C_{2-4}$ alkenyl, $C_{2-4}$ alkynyl, $C_{3-6}$ carbocyclic group or a 3 to 6 membered heterocyclic group;

each of $R^{1a}$, $R^{1b}$ is independently selected from F, CF$_3$, $C_{1-6}$ alkyl, $C_{2-6}$ alkenyl, $C_{2-6}$ alkynyl or a 3 to 6 membered heterocyclic group, preferably F, CF$_3$, $C_{2-4}$ alkenyl or $C_{2-4}$ alkynyl. The alkyl, alkenyl, alkynyl or heterocyclic group is optionally further substituted with 0 to 3 substituent(s) selected from the group consisting of F, Cl, Br, I, OH, CF$_3$, nitro, cyano, $C_{1-4}$ alkyl, $C_{1-4}$ alkoxy, $C_{2-4}$ alkenyl, $C_{2-4}$ alkynyl, $C_{3-6}$ carbocyclic group or a 3 to 6 membered heterocyclic group. The heterocyclic group contains 1 to 3 heteroatom(s) optionally selected from N, O or S;

$R^{z3}$ is independently selected from H, —C(=O)—$C_{1-4}$ alkyl, —C(=O)—$C_{3-6}$ carbocyclic group, —C(=O)O—$C_{1-4}$ alkyl, —C(=O)—$C_{3-4}$ carbocyclic group, —C(=O)O—$C_{3-6}$ carbocyclic group or —C(=O)O— (3 to 6 membered heterocyclic group), —S(=O)$_p$—$C_{1-4}$ alkyl, —S(=O)$_p$—$C_{3-6}$ carbocyclic group, —S(=O)$_p$— (3 to 6 membered heterocyclic group), —C(=O)NR$^{1g}$R$^{1h}$, —S(=O)$_p$—NR$^{1i}$R$^{1j}$ or a 3 to 6 membered heterocyclic group, preferably H, —C(=O)—$C_{1-4}$ alkyl, —C(=O)O—$C_{1-4}$ alkyl, —S(=O)$_p$—$C_{1-4}$ alkyl, —S(=O)$_p$—$C_{3-6}$ carbocyclic group, —C(=O)NR$^{1g}$R$^{1h}$ or a 3 to 6 membered heterocyclic group. The alkyl, alkenyl, alkynyl, carbocyclic or heterocyclic group is optionally further substituted with 0 to 3 substituent(s) selected from the group consisting of F, Cl, Br, I, OH, CF$_3$, nitro, cyano, amino, $C_{1-4}$ alkyl, $C_{1-4}$ alkoxy, $C_{2-4}$ alkenyl, $C_{2-4}$ alkynyl, $C_{3-6}$ carbocyclic group or a 3 to 6 membered heterocyclic group. The heterocyclic group contains 1 to 3 heteroatom(s) optionally selected from N, O or S;

each of $R^{1g}$, $R^{1h}$, $R^{1i}$, $R^{1j}$ is independently selected from H or $C_{1-6}$ alkyl, preferably H or $C_{1-4}$ alkyl;

alternatively, $R^{1g}$, $R^{1h}$ form a 3 to 10 membered heterocyclic ring, preferably form a 4 to 6 membered heterocyclic ring, with the nitrogen atom to which they are attached. The ring is optionally further substituted with substituent(s) selected from the group consisting of F, Cl, Br, I, OH, CF$_3$, cyano, nitro, $C_{1-4}$ alkyl, $C_{1-4}$ alkoxy, $C_{2-4}$ alkenyl, $C_{2-4}$ alkynyl or —S(=O)$_p$—$C_{1-4}$ alkyl. The heterocyclic group contains 1 to 3 heteroatom(s) selected from N, O or S;

q is selected from 0, 1, 2, 3 or 4; preferably 0 or 1;
p is selected from 0, 1 or 2; preferably 2;
a is selected from 0, 1, 2 or 3; preferably 3;

$R^4$ is independently selected from H, $C_{1-4}$ alkyl, $C_{2-4}$ alkenyl, $C_{2-4}$ alkynyl or —(CH$_2$)$_q$—$C_{3-6}$ carbocyclic group, preferably $C_{1-4}$ alkyl. The alkyl, alkenyl, alkynyl or carbocyclic group is optionally further substituted with 0 to 3 substituent(s) selected from the group consisting of F, Cl, Br, I, OH, CN, CF$_3$, NO$_2$, $C_{1-4}$ alkyl, $C_{1-4}$ alkoxy, $C_{2-4}$ alkenyl, $C_{2-4}$ alkynyl, $C_{3-6}$ carbocyclic group or a 3 to 6 membered heterocyclic group. The heterocyclic group contains 1 to 3 heteroatom(s) selected from N, O or S;

each of $R^2$, $R^3$, $R^7$, $R^8$ is independently selected from H, $C_{1-4}$ alkyl, —C(=O)O—$C_{1-4}$ alkyl, —C(=O)O—(CH$_2$)$_q$—$C_{3-6}$ carbocyclic group, —C(=O)O—(CH$_2$)$_q$— a 3 to 6 membered heterocyclic group or

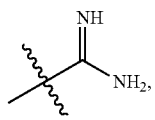 [SMILES: *C(=N)N]

preferably H, $C_{1-4}$ alkyl, —C(=O)O—$C_{1-4}$ alkyl, —C(=O)O—(CH$_2$)$_q$—$C_{3-6}$ carbocyclic group. The alkyl, carbocyclic or heterocyclic group is optionally further substituted with 0 to 3 substituent(s) selected from the group consisting of F, Cl, Br, I, OH, CF$_3$, nitro, cyano, $C_{1-4}$ alkyl, $C_{1-4}$ alkoxy, $C_{2-4}$ alkenyl, $C_{2-4}$ alkynyl, $C_{3-6}$ carbocyclic group or a 3 to 6 membered heterocyclic group. The heterocyclic group contains 1 to 3 heteroatom(s) optionally selected from N, O or S;

b is selected from 0, 1, 2, 3, 4 or 5, preferably 0 or 1;
c is selected from 0, 1, 2, 3, 4 or 5, preferably 0 or 1;
Each of $R^5$, $R^6$ is each independently selected from F, Cl, Br, I, CF$_3$, cyano, nitro, $C_{1-4}$ alkyl, or —NR$^{5f}$R$^{5g}$, preferably F, CF$_3$ or $C_{1-4}$ alkyl;

each of $R^{5f}$ and $R^{5g}$ is independently selected from H or $C_{1-4}$ alkyl.

In a preferred embodiment of the invention, a compound of the general formula (I) or a stereoisomer, hydrate, metabolite, solvate, pharmaceutically acceptable salt or cocrystal thereof, wherein:

each of m$_1$, m$_2$, m$_3$, m$_4$ is independently selected from 1 or 2;
each of n$_1$, n$_2$ is independently selected from 0, 1 or 2;
Z is selected from CR$^{z1}$R$^{z2}$ or NR$^{z3}$;
each of $R^{z1}$, $R^{z2}$ is independently selected from H, $C_{1-4}$ alkyl, —(CH$_2$)$_q$—C(=O)O—$C_{1-4}$ alkyl, —(CH$_2$)$_q$—NR$^{1e}$R$^{1f}$, —(CH$_2$)$_q$—COOH, —(CH$_2$)$_q$—CONH$_2$, $C_{3-6}$ carbocyclic group or a 3 to 6 membered heterocyclic group. The alkyl, carbocyclic or heterocyclic group is optionally further substituted with 0 to 5 substituent(s) selected from the group consisting of F, Cl, Br, I, OH, CF$_3$, =O, carboxyl, nitro, cyano, amino, $C_{1-4}$ alkyl, $C_{1-4}$ alkoxy, $C_{2-4}$ alkenyl, $C_{2-4}$ alkynyl, $C_{3-6}$ carbocyclic group or a 3 to 6 membered heterocyclic group. The heterocyclic group contains 1 to 3 heteroatom(s) optionally selected from N, O or S, and when the heteroatom is selected from S, it is optionally in form of S, S=O or S(=O)$_2$;

each of $R^{1e}$, $R^{1f}$ is independently selected from H, $C_{1-4}$ alkyl, —C(=O)O—$C_{1-4}$ alkyl or —C(=O)O—(CH$_2$)$_q$—$C_{3-6}$ carbocyclic group. The alkyl or carbocyclic group is optionally further substituted with 0 to 3 substituent(s) selected from the group consisting of F, Cl, Br, I, OH, CF$_3$, nitro, cyano, methyl, ethyl, methoxy, ethoxy, phenyl;

alternatively, $R^{z1}$ and $R^{z2}$ are capable of forming a 4 to 6 membered nitrogen-containing heterocyclic ring with a carbon atom to which they are attached. The ring is optionally further substituted with substituent of =O;

$R^{1a}$, $R^{1b}$ are independently selected from F, $CF_3$, methyl, ethyl, propanoyl or isopropyl;

$R^{z3}$ is each independently selected from H, —C(=O)—$C_{1-4}$ alkyl, —C(=O)—$C_{3-6}$ carbocyclic group, —C(=O)O—$C_{1-4}$ alkyl, —S(=O)$_p$—$C_{1-4}$ alkyl, —S(=O)$_p$—$C_{3-6}$ carbocyclic group, —C(=O)NR$^{1g}$R$^{1h}$, —S(=O)$_p$—NR$^{1i}$R$^{1j}$ or a 3 to 6 membered heterocyclic group. The alkyl, carbocyclic or heterocyclic group is optionally further substituted with 0 to 3 substituent(s) selected from the group consisting of F, Cl, Br, I, OH, $CF_3$, nitro, cyano, amino, methyl, ethyl, methoxy, ethoxy, cyclopropyl or phenyl. The heterocyclic group contains 1 to 3 heteroatom(s) selected from N, O or S;

each of $R^{1g}$, $R^{1h}$, $R^{1i}$, $R^{1j}$ is independently selected from H or $C_{1-4}$ alkyl;

Alternatively, $R^{1g}$, $R^{1h}$ form a 4 to 6 membered heterocyclic ring with the nitrogen atom to which they are attached. The ring is optionally further substituted with substituent(s) selected from the group consisting of F, Cl, Br, I, OH, $CF_3$, cyano, nitro, methyl, ethyl, methoxy, ethoxy or —S(=O)$_p$—$C_{1-4}$ alkyl(preferably —S(=O)$_p$-methyl, preferably —S(=O)$_p$-ethyl). The heterocyclic group contains 1 to 3 heteroatom(s) selected from N, O or S;

p is selected from 2;
q is selected from 0 or 1;
a is selected from 3;
$R^4$ is selected from propanoyl or isopropyl;
each of $R^2$, $R^3$, $R^7$, $R^8$ is independently selected from H, $C_{1-4}$ alkyl, —C(=O)O—$C_{1-4}$ alkyl or —C(=O)O-benzyl;
b is selected from 0;
c is selected from 0.

In a preferred embodiment of the invention, the invention provides a compound of the general formula (I), wherein the compound is selected from the compound of general formula (II) or a stereoisomer, hydrate, metabolite, solvate, pharmaceutically acceptable salt or cocrystal thereof, wherein:

(II)

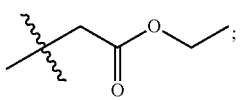 [SMILES: *CC(=O)OCC]

$R^1$ is selected from

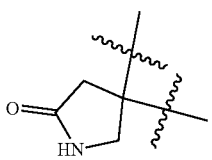 [SMILES: *C1(*)CNC(=O)C1]

each of $m_1$, $m_2$, $m_3$, $m_4$ is independently selected from 1 or 2;
each of $n_1$, $n_2$ is independently selected from 0 or 2;
$R^{1a}$, $R^{1b}$ are independently selected from F;
Z is selected from $CR^{z1}R^{z2}$ or $NR^{z3}$;
each of $R^{z1}$, $R^{z2}$ is independently selected from H, carboxyl

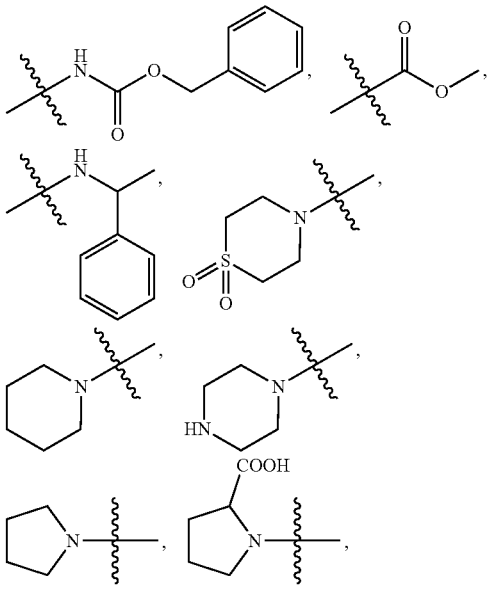

amino, —$CH_2NH_2$ or alternatively, $R^{z1}$ and $R^{z2}$ are capable of forming a lactam with the carbon atom to which they are attached;

$R^{z3}$ is each independently selected from H, —C(=O)—$C_{1-4}$ alkyl, —C(=O)—$C_{3-6}$ carbocyclic group, —C(=O)O—$C_{1-4}$ alkyl, —S(=O)$_p$—$C_{1-4}$ alkyl, —S(=O)$_p$—$C_{3-6}$ carbocyclic group, —C(=O)NR$^{1g}$R$^{1h}$, —S(=O)$_p$—NR$^{1i}$R$^{1j}$ or a 3 to 6 membered heterocyclic group. The alkyl, carbocyclic or heterocyclic group is optionally further substituted with 0 to 3 substituent(s) selected from the group consisting of F, Cl, Br, I, OH, $CF_3$, nitro, cyano, amino, methyl, ethyl, methoxy, ethoxy, cyclopropyl or phenyl. The heterocyclic group contains 1 to 3 heteroatom(s) selected from N, O or S;

each of $R^{1g}$, $R^{1h}$, $R^{1i}$, $R^{1j}$ is independently selected from H or $C_{1-4}$ alkyl;

Alternatively, $R^{1g}$, $R^{1h}$ form a 4 to 6 membered heterocyclic ring with the nitrogen atom to which they are attached. The ring is optionally further substituted with substituent(s) selected from the group consisting of F, $CF_3$, methyl, methoxy or $—S(=O)_p—C_{1-4}$ alkyl. The heterocyclic group contains 1 to 3 heteroatom(s) selected from N, O or S;

p is selected from 2;

each of $R^2$, $R^3$, $R^7$, $R^8$ is independently selected from H, methyl or $—C(=O)O$-tert-butyl.

In a preferred embodiment of the invention, the invention provides a compound of the general formula (II), or a stereoisomer, hydrate, metabolite, solvate, pharmaceutically acceptable salt or cocrystal thereof, wherein $R^1$ is selected from

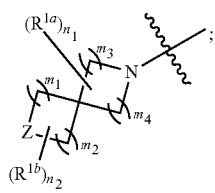

each of $m_1$, $m_2$, $m_3$, $m_4$ is independently selected from 1 or 2;

each of $n_1$, $n_2$ is independently selected from 0 or 2;

$R^{1a}$, $R^{1b}$ are selected from F;

Z is selected from $CR^{z1}R^{z2}$ or $NR^{z3}$;

each of $R^{z1}$, $R^{z2}$ is independently selected from H, carboxyl,

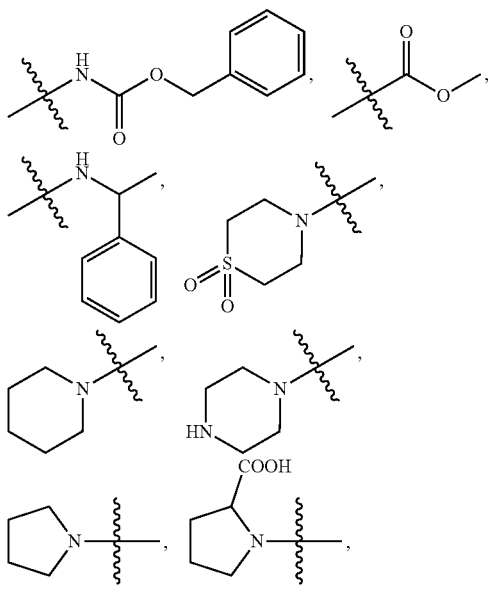

amino, $—CH_2NH_2$ or

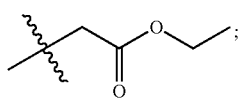 [SMILES: *CC(=O)OCC]

Alternatively, $R^{z1}$ and $R^{z2}$ are capable of forming a lactam

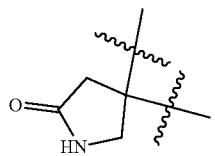 [SMILES: *C1(*)CNC(=O)C1]

with the carbon atom to which they are attached;

$R^{z3}$ is each independently selected from H,

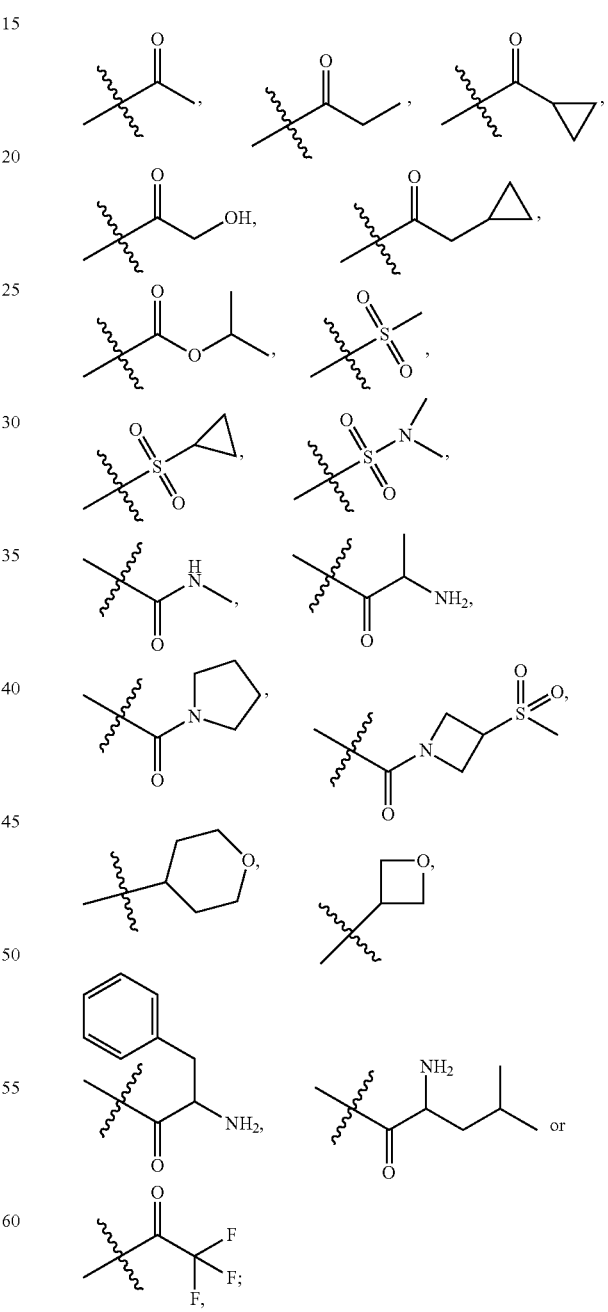

each of $R^2$, $R^3$, $R^7$, $R^8$ is independently selected from H, methyl or $—C(=O)O$-tert-butyl.

In a preferred embodiment of the invention, the invention provides a compound of the general formula (II), or a stereoisomer, hydrate, metabolite, solvate, pharmaceutically acceptable salt or cocrystal thereof, wherein:

$R^1$ is selected from

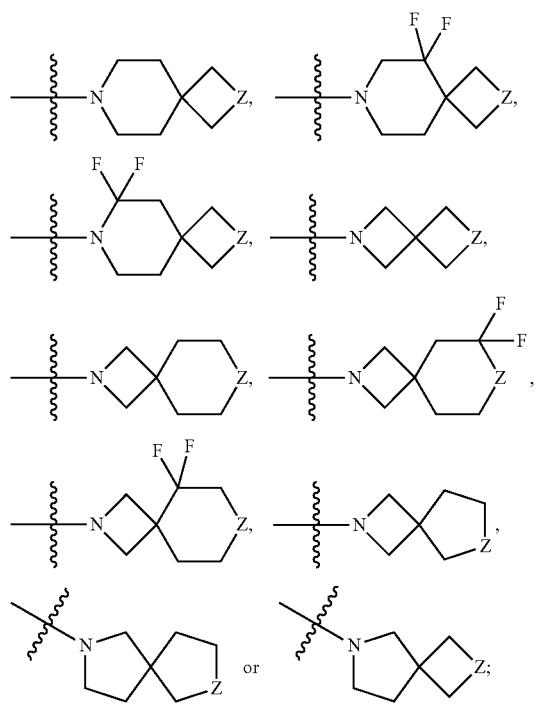

Z is selected from $CR^{z1}R^{z2}$ or $NR^{z3}$;

each of $R^{z1}$, $R^{z2}$ is independently selected from H, carboxyl,

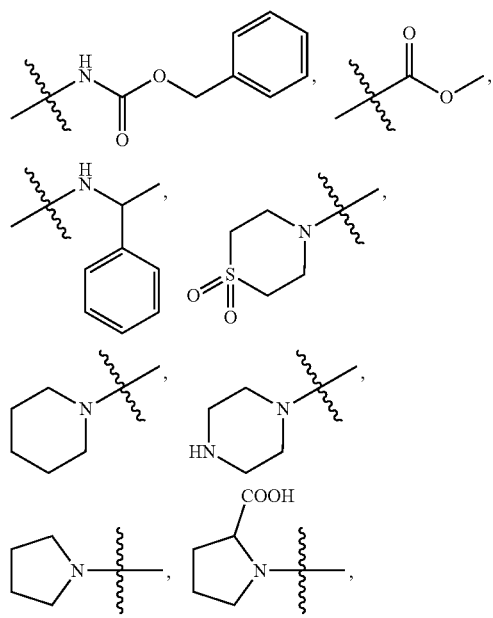

amino, —$CH_2NH_2$ or

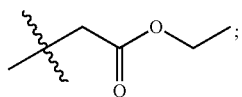 [SMILES: *CC(=O)OCC]

alternatively, $R^{z1}$ and $R^{z2}$ are capable of forming a lactam

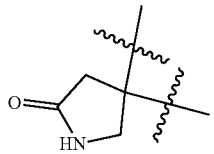 [SMILES: *C1(*)CNC(=O)C1]

with the carbon atom to which they are attached;

$R^{z3}$ is each independently selected from H,

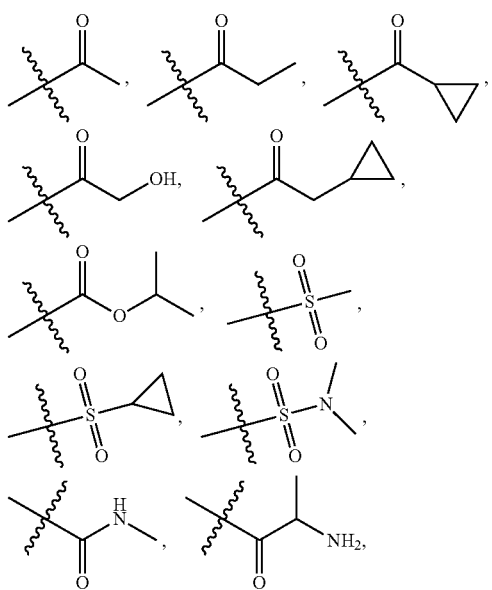

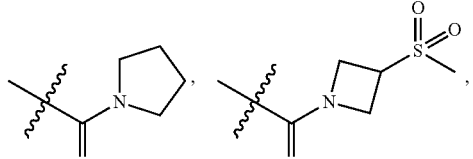

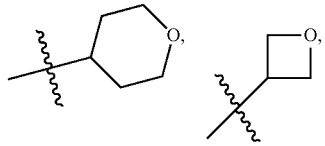

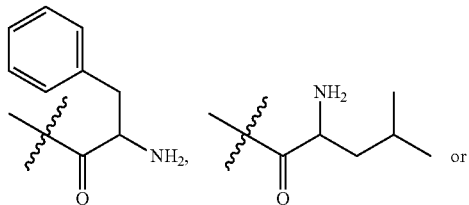

-continued

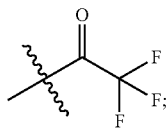

each of $R^2$, $R^3$, $R^7$, $R^8$ is independently selected from H, methyl or —C(=O)O-tert-butyl.

In a preferred embodiment of the invention, the invention provides a compound of the general formula (I) or (II), or a stereoisomer, hydrate, metabolite, solvate, pharmaceutically acceptable salt or cocrystal thereof, wherein the compound includes, but is not limited to, one of the compounds represented by the following structural formula:

compound 2

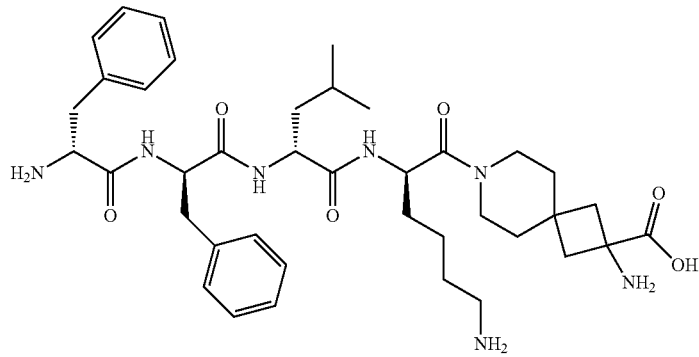

compound 3

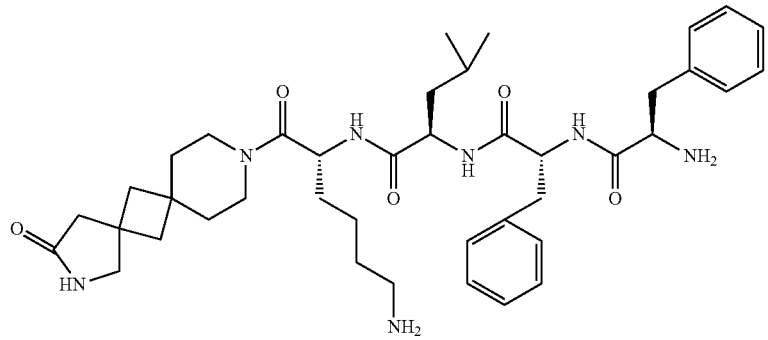

compound 4

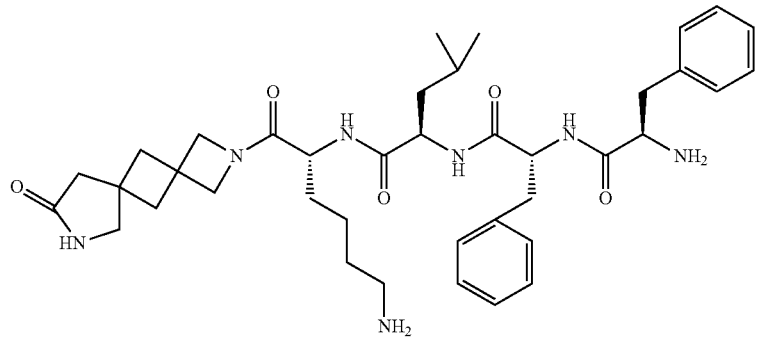

compound 6

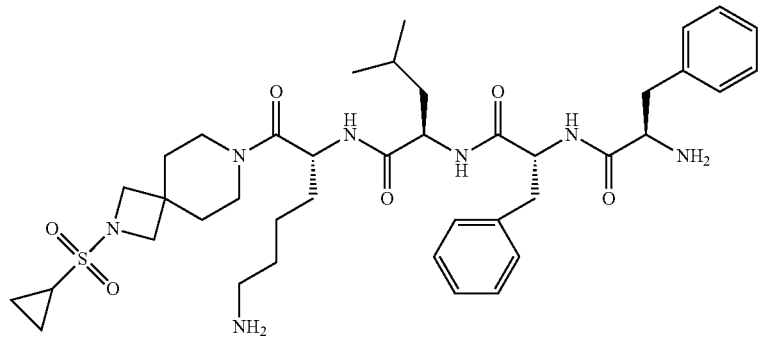

compound 7
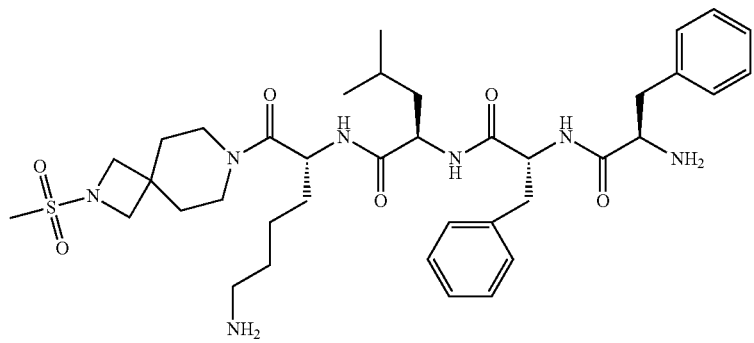
compound 8
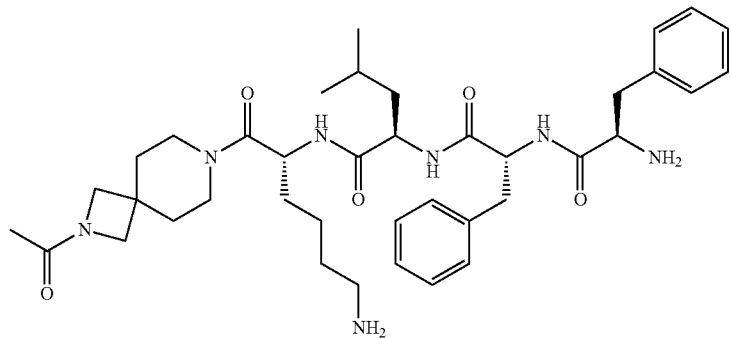
compound 9
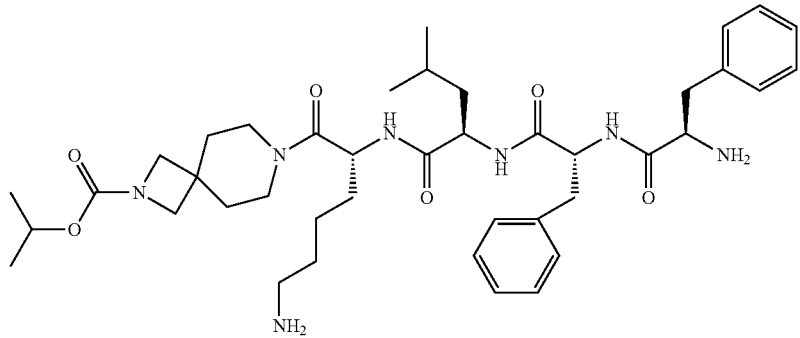
compound 10
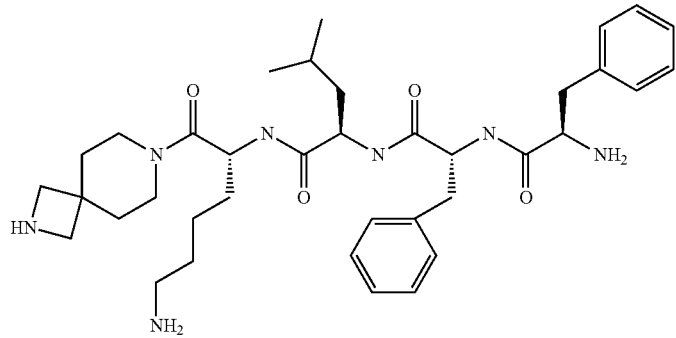

compound 11
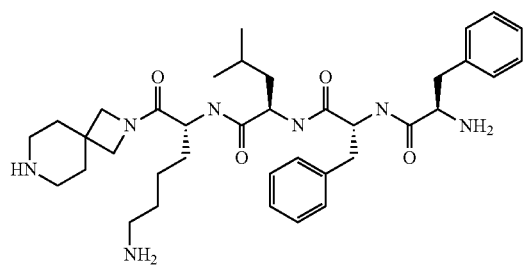
compound 12
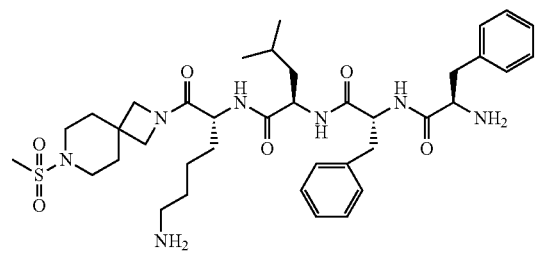
compound 13
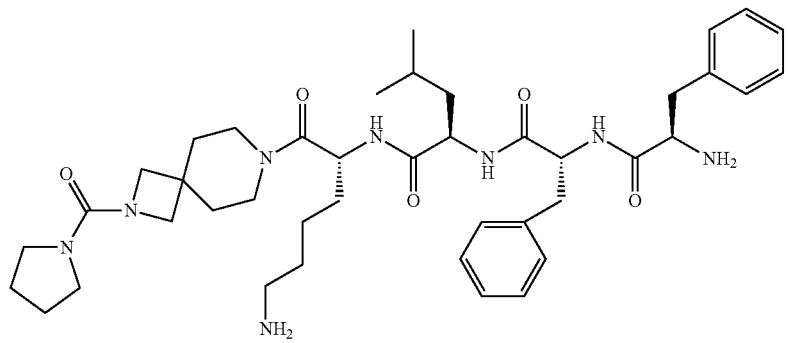
compound 14
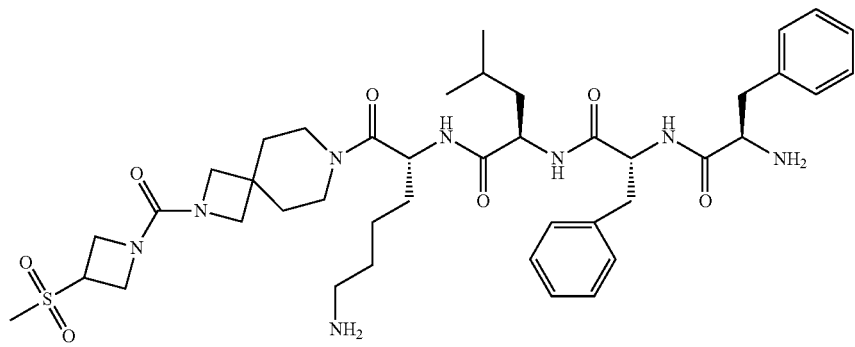
compound 15
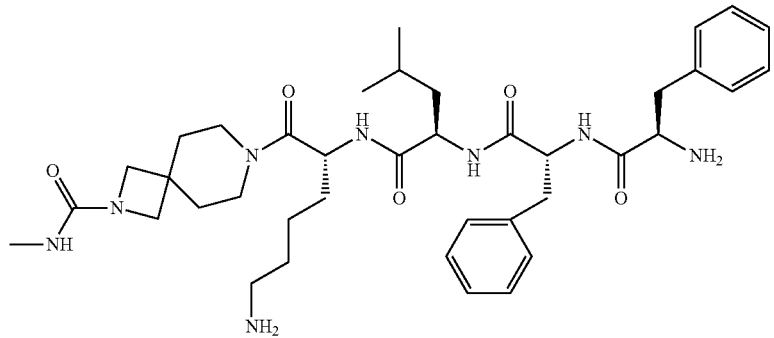

-continued
compound 16
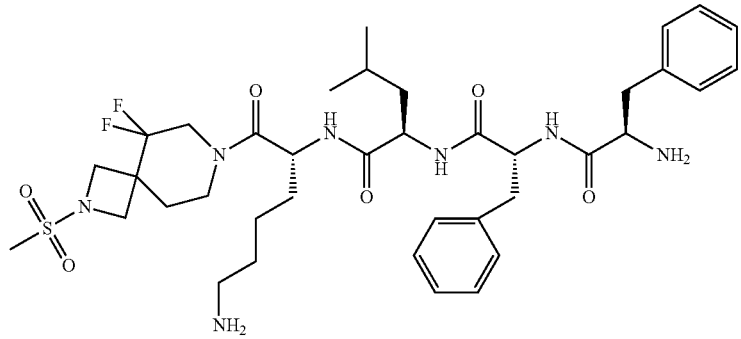
compound 17
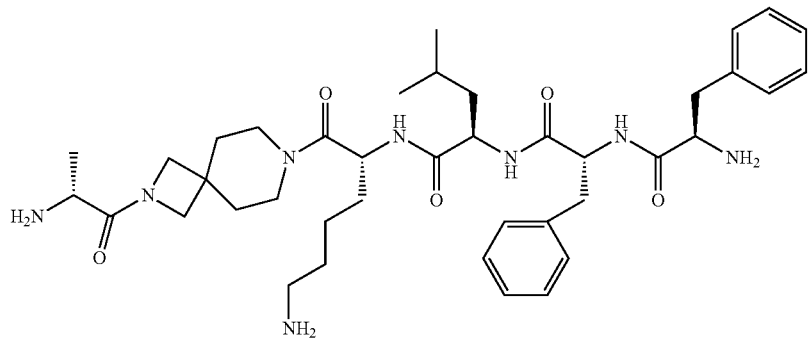
compound 18
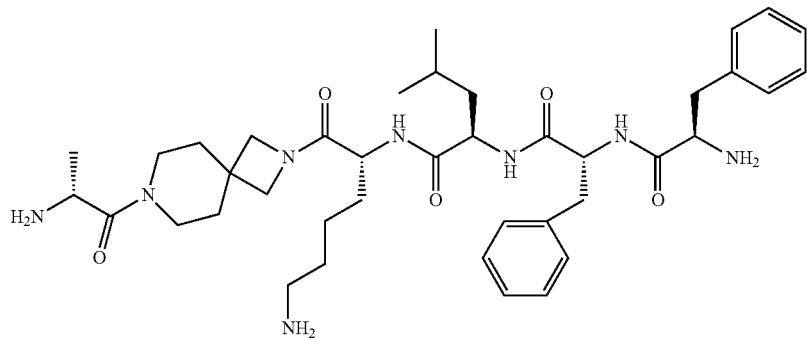
compound 19
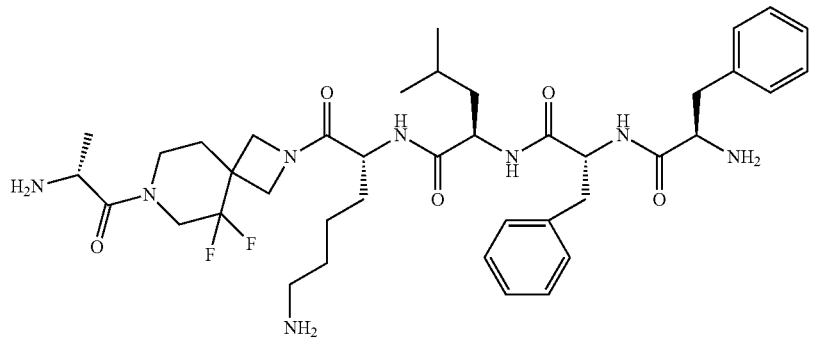

compound 20
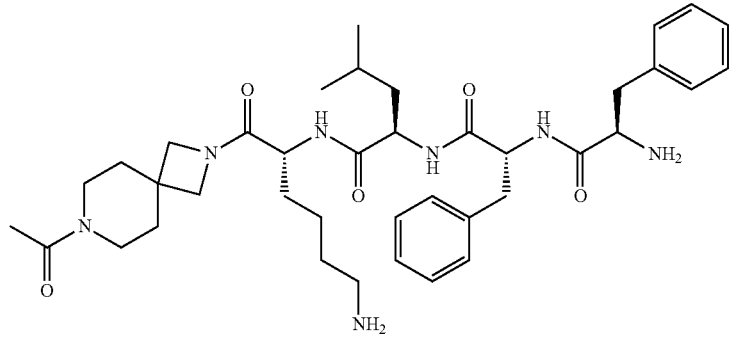
compound 21
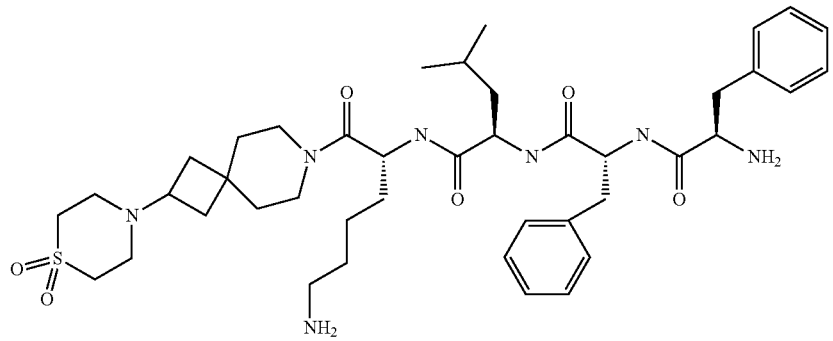
compound 22
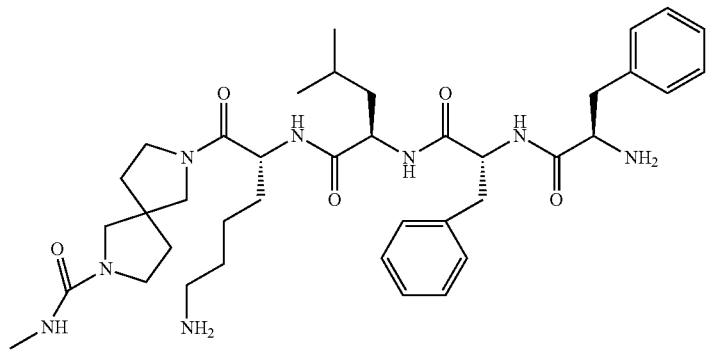
compound 23
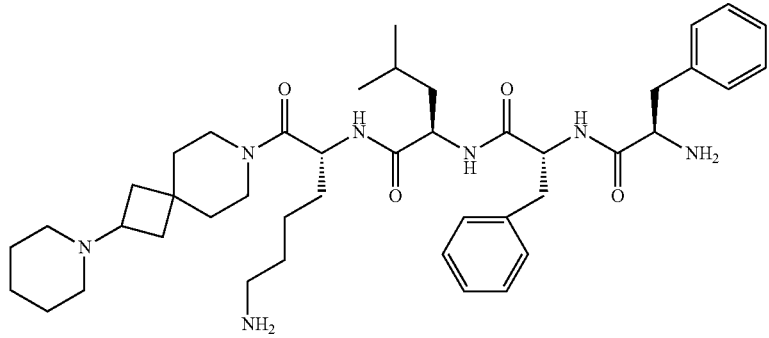

compound 24
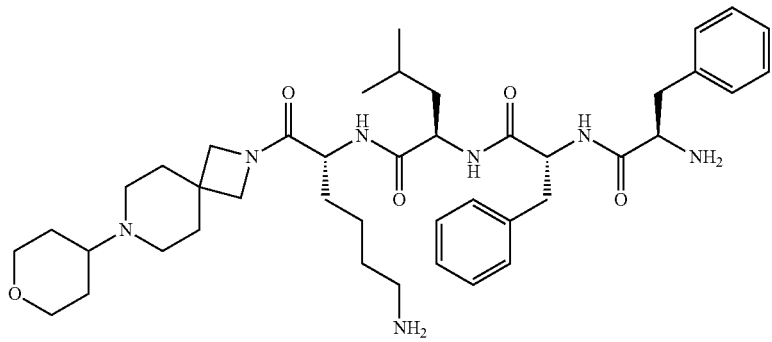
compound 25
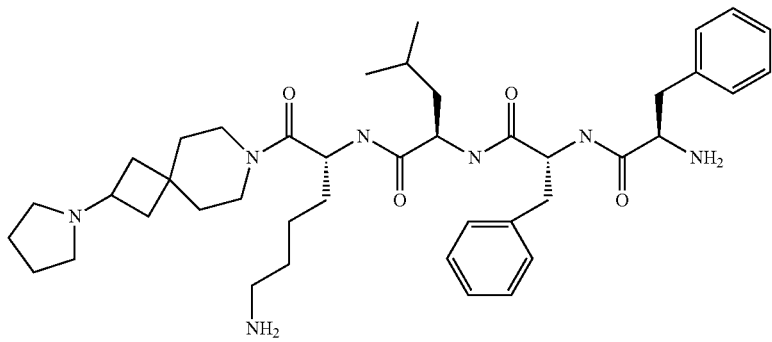
compound 26
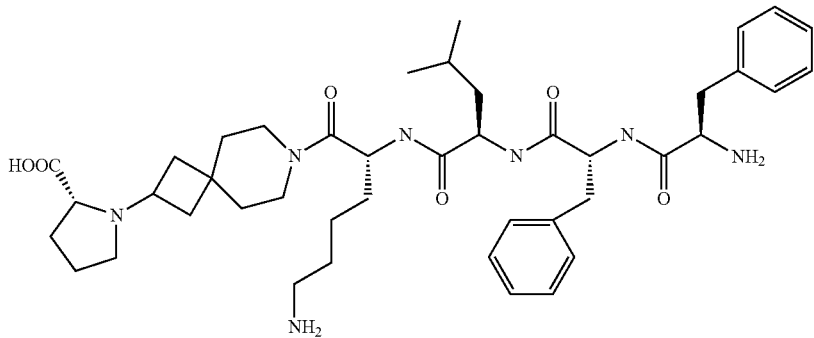
compound 27
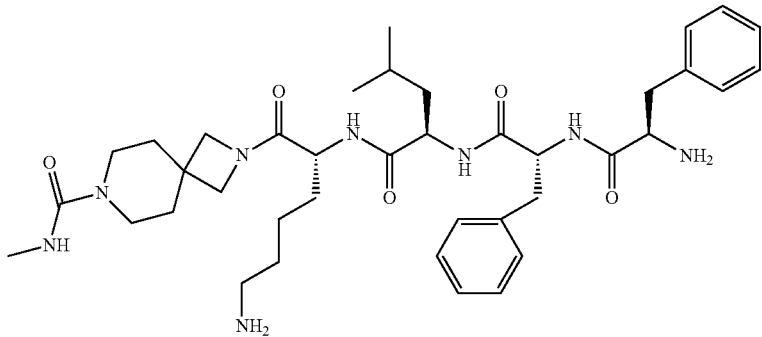

compound 28
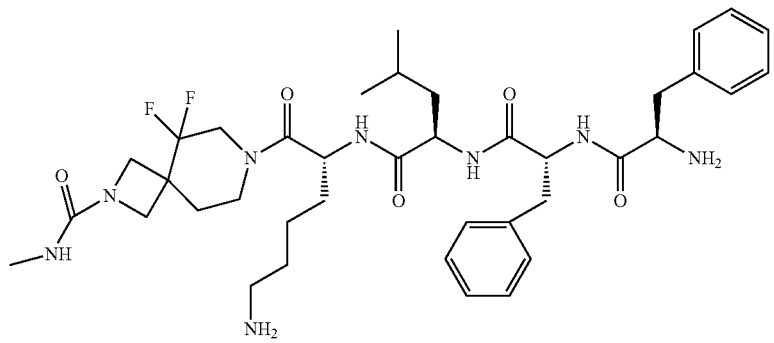
compound 29
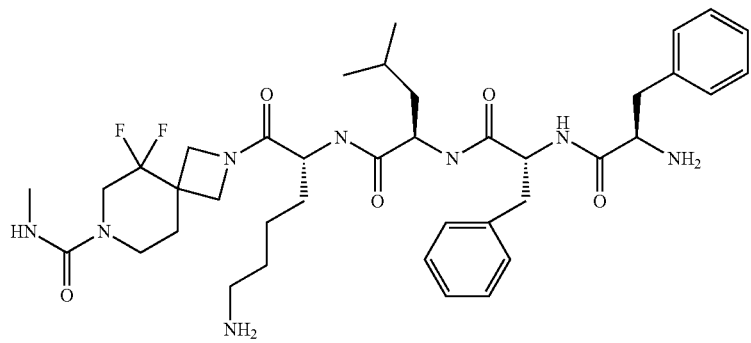
compound 30
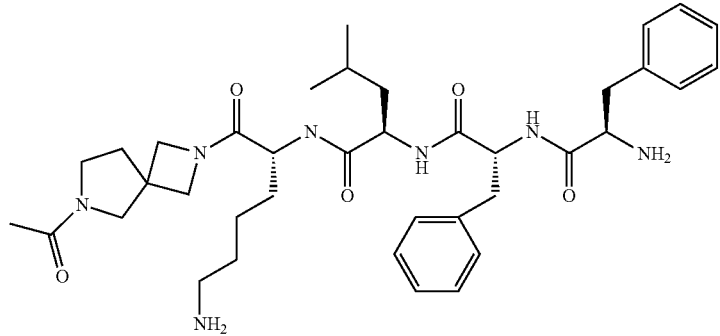
compound 31
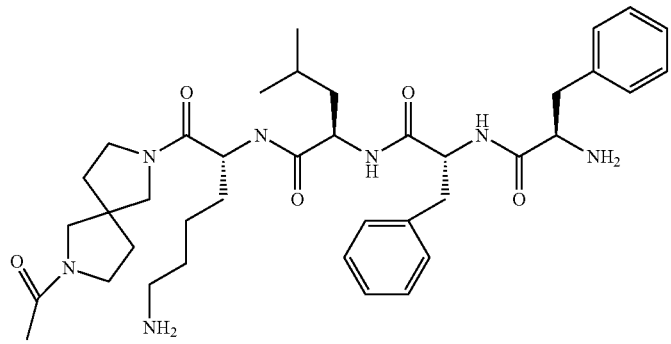

-continued
compound 32
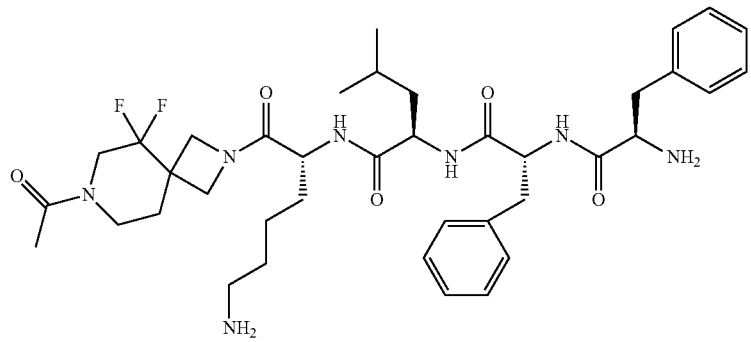
compound 33
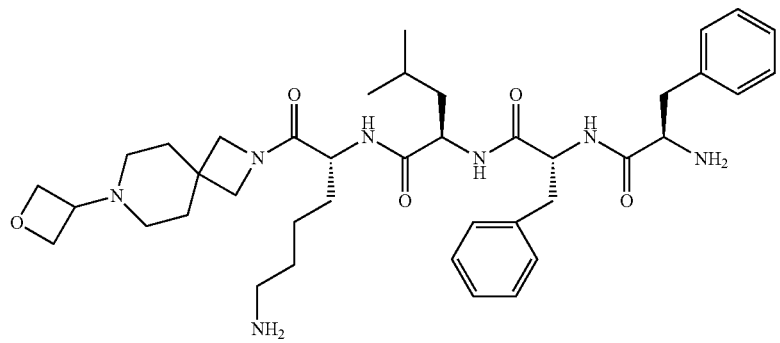
compound 34
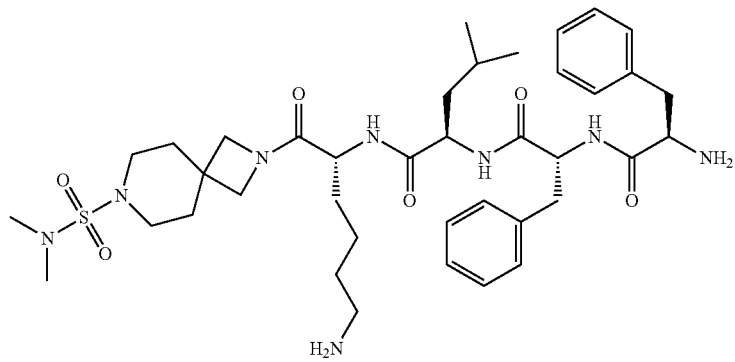
compound 35
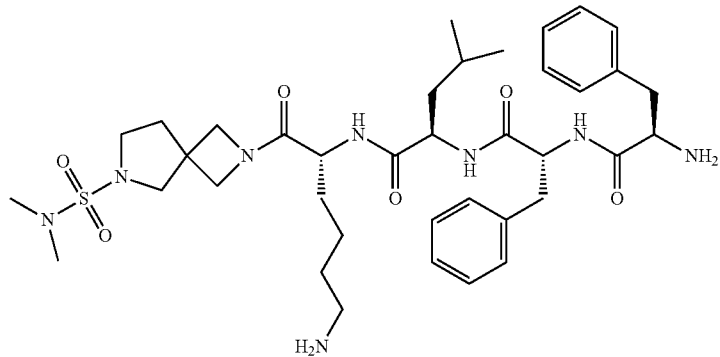

-continued
compound 36
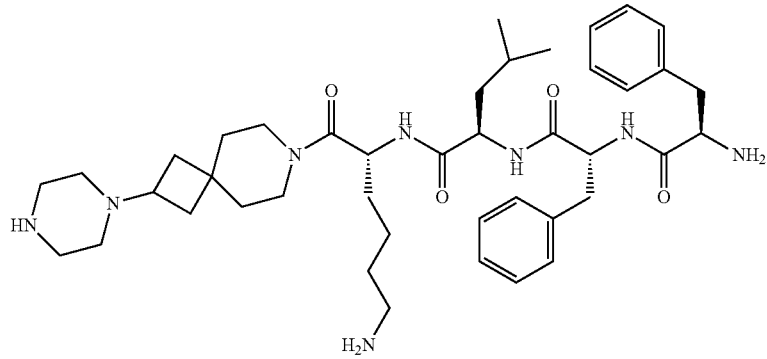
compound 37
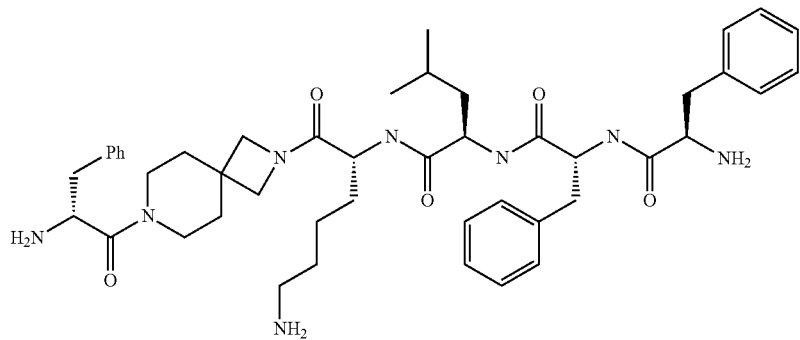
compound 38
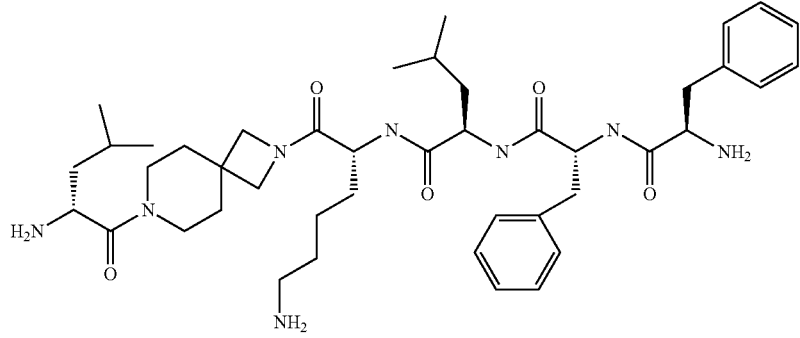
compound 39
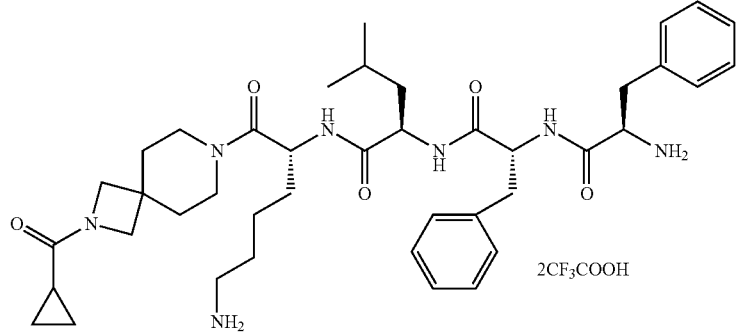

-continued compound 40

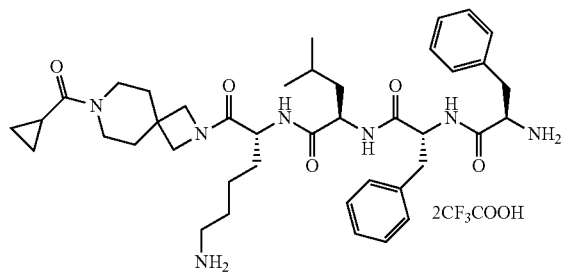

2CF₃COOH compound 41

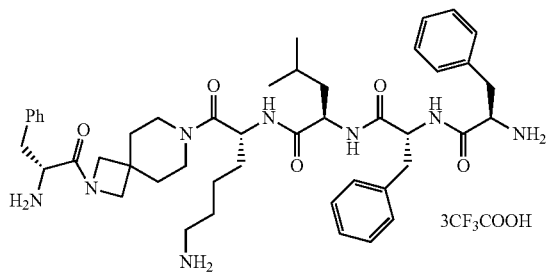

3CF₃COOH compound 42

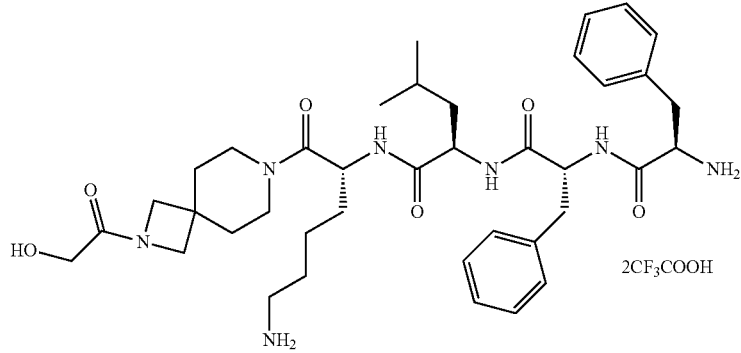

2CF₃COOH compound 43

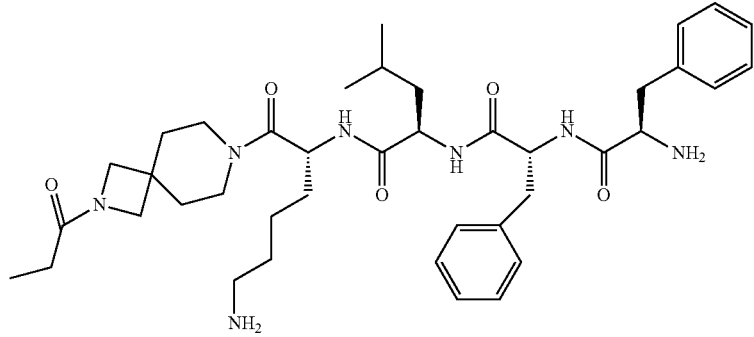

compound 44

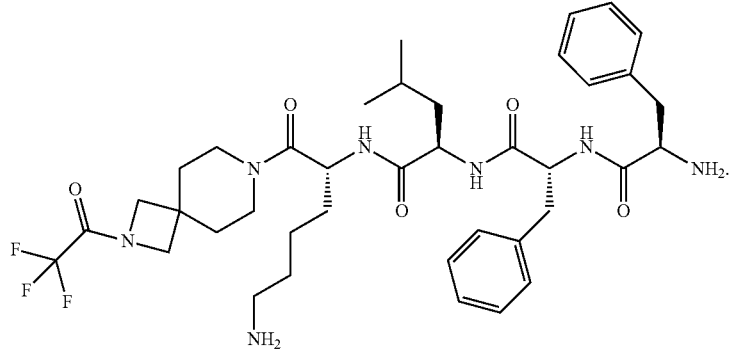

In one preferred embodiment of the invention, the invention provides a compound of the general formula (I) or (II), or a stereoisomer, hydrate, metabolite, solvate, pharmaceutically acceptable salt or cocrystal thereof. The pharmaceutically acceptable salt is selected from a trifluoroacetate.

The invention provides a pharmaceutical composition comprising a compound of the general formula (I) or (II), or a stereoisomer, hydrate, metabolite, solvate, pharmaceutically acceptable salt or cocrystal thereof, and one or more pharmaceutically acceptable carriers and/or excipients.

The use of a compound of the general formula (I) or (II) of the present invention, or a stereoisomer, hydrate, metabolite, solvate, pharmaceutically acceptable salt or cocrystal thereof or a pharmaceutical composition comprising the compound of the general formula (I) or (II), or a stereoisomer, hydrate, metabolite, solvate, pharmaceutically acceptable salt or cocrystal thereof in the manufacture of a medicament for the treatment or prevention of a disease or condition associated with a κ opioid receptor in a mammal.

In a preferred embodiment of the invention, wherein the κ opioid receptor-associated disease or condition is selected from the group consisting of pain, inflammation, itching, edema, hyponatremia, hypokalemia, ileus, cough and glaucoma.

In a preferred embodiment of the invention, wherein the pain is selected from the group consisting of neuropathic pain, physical pain, visceral pain and dermatalgia.

In a preferred embodiment of the invention, wherein the pain is selected from the group consisting of arthritis pain, kidney stone pain, hysterospasm, dysmenorrhea, endometriosis, dyspepsia, post-surgical pain, post-medical treatment pain, eye pain, otitis pain, fulminant cancer pain and pain associated with GI disorders.

The invention provides a method for treating or preventing a disease or condition associated with a κ opioid receptor in a mammal, the method comprising administering the compound of the general formula (I) or (II) or a stereoisomer, hydrate, metabolite, solvate, pharmaceutically acceptable salt or cocrystal thereof, or the pharmaceutical composition comprising the compound of the general formula (I) or (II), or a stereoisomer, hydrate, metabolite, solvate, pharmaceutically acceptable salt or cocrystal thereof. The κ opioid receptor-associated disease or condition is preferably selected from the group consisting of pain, inflammation, itching, edema, hyponatremia, hypokalemia, ileus, cough and glaucoma. The pain is preferably selected from the group consisting of neuropathic pain, somatic pain, visceral pain and dermatalgia; or the pain is preferably selected from the group consisting of arthritis pain, kidney stone pain, hysterospasm, dysmenorrhea, endometriosis, dyspepsia, post-surgical pain, post-medical treatment pain, eye pain, otitis pain, fulminant cancer pain and pain associated with GI disorders (gastrointestinal disorders).

Unless otherwise stated, the terms used in the specification and claims have the following meanings.

The carbon, hydrogen, oxygen, sulfur, nitrogen or halogen involved in the groups and compounds of the present invention include their isotopes, and the carbon, hydrogen, oxygen, sulfur, nitrogen or halogen involved in the groups and compounds of the present invention is optionally further replaced by one or more of their corresponding isotopes, wherein the isotopes of carbon include $^{12}C$, $^{13}C$ and $^{14}C$, the isotopes of hydrogen include protium (H), deuterium (D, also known as heavy hydrogen), tritium (T, also known as super-heavy hydrogen), the isotopes of oxygen include $^{16}O$, $^{17}O$ and $^{18}O$, the isotopes of sulfur include $^{32}S$, $^{33}S$, $^{34}S$ and $^{36}S$, the isotopes of nitrogen include $^{14}N$ and $^{15}N$, the isotopes of fluorine include $^{19}F$, the isotopes of chlorine include $^{35}Cl$ and $^{37}Cl$, the isotopes of bromine include $^{79}Br$ and $^{81}Br$.

An "alkyl" means a straight chain and branched chain monovalent saturated hydrocarbon group, and the straight and branched chain group has a main chain comprising 1 to 10 carbon atoms, preferably 1 to 8 carbon atoms, further preferably 1 to 6 carbon atoms, more preferably 1 to 4 carbon atoms, most preferably 1 to 2 carbon atoms. Examples of alkyl include, but are not limited to methyl, ethyl, n-propyl, isopropyl, n-butyl, isobutyl, sec-butyl, tert-butyl, n-pentyl, 2-pentyl, 3-pentyl, 2-methyl-2-butyl, 3-methyl-2-butyl, n-hexyl, n-heptyl, n-octyl, n-nonyl and n-decyl, etc. The alkyl may be further optionally substituted with 0, 1, 2, 3, 4 or 5 substituent(s) selected from the group consisting of F, Cl, Br, I, =O, hydroxyl, —$SR^{19}$, nitro, cyano, $C_{1-6}$ alkyl, $C_{1-6}$hydroxyl alkyl, $C_{1-6}$ alkoxy, $C_{2-6}$ alkenyl, $C_{2-6}$ alkynyl, $C_{3-8}$ carbocyclic group, 3 to 8 membered heterocyclic group, —$(CH_2)_a$—$C(=O)$—$R^{19}$, —$(CH_2)_k$—$C(=O)$—$O$—$R^{19}$, —$(CH_2)_k$—$C(=O)$—$NR^{19}R^{19a}$, —$(CH_2)_k$—$S(=O)_j$—$R^{19}$, —$O$—$C(=O)$—$O$—$R^{19}$ or —$NR^{19}R^{19a}$, wherein each of $R^{19}$ and $R^{19a}$ is independently selected from H, hydroxyl, amino, carboxyl, $C_{1-8}$ alkyl, $C_{1-8}$ alkoxy, $C_{2-8}$ alkenyl, $C_{2-8}$ alkynyl, 3 to 10 membered carbocyclic group, 4 to 10 membered heterocyclic group, 3 to 10 membered carbocyclyloxy group or 4 to 10 membered heterocyclic oxy group, k is selected from 0, 1, 2, 3, 4 or 5, j is selected from 0, 1 or 2. The alkyl, k, j, $R^{19}$ and $R^{19a}$, herein are as defined above.

An "alkylene" means a straight chain or branched chain divalent saturated hydrocarbon group, including —$(CH_2)_v$— (v is an integer from 1 to 10), and examples of alkylene include, but are not limited to, methylene, ethylene, propylene, butylene or the like. The alkylene may be further optionally substituted with 0, 1, 2, 3, 4 or 5 substituent(s) selected from the group consisting of F, Cl, Br, I, =O, hydroxyl, —$SR^{19}$, nitro, cyano, $C_{1-6}$ alkyl, $C_{1-6}$hydroxyl alkyl, $C_{1-6}$ alkoxy, $C_{2-6}$ alkenyl, $C_{2-6}$ alkynyl, $C_{3-8}$ carbocyclic group, 3 to 8 membered heterocyclic group, —$(CH_2)_a$—$C(=O)$—$R^{19}$, —$(CH_2)_k$—$C(=O)$—$O$—$R^{19}$, —$(CH_2)_k$—$C(=O)$—$NR^{19}R^{19a}$, —$(CH_2)_k$—$S(=O)_j$—$R^{19}$, —$O$—$C(=O)$—$O$—$R^{19}$ or —$NR^{19}R^{19a}$. When the number of substituent(s) in the alkylene group is 2 or more, the substituent(s) may be fused together to form a cyclic structure. The alkylene herein are as defined above.

An "alkoxy" means a monovalent group of an O-alkyl group, wherein alkyl is as defined herein, and examples of alkoxy include, but are not limited to methoxy, ethoxy, 1-propoxy, 2-propoxy, 1-butoxy, 2-methyl-1-propoxy, 2-butoxy, 2-methyl-2-propoxy, 1-pentyloxy, 2-pentyloxy, 3-pentyloxy, 2-methyl-2-butoxy, 3-methyl-2-butoxy, 3-methyl-1-butoxy and 2-methyl-1-butoxy and the like.

An "alkenyl" means a straight chain or branched chain monovalent unsaturated hydrocarbon group having at least 1, usually 1, 2 or 3 carbon-carbon double bonds, with a main chain thereof comprising 2 to 10 carbon atoms, further preferably 2 to 6 carbon atoms, more preferably 2 to 4 carbon atoms in the main chain. Examples of alkenyl include, but are not limited to vinyl, allyl, 1-propenyl, 2-propenyl, 1-butenyl, 2-butenyl, 3-butenyl, 1-pentenyl, 2-pentenyl, 3-pentenyl, 4-pentenyl, 1-methyl-1-butenyl, 2-methyl-1-butenyl, 2-methyl-3-butenyl, 1-hexenyl, 2-hexenyl, 3-hexenyl, 4-hexenyl, 5-hexenyl, 1-methyl-1-pentenyl, 2-methyl-1-pentenyl, 1-heptenyl, 2-heptenyl, 3-heptenyl, 4-heptenyl, 1-octenyl, 3-octenyl, 1-nonenyl, 3-nonenyl, 1-decenyl, 4-decenyl, 1,3-butadiene, 1,3-pentadiene, 1,4-pentadiene and 1,4-hexadiene and the like; The alkenyl may be further optionally substituted with 0, 1, 2, 3, 4 or 5 substituent(s) selected from the group consisting of F, Cl, Br, I, =O, hydroxyl, —$SR^{19}$, nitro, cyano, $C_{1-6}$ alkyl, $C_{1-6}$hydroxyl alkyl, $C_{1-6}$ alkoxy, $C_{2-6}$ alkenyl, $C_{2-6}$ alkynyl, $C_{3-8}$ carbocyclic group, 3 to 8 membered heterocyclic group, —$(CH_2)_a$—$C(=O)$—$R^{19}$, —$(CH_2)_k$—$C(=O)$—$O$—$R^{19}$, —$(CH_2)_k$—$C(=O)$—$NR^{19}R^{19a}$, —$(CH_2)_k$—$S(=O)_j$—$R^{19}$, —$O$—$C(=O)$—$O$—$R^{19}$ or —$NR^{19}R^{19a}$. The alkenyl herein is as defined above.

An "alkynyl" means a straight chain or branched chain monovalent unsaturated hydrocarbon group having at least 1, usually 1, 2 or 3 carbon-carbon triple bonds, with a main chain comprising 2 to 10 carbon atoms, further preferably 2 to 6 carbon atoms, more preferably 2 to 4 carbon atoms in the main chain. Examples of alkynyl include, but are not limited to ethynyl, 1-propynyl, 2-propynyl, butynyl, 2-butynyl, 3-butynyl, 1-methyl-2-propynyl, 4-pentynyl, 3-pentynyl, 1-methyl-2-butynyl, 2-hexynyl, 3-hexynyl, 2-heptynyl, 3-heptynyl, 4-heptynyl, 3-octynyl, 3-nonynyl and 4-decynyl and the like; The alkynyl may be further optionally substituted with 0, 1, 2, 3, 4 or 5 substituent(s) selected from the group consisting of F, Cl, Br, I, =O, hydroxyl, —$SR^{19}$, nitro, cyano, $C_{1-6}$ alkyl, $C_{1-6}$hydroxyl alkyl, $C_{1-6}$ alkoxy, $C_{2-6}$ alkenyl, $C_{2-6}$ alkynyl, $C_{3-8}$ carbocyclic group, 3 to 8 membered heterocyclic group, —$(CH_2)_a$—C(=O)—$R^{19}$, —$(CH_2)_k$—C(=O)—O—$R^{19}$, —$(CH_2)_k$—C(=O)—$NR^{19}R^{19a}$, —$(CH_2)_k$—S(=O)$_j$—$R^{19}$, —O—C(=O)—O—$R^{19}$ or —$NR^{19}R^{19a}$. The alkynyl herein is as defined above.

A "cycloalkyl" means a monovalent saturated carbocyclic hydrocarbon group, usually having from 3 to 10 carbon atoms, and non-limiting examples include cyclopropyl, cyclobutyl, cyclopentyl, cyclohexyl or cycloheptyl and the like. The cycloalkyl may be further optionally substituted with 0, 1, 2, 3, 4 or 5 substituent(s) selected from the group consisting of F, Cl, Br, I, =O, hydroxyl, —$SR^{19}$, nitro, cyano, $C_{1-6}$ alkyl, $C_{1-6}$hydroxyl alkyl, $C_{1-6}$ alkoxy, $C_{2-6}$ alkenyl, $C_{2-6}$ alkynyl, $C_{3-8}$ carbocyclic group, 3 to 8 membered heterocyclic group, —$(CH_2)_a$—C(=O)—$R^{19}$, —$(CH_2)_k$—C(=O)—O—$R^{19}$, —$(CH_2)_k$—C(=O)—$NR^{19}R^{19a}$, —$(CH_2)_k$—S(=O)$_j$—$R^{19}$, —O—C(=O)—O—$R^{19}$ or —$NR^{19}R^{19a}$. The cycloalkyl herein is as defined above.

A "carbocycly" means a saturated or unsaturated, aromatic or non-aromatic ring. The aromatic or non-aromatic ring may be a 3 to 10 membered monocyclic ring, a 4 to 12 membered bicyclic ring or a 10 to 15 membered tricyclic ring system. The carbocyclic group may be attached to a bridged ring or a spiro ring. Non-limiting examples include cyclopropyl, cyclobutyl, cyclopentyl, 1-cyclopentyl-1-alkenyl, 1-cyclopentyl-2-alkenyl, 1-cyclopentyl-3-alkenyl, cyclohexyl, 1-cyclohexyl-2-alkenyl, 1-cyclohexyl-3-alkenyl, cyclohexenyl, cyclohexadienyl, cycloheptyl, cyclooctyl, cyclononyl, cyclodecyl, cycloundecyl, cyclododecyl, phenyl or naphthyl. The carbocyclic group may be further optionally substituted with 0, 1, 2, 3, 4 or 5 substituent(s) selected from the group consisting of F, Cl, Br, I, =O, hydroxyl, —$SR^{19}$ nitro, cyano, $C_{1-6}$ alkyl, $C_{1-6}$hydroxyl alkyl, $C_{1-6}$ alkoxy, $C_{2-6}$ alkenyl, $C_{2-6}$ alkynyl, $C_{3-8}$ carbocyclic group, 3 to 8 membered heterocyclic group, —$(CH_2)_a$—C(=O)—$R^{19}$, —$(CH_2)_k$—C(=O)—O—$R^{19}$, —$(CH_2)_k$—C(=O)—$NR^{19}R^{19a}$, —$(CH_2)_k$—S(=O)$_j$—$R^{19}$, —O—C(=O)—O—$R^{19}$ or —$NR^{19}R^{19a}$. The carbocycle herein is as defined above.

A "heterocycle" means a saturated or unsaturated, aromatic or non-aromatic ring, and the aromatic or non-aromatic ring may be a 3 to 10 membered monocyclic, a 4 to 12 membered bicyclic or a 10 to 15 membered tricyclic system, and includes 1 to 4 hetero atoms selected from N, O or S, preferably a 3 to 8 membered heterocyclic group, and optionally substituted N, S in the ring of the heterocyclic group may be oxidized to various oxidation states. The heterocyclic group may be bonded to a hetero atom or a carbon atom, and the heterocyclic group may be bonded to a bridged or spiro ring. Non-limiting examples include epoxyethyl, epoxypropyl, azacyclopropyl, oxecyclobutyl, azacyclobutyl, thioheterobutyl, 1,3-dioxolanyl, 1,4-dioxolanyl, 1,3-dioxohexyl, azacycloheptyl, oxepanyl, thiocycloheptyl, oxazepinyl, diazepinyl, thiazepinyl, pyridyl, piperidinyl, homopiperidinyl, furyl, thienyl, pyranyl, N-alkylpyrrolyl, pyrimidinyl, pyrazinyl, pyridazinyl, piperazinyl, homopiperazinyl, imidazolyl, piperidinyl, morpholinyl, thiomorpholinyl, Oxathianyl, dihydrofuranyl, dihydropyranyl, dithiapentanyl, tetrahydrofuranyl, tetrahydrothienyl, tetrahydropyranyl, tetrahydrothyranyl, tetrahydropyrrolyl, tetrahydroimidazolyl, tetrahydrothiazolyl, tetrahydropyranyl, benzimidazolyl, benzopyridyl, pyrrolopyridyl, benzodihydrofuryl, 2-pyrrolinyl, 3-pyrrolinyl, dihydroindolyl, 2H-pyranyl, 4H-pyranyl, dioxane, 1,3-dioxolyl, pyrazolinyl, dithiaalkyl, dithiacenyl, dihydrothienyl, pyrazolidinyl, imidazolinyl, imidazolidinyl, 1,2,3,4-tetrahydroisoquinolinyl, 3-azabicyclo[3.1.0]hexyl, 3-azabicyclo[4.1.0]heptyl, azabicyclo[2.2.2]hexyl, 3H-indolylquinazinyl, N-pyridyl urea, 1,1-dioxothiomorpholinyl, azabicyclo[3.2.1]octyl, azabicyclo[5.2.0]nonanyl, oxatricyclo[5.3.1.1]dodecyl, azaadamantyl and oxaspiro[3.3]heptyl. The heterocyclic group may be further optionally substituted with 0, 1, 2, 3, 4 or 5 substituent(s) selected from the group consisting of F, Cl, Br, I, =O, hydroxyl, —$SR^{19}$, nitro, cyano, $C_{1-6}$ alkyl, $C_{1-6}$hydroxyl alkyl, $C_{1-6}$ alkoxy, $C_{2-6}$ alkenyl, $C_{2-6}$ alkynyl, $C_{3-8}$ carbocyclic group, 3 to 8 membered heterocyclic group, —$(CH_2)_a$—C(=O)—$R^{19}$, —$(CH_2)_k$—C(=O)—O—$R^{19}$, —$(CH_2)_k$—C(=O)—$NR^{19}R^{19a}$, —$(CH_2)_k$—S(=O)$_j$—$R^{19}$, —O—C(=O)—O—$R^{19}$ or —$NR^{19}R^{19a}$. The heterocycles herein are defined as described above.

The "optional" or "optionally" means that the subsequently described event or environment may but not necessary to occur, indicating a case where the event or environment occurs or does not occur. For example, "alkyl group optionally substituted with F" means that the alkyl group may, but need not to be substituted with F, indicating a case where the alkyl group is substituted with F and a case where the alkyl group is not substituted with F.

"Pharmaceutical composition" means a mixture of one or more of the compounds described herein or a physiologically/pharmaceutically acceptable salt thereof, or a stereoisomer, solvate, pharmaceutically acceptable salt or cocrystal thereof, and other constituents. Where other components comprise physiologically/pharmaceutically acceptable carriers and excipients.

"Stereoisomer" means isomers resulting from the spatial arrangement of atoms in a molecule, including cis and trans isomers, enantiomers and conformational isomers.

"Effective dose" means the amount of a compound that causes a physiological or medical response to a tissue, system or subject, which amount is sought. When administered to a subject, it is sufficient to prevent the occurrence or reduction of one or more symptoms of the diseases or conditions being treated to some extent.

"Solvate" means a compound of the invention or a salt thereof, which also includes a stoichiometric or non-stoichiometric amount of solvent bound by intermolecular non-covalent forces. When the solvent is water, it is a hydrate.

DETAILED DESCRIPTION

The technical solutions of the present invention are described in detail below with reference to the accompanying Drawings and Example, but the scope of the present invention includes them but not limited them.

The structure of the compound is determined by nuclear magnetic resonance (NMR) or (and) mass spectrometry (MS). The NMR shift (δ) is given in units of $10^{-6}$ (ppm). The NMR was measured using a nuclear magnetic apparatus (Bruker Avance III 400 and Bruker Avance 300), and the solvent for measurement was deuterated dimethyl sulfoxide (DMSO-$d_6$), deuterated chloroform (CDCl$_3$), deuterated methanol (CD$_3$OD), and the internal standard is tetramethylsilane (TMS).

MS is measured using (Agilent 6120B(ESI) and Agilent 6120B(APCI)).

HPLC is measured using an Agilent 1260DAD high pressure liquid chromatograph (Zorbax SB-C18 100×4.6 mm).

The thin layer chromatography silica gel plate is Yantai Yellow Sea HSGF254 or Qingdao GF254 silica gel plate. The silica gel plate used for thin layer chromatography (TLC) has a specification of 0.15 mm~0.20 mm, and the thin layer chromatography separation and purification product has a specification of 0.4 mm~0.5 mm.

Column chromatography generally uses Yantai Huanghai silica gel 200-300 mesh silica gel as the carrier.

The known starting materials of the present invention may be synthesized by or according to methods known in the art, or may be purchased from Titan Technology, Energy Chemical, Shanghai DEMO, Chengdu Kelong Chemical, Accela ChemBio Co. Ltd, and J&K Scientific Ltd, and the like.

The nitrogen atmosphere refers to the reaction bottle connected to a nitrogen balloon of about 1 L volume.

The hydrogen atmosphere refers to the reaction bottle connected to a hydrogen balloon of about 1 L volume.

The hydrogenation reaction is usually evacuated and charged with hydrogen, and the operation is repeated 3 times.

Unless specially indicated in the examples, all the reaction was allowed to proceed under a nitrogen atmosphere.

Unless specially indicated in the examples, all the solution means an aqueous solution.

Unless specially indicated in the examples, all the reaction temperature is room temperature.

The room temperature is optimal reaction temperature, ranging from 20° C. to 30° C.

Unless specially indicated in the examples, all the M is mol/L.

Boc refers to tert-butyloxycarbonyl group.
Cbz refers to benzyloxycarbonyl group.
THP refers to tetrahydropyranyl group.

Intermediate 1

(2R)-6-(tert-butoxycarbonylamino)-2-[[(2R)-2-[[(2R)-2-[[(2R)-2-(tert-butoxycarbonylamino)-3-phenyl-propanoyl]amino]-3-phenyl-propanoyl]amino]-4-methyl-pentanoyl]amino]hexanoic acid (Intermediate 1)

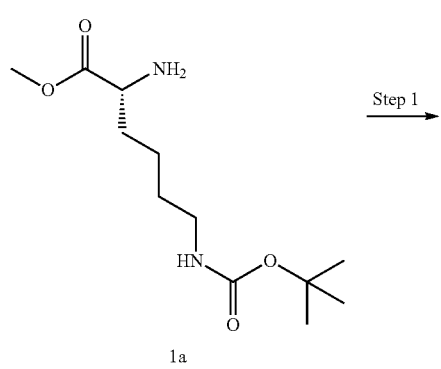

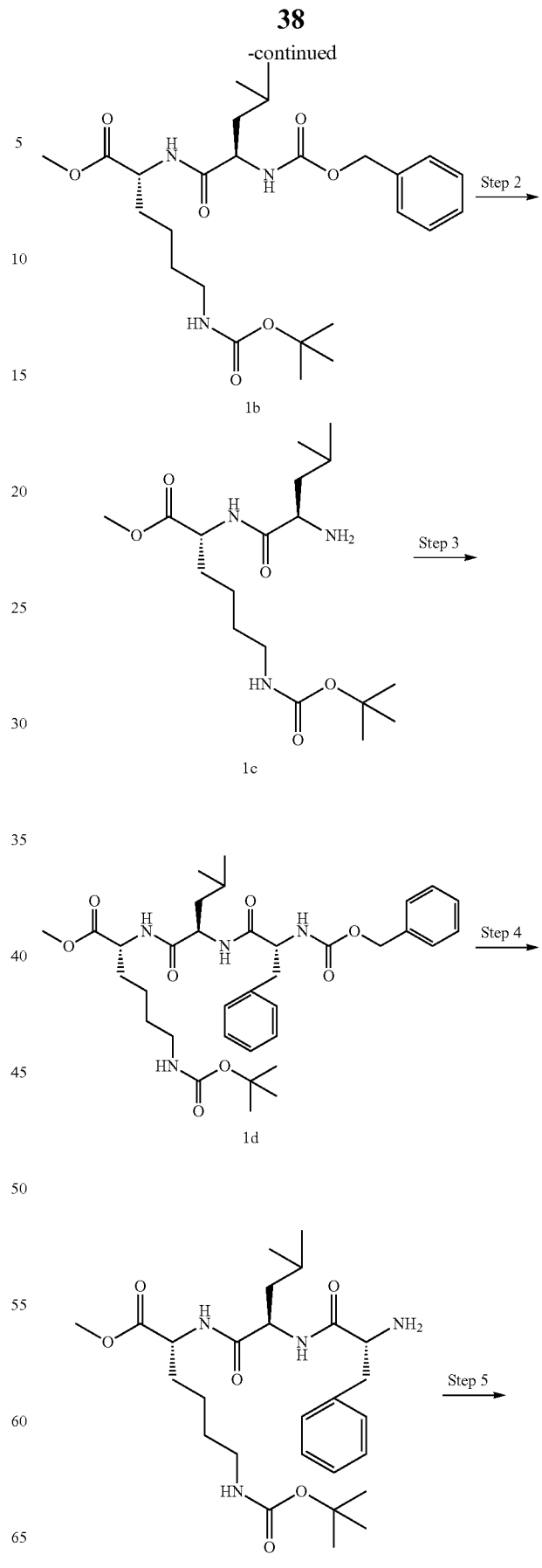

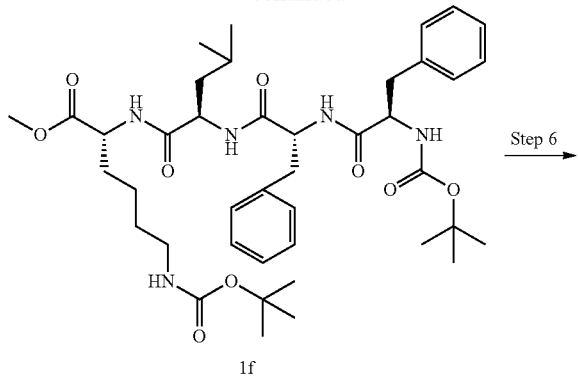

1f

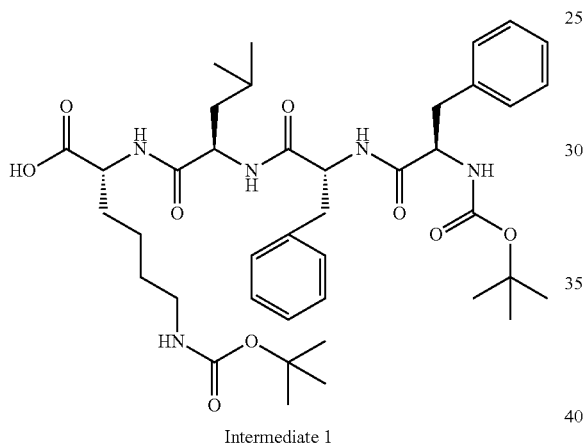

Intermediate 1

Step 1: methyl(2R)-2-[[(2R)-2-(benzyloxycarbonylamino)-4-methyl-pentanoyl]amino]-6-(tert-butoxycarbonylamino)hexanoate (1b)

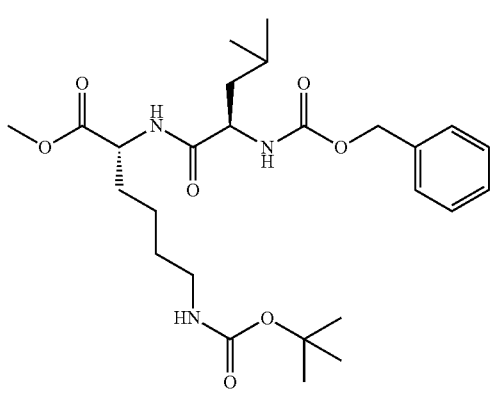 [SMILES: COC(=O)[C@@H](CCCCNC(=O)OC(C)(C)C)NC(=O)[C@@H](CC(C)C)NC(=O)OCc1ccccc1]

Methyl (2R)-2-amino-6-(tert-butoxycarbonylamino) hexanoate (1a) (2.6 g, 10 mmol) was dissolved in ethyl acetate (50 mL) at room temperature, and the temperature was cooled to 0° C. (2R)-2-(benzyloxycarbonylamino)-4-methyl-pentanoic acid (2.8 g, 11 mmol), 1-hydroxybenzotriazole (1.62 g, 12 mmol), 1-(3-dimethylaminopropyl)-3-ethylcarbodiimide hydrochloride (2.3 g, 12 mmol) were sequentially added to the reaction solution, and the temperature was raised to 25° C., and the reaction was allowed to proceed at this temperature for 15 h. 1M aqueous hydrochloric acid solution (25 mL) was added to the reaction solution to wash the reaction and the mixture was subjected to a liquid separation process. A saturated aqueous sodium bicarbonate solution (25 mL) was added to the organic phase, and the mixture was stirred for 30 minutes and the mixture was subjected to a liquid separation process. The organic phase was washed with 1M aqueous hydrochloric acid solution (25 mL), saturated aqueous sodium bicarbonate solution (25 mL), saturated aqueous sodium chloride solution (25 mL) in this order, and dried over anhydrous sodium sulfate (2 g). It was filtrated and the filtrate was concentrated under reduced pressure to obtain methyl (2R)-2-[[(2R)-2-(benzyloxycarbonylamino)-4-methyl-pentanoyl]amino]-6-(tert-butoxycarbonylamino) hexanoate (1b) as a white foamy solid (5.0 g, yield 99%).

Step 2: Methyl (2R)-2-[[(2R)-2-amino-4-methyl-pentanoyl]amino]-6-(tert-butoxycarbonylamino) hexanoate (1c)

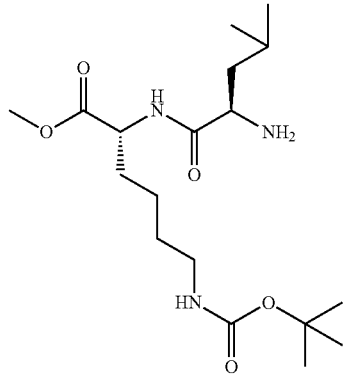 [SMILES: COC(=O)[C@@H](CCCCNC(=O)OC(C)(C)C)NC(=O)[C@H](N)CC(C)C]

Methyl(2R)-2-[[(2R)-2-(benzyloxycarbonylamino)-4-methyl-pentanoyl]amino]-6-(tert-butoxycarbonylamino) hexanoate (1b) (5.0 g, 10 mmol) was dissolved in ethyl acetate (50 mL) at room temperature, and 10% palladium on carbon (1 g, 20% w/w) was added to the reaction solution, and the atmosphere was replaced with hydrogen 3 times. The reaction was allowed to proceed in a hydrogen atmosphere at room temperature for 5 h. The reaction solution was filtered through diatomite (3 g), and the filtrate was concentrated under reduced pressure to obtain crude methyl (2R)-2-[[(2R)-2-amino-4-methyl-pentanoyl]amino]-6-(tert-butoxycarbonylamino)hexanoate (1c) as a white foamy solid (3.7 g, yield 99%) and used directly in the next reaction.

Step 3: Methyl(2R)-2-[[(2R)-2-[[(2R)-2-(benzyloxycarbonylamino)-3-phenyl-propanoyl]amino]-4-methyl-pentanoyl]amino]-6-(tert-butoxycarbonylamino)hexanoate (1d)

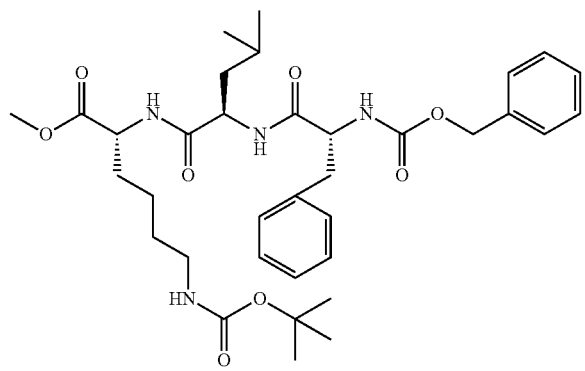 [SMILES: COC(=O)[C@@H](CCCCNC(=O)OC(C)(C)C)NC(=O)[C@@H](CC(C)C)NC(=O)[C@@H](Cc1ccccc1)NC(=O)OCc1ccccc1]

Crude Methyl (2R)-2-[[(2R)-2-amino-4-methyl-pentanoyl]amino]-6-(tert-butoxycarbonylamino) hexanoate (1c) (3.7 g, 9.9 mmol) was dissolved in ethyl acetate (50 mL) at room temperature, and the temperature was cooled to 0° C. (2R)-2-(benzyloxycarbonylamino)-3-phenyl-propanoic acid (3.3 g, 11 mmol), 1-hydroxybenzotriazole (1.62 g, 12 mmol), 1-(3-dimethylaminopropyl)-3-ethylcarbodiimide hydrochloride (2.3 g, 12 mmol) were sequentially added to the reaction solution, and the temperature was raised to 25° C., and the reaction was allowed to proceed at this temperature for 5 h. 1M aqueous hydrochloric acid (25 mL) was added to wash the reaction and the mixture was subjected to a liquid separation process. A saturated aqueous sodium bicarbonate solution (25 mL) was added to the organic phase, and the mixture was stirred for 30 minutes and the mixture was subjected to a liquid separation process. The organic phase was washed with 1M aqueous hydrochloric acid solution (25 mL), saturated aqueous sodium bicarbonate solution (25 mL), saturated aqueous sodium chloride solution (25 mL) in this order, and dried over anhydrous sodium sulfate (2 g). It was filtered and the filtrate was concentrated under reduced pressure to obtain crude methyl(2R)-2-[[(2R)-2-[[(2R)-2-(benzyloxycarbonylamino)-3-phenyl-propanoyl]amino]-4-methyl-pentanoyl]amino]-6-(tert-butoxycarbonylamino)hexanoate (1d) as a white foamy solid (3.0 g, yield 46%), and used directly in the next reaction.

Step 4: Methyl (2R)-2-[[(2R)-2-[[(2R)-2-amino-3-phenyl-propanoyl]amino]-4-methyl-pentanoyl]amino]-6-(tert-butoxycarbonylamino)hexanote (1e)

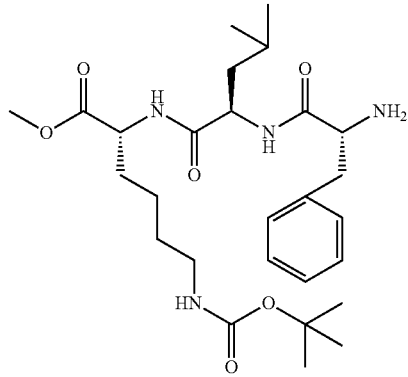 [SMILES: COC(=O)[C@@H](CCCCNC(=O)OC(C)(C)C)NC(=O)[C@@H](CC(C)C)NC(=O)[C@H](N)Cc1ccccc1]

Crude methyl (2R)-2-[[(2R)-2-[[(2R)-2-(benzyloxycarbonylamino)-3-phenyl-propanoyl]amino]-4-methyl-pentanoyl]amino]-6-(tert-butoxycarbonylamino)hexanoate (1d) (3.0 g, 4.58 mmol) was dissolved in ethyl acetate (50 mL) at room temperature, 10% palladium on carbon (1 g, 33% w/w) was added to the reaction solution, and the atmosphere was replaced with hydrogen 3 times. The reaction was allowed to proceed at room temperature for 5 h under a hydrogen atmosphere (balloon). The reaction solution was filtered through diatomite (3 g), and the filtrate was concentrated to dryness under reduced pressure. The ethyl acetate (6 mL) was added therein and the mixture was heated until dissolve. After adding petroleum ether (6 mL), the temperature was slowly dropped to room temperature to precipitate a solid, and filtered. The filter cake was dried at 50° C. under reduced pressure to obtain methyl (2R)-2-[[(2R)-2-[[(2R)-2-amino-3-phenyl-propanoyl]amino]-4-methyl-pentanoyl]amino]-6-(tert-butoxycarbonylamino)hexanoate (1e) as a white foamy solid (2.1 g, yield 88%).

Step 5: Methyl (2R)-6-(tert-butoxycarbonylamino)-2-[[(2R)-2-[[(2R)-2-[[(2R)-2-(tert-butoxycarbonylamino)-3-phenyl-propanoyl]amino]-3-phenyl-propanoyl]amino]-4-methyl-pentanoyl]amino]hexanoate (1f)

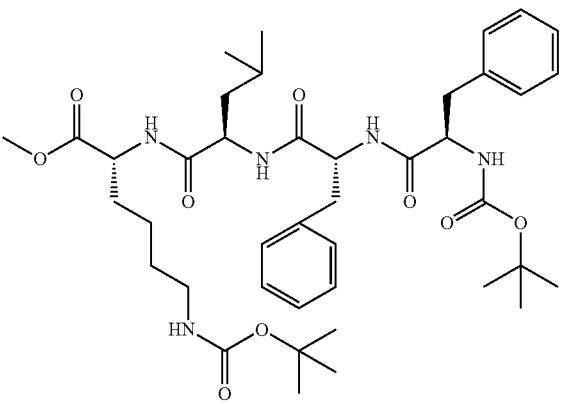 [SMILES: COC(=O)[C@@H](CCCCNC(=O)OC(C)(C)C)NC(=O)[C@@H](CC(C)C)NC(=O)[C@@H](Cc1ccccc1)NC(=O)[C@@H](Cc1ccccc1)NC(=O)OC(C)(C)C]

Methyl (2R)-2-[[(2R)-2-[[(2R)-2-amino-3-phenyl-propanoyl]amino]-4-methyl-pentanoyl]amino]-6-(tert-butoxycarbonylamino)hexanoate (1e) (2.1 g, 4.0 mmol) was dissolved in ethyl acetate (30 mL) at room temperature, and the temperature was dropped to 0° C. (2R)-2-(tert-butoxygencarbonyl)-3-phenyl-propanoic acid (1.3 g, 4.9 mmol), 1-hydroxybenzotriazole (0.65 g, 4.8 mmol), 1-(3-dimethylaminopropyl)-3-ethylcarbodiimide hydrochloride (1.1 g, 5.7 mmol) were sequentially added to the reaction solution, and the temperature was raised to 25° C., and the reaction was allowed to proceed at this temperature for 5 h. 1M aqueous hydrochloric acid (15 mL) was added to wash the reaction and the mixture was subjected to a liquid separation process. A saturated aqueous sodium bicarbonate solution (15 mL) was added to the organic phase, and the mixture was stirred for 30 minutes and the mixture was subjected to a liquid separation process. The organic phase was washed with 1M aqueous hydrochloric acid solution (15 mL), saturated aqueous sodium bicarbonate solution (15 mL), saturated aqueous sodium chloride solution (15 mL) in this order, and dried over anhydrous sodium sulfate. It was filtrated and the filtrate was concentrated under reduced pressure, and separated and purified by silica gel column chromatography (petroleum ether/ethyl acetate (v/v)=100:1-5:1) to obtain methyl (2R)-6-(tert-butoxycarbonylamino)-2-[[(2R)-2-[[(2R)-2-[[(2R)-2-(tert-butoxycarbonylamino)-3-phenyl-propanoyl]amino]-3-phenyl-propanoyl]amino]-4-methyl-pentanoyl]amino]hexanoate (1f) as a white foamy solid (2.3 g, yield 74%).

Step 6: (2R)-6-(tert-butoxycarbonylamino)-2-[[(2R)-2-[[(2R)-2-[[(2R)-2-(tert-butoxycarbonylamino)-3-phenyl-propanoyl]amino]-3-phenyl-propanoyl]amino]-4-methyl-pentanoyl]amino]hexanoic acid (Intermediate 1)

Methyl (2R)-6-(tert-butoxycarbonylamino)-2-[[(2R)-2-[[(2R)-2-[[(2R)-2-(tert-butoxycarbonylamino)-3-phenyl-propanoyl]amino]-3-phenyl-propanoyl]amino]-4-methyl-pentanoyl]amino]hexanoate (1f) (2.3 g, 3.0 mmol) was dissolved in methanol (20 mL) at room temperature. An aqueous sodium hydroxide (200 mg, 5.0 mmol) solution (20 mL) was added to the reaction solution, and the reaction was allowed to proceed at this temperature for 5 h. The reaction solution was adjusted to pH<4 with 1M aqueous hydrochloric acid solution, and then was extracted with ethyl acetate (40 mL), and the mixture was subjected to a liquid separation process The organic phase was dried over anhydrous sodium sulfate, filtered, and the filtrate was concentrated under reduced pressure to obtain (2R)-6-(tert-butoxycarbonylamino)-2-[[(2R)-2-[[(2R)-2-[[(2R)-2-(tert-butoxycarbonylamino)-3-phenyl-propanoyl]amino]-3-phenyl-propanoyl]amino]-4-methyl-pentanoyl]amino]hexanoic acid (Intermediate 1) as a white foamy solid (2.1 g, yield 93%).

Ms m/z (ESI): 752.5 [M−H]⁻;

$^1$H NMR (400 MHz, CDCl$_3$) δ 7.38-7.27 (m, 3H), 7.25-7.07 (m, 7H), 4.82-4.62 (m, 1H), 4.61-4.41 (m, 2H), 4.37-4.18 (m, 1H), 3.37-2.67 (m, 6H), 2.00-1.65 (m, 3H), 1.59-1.37 (m, 15H), 1.35-1.26 (m, 9H), 0.90-0.80 (m, 6H).

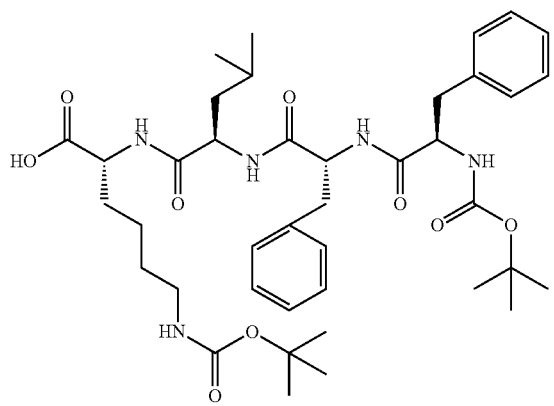 [SMILES: CC(C)C[C@@H](NC(=O)[C@@H](Cc1ccccc1)NC(=O)[C@@H](Cc1ccccc1)NC(=O)OC(C)(C)C)C(=O)N[C@H](CCCCNC(=O)OC(C)(C)C)C(=O)O]

Example 1: 2-amino-7-[(2R)-6-amino-2-[[(2R)-2-[[(2R)-2-[[(2R)-2-amino-3-phenyl-propanoyl]amino]-3-phenyl-propanoyl]amino]-4-methyl-pentanoyl]amino]hexanoyl]-7-azaspiro[3.5]nonane-2-carboxylic acid; tri-trifluoroacetate

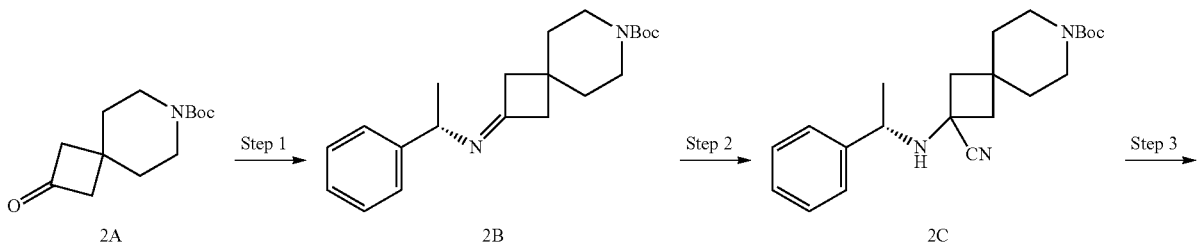

-continued
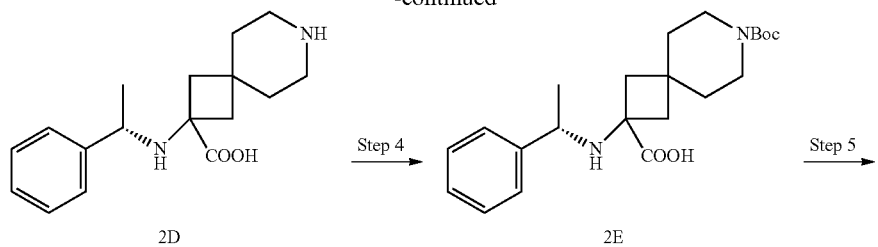
2D → Step 4 → 2E → Step 5 →
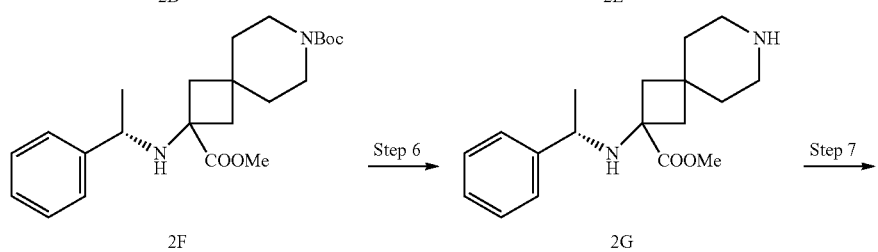
2F → Step 6 → 2G → Step 7 →
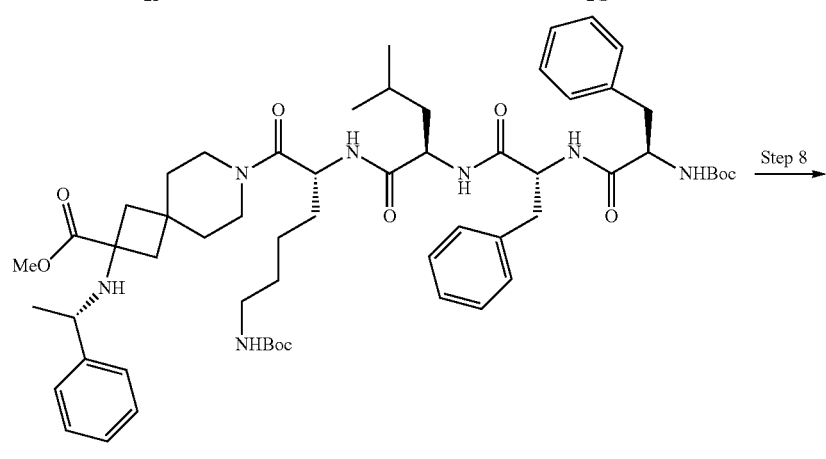
2H → Step 8 →
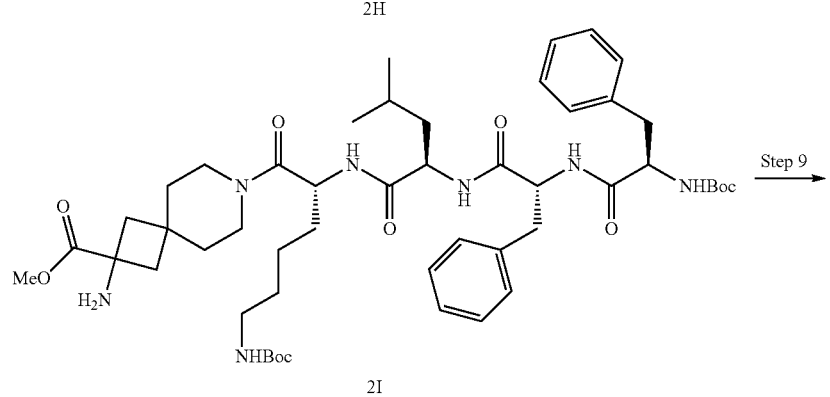
2I → Step 9 →
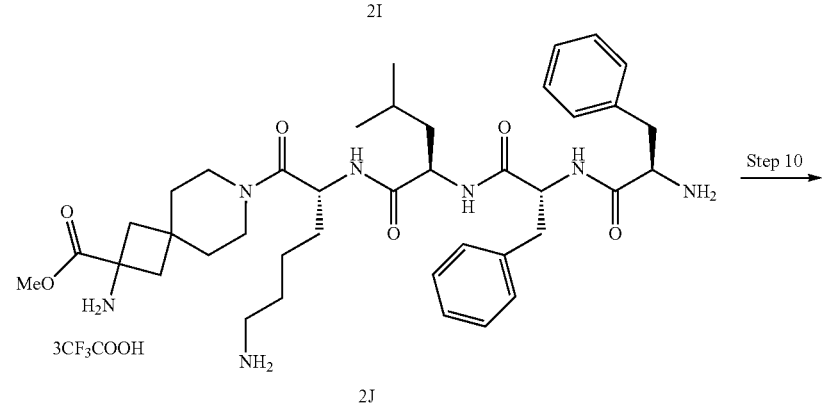
3CF₃COOH
2J → Step 10 →

-continued

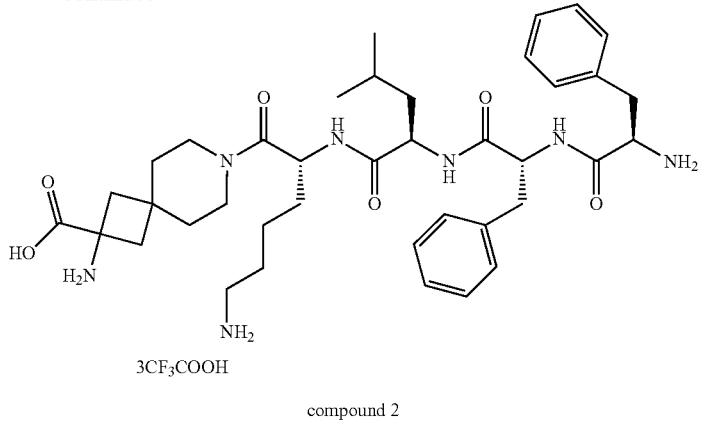

compound 2

Step 1: Tert-butyl 2-[(1S)-1-phenylethyl]imino-7-azaspiro[3.5]nonane-7-carboxylate (2B)

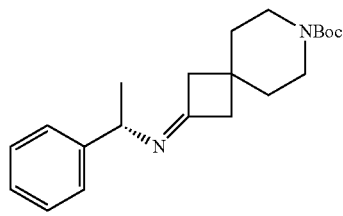 [SMILES: C[C@H](N=C1CC2(CCN(C(=O)OC(C)(C)C)CC2)C1)c1ccccc1]

Tert-butyl 2-oxo-7-azaspiro[3.5]nonane-7-carboxylate (2A) (7.2 g, 30 mmol), (1S)-1-phenethylamine (3.7 g, 31 mmol) were dissolved in toluene (100 mL), and p-toluenesulfonic acid (300 mg, 1.74 mmol) was added. A Dean-Stark apparatus was use for refluxing the system to separate water. After 6 h, the reaction solution was concentrated to dryness under reduced pressure to obtain crude tert-butyl 2-[(1S)-1-phenylethyl]imino-7-azaspiro[3.5]nonane-7-carboxylate (2B) as yellow foamy solid (10 g, yield 97%).

Step 2: Tert-butyl 2-cyano-2-[[(1 S)-1-phenylethyl]amino]-7-azaspiro[3.5]nonane-7-carboxylate (2C)

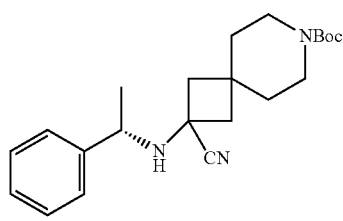 [SMILES: C[C@H](NC1(C#N)CC2(CCN(C(=O)OC(C)(C)C)CC2)C1)c1ccccc1]

Crude tert-butyl 2-[(1S)-1-phenylethyl]imino-7-azaspiro[3.5]nonane-7-carboxylate (2B) (10 g, 29.2 mmol) was dissolved in methanol (90 mL) at room temperature and cooled to 0° C. in an ice bath. Zinc chloride (210 mg, 1.54 mmol) was added under stirring, and trimethylsilyl cyanide (3 g, 30.2 mmol) was slowly added dropwise. The reaction was maintained at 0° C. for 3 h. The reaction solution was filtered, and the filtrate was concentrated under reduced pressure. The residue was separated and purified by silica gel column chromatography (petroleum ether:ethyl acetate (v/v)=4:1) to obtain tert-butyl 2-cyano-2-[[(1S)-1-phenylethyl]amino]-7-azaspiro[3.5]nonane-7-carboxylate (2C) as yellow foamy solid (4.7 g, yield 44%).

Step 3: 2-[[(1S)-1-phenylethyl]amino]-7-azaspiro[3.5]nonane-2-carboxylic acid (2D)

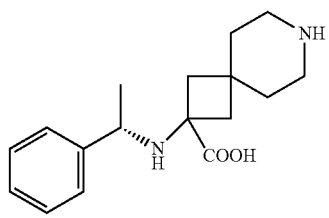 [SMILES: C[C@H](NC1(C(=O)O)CC2(CCNCC2)C1)c1ccccc1]

Tert-butyl 2-cyano-2-[[(1S)-1-phenylethyl]amino]-7-azaspiro[3.5]nonane-7-carboxylate (2C) (2 g, 5.4 mmol) was dissolved in concentrated hydrochloric acid (20 mL) at room temperature, and then the mixture was refluxed for 40 h. The temperature was reduced to room temperature, and the reaction solution was concentrated under reduced pressure to obtain crude 2-[[(1S)-1-phenylethyl]amino]-7-azaspiro[3.5]nonane-2-carboxylic acid (2D) as yellow oily liquid (1.5 g, yield 96%), and used directly in the next reaction.

Step 4: 7-tert-butoxycarbonyl-2-[[(1S)-1-phenylethyl]amino]-7-azaspiro[3.5]nonane-2-carboxylic acid (2E)

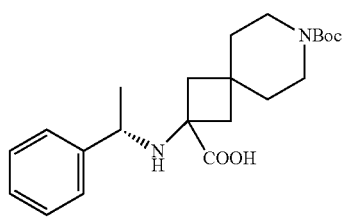 [SMILES: C[C@H](NC1(C(=O)O)CC2(CCN(C(=O)OC(C)(C)C)CC2)C1)c1ccccc1]

Crude 2-[[(1S)-1-phenylethyl]amino]-7-azaspiro[3.5]nonane-2-carboxylic acid (2D) (1 g, 3.47 mmol) was dissolved in tetrahydrofuran (10 mL) at room temperature. An aqueous sodium hydroxide (0.5 g, 12.5 mmol) solution (10 mL) was added, then di-tert-butyl dicarbonate (908 mg, 4.16 mmol) was added, and the reaction was allowed to proceed at room temperature for 6 h. The reaction solution was filtered to obtain crude 7-tert-butoxycarbonyl-2-[[(1S)-1-phenylethyl]amino]-7-azaspiro[3.5]nonane-2-carboxylic acid (2E) as white solid (0.8 g, yield 60%).

Step 5: O7-tert-butyl O2-methyl 2-[[(1S)-1-phenyl-ethyl]amino]-7-azaspiro[3.5]nonane-2,7-dicarboxylate (2F)

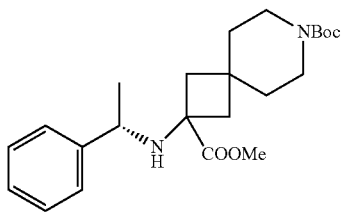 [SMILES: COC(=O)C1(N[C@@H](C)c2ccccc2)CC2(CCN(C(=O)OC(C)(C)C)CC2)C1]

7-tert-butoxycarbonyl-2-[[(1S)-1-phenylethyl]amino]-7-azaspiro[3.5]nonane-2-carboxylic acid (2E) (775 mg, 2.0 mmol) was dissolved in dichloromethane (10 mL) at room temperature, and methanol (10 mL) was added. 1-hydroxybenzotriazole (270 mg, 2.0 mmol), 1-(3-dimethylaminopropyl)-3-ethylcarbodiimide hydrochloride (0.6 g, 3.13 mmol) were sequentially added the solution under stirring at room temperature, and the system was allowed to react for 15 h. The reaction solution was concentrated under reduced pressure, and the residue was separated and purified by silica gel column chromatography (petroleum ether:ethyl acetate (v:v) =1:1) to obtain O7-tert-butylO2-methyl2-[[(1S)-1-phenyl-ethyl]amino]-7-azaspiro[3.5]nonane-2,7-dicarboxylate (2F) as light yellow foamy solid (560 mg, yield 70%).

Step 6: methyl 2-[[(1S)-1-phenylethyl]amino]-7-azaspiro[3.5]nonane-2-carboxylate (2G)

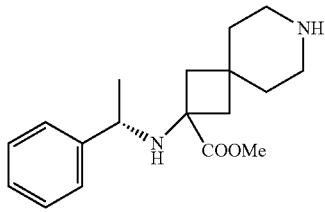 [SMILES: COC(=O)C1(N[C@@H](C)c2ccccc2)CC2(CCNCC2)C1]

O7-tert-butylO2-methyl2-[[(1S)-1-phenyl ethyl]amino]-7-azaspiro[3.5]nonane-2,7-dicarboxylate (2F) (500 mg, 1.24 mmol) was dissolved in dichloromethane (4.5 mL) at room temperature, and the temperature was lowered to 0° C. Trifluoroacetic acid (1.5 mL) was added, and the reaction was allowed to proceed at room temperature for 3 h. The reaction solution was concentrated under reduced pressure to obtain methyl 2-[[(1S)-1-phenylethyl]amino]-7-azaspiro[3.5]nonane-2-carboxylate (2G) as yellow oily liquid (320 mg, yield 85%).

Step 7: methyl 7-[(2R)-6-(tert-butoxycarbonylamino)-2-[[(2R)-2-[[(2R)-2-[[(2R)-2-(tert-butoxycarbonylamino)-3-phenyl-propanoyl]amino]-3-phenyl-propanoyl]amino]-4-methyl-pentanoyl]amino]hexanoyl]-2-[[(1 S)-1-phenylethyl]amino]-7-azaspiro[3.5]nonane-2-carboxylate

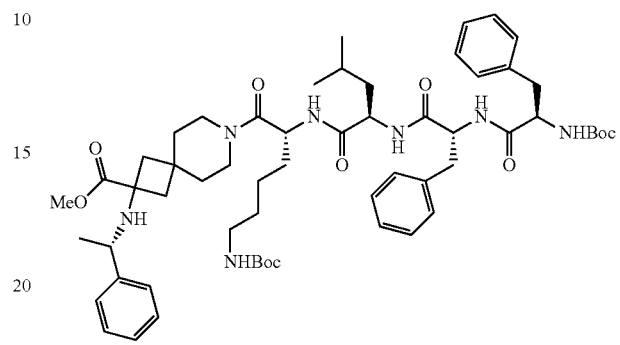

Methyl 2-[[(1S)-1-phenylethyl]amino]-7-azaspiro[3.5]nonane-2-carboxylate (2G) (300 mg, 1.0 mmol) was dissolved in dichloromethane (10 mL) at room temperature, and intermediate 1 (753 mg, 1.0 mmol) was added. 1-hydroxybenzotriazole (135 mg, 1.0 mmol), 1-(3-dimethylaminopropyl)-3-ethylcarbodiimide hydrochloride (0.23 g, 1.2 mmol) were sequentially added under stirring at room temperature, and the system was allowed to react for 15 h. The reaction solution was concentrated under reduced pressure, and the residue was separated and purified by silica gel column chromatography (dichloromethane:methanol (v:v) =50:1). The eluent was collected and concentrated under reduced pressure to obtain methyl 7-[(2R)-6-(tert-butoxycarbonylamino)-2-[[(2R)-2-[[(2R))-2-[[(2R)phenyl-propanoyl]amino]-3-phenyl-propanoyl]amino]-4-methyl-pentanoyl]amino]hexanoyl]-2-[[(1S)-1-phenylethyl]amino]-7-azaspiro[3.5]nonane-2-carboxylate (2H) as a white foamy solid (710 mg, yield 69%).

Step 8: methyl 2-amino-7-[(2R)-6-(tert-butoxycarbonylamino)-2-[[(2R)-2-[[(2R)-2-[[(2R)-2-(tert-butoxycarbonylamino)-3-phenyl-propanoyl]amino]-3-phenyl-propanoyl]amino]-4-methyl-pentanoyl]amino]hexanoyl]-7-azaspiro[3.5]nonane-2-carboxylate (2I)

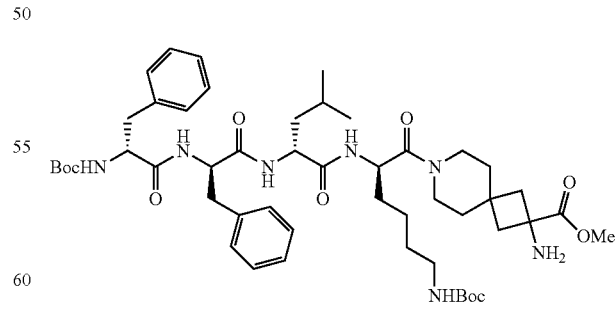

Methyl7-[(2R)-6-(tert-butoxycarbonylamino)-2-[[(2R)-2-[[(2R))-2-[[(2R)phenyl-propanoyl]amino]-3-phenyl-propanoyl]amino]-4-methyl-pentanoyl]amino]hexanoyl]-2-[[(1 S)-1-phenylethyl]amino]-7-azaspiro[3.5]nonane-2-carboxylate (2H) (700 mg, 0.7 mmol) was dissolved in ethyl acetate (10 mL) at room temperature, and palladium on carbon (0.1 g, 20 wt %) was added to the reaction solution. The atmosphere was replaced with hydrogen 3 times, and the reaction was allowed to proceed at room temperature for 5 h under a hydrogen atmosphere (balloon). The reaction solution was filtered through diatomite, and the filtrate was concentrated to dryness. The residue was separated and purified by silica gel column chromatography (dichloromethane:methanol (v:v)=50:1), to obtain methyl 2-amino-7-[(2R)-6-(tert-butoxycarbonylamino)-2-[[(2R)-2-[[(2R)-2-[[(2R)-2-(tert-butoxycarbonylamino)-3-phenyl-propanoyl]amino]-3-phenyl-propanoyl]amino]-4-methyl-pentanoyl]amino]hexanoyl]-7-azaspiro[3.5]nonane-2-carboxylate (2I) as a white foamy solid (370 mg, yield 60%).

Step 9: methyl 2-amino-7-[(2R)-6-amino-2-[[(2R)-2-[[(2R)-2-[[(2R)-2-amino-3-phenyl-propanoyl]amino]-3-phenyl-propanoyl]amino]-4-methyl-pentanoyl]amino]hexanoyl]-7-azaspiro[3.5]nonane-2-carboxylate; 2,2,2-trifluoroacetic acid (2J)

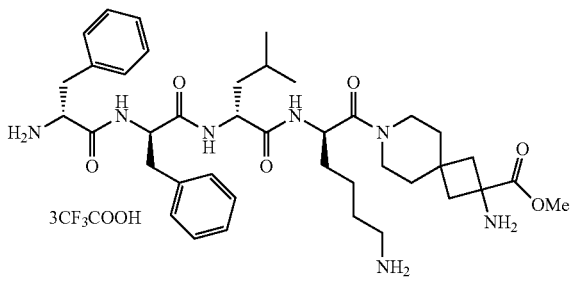 [SMILES: COC(=O)C1(N)CC2(CCN(C(=O)[C@@H](CCCCN)NC(=O)[C@@H](CC(C)C)NC(=O)[C@@H](Cc3ccccc3)NC(=O)[C@H](N)Cc3ccccc3)CC2)C1]

Methyl 2-amino-7-[(2R)-6-(tert-butoxycarbonylamino)-2-[[(2R)-2-[[(2R)-2-[[(2R)-2-(tert-butoxycarbonylamino)-3-phenyl-propanoyl]amino]-3-phenyl-propanoyl]amino]-4-methyl-pentanoyl]amino]hexanoyl]-7-azaspiro[3.5]nonane-2-carboxylate (2I) (370 mg, 0.4 mmol) was dissolved in dichloromethane (3 mL) at room temperature, and the temperature was lowered to 0° C. Trifluoroacetic acid (1 mL) was added and the temperature was raised to room temperature and the system was allowed to react for 3 h. The reaction solution was concentrated to dryness under reduced pressure to obtain crude 2-amino-7-[(2R)-6-amino-2-[[(2R)-2-[[(2R)-2-[[(2R)-2-amino-3-phenyl-propanoyl]amino]-3-phenyl-propanoyl]amino]-4-methyl-pentanoyl]amino]hexanoyl]-7-azaspiro[3.5]nonane-2-carboxylate; tri-trifluoroacetic acid (2J) as yellow oily liquid (305 mg, yield 72%).

Step 10: 2-amino-7-[(2R)-6-amino-2-[[(2R)-2-[[(2R)-2-[[(2R)-2-amino-3-phenyl-propanoyl]amino]-3-phenyl-propanoyl]amino]-4-methyl-pentanoyl]amino]hexanoyl]-7-azaspiro[3.5]nonane-2-carboxylic acid; tri-trifluoroacetic acid (compound 2)

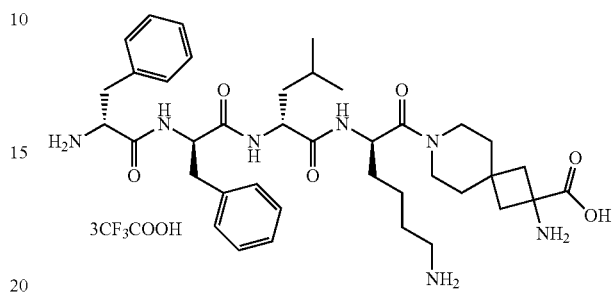

Sodium hydroxide (50 mg, 1.25 mmol) was dissolved in water (2 mL) at room temperature, and crude 2-amino-7-[(2R)-6-amino-2-[[(2R)-2-[[(2R)-2-[[(2R)-2-amino-3-phenyl-propanoyl]amino]-3-phenyl-propanoyl]amino]-4-methyl-pentanoyl]amino]hexanoyl]-7-azaspiro[3.5]nonane-2-carboxylate; tri-trifluoroacetic acid (2J) (305 mg, 0.288 mmol) was added. The system was allowed to react for 5 h at room temperature. The reaction solution was concentrated to dryness under reduced pressure, and separated and purified by preparative liquid chromatography (preparation conditions:instrument: Gilson GX-281; column: Xbridge C18, 150 mmol)[[(2R)-2-met; mobile phase: A for ACN and B for H2O; isocratic: A 65%; flow rate: 30 mL/min; back pressure: 1000 PSI; column temperature: 30° C.; wavelength: 210 nm; period: 18 min; sample preparation: the compound dissolved in 12 mL methanol; injection: 0.9 mL/needle). The preparation solution was concentrated under reduced pressure to remove most of the solvent, and lyophilized to obtain 2-amino-7-[(2R)-6-amino-2-[[(2R)-2-[[(2R)-2-[[(2R)-2-amino-3-phenyl-propanoyl]amino]-3-phenyl-propanoyl]amino]-4-methyl-pentanoyl]amino]hexanoyl]-7-azaspiro[3.5]nonane-2-carboxylic acid; tri-trifluoroacetic acid (compound 2) (92 mg, yield 31%).

MS m/z (ESI): 360.8[M+2H]$^+$/2;

$^1$H NMR (400 MHz, D$_2$O) δ7.44-7.18 (m, 10H), 4.65 (t, 1H), 4.33-4.18 (m, 2H), 3.58 (br, 2H), 3.52-3.41 (m, 1H), 3.41-3.29 (m, 1H), 3.17 (d, 2H), 3.10-2.90 (m, 4H), 2.70-2.46 (m, 2H), 2.32-2.18 (m, 2H), 2.05-1.28 (m, 14H), 0.98-0.84 (m, 6H).

compound 2-1 (compound 2 in free form):

The compound 2 (7.3 g, 6.88 mmol) was pass through an ion exchange resin (300 mL) (eluted by water ~3.3% ammonia), and the received elution solution was concentrated under reduced pressure (concentrated under reduced pressure to 100 mL at 60° C.) and further lyophilized to obtain the compound 2-1 as white solid (4.5 g, yield 90.8%).

MS m/z=720.5 [M+2H]$^+$;

$^1$HNMR (400 MHz, D$_2$O) δ 7.34-7.22 (m, 6H), 7.18-7.06 (m, 4H), 4.78-4.72 (m, 1H), 4.55 (t, 1H), 4.25 (t, 1H), 3.65-3.46 (m, 3H), 3.45-3.25 (m, 2H), 3.09-2.97 (m, 1H), 2.95-2.84 (m, 3H), 2.85-2.73 (m, 2H), 2.51-2.33 (m, 2H), 2.00-1.83 (m, 2H), 1.82-1.25 (m, 13H), 0.96-0.78 (m, 6H).

Example 2: (2R)—N-[(1R)-5-amino-1-(2-oxo-3,10-diazadispiro[4.1.5^{7}.1^{5}]tridecane-10-carbonyl)pentyl]-2-[[(2R)-2-[[(2R)-2-amino-3-phenyl-propanoyl]amino]-3-phenyl-propanoyl]amino]-4-methyl-pentanamide; di-trifluoroacetic acid (compound 3)
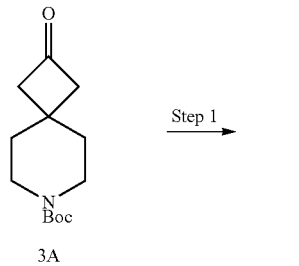
3A
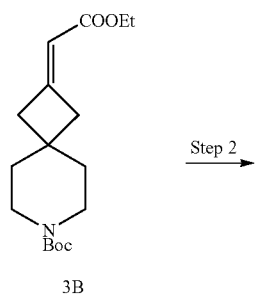
3B
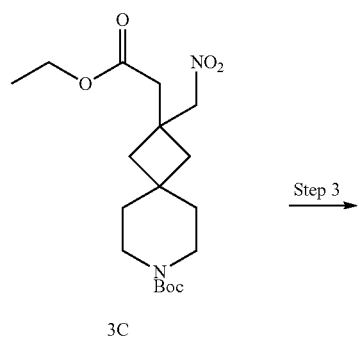
3C
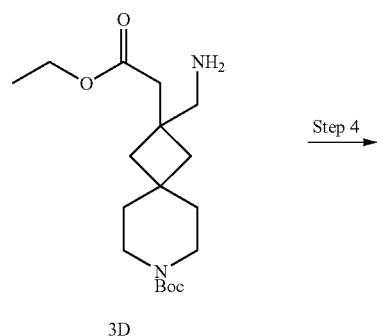
3D
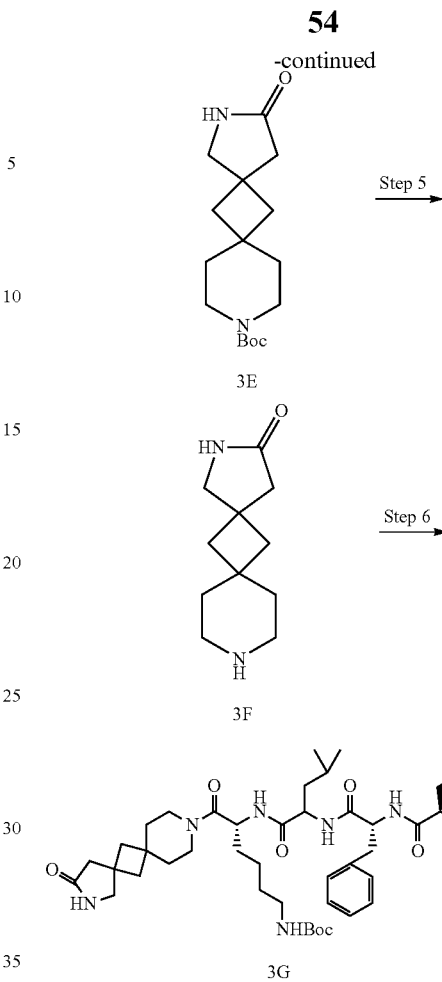
3E
3F
3G
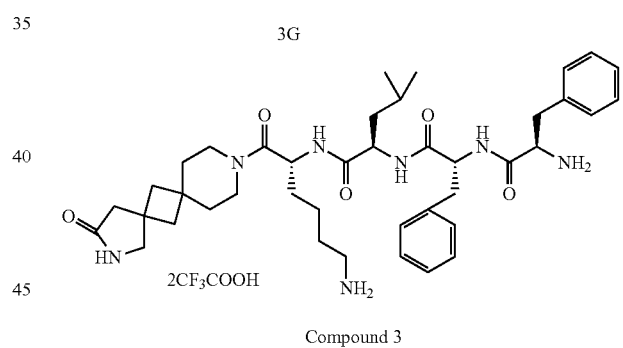
Compound 3
Step 1: tert-butyl 2-(2-ethoxy-2-oxo-ethylidene)-7-azaspiro[3.5]nonane-7-carboxylate (3B)
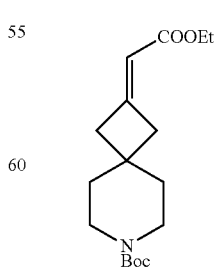
Tetrahydrofuran (50 mL) was added to a reaction flask, and sodium hydride (1.3 g, 54.2 mmol) was added under nitrogen protection. It was cooled to 0° C. in an ice-water bath, and triethyl phosphonoacetate (6.9 g, 31 mmol) was slowly added dropwise. After the addition, the reaction was carried out at 0° C. for 20 minutes. It was cooled to −5 to 0° C. and tert-butyl 2-oxo-7-azaspiro[3.5]nonane-7-carboxylate (3A) (5 g, 20.9 mmol) in tetrahydrofuran (20 mL) was slowly added dropwise. After the addition, the temperature was raised to room temperature and reacted for 1 h. A saturated aqueous sodium chloride solution (50 mL) was added, and the mixture was extracted with ethyl acetate (50 mL×2). The organic layers were combined, and the organic layers were dried over anhydrous sodium sulfate, filtered, and the filtrate was concentrated under reduced pressure to obtain crude tert-butyl 2-(2-ethoxy-2-oxo-ethylidene)-7-azaspiro[3.5]nonane-7-carboxylate (3B) as light yellow oily liquid (6.0 g, yield 92.8%), and used directly in the next step.

Step 2: tert-butyl 2-(2-ethoxy-2-oxo-ethyl)-2-(nitromethyl)-7-azaspiro[3.5]nonane-7-carboxylate (3C)

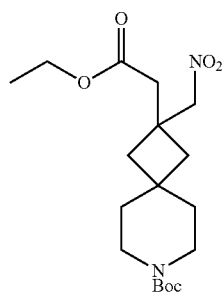 [SMILES: CCOC(=O)CC1(C[N+](=O)[O-])CC2(CCN(C(=O)OC(C)(C)C)CC2)C1]

Tert-butyl 2-(2-ethoxy-2-oxo-ethylidene)-7-azaspiro[3.5]nonane-7-carboxylate (3B) was added to a reaction flask, and tetrahydrofuran (60 mL) was added. It was dissolved completely at room temperature under stirring, then nitromethane (6.0 g, 98.3 mmol) and tetrabutylammonium fluoride (7.85 g, 30 mmol) were added. After the addition, the reaction was heated reflux for 5 h. The reaction solution was cooled to room temperature, and ethyl acetate (150 mL) was added, and a saturated aqueous sodium chloride solution (100 mL×1) was used for washing and separation. The organic phase was dried over anhydrous sodium sulfate, filtered, and concentrated to dryness under reduced pressure. The residue was separated and purified by silica gel column chromatography (petroleum ether:ethyl acetate (v:v)=10:1) to obtain tert-butyl 2-(2-ethoxy-2-oxo-ethyl)-2-(nitromethyl)-7-azaspiro[3.5]nonane-7-carboxylate (3C) as colorless transparent oily liquid (6.5 g, yield 90%).

Step 3: Tert-butyl2-(aminomethyl)-2-(2-ethoxy-2-oxo-ethyl)-7-azaspiro[3.5]nonane-7-carboxylate (3D)

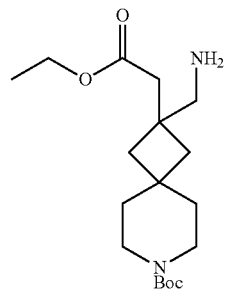

Tert-butyl 2-(2-ethoxy-2-oxo-ethyl)-2-(nitromethyl)-7-azaspiro[3.5]nonane-7-carboxylate (3C) (6.5 g, 18 mmol) was added to a reaction flask, and ethanol (75 mL) and water (25 mL), iron powder (4.9 g, 88 mmol) and ammonium chloride (4.7 g, 88.00 mmol) were added, and the reaction was refluxed for 5 h. The temperature was cooled to room temperature, and the reaction system was concentrated to 20 mL. Water (30 mL) was added, the pH was adjusted to greater than 10 with ammonia water, and extracted with dichloromethane (50 mL×2). The organic phases were combined, and the organic phases were concentrated to dryness under reduced pressure to obtain tert-butyl 2-(aminomethyl)-2-(2-ethoxy-2-oxo-ethyl)-7-azaspiro[3.5]nonane-7-carboxylate (3D) as light yellow oily liquid (5.1 g, yield 85%).

Step 4: tert-butyl 2-oxo-3,10-diazadispiro[4.1.5^{7}.1^{5}]tridecane-10-carboxylate (3E)

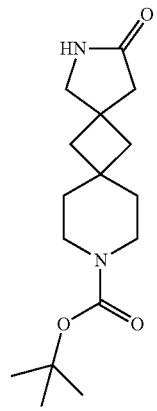 [SMILES: CC(C)(C)OC(=O)N1CCC2(CC1)CC1(CNC(=O)C1)C2]

Tert-butyl2-(aminomethyl)-2-(2-ethoxy-2-oxo-ethyl)-7-azaspiro[3.5]nonane-7-carboxylate (3D) (3 g, 8.8 mmol) was added to a reaction flask, aqueous sodium hydroxide (400 mg, 10 mmol) solution (30 mL) was added, and the system was allowed to react at room temperature for 5 h. The reaction solution was filtered to obtain tert-butyl 2-oxo-3,10-diazaspiro[4.1.5^{7}.1^{5}]tridecane-10-carboxylate (3E) as white solid (2.10 g, yield 81%).

Step 5: 3,10-diazadispiro[4.1.5^{7}.1^{5}]tridecan-2-one (3F)

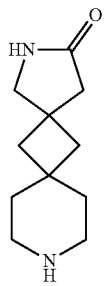

Tert-butyl 2-oxo-3,10-diazaspiro[4.1.5^{7}.1^{5}]tridecane-10-carboxylate (3E) (1 g, 3.4 mmol) was dissolved in dichloromethane (9 mL), and trifluoroacetic acid (3 mL) was added. The reaction was allowed to proceed at room temperature for 5 h to fully reacted. The reaction solution was concentrated to dryness under reduced pressure, water (20 mL) was added, and the system was adjusted to pH>10 with a 2 M aqueous sodium hydroxide solution. It was extracted with dichloromethane (20 mL×2) and the mixture was subjected to a liquid separation process. The organic phases were combined and concentrated under reduced pressure to obtain crude 3,10-diazaspiro[4.1.5^{7}.1^{5}]tridecane-2-one (3F) as yellow oily liquid (0.6 g, yield 85%).

Step 6: tert-butyl N-[(1R)-1-benzyl-2-[[(1R)-1-benzyl-2-[[(1R)-1-[[(1R)-5-(tert-butoxycarbonylamino)-1-(2-oxo-3,10-diazadispiro[4.1.5^{7}.1^{5}]tridecane-10-carbonyl)pentyl]carbamoyl]-3-methyl-butyl]amino]-2-oxo-ethyl]amino]-2-oxo-ethyl]carbamate (3G)

Dichloromethane (30 mL) was added to a reaction flask under nitrogen protection, and intermediate 1 (2.25 g, 2.98 mmol), crude 3,10-diazaspiro[4.1.5^{7}.1^{5}]tridecane-2-one (3F) (0.6 g, 2.88 mmol), 1-hydroxybenzotriazole (0.39 g, 2.89 mmol), 1-(3-dimethylaminopropyl)-3-ethylcarbodiimide hydrochloride (0.83 g, 4.33 mmol) were added. The system was allowed to react at room temperature for 15 h. Then water (20 mL) was added, and it was extracted with ethyl acetate (30 mL×3), and the layers were separated and the organic phases were combined. The organic phases were dried over anhydrous sodium sulfate, filtered, and the filtrate was concentrated under reduced pressure. The residue was separated and purified by silica gel column chromatography (dichloromethane:methanol (v:v)=20:1) to obtain tert-butyl N-[(1R)-1-benzyl-2-[[(1R)-1-benzyl-2-[[(1R)-1-[[(1R)-5-(tert-butoxycarbonylamino)1-(2-oxo-3,10-diazaspiro[4.1.5^{7}.1^{5}]tridecane-10-carbonyl)pentyl]carbamoyl]-3-methyl-butyl]amino]-2-oxo-ethyl]amino]-2-oxo-ethyl]carbamate (3G) as a white foamy solid (1.77 g, yield 73.2%).

Step 7: (2R)—N-[(1R)-5-amino-1-(2-oxo-3,10-diazadispiro[4.1.5^{7}.1^{5}]tridecane-10-carbonyl)pentyl]-2-[[(2R)-2-[[(2R)-2-amino-3-phenyl-propanoyl]amino]-3-phenyl-propanoyl]amino]-4-methyl-pentanamide; di-trifluoroacetic acid (compound 3)

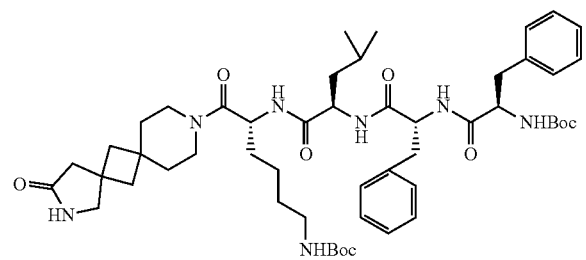 [SMILES: CC(C)C[C@@H](NC(=O)[C@@H](Cc1ccccc1)NC(=O)[C@@H](Cc1ccccc1)NC(=O)OC(C)(C)C)C(=O)N[C@H](CCCCNC(=O)OC(C)(C)C)C(=O)N1CCC2(CC1)CC1(CNC(=O)C1)C2]

Tert-butyl N-[(1R)-1-benzyl-2-[[(1R)-1-benzyl-2-[[(1R)-1-[[(1R)-5-(tert-butoxycarbonylamino)1-(2-oxo-3,10-diazaspiro[4.1.5^{7}.1^{5}]tridecane-10-carbonyl)pentyl]carbamoyl]-3-m ethyl-butyl]amino]-2-oxo-ethyl]amino]-2-oxo-ethyl]carbamate (3G) (0.90 g, 1 mmol) and dichloromethane (21 mL) were added to a reaction flask under nitrogen protection, and trifluoroacetic acid (7 mL) was added under stirring. The reaction was allowed to proceed at room temperature for 3 h. The reaction solution was concentrated to dryness under reduced pressure, and the residue was separated and purified (preparation conditions: instrument: Gilson GX-281; column: Xbridge C18, 150×30 mm I.D., 5 μm; mobile phase: A for ACN and B for H2O; isocratic: A 65%; flow rate: 30 mL/min; back pressure: 1000 PSI; column temperature: 30° C.; wavelength: 210 nm; period: 18 min; sample preparation: the compound dissolved in 12 mL methanol; injection: 0.9 mL/needle). The preparation was concentrated under reduced pressure to remove most of the solvent, and lyophilized to obtain (2R)—N-[(1R)-5-amino-1-(2-oxo-3,10-diazaspiro[4.1.5^{7}.1^{5}]tridecane-10-carbonyl)pentyl]-2-[[(2R)-2-[[(2R)-2-amino-3-phenyl-propanoyl]amino]-3-phenyl-propanoyl]amino]-4-methy 1-pentanamide; di-trifluoroacetic acid (compound 3) as white solid (0.98 g, yield 54%).

MS m/z (ESI): 365.9[M+2H]$^+$/2;

$^1$H NMR (400 MHz, DMSO-d$_6$) δ 8.86-8.67 (m, 1H), 8.40-8.23 (m, 1H), 8.14-8.01 (m, 3H), 7.84-7.72 (m, 2H), 7.52-7.42 (m, 1H), 7.37-7.15 (m, 10H), 4.76-3.94 (m, 4H), 3.59-2.65 (m, 12H), 2.29-2.15 (m, 2H), 1.93-1.19 (m, 17H), 0.88 (dd, 6H).

Example 3: (2R)—N-[(1R)-5-amino-1-(9-oxo-2,8-diazadispiro[3.1.4^{6}.1^{4}]undecane-2-carbonyl)pentyl]-2-[[(2R)-2-[[(2R)-2-amino-3-phenyl-propanoyl]amino]-3-phenyl-propanoyl]amino]-4-methyl-pentanamide; di-trifluoroacetic acid (compound 4)
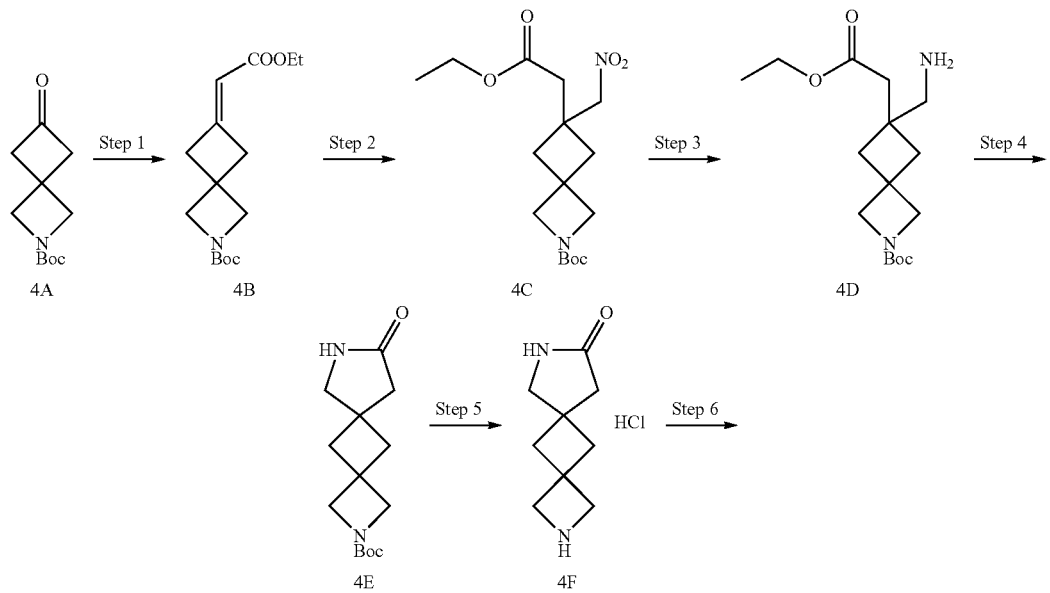

Step 1: tert-butyl 6-(2-ethoxy-2-oxo-ethylidene)-2-azaspiro[3.3]heptane-2-carboxylate (4B)

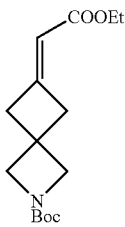 [SMILES: CCOC(=O)C=C1CC2(C1)CN(C(=O)OC(C)(C)C)C2]

Tetrahydrofuran (50 mL) was added to a reaction flask, and sodium hydride (2.5 g, 59.2 mmol) was added. It was cooled to 0° C. in an ice-water bath, and triethyl phosphonoacetate (7.96 g, 35.5 mmol) was slowly added dropwise. The reaction was allowed to proceed at 0° C. for 20 min after the addition. Then it was cooled to −5 to 0° C., and tert-butyl 6-oxo-2-azaspiro[3.3]heptane-2-carboxylate (4A) (5 g, 23.7 mmol) in tetrahydrofuran (20 mL) was slowly added dropwise. After the addition, the reaction was allowed to proceed at room temperature for 1 h. Then, a saturated sodium chloride aqueous solution (50 mL) was added to the reaction solution, and the mixture was extracted with ethyl acetate (50 mL×2), and the mixture was subjected to a liquid separation process. The organic phases were combined. The organic phase was dried over anhydrous sodium sulfate, filtered, and the filtrate was concentrated under reduced pressure to obtain crude tert-butyl 6-(2-ethoxy-2-oxo-ethylidene)-2-azaspiro[3.3]heptane-2-carboxylate (4B) as yellow oily liquid (5.5 g, yield 83%), and used directly in the next step.

Step 2: tert-butyl 6-(2-ethoxy-2-oxo-ethyl)-6-(nitromethyl)-2-azaspiro[3.3]heptane-2-carboxylate (4C)

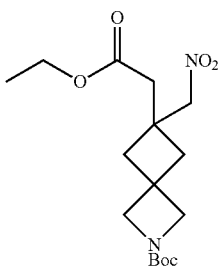 [SMILES: CCOC(=O)CC1(C[N+](=O)[O-])CC2(CN(C(=O)OC(C)(C)C)C2)C1]

Crude tert-butyl 6-(2-ethoxy-2-oxo-ethylidene)-2-azaspiro[3.3]heptane-2-carboxylate (4B) was added to a reaction flask, and tetrahydrofuran (60 mL) was added. The system was stirred to dissolve completely at room temperature, then nitromethane (6.0 g, 98.3 mmol) and tetrabutylammonium fluoride (7.85 g, 30 mmol) were added. After the addition was completed, the reaction was heated reflux for 5 h. The reaction solution was cooled to room temperature, ethyl acetate (150 mL) was added thereto, and the mixture was washed with a saturated aqueous sodium chloride solution (100 mL) and the mixture was subjected to a liquid separation process. The organic phase was dried over anhydrous sodium sulfate, filtered, and the filtrate was concentrated under reduced pressure. The residue was separated and purified by silica gel column chromatography (petroleum ether:ethyl acetate (v:v)=4:1), to obtain tert-butyl 6-(2-ethoxy-2-oxo-ethyl)-6-(nitromethyl)-2-azaspiro[3.3] heptane-2-carboxylate (4C) as colorless transparent oily liquid (5.1 g, yield 76%).

Step 3: tert-butyl6-(aminomethyl)-6-(2-ethoxy-2-oxo-ethyl)-2-azaspiro[3.3]heptane-2-carboxylate (4D)

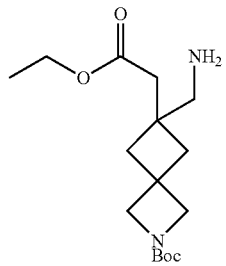 [SMILES: CCOC(=O)CC1(CN)CC2(CN(C(=O)OC(C)(C)C)C2)C1]

Tert-butyl6-(2-ethoxy-2-oxo-ethyl)-6-(nitromethyl)-2-azaspiro[3.3]heptane-2-carboxylate (4C) (5.1 g, 15 mmol) was added to a reaction flask, ethanol (75 mL), water (25 mL), iron powder (4.2 g, 74 mmol) and ammonium chloride (4.0 g, 74 mmol) were added, and the reaction was heated reflux for 5 h. The temperature was lowered to room temperature, and the reaction system was concentrated to about 20 mL. Water (30 mL) was added, then the pH was adjusted to greater than 10 with ammonia, extract with dichloromethane (50 mL×2), and the mixture was subjected to a liquid separation process. The organic phases were combined and the organic phases were concentrated under reduced pressure to obtain crude tert-butyl 6-(aminomethyl)-6-(2-ethoxy-2-oxo-ethyl)-2-azaspiro[3.3]heptane-2-carboxylate (4D) (4.6 g, yield 99%), and used directly in the next step.

Step 4: tert-butyl 9-oxo-2,8-diazadispiro[3.1.4^{6}.1^{4}]undecane-2-carboxylate (4E)

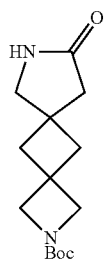

Crude tert-butyl 6-(aminomethyl)-6-(2-ethoxy-2-oxoethyl)-2-azaspiro[3.3]heptane-2-carboxylate (4D) (4.6 g, 15 mmol) was added to a reaction flask. An aqueous sodium hydroxide (600 mg, 15 mmol) solution (45 mL) was added, and the mixture was reacted at room temperature for 5 h. The reaction solution was filtered to obtain tert-butyl9-oxo-2,8-diazaspiro[3.1.4^{6}.1^{4}]undecane-2-carboxylate (4E) as white solid (2.90 g, yield 74%).

Step 5: 2,8-diazadispiro[3.1.4^{6}.1^{4}]undecan-9-one; hydrchloride (4F)

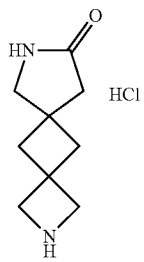

Tert-butyl 9-oxo-2,8-diazaspiro[3.1.4^{6}.1^{4}]undecane-2-carboxylate (4E) (2 g, 7.5 mmol) was dissolved in 4N HCl-isopropanol solution (9 mL), and the system was allowed to react at room temperature for 5 h. The reaction solution was concentrated to dryness under reduced pressure, to obtain crude 2,8-diazaspiro[3.1.4^{6}.1^{4}]undecane-9-one; hydrochloride (4F) as white solid (0.95 g, yield 62%), and used directly in the next step.

Step 6: tert-butyl N-[(1R)-1-benzyl-2-[[(1R)-1-benzyl-2-[[(1R)-1-[[(1R)-5-(tert-butoxycarbonylamino)-1-(9-oxo-2,8-diazadispiro[3.1.4^{6}.1^{4}]undecane-2-carbonyl)pentyl]carbamoyl]-3-methyl-butyl]amino]-2-oxo-ethyl]amino]-2-oxo-ethyl]carbamate (4G)

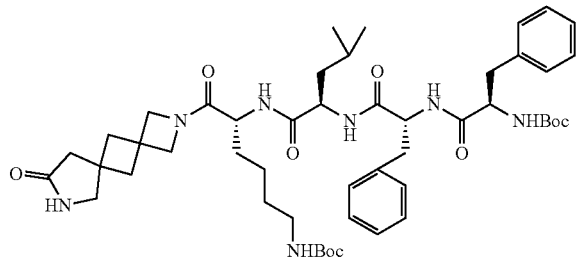 [SMILES: CC(C)C[C@@H](NC(=O)[C@@H](Cc1ccccc1)NC(=O)[C@@H](Cc1ccccc1)NC(=O)OC(C)(C)C)C(=O)N[C@H](CCCCNC(=O)OC(C)(C)C)C(=O)N1CC2(C1)CC1(CNC(=O)C1)C2]

Dichloromethane (30 mL) was added to a reaction flask under nitrogen protection, and intermediate 1 (2.25 g, 2.98 mmol), 2,8-diazaspiro[3.1.4^{6}.1^{4}]undecane-9-one; hydrochloride (4F) (0.6 g, 3.0 mmol), 1-hydroxybenzotriazole (0.39 g, 2.89 mmol), 1-(3-dimethylaminopropyl)-3-ethylcarbodiimide hydrochloride (0.83 g, 4.33 mmol) were added. The reaction was allowed to proceed at room temperature for 15 h. Then water (20 mL) was added, and the mixture was extracted with ethyl acetate (30 mL×3) and the mixture was subjected to a liquid separation process. The organic phases were combined, and the organic phases were dried over anhydrous sodium sulfate, filtered, and the filtrate was concentrated under reduced pressure. The residue was separated and purified by silica gel column chromatography (dichloromethane:methanol (v:v)=10:1) to obtain tert-butyl N-[(1R)-1-benzyl-2-[[(1R)-1-benzyl-2-[[(1R)-1-[[(1R)-5-(tert-butoxycarbonylamino)1-(9-oxo-2,8-diazaspiro[3.1.4^{6}.1^{4}]undecane-2-carbonyl)pentyl]carbamoyl]-3-methyl-butyl]amino]-2-oxo-ethyl]amino]-2-oxo-ethyl]carbamate (4G) as a white foamy solid (1.9 g, yield 70%).

Step 7: (2R)—N-[(1R)-5-amino-1-(9-oxo-2,8-diazadispiro[3.1.4^{6}.1^{4}]undecane-2-carbonyl)pentyl]-2-[[(2R)-2-[[(2R)-2-amino-3-phenyl-propanoyl]amino]-3-phenyl-propanoyl]amino]-4-methyl-1-pentanamide; di-trifluoroacetic acid (compound 4)

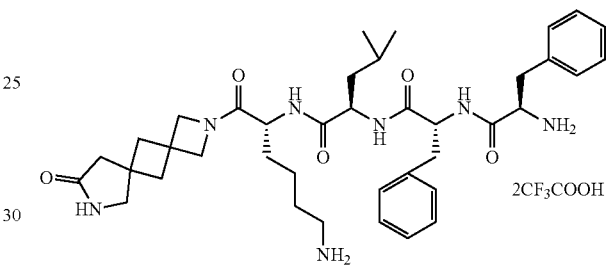

Tert-butylN-[(1R)-1-benzyl-2-[[(1R)-1-benzyl-2-[[(1R)-1-[[(1R)-5-(tert-butoxycarbonylamino)1-(9-oxo-2,8-diazaspiro[3.1.4^{6}.1^{4}]undecane-2-carbonyl)pentyl]carbamoyl]-3-methyl-butyl]amino]-2-oxo-ethyl]amino]-2-oxo-ethyl]carbamate (4G) (1.7 g, 1.9 mmol) and dichloromethane (21 mL) were added to a reaction flask under nitrogen protection. Trifluoroacetic acid (7 mL) was added under stirring, and the reaction was allowed to proceed at room temperature for 3 h. The reaction solution was concentrated to dryness under reduced pressure, and the residue was separated and purified by preparative chromatography (preparation conditions: instrument: Gilson GX-281; column: Xbridge C18, 150×30 mm I.D., 5 μm; mobile phase: A for ACN and B for H$_2$O; isocratic: A 65%; flow rate: 30 mL/min; back pressure: 1000 PSI; column temperature: 30° C.; wavelength: 210 nm; period: 18 min; sample preparation: the compound dissolved in 12 mL methanol; injection: 0.9 mL/needle). The preparation was concentrated under reduced pressure to remove most of the solvent, and lyophilized to obtain (2R)—N-[(1R)-5-amino-1-(9-oxo-2,8-diazaspiro[3.1.4^{6}.1^{4}]undecane-2-carbonyl)pentyl]-2-[[(2R)-2-[[(2R)-2-amino-3-phenyl-propanoyl]amino]-3-phenyl-propanoyl]amino]-4-methyl-pentanamide; di-trifluoroacetic acid (compound 4) as white solid (0.7 g, yield 40%).

MS m/z (ESI): 351.8 [M+2H]$^+$/2;

$^1$H NMR (400 MHz, DMSO-d$_6$) δ 8.76 (d, 1H), 8.32 (d, 1H), 8.11-7.97 (m, 4H), 7.85-7.69 (m, 3H), 7.50 (s, 1H), 7.33-7.18 (m, 10H), 4.74-3.74 (m, 8H), 3.24-2.63 (m, 8H), 2.27-2.05 (m, 6H), 1.71-1.17 (m, 9H), 0.89 (dd, 6H).

Example 4: (2R)—N-[(1R)-5-amino-1-(2-cyclopropylsulfonyl-2,7-diazaspiro[3.5]nonane-7-carbonyl)pentyl]-2-[[(2R)-2-[[(2R)-2-amino-3-phenyl-propanoyl]amino]-3-phenyl-propanoyl]amino]-4-methyl-pentanamide (compound 6)
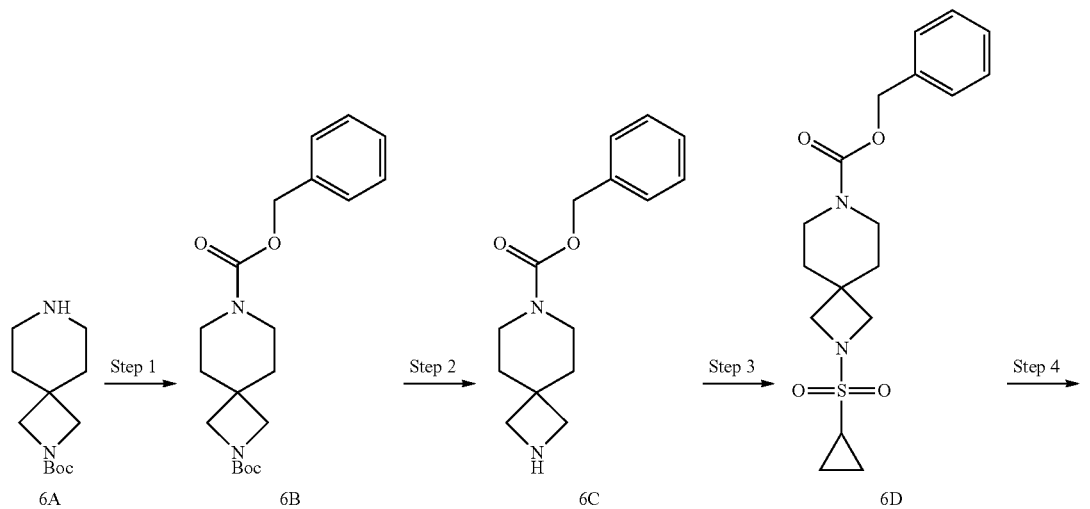
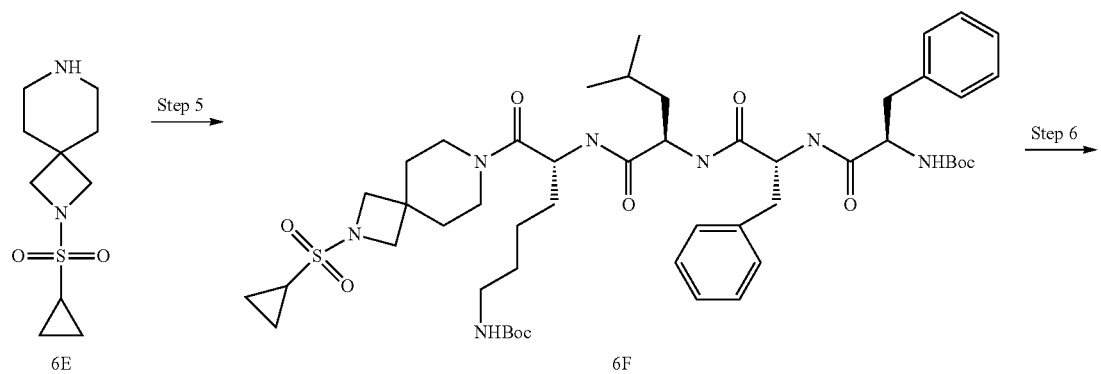
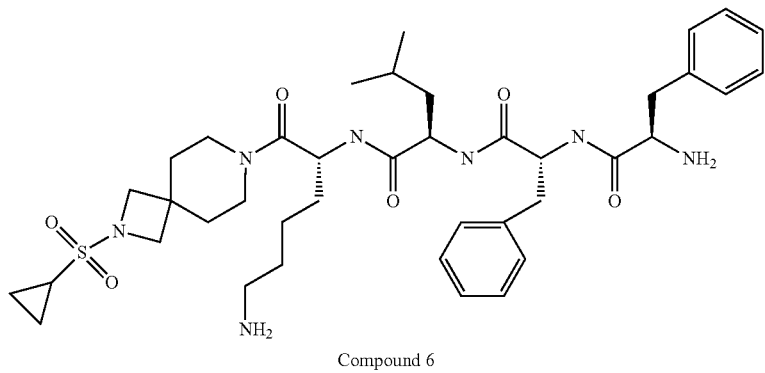
Compound 6

Step 1: 7-benzyl 2-tert-butyl 2,7-diazaspiro[3.5]nonane-2,7-dicarboxylate (6B)

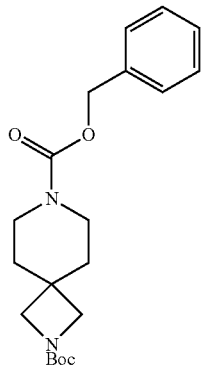 [SMILES: CC(C)(C)OC(=O)N1CC2(CCN(C(=O)OCc3ccccc3)CC2)C1]

Triethylamine (0.15 mL, 1.1 mmol) was added dropwise into a tert-butyl 2,7-diazaspiro[3.5]nonane-2-carboxylate (6A) (0.23 g, 1 mmol) in a solution of tetrahydrofuran (5 mL) in a 50 mL single-necked bottle at 0° C. After the dropwise addition, benzyl chloroformate (340 mg, 2 mmol) was added and stirred for 10 min. The temperature was raised to room temperature and stirring was continued for 1 h. The reaction solution was filtered through diatomite and the filtrate was concentrated under reduced pressure to obtain 7-benzyl 2-tert-butyl-2,7-diazaspiro[3.5]nonane-2,7-dicarboxylate (6B) as colorless oily product (362 mg, yield 99%).

MS m/z=383.2 [M+Na]$^+$;

$^1$H NMR (400 MHz, CDCl$_3$) δ 7.34-7.32 (m, 5H), 5.12 (s, 2H), 3.64 (s, 4H), 3.43 (dd, 4H), 1.77-1.61 (m, 4H), 1.44 (s, 9H).

Step 2: benzyl 2,7-diazaspiro[3.5]nonane-7-carboxylate (6C)

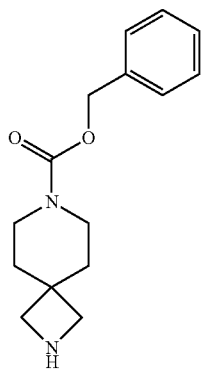 [SMILES: O=C(OCc1ccccc1)N1CCC2(CC1)CNC2]

7-benzyl 2-tert-butyl-2,7-diazaspiro[3.5]nonane-2,7-dicarboxylate (6B) (0.36 g, 1 mmol) and dichloromethane (7 mL) were added in a 50 mL reaction flask, and trifluoroacetic acid (1 mL) was added dropwise at room temperature. After the addition, the reaction was allowed to proceed at room temperature for 3 h. The reaction solution was directly concentrated under reduced pressure to obtain crude benzyl 2,7-diazaspiro[3.5]nonane-7-carboxylate (6C) as yellow oily liquid (260 mg, yield 100%), and used directly in the next reaction.

MS m/z=261.2 [M+H]$^+$;

Step 3: benzyl 2-cyclopropylsulfonyl-2,7-diazaspiro[3.5]nonane-7-carboxylate (6D)

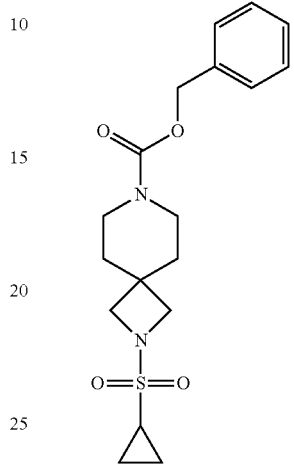

Crude benzyl 2,7-diazaspiro[3.5]nonane-7-carboxylate (6C) (260 mg, 1 mmol), triethylamine (200 mg, 2 mmol) and dichloromethane (7 mL) were added in a 50 mL reaction flask. The solution was cooled to 0° C. in an ice bath, and cyclopropylsulfonyl chloride (170 mg, 1.2 mmol) was added dropwise. After the addition, the temperature was raised to room temperature for 4 h. The reaction system was then quenched with saturated sodium bicarbonate (10 mL), extracted with ethyl acetate (5 mL×3), and the organic phases were combined. The organic phases were dried over anhydrous sodium sulfate, filtered, and the filtrate was concentrated under reduced pressure. The residue was separated and purified by silica gel column chromatography (petroleum ether:ethyl acetate (v:v)=4:1) to obtain benzyl 2-cyclopropylsulfonyl-2,7-diazaspiro[3.5]nonane-7-carboxylate compound (6D) as white solid (360 mg, yield 99%).

MS m/z=365.2 [M+H]$^+$;

$^1$H NMR (400 MHz, CDCl$_3$) δ 7.43-7.28 (m, 5H), 5.12 (s, 2H), 3.70 (s, 4H), 3.53-3.36 (m, 4H), 2.41-2.22 (m, 1H), 1.85-1.69 (m, 4H), 1.19-1.09 (m, 2H), 1.04-0.93 (m, 2H).

Step 4: 2-cyclopropylsulfonyl-2,7-diazaspiro[3.5]nonane (6E)

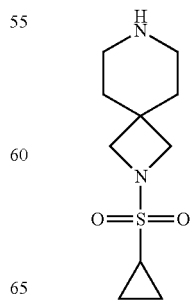

Benzyl 2-cyclopropylsulfonyl-2,7-diazaspiro[3.5]nonane-7-carboxylate (6D) (360 mg, 0.99 mmol), palladium on carbon (72 mg, 20 wt %) and ethyl acetate (10 mL) were added in a 50 mL reaction flask. The atmosphere was replaced with hydrogen 3 times, and the reaction was allowed to proceed at room temperature for 2 h under a hydrogen (balloon) atmosphere. The reaction solution was filtered through diatomite, and the filtrate was concentrated under reduced pressure to obtain 2-cyclopropylsulfonyl-2,7-diazaspiro[3.5]nonane (6E) as light yellow solid (210 mg, yield 92%), and used directly in the next reaction.

Step 5: tert-butyl N-[(1R)-1-benzyl-2-[[(1R)-1-benzyl-2-[[(1R)-1-[[(1R)-5-(tert-butoxycarbonylamino)-1-(2-cyclopropylsulfonyl-2,7-diazaspiro[3.5]nonane-7-carbonyl)pentyl]carbamoyl]-3-methyl-butyl]amino]-2-oxo-ethyl]amino]-2-oxo-ethyl]carbamate (6F)

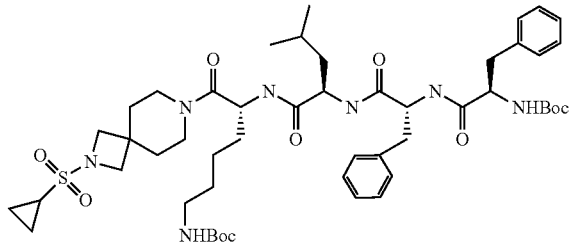 [SMILES: CC(C)C[C@@H](NC(=O)[C@@H](Cc1ccccc1)NC(=O)[C@@H](Cc1ccccc1)NC(=O)OC(C)(C)C)C(=O)N[C@H](CCCCNC(=O)OC(C)(C)C)C(=O)N1CCC2(CC1)CN(S(=O)(=O)C1CC1)C2]

2-cyclopropylsulfonyl-2,7-diazaspiro[3.5]nonane (6E) (161 mg, 0.7 mmol), 1-(3-dimethylaminopropyl)-3-ethyl-carbodiimide hydrochloride (124 mg, 0.8 mmol), 1-hydroxybenzotriazole (108 mg, 0.8 mmol), intermediate 1 (500 mg, 0.7 mmol) and dichloromethane (30 mL) were added in a 50 mL reaction flask, and the system was allowed to react at room temperature for 5 h. The reaction solution was concentrated under reduced pressure and the residue was separated and purified by silica gel column chromatography (petroleum ether:ethyl acetate (v:v)=1:2) to obtain tert-butyl N-[(1R)-1-benzyl-2-[[(1R)-1-benzyl-2-[[(1R)-1-[[(1R)-5-(tert-butoxycarbonylamino)-1-(2-cyclopropylsulfonyl-2,7-diazaspiro[3.5]nonane-7-carbonyl)pentyl]carbamoyl]-3-methyl-butyl]amino]-2-oxo-ethyl]amino]-2-oxo-ethyl]carbamate (6F) as white solid (610 mg, yield 95%).

Step 6: (2R)—N-[(1R)-5-amino-1-(2-cyclopropylsulfonyl-2,7-diazaspiro[3.5]nonane-7-carbonyl)pentyl]-2-[[(2R)-2-[[(2R)-2-amino-3-phenyl-propanoyl]amino]-3-phenyl-propanoyl]amino]-4-methyl-pentanamide (compound 6)

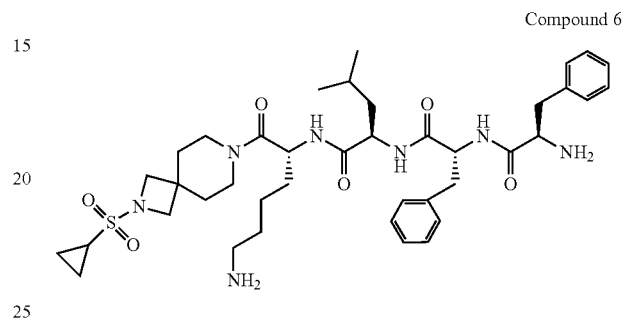

Tert-butylN-[(1R)-1-benzyl-2-[[(1R)-1-benzyl-2-[[(1R)-1-[[(1R)-5-(tert-butoxycarbonylamino)1-(2-cyclopropylsulfonyl-2,7-diazaspiro[3.5]nonane-7-carbonyl)pentyl]carbamoyl]-3-methyl-butyl]amino]-2-oxo-ethyl]amino]-2-oxo-ethyl]carbamate (6F) (300 mg, 0.31 mmol) and trifluoroacetic acid (2 mL) was added in a 50 mL reaction flask, and the system was allowed to react at room temperature for 2 h. The reaction solution was concentrated under reduced pressure and the residue was separated and purified by preparative liquid chromatography (preparation conditions: instrument: Gilson GX-281; column: Xbridge C18, 150×30 mm I.D., 5 μm; mobile phase: A for ACN and B for $H_2O$; isocratic: A 65%; flow rate: 30 mL/min; back pressure: 1000 PSI; column temperature: 30° C.; wavelength: 210 nm; period: 18 min; sample preparation: the compound dissolved in 12 mL methanol; injection: 0.9 mL/needle). The preparation was concentrated under reduced pressure to remove most of the solvent and lyophilized to obtain a white powdery compound. Then, the ion-exchange resin (eluted with water to 3.3% ammonia) was used to concentrate the received elution solution under reduced pressure (concentrated under reduced pressure to 25 mL at 60° C.), and further lyophilized to obtain (2R)—N-[(1R)-5-amino-1-(2-cyclopropylsulfonyl-2,7-diazaspiro[3.5]nonane-7-carbonyl)pentyl]-2-[[(2R)-2-[[(2R)-2-amino-3-phenyl-propanoyl]amino]-3-phenyl-propanoyl]amino]-4-methyl-pentanamide (compound 6) as white solid (153 mg, yield 63%).

MS m/z=383.8 $[M+2H]^+/2$;

$^1$H NMR (400 MHz, $D_2O$) δ 7.40-7.24 (m, 6H), 7.16 (dd, 4H), 4.72-4.73 (m, 1H), 4.58-4.52 (m, 1H), 4.25 (t, 1H), 3.84 (dd, 4H), 3.67-3.55 (m, 3H), 3.46-3.45 (m, 1H), 3.35-3.34 (m, 1H), 3.03 (dd, 1H), 2.91 (dd, 3H), 2.82 (d, 2H), 2.69 (ddd, 1H), 1.85-1.86 (m, 3H), 1.670-1.66 (m, 5H), 1.51-1.49 (m, 3H), 1.38-1.36 (m, 2H), 1.23-1.06 (m, 4H), 0.88 (dd, 6H).

Example 5: (2R)—N-[(1R)-5-amino-1-(2-methyl-sulfonyl-2,7-diazaspiro[3.5]nonane-7-carbonyl)pentyl]-2-[[(2R)-2-[[(2R)-2-amino-3-phenyl-propanoyl]amino]-3-phenyl-propanoyl]amino]-4-methyl-pentanamide; di-trifluoroacetate (compound 7)

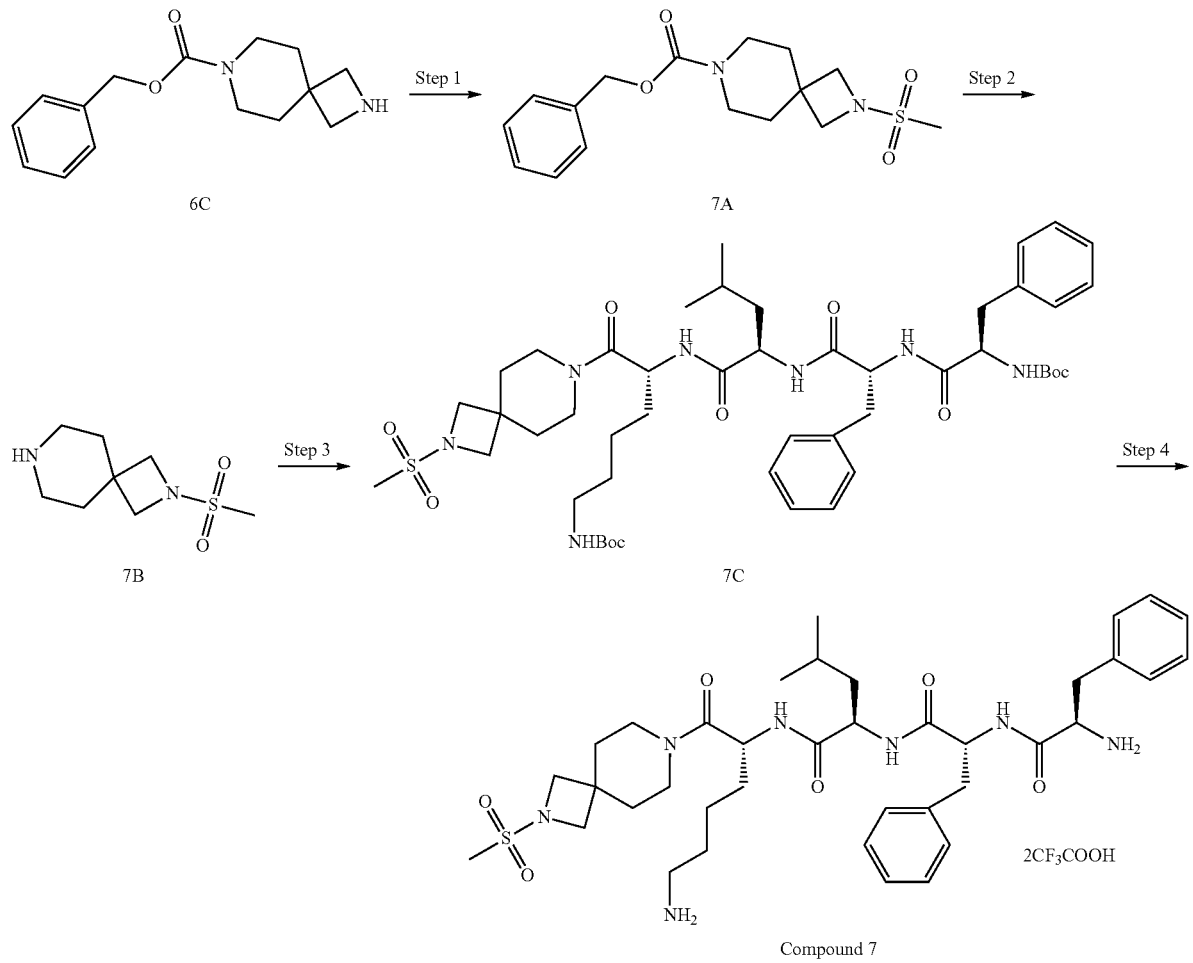

Step 1: benzyl 2-methylsulfonyl-2,7-diazaspiro[3.5]nonane-7-carboxylate (7A)

Benzyl 2,7-diazaspiro[3.5]nonane-7-carboxylate (6C) (330 mg, 1.3 mmol), triethylamine (263 mg, 2.6 mmol) and dichloromethane (20 mL) were added in a 50 mL reaction flask and stirred to dissolve. After cooling to −10° C., methanesulfonyl chloride (164 mg, 1.43 mmol) was added dropwise, and the reaction was allowed to proceed for 4 h. Then the temperature was raised to room temperature. The reaction solution was washed with saturated aqueous sodium bicarbonate solution (60 mL), 3N aqueous hydrochloric acid solution (60 mL), and the mixture was subjected to a liquid separation process. The organic phases were dried over anhydrous sodium sulfate, filtered, and the filtrate was concentrated under reduced pressure. The residue was separated and purified by silica gel column chromatography (petroleum ether:ethyl acetate (v:v)=1:1) to obtain benzyl 2-methylsulfonyl-2,7-diazaspiro[3.5]nonane-7-carboxylate (7A) as light yellow oily substance (236 mg, yield 54.6%).

MS m/z=339.0 [M+H]$^+$;

$^1$H NMR (400 MHz, CDCl$_3$) δ 7.41-7.28 (m, 5H), 5.12 (s, 2H), 3.68 (s, 4H), 3.50-3.38 (m, 4H), 2.86 (s, 3H), 1.83-1.70 (m, 4H).

Step 2: 2-methylsulfonyl-2,7-diazaspiro[3.5]nonane (7B)

Benzyl 2-methylsulfonyl-2,7-diazaspiro[3.5]nonane-7-carboxylate (7A) (236 mg, 0.7 mmol), palladium on carbon (40 mg, 20 wt %) and methanol (20 mL) were added in a 50 mL reaction flask. The atmosphere was replaced with hydrogen 3 times, and the reaction was allowed to proceed at room temperature for 8 h under a hydrogen (balloon) atmosphere. The reaction solution was then filtered through diatomite, and the filtrate was concentrated under reduced pressure to obtain crude 2-methylsulfonyl-2,7-diazaspiro[3.5]nonane (7B) as light yellow solid (133 mg, yield 100%), and used directly in the next reaction.

MS m/z=205.1 [M+1]$^+$;

Step 3: tert-butylN-[(1R)-1-benzyl-2-[[(1R)-1-benzyl-2-[[(1R)-1-[[(1R)-5-(tert-butoxy carbonylamino)-1-(2-methylsulfonyl-2,7-diazaspiro[3.5]nonane-7-carbonyl)pentyl]carbamoyl]-3-methyl-butyl]amino]-2-oxo-ethyl]amino]-2-oxo-ethyl] carbamate (7C)

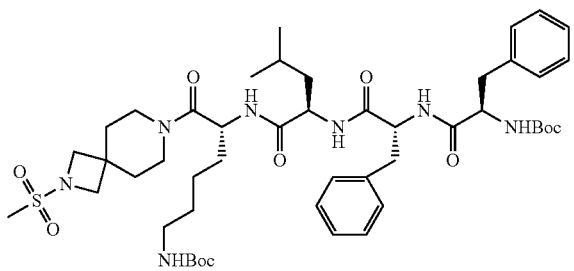 [SMILES: CC(C)C[C@@H](NC(=O)[C@@H](Cc1ccccc1)NC(=O)[C@@H](Cc1ccccc1)NC(=O)OC(C)(C)C)C(=O)N[C@H](CCCCNC(=O)OC(C)(C)C)C(=O)N1CCC2(CC1)CN(S(C)(=O)=O)C2]

Crude 2-methylsulfonyl-2,7-diazaspiro[3.5]nonane (7B) (133 mg, 0.65 mmol), 1-(3-dimethylaminopropyl)-3-ethyl-carbodiimide hydrochloride (374 mg, 1.95 mmol), 1-hydroxybenzotriazole (96.6 mg, 0.72 mmol), intermediate 1 (490 mg, 0.65 mmol) and dichloromethane (30 mL) were added in a 50 mL reaction flask, and the system was allowed to react at room temperature for 5 h. Then the reaction solution was concentrated under reduced pressure and the residue was separated and purified by silica gel column chromatography (petroleum ether:ethyl acetate (v:v)=1:2) to obtain tert-butyl N-[(1R)-1-benzyl-2-[[(1R)-1-benzyl-2-[[(1R)-1-[[(1R)-5-(tert-butoxycarbonylamino)-1-(2-methylsulfonyl-2,7-diazaspiro[3.5]nonane-7-carbonyl)pentyl]carbamoyl]-3-methyl-butyl]amino]-2-oxo-ethyl]amino]-2-oxo-ethyl]carbamate (7C) as light yellow solid (317 mg, yield 52%).

Step 4: (2R)—N-[(1R)-5-amino-1-(2-methylsulfonyl-2,7-diazaspiro[3.5]nonane-7-carbonyl)pentyl]-2-[[(2R)-2-[[(2R)-2-amino-3-phenyl-propanoyl]amino]-3-phenyl-propanoyl]amino]-4-methyl-pentanamide (compound 7)

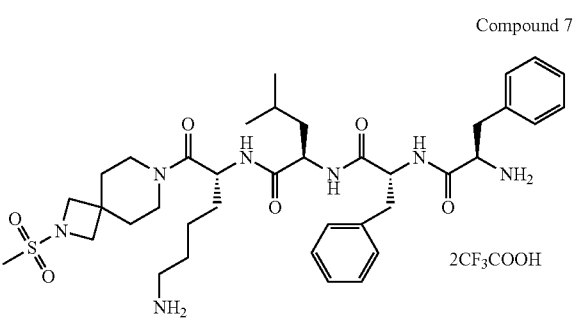 [SMILES: CC(C)C[C@@H](NC(=O)[C@@H](Cc1ccccc1)NC(=O)[C@H](N)Cc1ccccc1)C(=O)N[C@H](CCCCN)C(=O)N1CCC2(CC1)CN(S(C)(=O)=O)C2]

Compound 7

Tert-butyl N-[(1R)-1-benzyl-2-[[(1R)-1-benzyl-2-[[(1R)-1-[[(1R)-5-(tert-butoxycarbonylamino)-(2-methylsulfonyl-2,7-diazaspiro[3.5]nonane-7-carbonyl)pentyl]carbamoyl]-3-methyl-butyl]amino]-2-oxo-ethyl]amino]-2-oxo-ethyl] carbamate (7C) (317 mg, 0.34 mmol) and trifluoroacetic acid (2 mL) were added in a 50 mL reaction flask, and the system was allowed to react at room temperature for 2 h. Then the reaction solution was concentrated under reduced pressure and the residue was separated and purified by preparative liquid chromatography (preparation conditions: instrument: Gilson GX-281; column: Xbridge C18, 150×30 mm I.D., 5 μm; mobile phase: A for ACN and B for H$_2$O; isocratic: A 65%; flow rate: 30 mL/min; back pressure: 1000 PSI; column temperature: 30° C.; wavelength: 210 nm; period: 18 min; sample preparation: the compound dissolved in 12 mL methanol; injection: 0.9 mL/needle). The preparation was collected, and concentrated under reduced pressure to remove most of the organic solvent, and lyophilized to obtain (2R)—N-[(1R)-5-amino-1-(2-methylsulfonyl-2,7-diazaspiro[3.5]nonane-7-carbonyl)pentyl]-2-[[(2R)-2-[[(2R)-2-amino-3-phenyl-propanoyl]amino]-3-phenyl-propanoyl]amino]-4-methyl-pentanamide (compound 7) as white powder (217 mg, yield 66.5%).

MS m/z=370.8 [M+2H]$^+$/2;

$^1$H NMR (400 MHz, D$_2$O) δ 7.43-7.27 (m, 6H), 7.25-7.20 (m, 4H), 4.67-4.62 (m, 2H), 4.33-4.20 (m, 2H), 3.87-3.71 (m, 4H), 3.69-3.56 (m, 2H), 3.53-3.41 (m, 1H), 3.40-3.29 (m, 1H), 3.23-3.12 (m, 2H), 3.11-3.07 (m, 3H), 3.07-2.91 (m, 4H), 1.94-1.78 (m, 3H), 1.78-1.60 (m, 5H), 1.58-1.48 (m, 3H), 1.46-1.28 (m, 2H), 0.98-0.82 (m, 6H).

Example 6: (2R)—N-[(1R)-1-(2-acetyl-2,7-diaz-aspiro[3.5]nonane-7-carbonyl)-5-amino-pentyl]-2-[[(2R)-2-[[(2R)-2-amino-3-phenyl-propanoyl]amino]-3-phenyl-propanoyl]amino]-4-methyl-pentanamide; di-trifluoroacetic acid (compound 8)
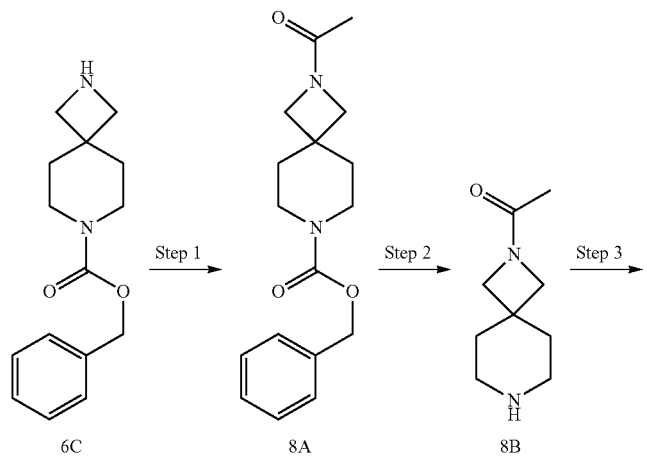
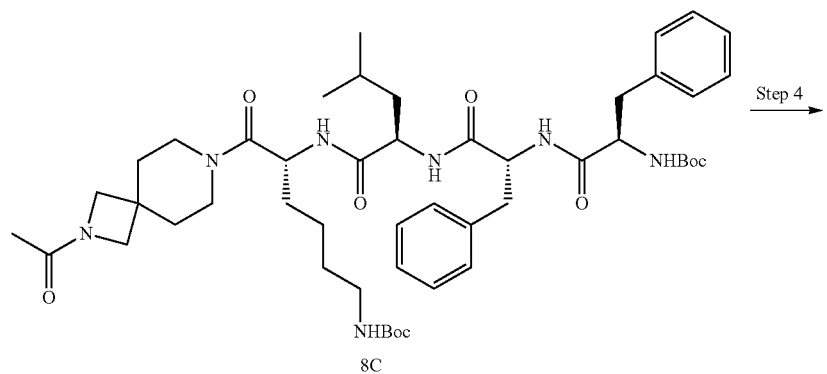
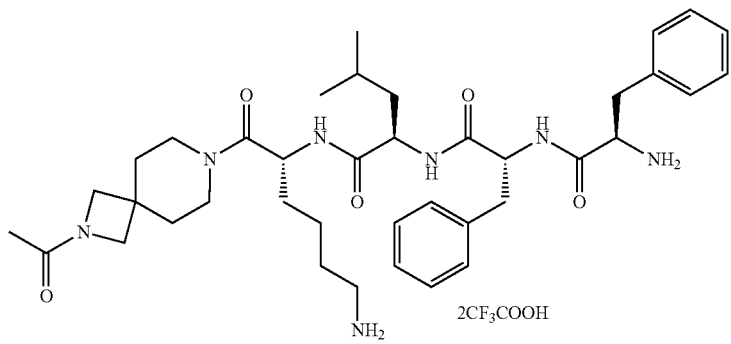
Compound 8

Step 1: benzyl 2-acetyl-2,7-diazaspiro[3.5]nonane-7-carboxylate (8A)

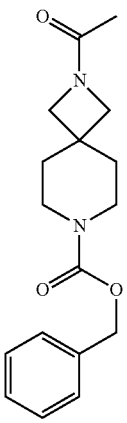

Benzyl 2,7-diazaspiro[3.5]nonane-7-carboxylate (6C) (520 mg, 2.0 mmol) was dissolved in dichloromethane (5 mL) under nitrogen protection in a 50 mL reaction flask and triethylamine (607 mg, 6.0 mmol) was added under stirring. Then the temperature was dropped to −20° C., and acetyl chloride (314 mg, 4.0 mmol) was added dropwise. After the addition, the temperature was naturally raised to room temperature and stirred for 2 h. Then a 0.5 M dilute aqueous hydrochloric acid solution (20 mL) was added to the reaction, and the layers were separated under stirring and the mixture was subjected to a liquid separation process. The aqueous layer was extracted with dichloromethane (20 mL×2), and the organic phases were combined. The organic phases were dried over anhydrous sodium sulfate, filtered, and the filtrate was concentrated under reduced pressure. The residue was separated and purified by silica gel column chromatography (pure ethyl acetate) to obtain benzyl 2-acetyl-2,7-diazaspiro[3.5]nonane-7-carboxylate compound (8A) as light yellow oily liquid (440 mg, yield 72.8%).

Step 2: 1-(2,7-diazaspiro[3.5]nonan-2-yl)ethanone (8B)

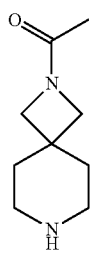

Benzyl 2-acetyl-2,7-diazaspiro[3.5]nonane-7-carboxylate (8A) (440 mg, 1.46 mmol) was added to a mixed solution of ethyl acetate (5 mL) and methanol (2 mL) in a 50 mL reaction flask. Then palladium on carbon (80 mg, 20 wt %) was added, and the system was stirred under a hydrogen (balloon) atmosphere at room temperature for 2 h. The reaction solution was then filtered, and the filtrate was concentrated under reduced pressure to obtain crude 1-(2, 7-diazaspiro[3.5]nonan-2-yl)ethanone (8B) as light yellow oily liquid (250 mg, yield 99%), and used directly in the next reaction.

Step 3: tert-butylN-[(1R)-2-[[(1R)-2-[[(1R)-1-[[(1R)-1-(2-acetyl-2,7-diazaspiro[3.5]nonane-7-carbonyl)-5-(tert-butoxycarbonylamino)pentyl]carbamoyl]-3-methyl-butyl]amino]-1-benzyl-2-oxo-ethyl]amino]-1-benzyl-2-oxo-ethyl]carbamate (8C)

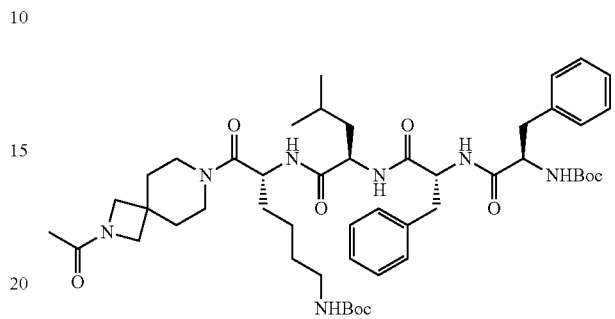

Crude 1-(2,7-diazaspiro[3.5]nonan-2-yl)ethanone (8B) (200 mg, 1.19 mmol) was added in ethyl acetate (10 mL) in a 50 mL reaction flask under nitrogen protection. It was cooled to 0° C. in an ice bath, then intermediate 1 (867 mg, 1.15 mmol), 1-(3-dimethylaminopropyl)-3-ethylcarbodiimide hydrochloride (331 mg, 1.73 mmol), 1-hydroxybenzotriazole (186 mg, 1.38 mmol) were added. After the addition, the reaction was allowed to proceed at room temperature for 1.5 h. Subsequently, a 1N aqueous hydrochloric acid solution (15 mL) was added to the reaction solution, and the mixture was stirred and then subjected to a liquid separation process. A saturated aqueous sodium carbonate solution (15 mL) was added to the organic phase, and the mixture was stirred for 30 minutes and then subjected to a liquid separation process. The organic phase was washed with a saturated sodium chloride aqueous solution (15 mL), dried over anhydrous sodium sulfate, filtered, and the filtrate was concentrated under reduced pressure to obtain crude tert-butyl N-[(1R)-2-[[(1R)-2-[[(1R)-1-[[(1R)-1-(2-acetyl-2,7-diazaspiro[3.5]nonane--7-carbonyl)-5-(tert-butoxycarbonylamino)pentyl]carbamoyl]-3-methyl-butyl]amino]-1-benzyl-2-oxo-ethyl]amino]-1-benzyl-2-oxo-ethyl] carbamate (8C) as light yellow foamy solid (1.04 g, yield 99%), and used directly in the next reaction.

Step 4: (2R)—N-[(1R)-1-(2-acetyl-2,7-diazaspiro[3.5]nonane-7-carbonyl)-5-amino-pentyl]-2-[[(2R)-2-[[(2R)-2-amino-3-phenyl-propanoyl]amino]-3-phenyl-propanoyl]amino]-4-methyl-pentanamide; di-trifluoroacetic acid (compound 8)

Compound 8

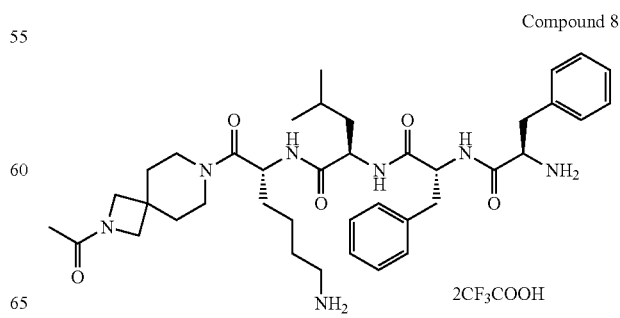

Crude tert-butyl N-[(1R)-2-[[(1R)-2-[[(1R)-1-[[(1R)-1-(2-acetyl-2,7-diazaspiro[3.5]nonane--7-carbonyl)-5-(tert-butoxycarbonylamino)pentyl]carbamoyl]-3-methyl-butyl]amino]-1-benzyl-2-oxo-ethyl]amino]-1-benzyl-2-oxo-ethyl]carbamate (8C) (1.04 g, 1.15 mmol) was dissolved in dichloromethane (7.5 mL), and trifluoroacetic acid (3.5 mL) was added. The system was stirred at room temperature for 1 h. Subsequently, the reaction solution was concentrated under reduced pressure. After the residue was separated and purified by preparative liquid chromatography (preparation conditions: instrument: Gilson GX-281; column: Xbridge C18, 150×30 mm I.D., 5 μm; mobile phase: A for ACN and B for H$_2$O; isocratic: A 65%; flow rate: 30 mL/min; back pressure: 1000 PSI; column temperature: 30° C.; wavelength: 210 nm; period: 18 min; sample preparation: the compound dissolved in 12 mL methanol; injection: 0.9 mL/needle), the preparation was collected, and concentrated under reduced pressure to remove most of the organic solvent, and lyophilized to obtain (2R)—N-[(1R)-1-(2-acetyl-2,7-diazaspiro[3.5]nonane-7-carbonyl)-5-amino-pentyl]-2-[[(2R)-2-[[(2R)-2-amino-3-phenyl-propanoyl]amino]-3-phenyl-propanoyl]amino]-4-methyl-pentanamide; di-trifluoroacetic acid (compound 8) as white solid (460 mg, two-step yield 42.9%).

MS m/z (ESI): 352.8[M+2H]$^+$/2;

$^1$H NMR (400 MHz, D$_2$O) δ 7.49-7.00 (m, 10H), 4.66-4.49 (m, 2H), 4.30-3.93 (m, 4H), 3.79-3.54 (m, 4H), 3.52-3.25 (m, 2H), 3.22-2.90 (m, 6H), 1.92-1.27 (m, 16H), 1.02-0.75 (m, 6H).

compound 8-1:

The compound 8 (1.0 g, 1.07 mmol) was passed through an ion exchange resin (60 mL) (eluted by water ~3.3% ammonia), and the received elution solution was concentrated under reduced pressure (concentrated under reduced pressure to 100 mL at 60° C.) and further lyophilized to obtain the compound 8-1 as the free form of compound 8 as white solid (451 mg, yield 60.0%).

MS m/z (ESI): 352.8[M+2H]$^+$/2;

$^1$H NMR (400 MHz, D$_2$O) δ 7.45-7.32 (m, 6H), 7.23 (dd, 4H), 4.85-4.75 (m, 1H), 4.64 (t, 1H), 4.35 (t, 1H), 4.07 (d, 2H), 3.83 (d, 2H), 3.74-3.63 (m, 3H), 3.62-3.50 (m, 1H), 3.50-3.39 (m, 1H), 3.17-2.65 (m, 6H), 2.01-1.66 (m, 9H), 1.65-1.30 (m, 7H), 0.96 (dd, 6H).

Example 7: isopropyl 7-[(2R)-6-amino-2-[[(2R)-2-[[(2R)-2-[[(2R)-2-amino-3-phenyl-propanoyl]amino]-3-phenyl-propanoyl]amino]-4-methyl-pentanoyl]amino]hexanoyl]-2,7-diazaspiro[3.5]nonane-2-carboxylate; di-trifluoroacetic acid (compound 9)

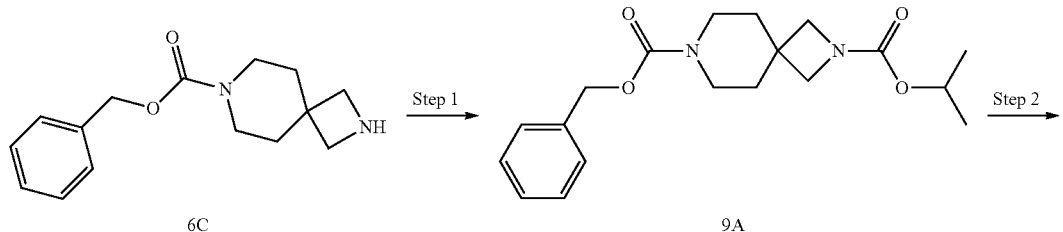

6C → Step 1 → 9A → Step 2 →

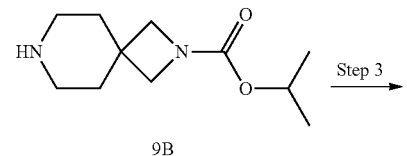

9B → Step 3 →

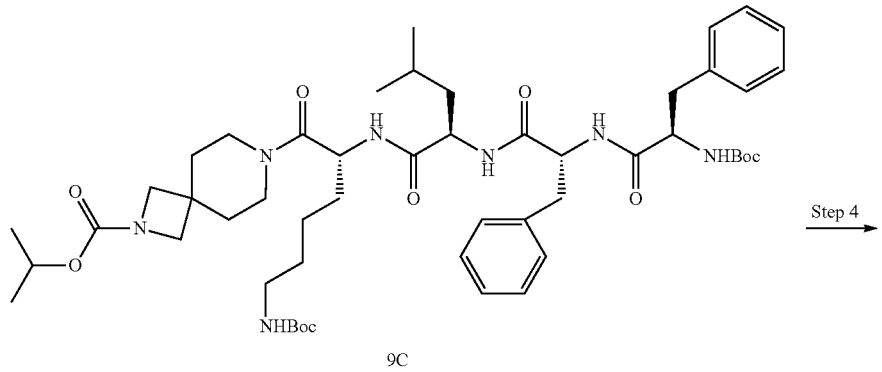

9C → Step 4 →

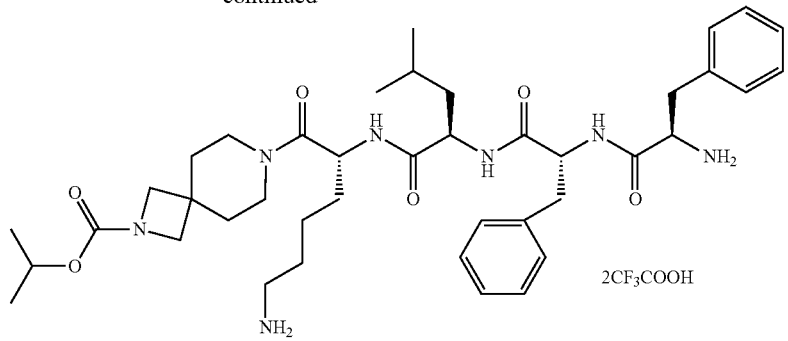

Compound 9

Step 1: O7-benzyl O2-isopropyl 2,7-diazaspiro[3.5]nonane-2,7-dicarboxylate (9A)

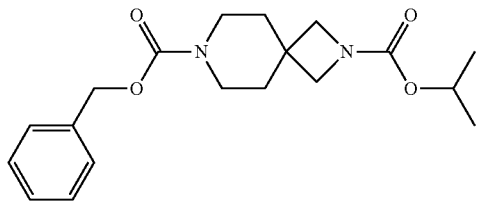 [SMILES: CC(C)OC(=O)N1CC2(CCN(C(=O)OCc3ccccc3)CC2)C1]

Benzyl 2,7-diazaspiro[3.5]nonane-7-carboxylate (6C) (310 mg, 1.2 mmol), triethylamine (364 mg, 3.6 mmol) and dichloromethane (20 mL) were added in a 50 mL single-necked flask, and it was dissolved under stirring at room temperature. Then it was cooled to −10° C., and isopropyl chloroformate (146 mg, 1.2 mmol) was added dropwise. After the addition, the temperature was raised to room temperature, and the reaction was allowed to proceed for 4 h. The reaction system was sequentially washed with saturated aqueous sodium bicarbonate solution (60 mL), 3M aqueous hydrochloric acid solution (60 mL) and the mixture was subjected to a liquid separation process. The organic phases were dried over anhydrous sodium sulfate, filtered, and the filtrate was concentrated under reduced pressure. The residue was separated and purified by silica gel column chromatography (petroleum ether:ethyl acetate (v:v)=1:1) to obtain O7-benzyl O-isopropyl 2,7-diazaspiro[3.5]nonane-2,7-dicarboxylate compound (9A) as light yellow oily liquid (279 mg, yield 68%).

MS m/z=347.2 [M+H]$^+$;

$^1$H NMR (400 MHz, CDCl$_3$) δ 7.38-7.30 (m, 5H), 5.12 (s, 2H), 4.95-4.80 (m, 1H), 3.68 (s, 4H), 3.47-3.39 (m, 4H), 1.75-1.68 (m, 4H), 1.23 (d, 6H).

Step 2: isopropyl 2,7-diazaspiro[3.5]nonane-2-carboxylate (9B

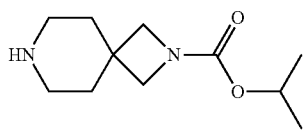

O7-benzyl O-isopropyl 2,7-diazaspiro[3.5]nonane-2,7-dicarboxylate (9A) (260 mg, 0.75 mmol), palladium on carbon (52 mg, 20 wt % l) and methanol (20 mL) were added in a 50 mL single-necked flask. The atmosphere was replaced with hydrogen 3 times, and the mixture reacted at room temperature for 8 h under a hydrogen (balloon) atmosphere. Then the reaction solution was filtered through diatomite, and the filtrate was concentrated under reduced pressure to obtain crude isopropyl 2,7-diazaspiro[3.5]nonane-2-carboxylate (9B) as light yellow solid (159 mg, yield 100%), and used directly in the next reaction.

MS m/z=213.2 [M+1].

Step 3: Isopropyl 7-[(2R)-6-(tert-butoxycarbonylamino)-2-[[(2R)-2-[[(2R)-2-[[(2R)-2-(tert-butoxycarbonylamino)-3-phenyl-propanoyl]amino]-3-phenyl-propanoyl]amino]-4-methyl-pentanoyl]amino]hexanoyl]-2,7-diazaspiro[3.5]nonane-2-carboxylate (9C)

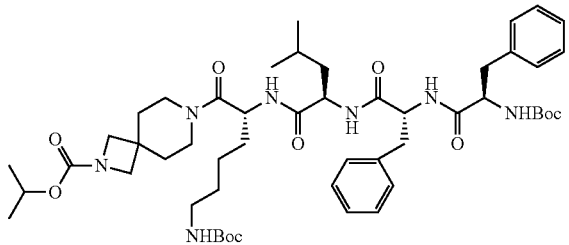 [SMILES: CC(C)C[C@@H](NC(=O)[C@@H](Cc1ccccc1)NC(=O)[C@@H](Cc1ccccc1)NC(=O)OC(C)(C)C)C(=O)N[C@H](CCCCNC(=O)OC(C)(C)C)C(=O)N1CCC2(CC1)CN(C(=O)OC(C)C)C2]

Crude isopropyl 2,7-diazaspiro[3.5]nonane-2-carboxylate (9B) (159 mg, 0.75 mmol), 1-(3-dimethylaminopropyl)-3-ethylcarbodiimide hydrochloride (374 mg, 1.95 mmol), 1-hydroxybenzotriazole (110 mg, 0.81 mmol), intermediate 1 (565 mg, 0.75 mmol) and dichloromethane (30 mL) were added in a 50 mL single-necked flask, and the system was allowed to react at room temperature for 5 h. Then the reaction solution was concentrated under reduced pressure. The residue was separated and purified by silica gel column chromatography (petroleum ether:ethyl acetate (v:v)=1:2) to obtain isopropyl 7-[(2R)-6-(tert-butoxycarbonylamino)-2-[[(2R)-2-[[(2R)-2-[[(2R)-2-(tert-butoxycarbonylamino)-3-phenyl-propanoyl]amino]-3-phenyl-propanoyl]amino]-4-methylpentanoyl]amino]hexanoyl]-2,7-diazaspiro[3.5]nonane-2-carboxylate (9C) as light yellow solid (556 mg, yield 78%).

Step 4: isopropyl 7-[(2R)-6-amino-2-[[(2R)-2-[[(2R)-2-[[(2R)-2-amino-3-phenyl-propanoyl]amino]-3-phenyl-propanoyl]amino]-4-methyl-pentanoyl]amino]hexanoyl]-2,7-diazaspiro[3.5]nonane-2-carboxylate; di-trifluoroacetic acid (compound 9)

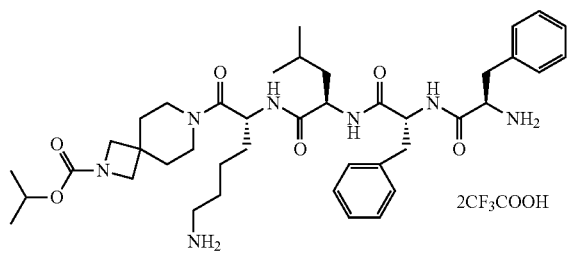 [SMILES: CC(C)C[C@@H](NC(=O)[C@@H](Cc1ccccc1)NC(=O)[C@H](N)Cc1ccccc1)C(=O)N[C@H](CCCCN)C(=O)N1CCC2(CC1)CN(C(=O)OC(C)C)C2]

Isopropyl 7-[(2R)-6-(tert-butoxycarbonylamino)-2-[[(2R)-2-[[(2R)-2-[[(2R)-2-(tert-butoxycarbonylamino)-3-phenyl-propanoyl]amino]-3-phenyl-propanoyl]amino]-4-methylpentanoyl]amino]hexanoyl]-2,7-diazaspiro[3.5]nonane-2-carboxylate (9C) (317 mg, 0.334 mmol) and trifluoroacetic acid (2 mL) were added in a 50 mL single-necked flask, and the system was allowed to react at room temperature for 2 h. Then the reaction solution was concentrated under reduced pressure, and the residue was purified by preparative liquid chromatography (preparation conditions: instrument: Gilson GX-281; column: Xbridge C18, 150×30 mm I.D., 5 μm; mobile phase: A for ACN and B for $H_2O$; isocratic: A 65%; flow rate: 30 mL/min; back pressure: 1000 PSI; column temperature: 30° C.; wavelength: 210 nm; period: 18 min; sample preparation: the compound dissolved in 12 mL methanol; injection: 0.9 mL/needle). The preparation was concentrated under reduced pressure to remove most of the solvent, and lyophilized to obtain isopropyl 7-[(2R)-6-amino-2-[[(2R)-2-[[(2R)-2-[[(2R)-2-amino-3-phenyl-propanoyl]amino]-3-phenyl-propanoyl]amino]-4-methyl-pentanoyl]amino]hexanoyl]-2,7-diazaspiro[3.5]nonane-2-carboxylat e; di-trifluoroacetic acid (compound 9) as white powdery product (326 mg, yield 98%).

MS m/z=374.9[M+2H]$^+$/2;

$^1$HNMR (400 MHz, $D_2O$) δ 7.50-7.14 (m, 10H), 4.89-4.78 (m, 1H), 4.66 (t, 1H), 4.30 (t, 1H), 4.22 (t, 1H), 3.89-3.74 (m, 4H), 3.69-3.54 (m, 2H), 3.54-3.41 (m, 1H), 3.41-3.28 (m, 1H), 3.21-3.11 (m, 2H), 3.11-2.90 (m, 4H), 1.93-1.30 (m, 14H), 1.27 (d, 6H), 0.93 (q, 6H).

Example 8: (2R)—N-[(1R)-5-amino-1-(2,7-diazaspiro[3.5]nonane-7-carbonyl)pentyl]-2-[[(2R)-2-[[(2R)-2-amino-3-phenyl-propanoyl]amino]-3-phenyl-propanoyl]amino]-4-methyl-pentanamide; tri-trifluoroacetic acid (compound 10)

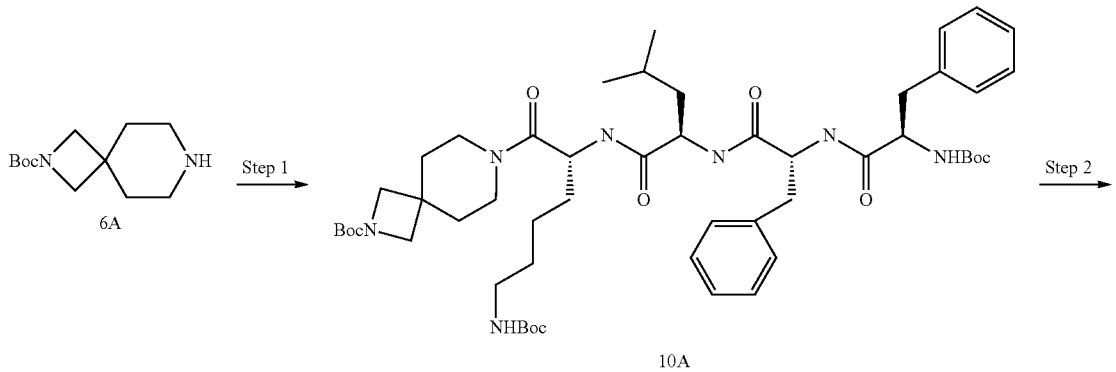

10A

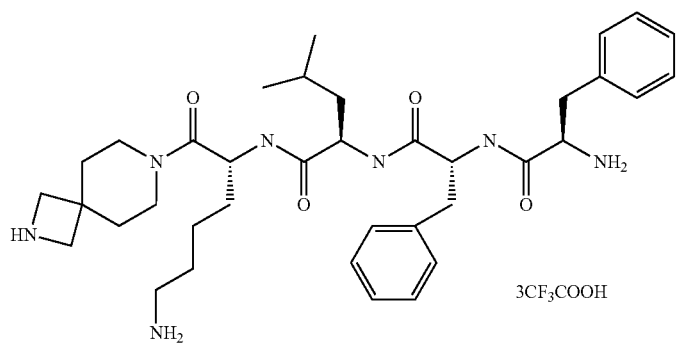

Compound 10

Step 1: tert-butyl 7-[(2R)-6-(tert-butoxycarbonylamino)-2-[[(2R)-2-[[(2R)-2-[[(2R)-2-(tert-butoxycarbonylamino)-3-phenyl-propanoyl]amino]-3-phenyl-propanoyl]amino]-4-methyl-pentanoyl]amino]hexanoyl]-2,7-diazaspiro[3.5]nonane-2-carboxylate (10A)

Step 2: (2R)—N-[(1R)-5-amino-1-(2,7-diazaspiro[3.5]nonane-7-carbonyl)pentyl]-2-[[(2R)-2-[[(2R)-2-amino-3-phenyl-propanoyl]amino]-3-phenyl-propanoyl]amino]-4-methyl-pentanamide; tri-trifluoroacetic acid (compound 10)

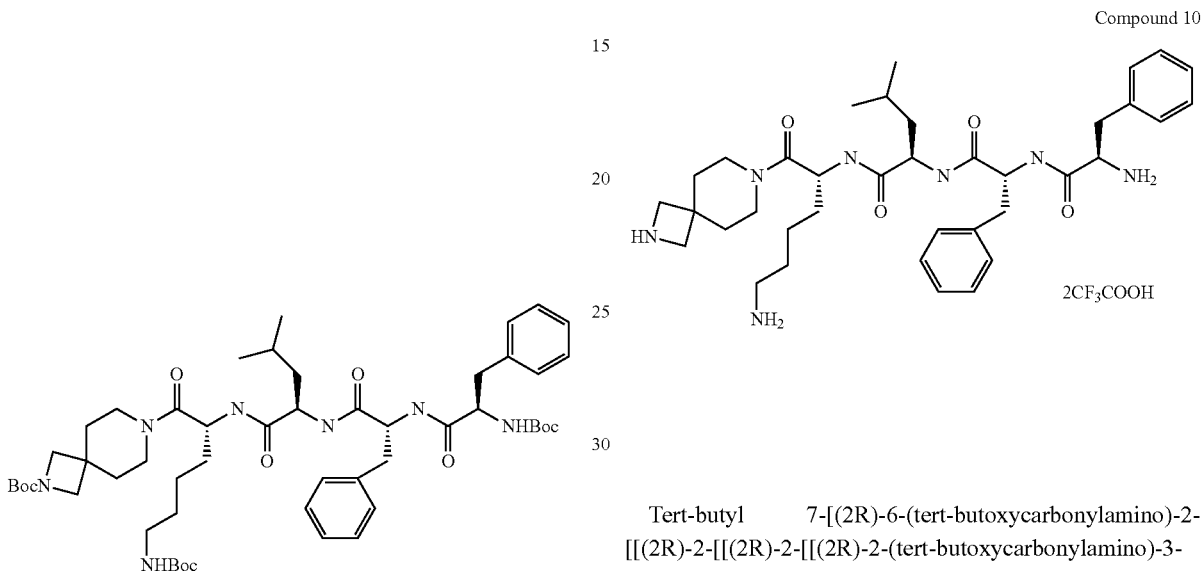

Compound 10

Tert-butyl 2,7-diazaspiro[3.5]nonane-2-carboxylate (6A) (0.11 g, 0.5 mmol), 1-(3-dimethylaminopropyl)-3-ethylcarbodiimide hydrochloride (115 mg, 0.6 mmol), 1-hydroxybenzotriazole (81 mg, 0.6 mmol), intermediate 1 (378 mg, 0.5 mmol) and dichloromethane (30 mL) were added in a 50 mL single-necked flask, and the system was allowed to react at room temperature for 5 h. Then the reaction solution was concentrated under reduced pressure. The residue was separated and purified by silica gel column chromatography (petroleum ether:ethyl acetate (v:v)=1:2) to obtain tert-butyl 7-[(2R)-6-(tert-butoxycarbonylamino)-2-[[(2R)-2-[[(2R)-2-[[(2R)-2-(tert-butoxycarbonylamino)-3-phenyl-propanoyl]amino]-3-phenyl-propanoyl]amino]-4-methyl-pentanoyl]amino]hexanoyl]-2,7-diazaspiro[3.5]nonane-2-carboxylate (10A) as white solid (450 mg, yield 93%).

Tert-butyl 7-[(2R)-6-(tert-butoxycarbonylamino)-2-[[(2R)-2-[[(2R)-2-[[(2R)-2-(tert-butoxycarbonylamino)-3-phenyl-propanoyl]amino]-3-phenyl-propanoyl]amino]-4-methyl-pentanoyl]amino]hexanoyl]-2,7-diazaspiro[3.5]nonane-2-carboxylate (10A) (450 mg, 0.468 mmol) and trifluoroacetic acid (2 mL) were added in a 50 mL single-necked flask, and the system was allowed to react at room temperature for 2 h. Then the reaction solution was concentrated under reduced pressure, the residue was purified by preparative liquid chromatography (preparation conditions: instrument: Gilson GX-281; column: Xbridge C18, 150×30 mm I.D., 5 μm; mobile phase: A for ACN and B for H$_2$O; isocratic: A 65%; flow rate: 30 mL/min; back pressure: 1000 PSI; column temperature: 30° C.; wavelength: 210 nm; period: 18 min; sample preparation: the compound dissolved in 12 mL methanol; injection: 0.9 mL/needle). The preparation was concentrated under reduced pressure to remove most of the solvent, and lyophilized to obtain (2R)—N-[(1R)-5-amino-1-(2,7-diazaspiro[3.5]nonane-7-carbonyl)pentyl]-2-[[(2R)-2-[[(2R)-2-amino-3-phenyl-propanoyl]amino]-3-phenyl-propanoyl]amino]-4-methyl-pentanamide; tri-trifluoroacetic acid (compound 10) as white powdery product (358 mg, yield 76%).

MS m/z=331.8 [M-2CF$_3$COOH+2H]$^+$/2;

$^1$H NMR (400 MHz, D$_2$O) δ 7.48-7.10 (m, 10H), 4.65-4.61 (m, 2H), 4.28-4.20 (m, 2H), 3.93 (d, 4H), 3.70-3.57 (m, 2H), 3.52-3.39 (m, 1H), 3.39-3.27 (m, 1H), 3.15 (d, 2H), 3.02-2.94 (m, 4H), 1.98-1.87 (m, 3H), 1.82-1.60 (m, 5H), 1.51-1.50 (m, 3H), 1.44-1.36 (m, 2H), 0.89 (dd, 6H).

Example 9: (2R)—N-[(1R)-5-amino-1-(2,7-diazaspiro[3.5]nonane-2-carbonyl)pentyl]-2-[[(2R)-2-[[(2R)-2-amino-3-phenyl-propanoyl]amino]-3-phenyl-propanoyl]amino]-4-methyl-pentanamide; tri-trifluocroacetic acid (compound 11)
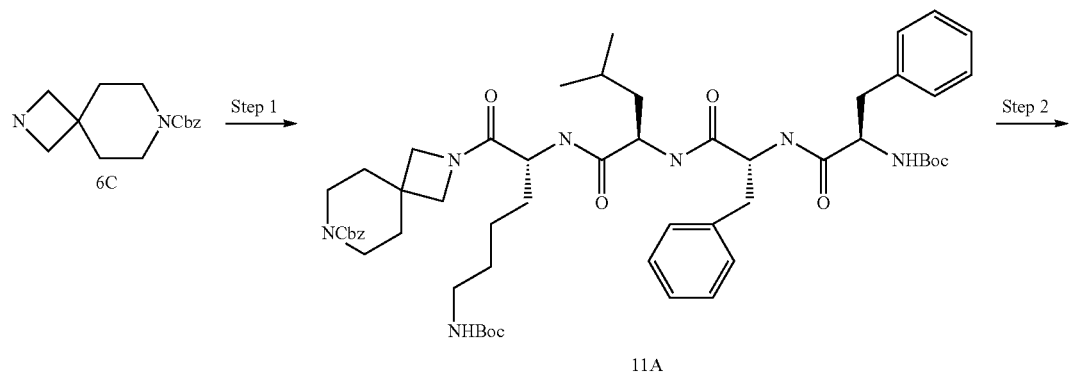
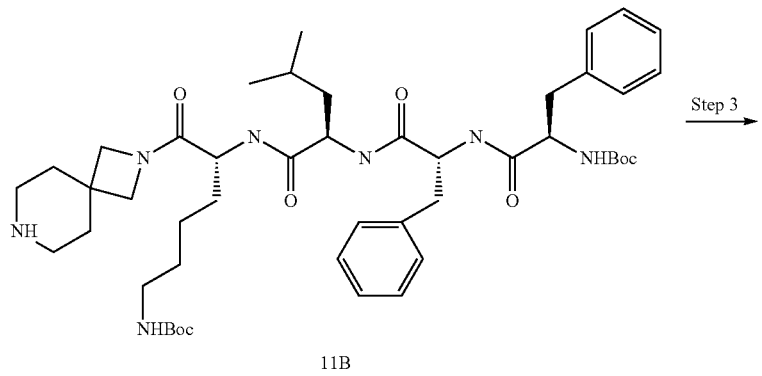
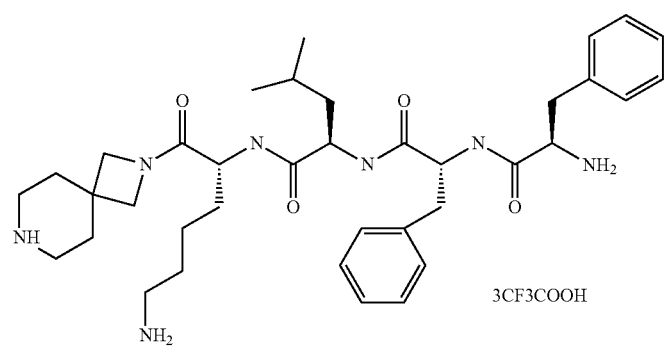

Step 1: Benzyl2-[(2R)-6-(tert-butoxycarbo-nylamino)-2-[[(2R)-2-[[(2R)-2-[[(2R)-2-(tert-butoxycarbonylamino)-3-phenyl-propanoyl]amino]-3-phenyl- propanoyl]amino]-4-methyl-pentanoyl]amino]hexanoyl]-2,7-diazaspiro[3.5]nonane-7-carboxylate (11A)

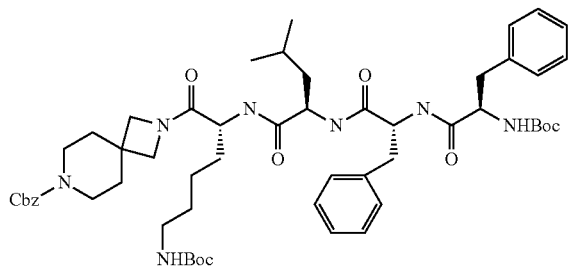 [SMILES: CC(C)C[C@@H](NC(=O)[C@@H](Cc1ccccc1)NC(=O)[C@@H](Cc1ccccc1)NC(=O)OC(C)(C)C)C(=O)N[C@H](CCCCNC(=O)OC(C)(C)C)C(=O)N1CC2(CCN(C(=O)OCc3ccccc3)CC2)C1]

Benzyl 2,7-diazaspiro[3.5]nonane-7-carboxylate (6C) (0.26 g, 1 mmol), 1-(3-dimethylaminopropyl)-3-ethylcarbodiimide hydrochloride (230 mg, 1.2 mmol), 1-hydroxybenzotriazole (162 mg, 1.2 mmol), intermediate 1 (0.75 g, 1 mmol) and dichloromethane (30 mL) were added in a 50 mL single-necked flask and the system was allowed to react at room temperature for 5 h. Then the reaction solution was concentrated under reduced pressure and the residue was separated and purified by silica gel column chromatography (petroleum ether:ethyl acetate (v:v)=1:2) to obtain benzyl 2-[(2R)-6-(tert-butoxycarbonylamino)-2-[[(2R))-2-[[(2R)-2-(tert-butoxycarbonylamino]-3-phenyl-propanoyl]amino]-3-phenyl- propanoyl]amino]-4-methyl-pentanoyl]amino]hexanoyl]-2,7-diazaspiro[3.5]nonane-7-carboxylate (11A) as white solid (850 mg, yield 85%).

Step 2: tert-butyl N-[(1R)-1-benzyl-2-[[(1R)-1-benzyl-2-[[(1R)-1-[[(1R)-5-(tert-butoxycarbonylamino)-1-(2,7-di azaspiro[3.5]nonane-2-carbonyl)pentyl]carbamoyl]-3-methyl-butyl]amino]-2-oxo-ethyl]amino]-2-oxo-ethyl]carbamate (11B)

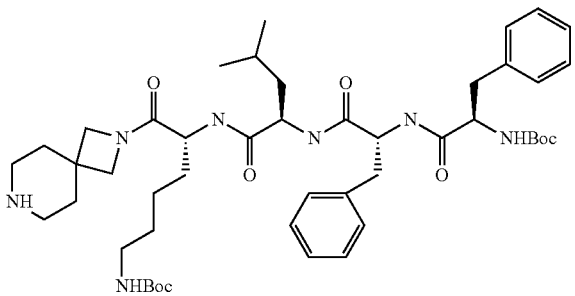 [SMILES: CC(C)C[C@@H](NC(=O)[C@@H](Cc1ccccc1)NC(=O)[C@@H](Cc1ccccc1)NC(=O)OC(C)(C)C)C(=O)N[C@H](CCCCNC(=O)OC(C)(C)C)C(=O)N1CC2(CCNCC2)C1]

Benzyl 2-[(2R)-6-(tert-butoxycarbonylamino)-2-[[(2R)-2-[[(2R))-2-[[(2R)-2-(tert-butoxycarbonylamino]-3-phenyl-propanoyl]amino]-3-phenyl-propanoyl]amino]-4-methyl-pentanoyl]amino]hexanoyl]-2,7-diazaspiro[3.5]nonane-7-carboxylate (11A) (850 mg, 0.85 mmol), palladium on carbon (170 mg, 20 wt %) and methanol (20 mL) were added in a 50 mL single-necked flask. The atmosphere was replaced with hydrogen 3 times, and the reaction was allowed to proceed at room temperature for 8 h under a hydrogen (balloon) atmosphere. Then the reaction solution was filtered through diatomite, and the filtrate was concentrated under reduced pressure to obtain crude tert-butyl N-[(1R)-1-benzyl-2-[[(1R)-1-benzyl-2-[[(1R)-1-[[(1R)-5-(tert-butoxycarbonylamino)-1-(2,7-diazaspiro[3.5]nonane-2-carbonyl)pentyl]carbamoyl]-3-methyl-butyl]amino]-2-oxo-ethyl]amino]-2-oxo-ethyl]carbamate (11B) as white solid (580 mg, yield 79%), and used directly in the next reaction.

Step 3: (2R)—N-[(1R)-5-amino-1-(2,7-diazaspiro[3.5]nonane-2-carbonyl)pentyl]-2-[[(2R)-2-[[(2R)-2-amino-3-phenyl-propanoyl]amino]-3-phenyl-propanoyl]amino]-4-methyl-pentanamide; tri-trifluoroacetic acid (compound 11)

Compound 11

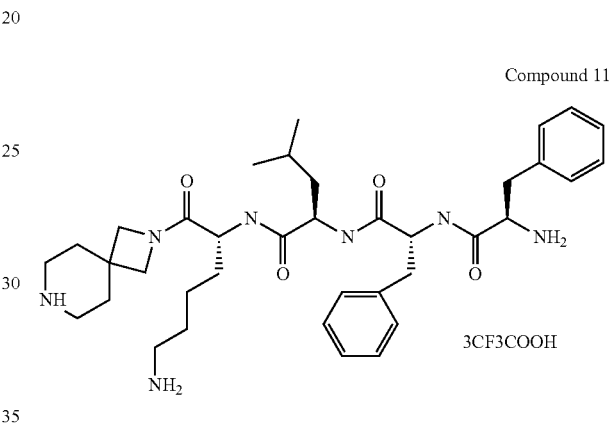

3CF3COOH

Tert-butyl N-[(1R)-1-benzyl-2-[[(1R)-1-benzyl-2-[[(1R)-1-[[(1R)-5-(tert-butoxycarbonylamino)-1-(2,7-di azaspiro[3.5]nonane-2-carbonyl)pentyl]carbamoyl]-3-methyl-butyl]amino]-2-oxo-ethyl]amino]-2-oxo-ethyl]carbamate (11B) (0.5 g, 0.58 mmol) and trifluoroacetic acid (2 mL) were added in a 50 mL single-necked flask, and the system was allowed to react at room temperature for 2 h. Then the reaction solution was concentrated under reduced pressure, and the residue was purified by preparative liquid chromatography (preparation conditions: instrument: Gilson GX-281; column: Xbridge C18, 150×30 mm I.D., 5 μm; mobile phase: A for ACN and B for H$_2$O; isocratic: A 65%; flow rate: 30 mL/min; back pressure: 1000 PSI; column temperature: 30° C.; wavelength: 210 nm; period: 18 min; sample preparation: the compound dissolved in 12 mL methanol; injection: 0.9 mL/needle). The preparation was concentrated under reduced pressure to remove most of the solvent, and lyophilized to obtain (2R)—N-[(1R)-5-amino-1-(2,7-diazaspiro[3.5]nonane-2-carbonyl)pentyl]-2-[[(2R)-2-[[(2R)-2-amino-3-phenyl-propanoyl]amino]-3-phenyl-propanoyl]amino]-4-methyl-pentanamide; tri-trifluoroacetic acid (compound 11) as white powdery product (380 mg, yield 66%).

MS m/z=331.8 [M-2CF$_3$COOH+2H]$^+$/2;

1H NMR (400 MHz, D$_2$O) δ 7.43-7.13 (m, 10H), 4.61 (t, 1H), 4.28-4.06 (m, 5H), 3.84-3.74 (m, 2H), 3.19-3.14 (m, 6H), 2.99-2.95 (m, 4H), 2.09-1.94 (m, 4H), 1.79-1.61 (m, 4H), 1.55-1.31 (m, 5H), 0.89 (dd, 6H).

Example 10: 2R)—N-[(1R)-5-amino-1-(7-methyl-sulfonyl-2,7-diazaspiro[3.5]nonane-2-carbonyl)pentyl]-2-[[(2R)-2-[[(2R)-2-amino-3-phenyl-propanoyl]amino]-3-phenyl-propanoyl]amino]-4-methyl-pentanamide; di-trifluoroacetic acid (compound 12)

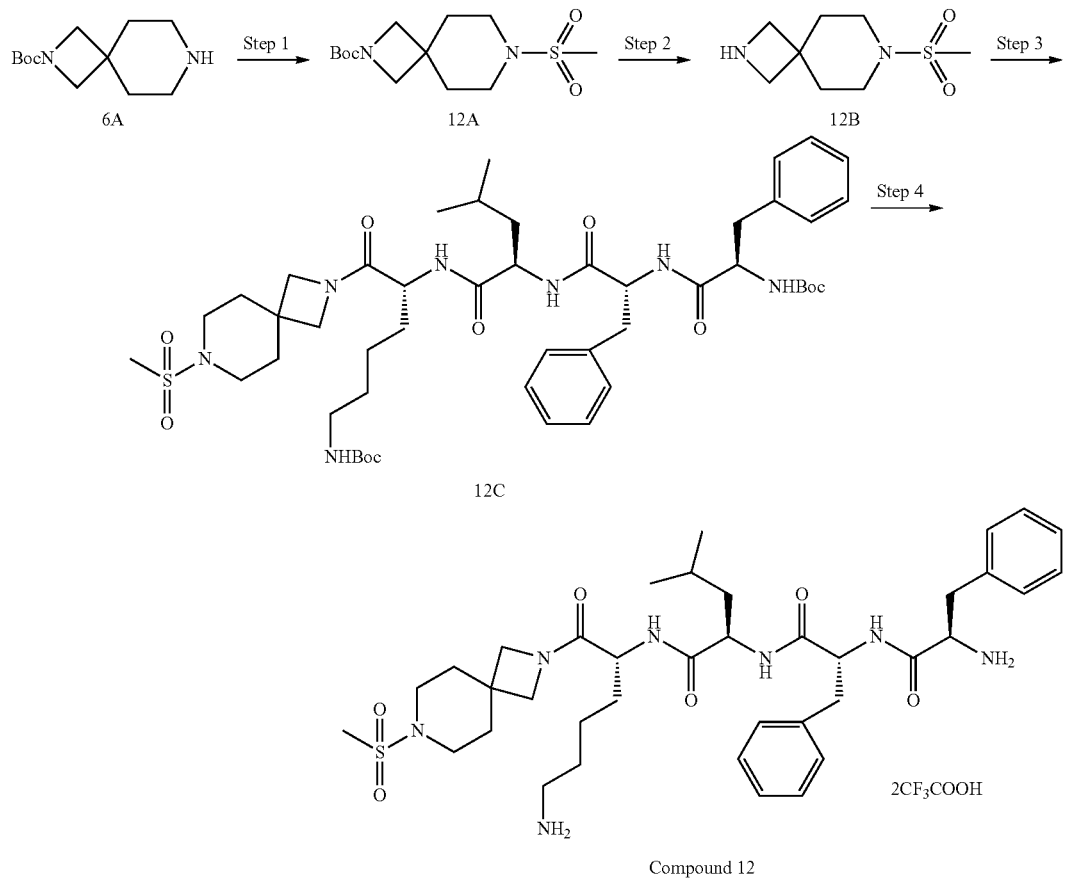

Step 1: tert-butyl 7-methylsulfonyl-2,7-diazaspiro[3.5]nonane-2-carboxylate (12A)

Tert-butyl 2,7-diazaspiro[3.5]nonane-2-carboxylate (6A) (0.23 g, 1 mmol), triethylamine (210 mg, 2.0 mmol) and dichloromethane (7 mL) were added in a 50 mL reaction flask, and dissolved under stirring. After cooling to −10° C., methanesulfonyl chloride (140 mg, 1.2 mmol) was added dropwise, and the system was allowed to react for 4 h. Then the temperature was raised to room temperature, and the reaction system was quenched with a saturated aqueous sodium bicarbonate solution (10 mL), and extracted with ethyl acetate (5 mL×3), and the organic phases were combined. The organic phases were dried over anhydrous sodium sulfate, filtered, and the filtrate was concentrated under reduced pressure. The residue was separated and purified by silica gel column chromatography (petroleum ether:ethyl acetate (v:v)=4:1) to obtain tert-butyl 7-methylsulfonyl-2,7-diazaspiro[3.5]nonane-2-carboxylate (12A) as light yellow oily substance (250 mg, yield 81%).

MS m/z=327.2[M+Na]$^+$.

Step 2: 7-methylsulfonyl-2,7-diazaspiro[3.5]nonane (12B)

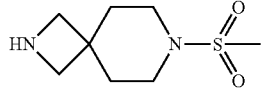

Tert-butyl 7-methylsulfonyl-2,7-diazaspiro[3.5]nonane-2-carboxylate (12A) (0.25 g, 0.81 mmol) and dichloromethane (7 mL) were added in a 50 mL reaction flask, and trifluoroacetic acid (1 mL) was added dropwise at room temperature. After the addition, the system was allowed to react at room temperature for 3 h. The reaction solution was directly concentrated under reduced pressure to obtain crude 7-methylsulfonyl-2,7-diazaspiro[3.5]nonane (12B) as light yellow oily liquid (165 mg, yield 100%), and used directly in the next reaction.

Step 3: tert-butyl N-[(1R)-1-benzyl-2-[[(1R)-1-benzyl-2-[[(1R)-1-[[(1R)-5-(tert-butoxycarbonylamino)-1-(7-methylsulfonyl-2,7-diazaspiro[3.5]nonane-2-carbonyl)pentyl]carbamoyl]-3-methyl-butyl]amino]-2-oxo-ethyl]amino]-2-oxo-ethyl]carbamate (12C)

Step 4: (2R)—N-[(1R)-5-amino-1-(7-methylsulfonyl-2,7-diazaspiro[3.5]nonane-2-carbonyl)pentyl]-2-[[(2R)-2-[[(2R)-2-amino-3-phenyl-propanoyl]amino]-3-phenyl-propanoyl]amino]-4-methyl-pentanamide; di-trifluoroacetic acid (compound 12)

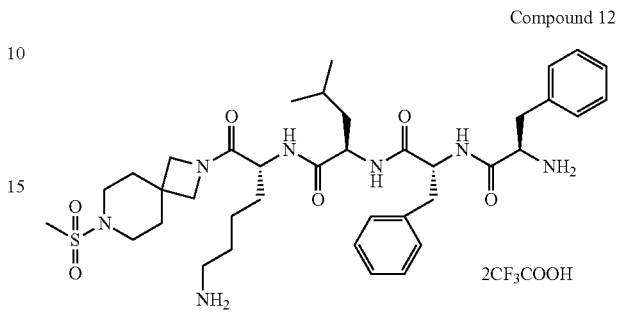

Compound 12

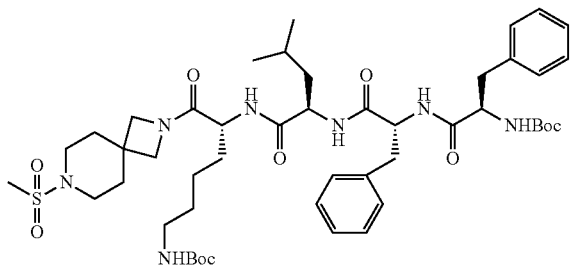 [SMILES: CC(C)C[C@@H](NC(=O)[C@@H](Cc1ccccc1)NC(=O)[C@@H](Cc1ccccc1)NC(=O)OC(C)(C)C)C(=O)N[C@H](CCCCNC(=O)OC(C)(C)C)C(=O)N1CC2(CCN(S(C)(=O)=O)CC2)C1]

Crude 7-methylsulfonyl-2,7-diazaspiro[3.5]nonane (12B) (165 mg, 0.75 mmol), 1-(3-dimethylaminopropyl)-3-ethyl-carbodiimide hydrochloride (192 mg, 1 mmol), 1-hydroxy-benzotriazole (135 mg, 1 mmol), intermediate 1 (610 mg, 0.81 mmol) and dichloromethane (30 mL) were added in a 50 mL single-necked flask, and the system was allowed to react at room temperature for 5 h. Then the reaction solution was concentrated under reduced pressure, and the residue was separated and purified by silica gel column chromatography (petroleum ether:ethyl acetate (v:v)=1:2) to obtain tert-butyl N-[(1R)-1-benzyl-2-[[(1R)-1-benzyl-2-[[(1R)-1-[[(1R)-5-(tert-butoxycarbonylamino)-1-(7-methylsulfonyl-2,7-diazaspiro[3.5]nonane-2-carbonyl)pentyl]carbamoyl]-3-methyl-butyl]amino]-2-oxo-ethyl]amino]-2-oxo-ethyl] carbamate (12C) as white solid (630 mg, yield 82.7%).

Tert-butyl N-[(1R)-1-benzyl-2-[[(1R)-1-benzyl-2-[[(1R)-1-[[(1R)-5-(tert-butoxycarbonylamino)-1-(7-methylsulfonyl-2,7-diazaspiro[3.5]nonane-2-carbonyl)pentyl]carbamoyl]-3-methyl-butyl]amino]-2-oxo-ethyl]amino]-2-oxo-ethyl]carbamate (12C) (630 mg, 0.34 mmol) and trifluoroacetic acid (2 mL) were added in a 50 mL reaction flask, and the system was allowed to react at room temperature for 2 h. Then the reaction solution was concentrated under reduced pressure, and the residue was separated and purified by preparative liquid chromatography (preparation conditions: instrument: Gilson GX-281; column: Xbridge C18, 150×30 mm I.D., 5 µm; mobile phase: A for ACN and B for H$_2$O; isocratic: A 65%; flow rate: 30 mL/min; back pressure: 1000 PSI; column temperature: 30° C.; wavelength: 210 nm; period: 18 min; sample preparation: the compound dissolved in 12 mL methanol; injection: 0.9 mL/needle). The preparation was concentrated under reduced pressure to remove most of the solvent, and lyophilized to obtain (2R)—N-[(1R)-5-amino-1-(7-methylsulfonyl-2,7-diazaspiro[3.5]nonane-2-carbonyl)pentyl]-2-[[(2R)-2-[[(2R)-2-amino-3-phenyl-propanoyl]amino]-3-phenyl-propanoyl]amino]-4-methyl-pentanamide; di-trifluoroacetic acid (compound 12) as white powder (410 mg, yield 63.2%).

MS m/z=370.8[M+2H]$^+$/2;

$^1$H NMR (400 MHz, D$_2$O) δ 7.43-7.15 (m, 10H), 4.61 (t, 1H), 4.33-3.96 (m, 5H), 3.79-3.69 (m, 2H), 3.25-3.13 (m, 7H), 3.02-2.93 (m, 6H), 1.91-1.86 (m, 3H), 1.70-1.64 (m, 3H), 1.56-1.31 (m, 5H), 1.25 (t, 2H), 0.89 (dd, 6H).

Example 11: (2R)-2-[[(2R)-2-[[(2R)-2-amino-3-phenyl-propanoyl]amino]-3-phenyl-propanoyl]amino]-N-[(1R)-5-amino-1-[2-(pyrrolidin-1-carbonyl)-2,7-diazaspiro[3.5]nonane-7-carbonyl]pentyl]-4-methyl-pentanamide; di-trifluoroacetic acid (compound 13)

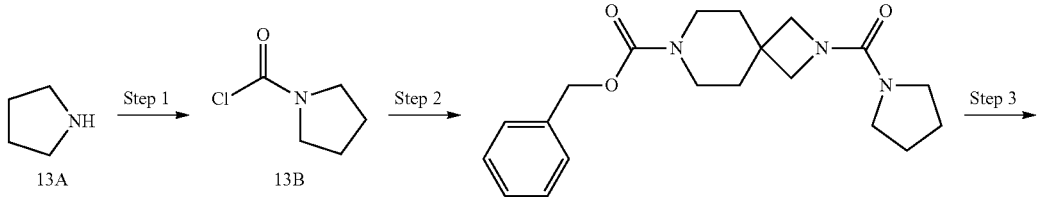

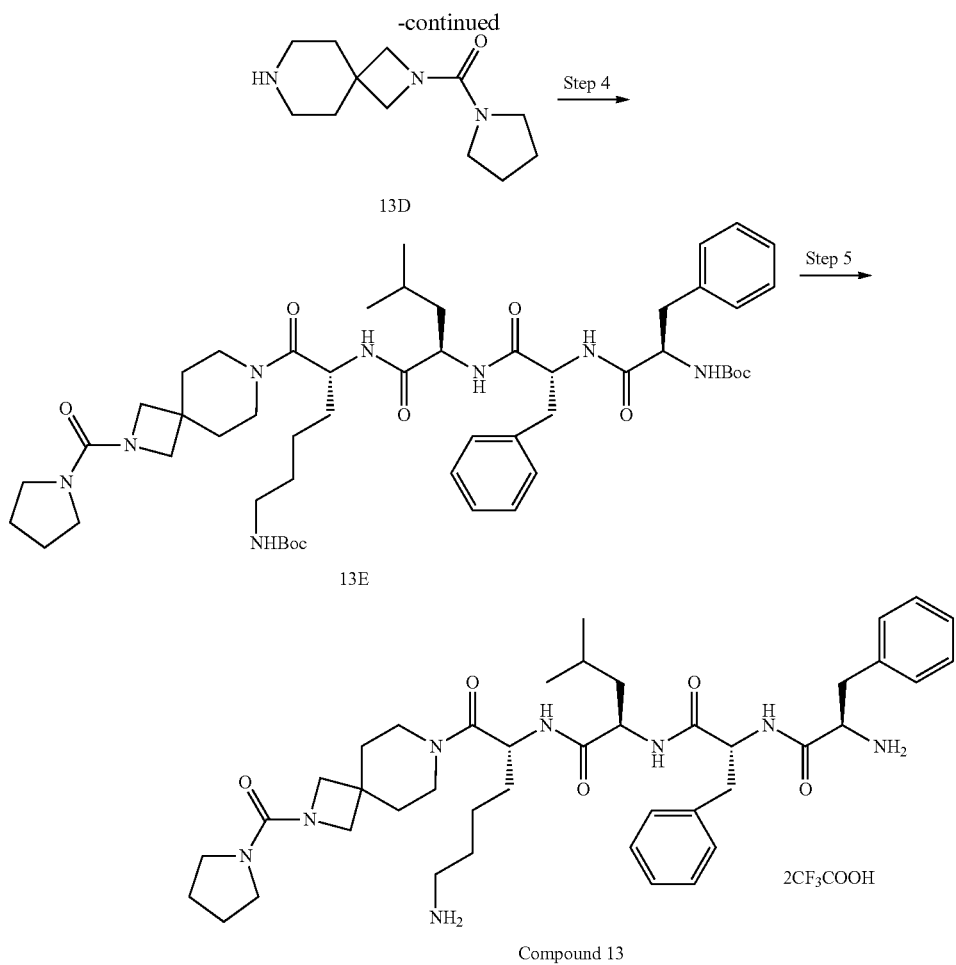

Compound 13

Step 1: pyrrolidin-1-carbonyl chloride (13B)

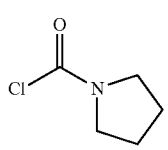

Step 2: benzyl 2-(pyrrolidin-1-carbonyl)-2,7-diazaspiro[3.5]nonane-7-carboxylate (13C)

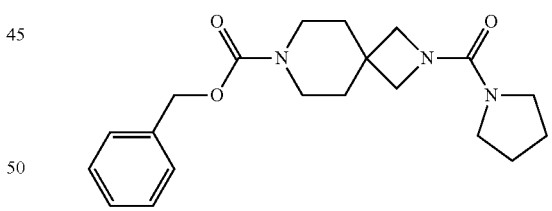

NaHCO$_3$ (5.04 g, 60 mmol), triphosgene (5.94 g, 20 mmol) and dichloromethane (10 mL) were added in a 50 mL single-necked flask. The reaction solution was cooled to 10° C. and then pyrrolidin (2.16 g, 30.4 mmol) was slowly added dropwise. After the addition, the temperature was returned to room temperature and reacted overnight. The reaction solution was filtered, and the filtrate was concentrated under reduced pressure, and the residue was separated and purified by silica gel column chromatography (petroleum ether:ethyl acetate (v:v)=3:1), to obtain pyrrolidin-1-carbonyl chloride (13B) as colorless oily substance (2.07 g, yield 51.65%). $^1$HNMR (400 MHz, CDCl$_3$) δ 3.62-3.56 (m, 2H), 3.54-3.44 (m, 2H), 2.02-1.90 (m, 4H).

Benzyl 2,7-diazaspiro[3.5]nonane-7-carboxylate (6C) (350 mg, 1.3 mmol), triethylamine (408 mg, 4.03 mmol) and dichloromethane (20 mL) were added in a 50 mL single-necked flask, and it was dissolved under stirring at room temperature. Then the reaction solution was cooled to 0° C., and pyrrolidin-1-carbonyl chloride (13B) (123 mg, 0.92 mmol) was added dropwise. After the addition, the temperature was raised to room temperature, and the reaction was allowed to proceed for 4 h. The reaction solution was sequentially washed with a saturated aqueous sodium bicarbonate solution (60 mL), 3 mol/L aqueous hydrochloric acid solution (60 mL) and the mixture was subjected to a liquid separation process. The organic phases were dried over anhydrous sodium sulfate, filtered, and the filtrate was concentrated under reduced pressure to obtain crude benzyl 2-(pyrrolidin-1-carbonyl)-2,7-diazaspiro[3.5]nonane-7-carboxylate (13C) as light yellow oily liquid (460 mg, yield 100%).

MS m/z=358.2 [M+H]$^+$.

Step 3: 2,7-diazaspiro[3.5]nonan-2-yl(pyrrolidin-1-yl)methanone (13D)

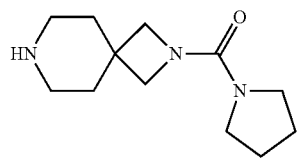 [SMILES: O=C(N1CCCC1)N1CC2(CCNCC2)C1]

Crude benzyl 2-(pyrrolidin-1-carbonyl)-2,7-diazaspiro[3.5]nonane-7-carboxylate (13C) (460 mg, 1.3 mmol), palladium hydroxide/carbon (100 mg, 20 wt %) and isopropanol (20 mL) were added in a 50 mL single-necked flask. The atmosphere was replaced with hydrogen 3 times, and it was heated to 100° C. in the oil bath for 8 h under a hydrogen (balloon) atmosphere. Then the reaction solution was filtered through diatomite, and the filtrate was concentrated under reduced pressure to obtain crude 2,7-diazaspiro[3.5]nonan-2-yl(pyrrolidin-1-yl)methanone (13D) as light yellow solid (290 mg, yield 100%), and used directly in the next reaction.

MS m/z=224.3 [M+H]$^+$.

Step 4: tert-butylN-[(1R)-1-benzyl-2-[[(1R)-1-benzyl-2-[[(1R)-1-[[(1R)-5-(tert-butoxycarbonylamino)-1-[2-(pyrrolidin-1-carbonyl)-2,7-diazaspiro[3.5]nonane-7-carbonyl]pentyl]carbamoyl]-3-methyl-butyl]amino]-2-oxo-ethyl]amino]-2-oxo-ethyl]carbamate (13E)

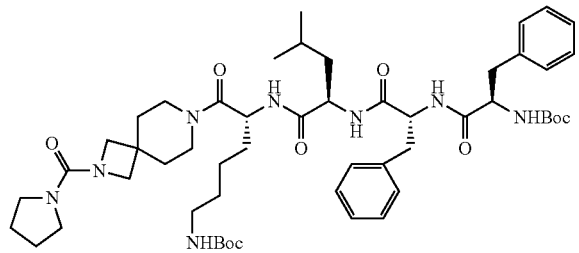 [SMILES: CC(C)C[C@@H](NC(=O)[C@@H](Cc1ccccc1)NC(=O)[C@@H](Cc1ccccc1)NC(=O)OC(C)(C)C)C(=O)N[C@H](CCCCNC(=O)OC(C)(C)C)C(=O)N1CCC2(CC1)CN(C(=O)N1CCCC1)C2]

Crude 2,7-diazaspiro[3.5]nonan-2-yl(pyrrolidin-1-yl)methanone (13D) (167 mg, 0.75 mmol), 1-(3-dimethylaminopropyl)-3-ethylcarbodiimide hydrochloride (374 mg, 1.95 mmol), 1-hydroxybenzotriazole (108 mg, 0.81 mmol), intermediate 1 (556 mg, 0.75 mmol) and dichloromethane (30 mL) were added sequentially in a 50 mL reaction flask. After the addition, the system was allowed to react at room temperature for 5 h. The reaction solution was concentrated under reduced pressure and the residue was separated and purified by silica gel column chromatography (petroleum ether:ethyl acetate (v:v)=1:2) to obtain tert-butyl N-[(1R)-1-benzyl-2-[[(1R)-1-benzyl-2-[[(1R)-1-[[(1R)-5-(tert-bu toxycarbonylamino)-1-[2-(pyrrolidin-1-carbonyl)-2,7-diazaspiro[3.5]nonane-7-carbonyl]pentyl]carbamoyl]-3-methyl-butyl]amino]-2-oxo-ethyl]amino]-2-oxo-ethyl]carbamate (13E) as white solid (360 mg, yield 29%).

Step 5: (2R)-2-[[(2R)-2-[[(2R)-2-amino-3-phenyl-propanoyl]amino]-3-phenyl-propanoyl]amino]-N-[(1R)-5-amino-1-[2-(pyrrolidin-1-carbonyl)-2,7-diazaspiro[3.5]nonane-7-carbonyl]pentyl]-4-methyl-pentanamide; di-trifluoroacetic acid (compound 13)

Compound 13

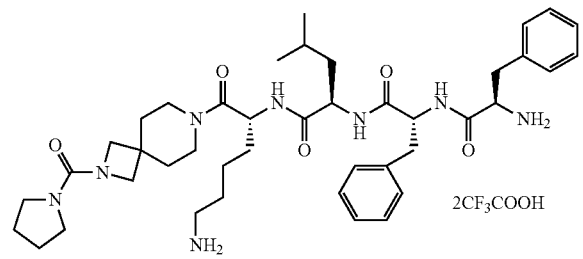

Tert-butyl N-[(1R)-1-benzyl-2-[[(1R)-1-benzyl-2-[[(1R)-1-[[(1R)-5-(tert-butoxycarbonylamino)-1-[2-(pyrrolidin-1-carbonyl)-2,7-diazaspiro[3.5]nonane-7-carbonyl]pentyl]carbamoyl]-3-methyl-butyl]amino]-2-oxo-ethyl]amino]-2-oxo-ethyl]carbamate (13E) (360 mg, 0.38 mmol) and dichloromethane (10 mL) were added in a 50 mL reaction flask, and trifluoroacetic acid (3 mL) was added dropwise at room temperature. After the addition, the system was allowed to react for 2 h. The reaction solution was concentrated under reduced pressure and the residue was separated and purified by preparative liquid chromatography (preparation conditions: instrument: Gilson GX-281; column: Xbridge C18, 150×30 mm I.D., 5 μm; mobile phase: A for ACN and B for H$_2$O; isocratic: A 65%; flow rate: 30 mL/min; back pressure: 1000 PSI; column temperature: 30° C.; wavelength: 210 nm; period: 18 min; sample preparation: the compound dissolved in 12 mL methanol; injection: 0.9 mL/needle). The preparation was concentrated under reduced pressure to remove most of the solvent, and lyophilized to obtain (2R)-2-[[(2R)-2-[[(2R)-2-amino-3-phenyl-propanoyl]amino]-3-phenyl-propanoyl]amino]-N-[(1R)-5-amino-1-[2-(pyrrolidin-1-carbonyl)-2,7-diazaspiro[3.5]nonane-7-carbonyl]pentyl]-4-methyl-pentanamide; di-trifluoroacetic acid (compound 13) as white solid (169 mg, yield 45.6%).

MS m/z=380.4 [M+2H]$^+$/2.

$^1$HNMR (400 MHz, DMSO-d$_6$) δ 8.75 (d, 1H), 8.35 (d, 1H), 8.09 (d, 1H), 8.01 (br, 3H), 7.73 (br, 3H), 7.34-7.17 (m, 10H), 4.71-4.60 (m, 2H), 4.40-4.32 (m, 1H), 4.08-3.96 (m, 2H), 3.73-3.23 (m, 8H), 3.16-3.01 (m, 3H), 2.98-2.86 (m, 1H), 2.85-2.69 (m, 3H), 1.82-1.69 (m, 4H), 1.69-1.42 (m, 11H), 1.36-1.22 (m, 2H), 0.89 (dd, 6H).

Example 12: (2R)—N-[(1R)-5-amino-1-[2-(3-methylsulfonylazetidine-1-carbonyl)-2,7-diazaspiro[3.5]nonane-7-carbonyl]pentyl]-2-[[(2R)-2-[[(2R)-2-amino-3-phenyl-propanoyl]amino]-3-phenyl-propanoyl]amino]-4-methyl-pentanamide; di-trifluoroacetic acid (compound 14)
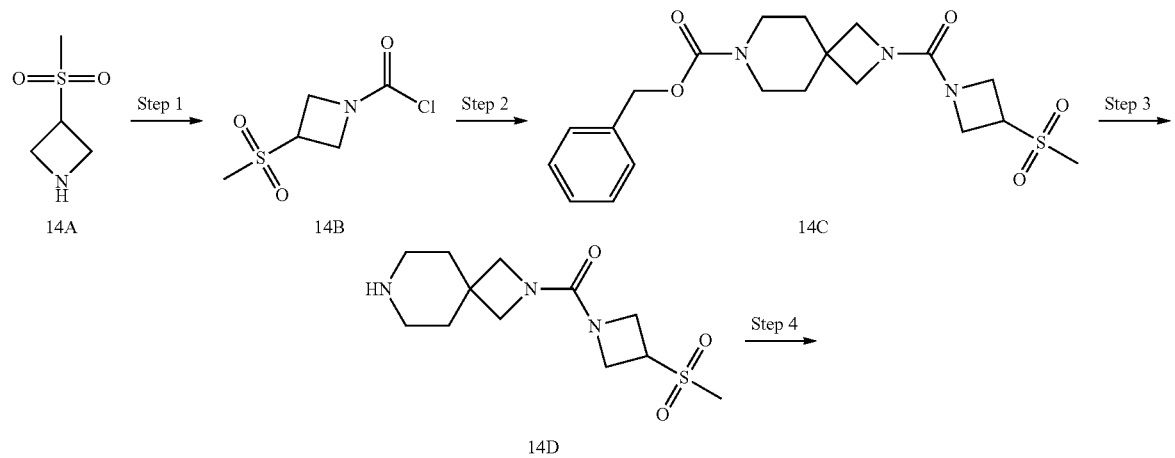
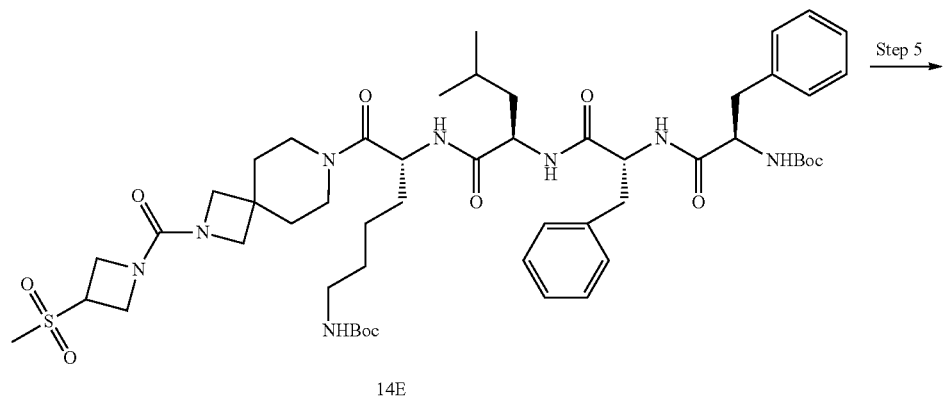
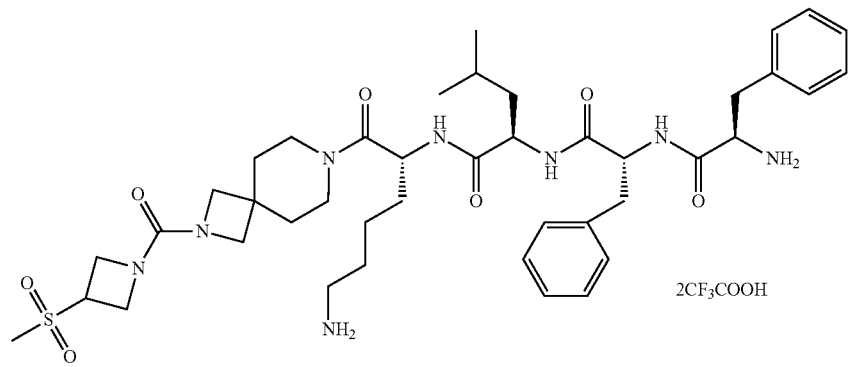
Compound 14

Step 1: 3-methylsulfonylazetidine-1-carbonyl chloride (14B)

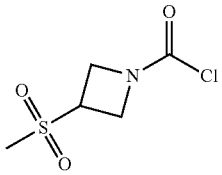

NaHCO₃ (756 mg, 9.0 mmol), triphosgene (0.89 g, 4.5 mmol) and dichloromethane (8 mL) were added in a 50 mL single-necked flask. The reaction solution was cooled to −10° C., and then 3-methylsulfonylazetidine hydrochloride (772 mg, 4.5 mmol) was slowly added dropwise. After the addition, the temperature was returned to the temperature was returned to room temperature and reacted overnight. The reaction solution was filtered, concentrated under reduced pressure, and the residue was separated and purified by silica gel column chromatography (petroleum ether:ethyl acetate (v:v)=1:1) to obtain as colorless oily substance, 3-methylsulfonylazetidine-1-carbonyl chloride (14B) (494 mg, yield 50%).

$^1$H NMR (400 MHz, CDCl₃) δ 4.62-4.32 (m, 4H), 4.07-3.92 (m, 1H), 2.93 (s, 3H).

Step 2: benzyl 2-(3-methylsulfonylazetidine-1-carbonyl)-2,7-diazaspiro[3.5]nonane-7-carboxylate (14C)

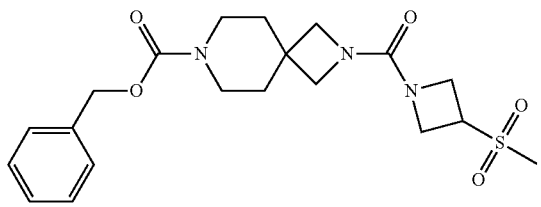 [SMILES: CS(=O)(=O)C1CN(C(=O)N2CC3(CCN(C(=O)OCc4ccccc4)CC3)C2)C1]

Benzyl 2,7-diazaspiro[3.5]nonane-7-carboxylate (6C) (350 mg, 1.3 mmol), triethylamine (406 mg, 4.01 mmol) and dichloromethane (20 mL) were added in a 50 mL single-necked flask, and it was dissolved under stirring at room temperature. Then the reaction solution was cooled to 0° C., and 3-methylsulfonylazetidine-1-carbonyl chloride (14B) (293 mg, 1.48 mmol) was added dropwise. After the addition, the temperature was raised to room temperature, and the system was allowed to react for 4 h. The reaction solution was sequentially washed with a saturated aqueous sodium bicarbonate solution (60 mL), 3 mol/L aqueous hydrochloric acid solution (60 mL) and separated. The organic phases were dried over anhydrous sodium sulfate, filtered, and the filtrate was concentrated under reduced pressure. The residue was separated and purified by preparative liquid chromatography (preparation conditions: instrument: Gilson GX-281; column: Xbridge C18, 150×30 mm I.D., 5 μm; mobile phase: A for ACN and B for H₂O; isocratic: A 65%; flow rate: 30 mL/min; back pressure: 1000 PSI; column temperature: 30° C.; wavelength: 210 nm; period: 18 min; sample preparation: the compound dissolved in 12 mL methanol; injection: 0.9 mL/needle) to obtain benzyl 2-(3-methylsulfonylazetidine-1-carbonyl)-2,7-diazaspiro[3.5]nonane-7-carboxylate (14C) as white solid (300 mg, yield 55%).

MS m/z=422.2 [M+H]⁺;
$^1$HNMR (400 MHz, CDCl₃) δ 7.41-7.28 (m, 5H), 5.12 (s, 2H), 4.30-4.19 (m, 4H), 4.00-3.89 (m, 1H), 3.69 (s, 4H), 3.49-3.36 (m, 4H), 2.90 (s, 3H), 1.79-1.67 (m, 4H).

Step 3: 2,7-diazaspiro[3.5]nonan-2-yl-(3-methylsulfonylazetidin-1-yl)methanone (14D)

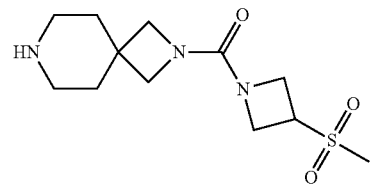 [SMILES: CS(=O)(=O)C1CN(C(=O)N2CC3(CCNCC3)C2)C1]

Benzyl 2-(3-methylsulfonylazetidine-1-carbonyl)-2,7-diazaspiro[3.5]nonane-7-carboxylate (14C) (300 mg, 0.7 mmol), palladium hydroxide/carbon (60 mg, 20 wt %) and isopropanol (20 mL) were added sequentially in a 50 mL single-necked flask. The atmosphere was replaced with hydrogen 3 times, and it was heated to 100° C. in the oil bath and reacted for 8 h under a hydrogen (balloon) atmosphere. Then the reaction solution was filtered through diatomite, and the filtrate was concentrated under reduced pressure to obtain crude 2,7-diazaspiro[3.5]nonan-2-yl-(3-methylsulfonylazetidin-1-yl)methanone (14D) as light yellow solid (202 mg, yield 100%), and used directly in the next reaction.

MS m/z=288.1 [M+H]⁺.

Step 4: tert-butyl N-[(1R)-1-benzyl-2-[[(1R)-1-benzyl-2-[[(1R)-1-[[(1R)-5-(tert-butoxy carbonylamino)-1-[2-(3-methylsulfonylazetidine-1-carbonyl)-2,7-diazaspiro[3.5]nonane-7-carbonyl]pentyl]carbamoyl]-3-methyl-butyl]amino]-2-oxo-ethyl]amino]-2-oxo-ethyl]carbamate (14E)

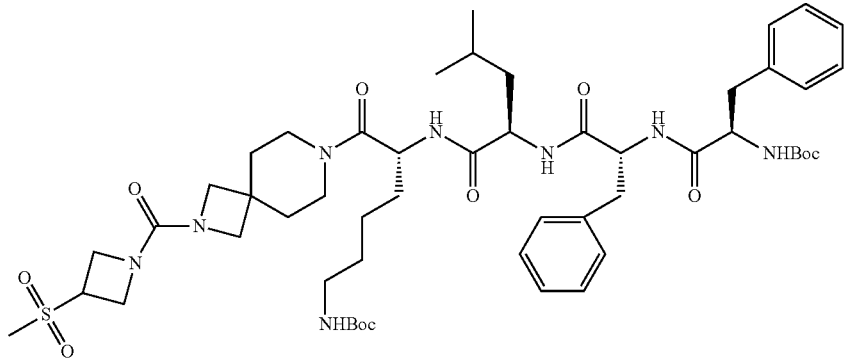 [SMILES: CC(C)C[C@@H](NC(=O)[C@@H](Cc1ccccc1)NC(=O)[C@@H](Cc1ccccc1)NC(=O)OC(C)(C)C)C(=O)N[C@H](CCCCNC(=O)OC(C)(C)C)C(=O)N1CCC2(CC1)CN(C(=O)N1CC(S(C)(=O)=O)C1)C2]

Crude 2,7-diazaspiro[3.5]nonan-2-yl-(3-methylsulfonylazetidine-1-yl)methanone (14D) (202 mg, 0.7 mmol), 1-(3-dimethylaminopropyl)-3-ethylcarbodiimide hydrochloride (402 mg, 2.10 mmol), 1-hydroxybenzotriazole (115 mg, 0.85 mmol), intermediate 1 (536 mg, 0.71 mmol) and dichloromethane (30 mL) were added sequentially in a 50 mL reaction flask. After the addition, the system was allowed to react at room temperature for 5 h. The reaction solution was concentrated under reduced pressure and the residue was separated and purified by silica gel column chromatography (dichloromethane:methanol (v:v)=40:1) to obtain tert-butyl N-[(1R)-1-benzyl-2-[[(1R)-1-benzyl-2-[[(1R)-1-[[(1R)-5-(tert-butoxycarbonylamino)-1-[2-(3-methylsulfonylazetidine-1-carbonyl)-2,7-diazaspiro[3.5]nonane-7-carbonyl]pentyl]carbamoyl]-3-methyl-butyl]amino]-2-oxo-ethyl]amino]-2-oxo-ethyl]carbamate (14E) as light yellow solid (686 mg, yield 96%).

Step 5: (2R)—N-[(1R)-5-amino-1-[2-(3-methylsulfonylazetidine-1-carbonyl)-2,7-diazaspiro[3.5]nonane-7-carbonyl]pentyl]-2-[[(2R)-2-[[(2R)-2-amino-3-phenyl-propanoyl]amino]-3-phenyl-propanoyl]amino]-4-methyl-pentanamide;2,2,2-trifluoroacetic acid (compound 14)

was allowed to react at room temperature for 2 h. The reaction solution was concentrated under reduced pressure and the residue was separated and purified by preparative liquid chromatography (preparation conditions: instrument: Gilson GX-281; column: Xbridge C18, 150×30 mm I.D., 5 μm; mobile phase: A for ACN and B for H₂O; isocratic: A 65%; flow rate: 30 mL/min; back pressure: 1000 PSI; column temperature: 30° C.; wavelength: 210 nm; period: 18 min; sample preparation: the compound dissolved in 12 mL methanol; injection: 0.9 mL/needle). The preparation was concentrated under reduced pressure to remove most of the solvent, and lyophilized to obtain (2R)—N-[(1R)-5-amino-1-[2-(3-methylsulfonylazetidine-1-carbonyl)-2,7-diazaspiro[3.5]nonane-7-carbonyl]pentyl]-2-[[(2R)-2-[[(2R)-2-amino-3-phenyl-propanoyl]amino]-3-phenyl-propanoyl]amino]-4-methyl-pentanamide; di-trifluoroacetic acid (compound 14) as white solid (330 mg, yield 41.3%).

MS m/z=412.3 [M+2H]⁺/2;

¹HNMR (400 MHz, D₂O) δ 7.44-7.18 (m, 10H), 4.66 (t, 1H), 4.47-4.16 (m, 7H), 3.90-3.72 (m, 4H), 3.69-3.55 (m, 2H), 3.53-3.41 (m, 1H), 3.39-3.27 (m, 1H), 3.24-3.14 (m,

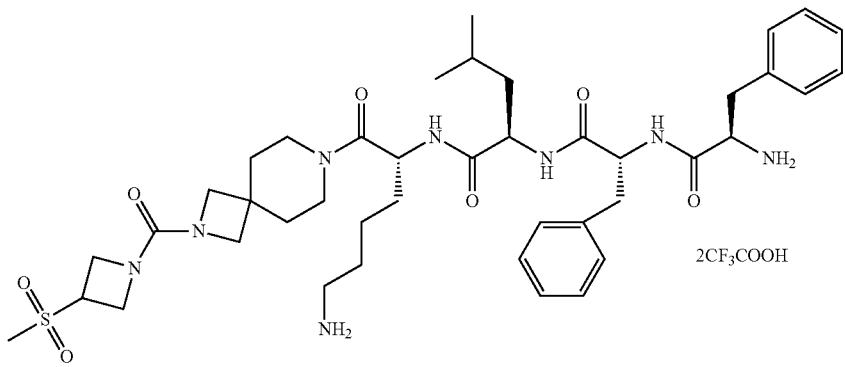

Compound 14

2H), 3.10 (s, 3H), 3.09-2.90 (m, 4H), 1.94-1.26 (m, 14H), 0.92 (d, 6H).

Tert-butyl N-[(1R)-1-benzyl-2-[[(1R)-1-benzyl-2-[[(1R)-1-[[(1R)-5-(tert-butoxycarbonylamino)-1-[2-(3-methylsulfonylazetidine-1-carbonyl)-2,7-diazaspiro[3.5]nonane-7-carbonyl]pentyl]carbamoyl]-3-methyl-butyl]amino]-2-oxo-ethyl]amino]-2-oxo-ethylcarbamate (14E) (680 mg, 0.66 mmol) and dichloromethane (10 mL) were added in a 50 mL reaction flask, and trifluoroacetic acid (3 mL) was added dropwise at room temperature. After the addition, the system Example 13: 7-[(2R)-6-amino-2-[[(2R)-2-[[(2R)-2-amino-3-phenyl-propanoyl]amino]-3-phenyl-propanoyl]amino]-4-methyl-pentanoyl]amino]hexanoyl]-N-methyl-2,7-diazaspiro[3.5]nonane-2-carboxamide;2,2,2-trifluoroacetic acid (compound 15)

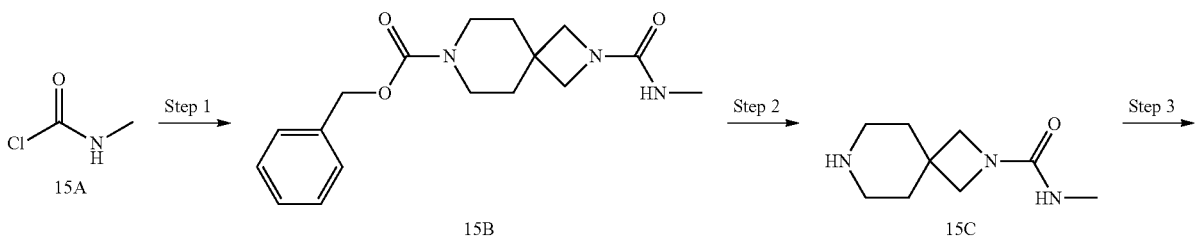

-continued

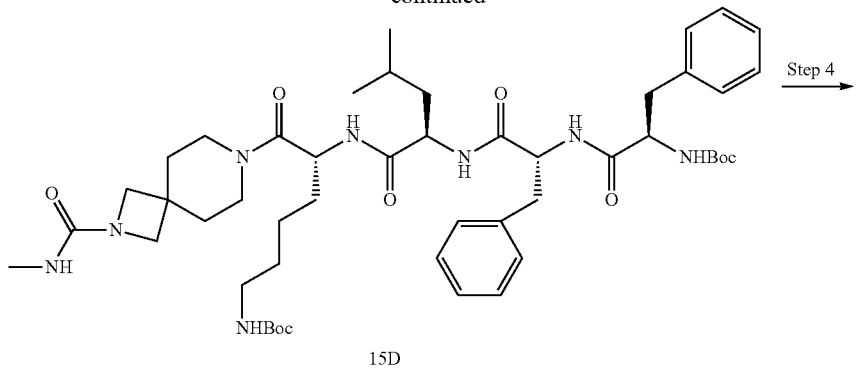

15D

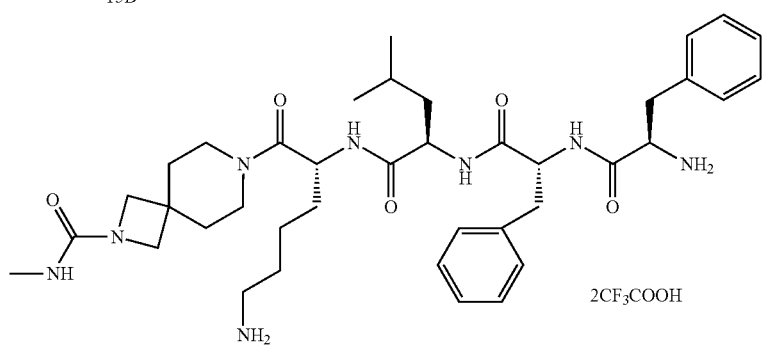

Compound 15

Step 1: benzyl 2-(methylcarbamoyl)-2,7-diazaspiro 3.5 nonane-7-carboxylate (15B)

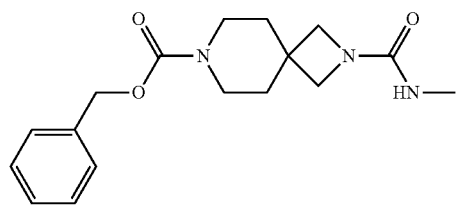 [SMILES: CNC(=O)N1CC2(CCN(C(=O)OCc3ccccc3)CC2)C1]

Benzyl 2,7-diazaspiro[3.5]nonane-7-carboxylate (6C) (310 mg, 1.2 mmol), triethylamine (364 mg, 3.6 mmol) and dichloromethane (20 mL) were added in a 50 mL single-necked flask, and it was dissolved under stirring at room temperature. Then the reaction solution was cooled to 0° C., and methylaminoformyl chloride (15A) (123 mg, 1.32 mmol) was added dropwise. After the addition, the temperature was raised to room temperature, and the reaction was allowed to proceed for 4 h. The reaction solution was sequentially washed with saturated aqueous sodium bicarbonate solution (60 mL), 3 mol/L aqueous hydrochloric acid solution (60 mL) and separated. The organic phases were dried over anhydrous sodium sulfate, filtered, and the filtrate was concentrated under reduced pressure to obtain crude benzyl 2-(methylcarbamoyl)-2,7-diazaspiro[3.5]nonane-7-carboxylate (15B) as yellow oily substance (440 mg, yield 100%).

MS m/z=318.2 [M+H]+;

$^1$HNMR (400 MHz, CDCl$_3$) δ 7.39-7.28 (m, 5H), 5.12 (s, 2H), 3.66 (s, 4H), 3.50-3.36 (m, 4H), 2.79 (s, 3H), 1.82-1.63 (m, 4H).

Step 2: N-methyl-2,7-diazaspiro[3.5]nonane-2-carboxamide (15C)

Crude benzyl 2-(methylcarbamoyl)-2,7-diazaspiro[3.5] nonane-7-carboxylate (15B) (260 mg, 0.82 mmol), palladium hydroxide/carbon (50 mg, 20 wt %) and isopropanol (20 mL) were added sequentially in a 50 mL single-necked flask. The atmosphere was replaced with hydrogen 3 times, and the reaction was heated to 100° C. in the oil bath and reacted for 8 h under hydrogen (balloon) atmosphere. Then the reaction solution was filtered through diatomite, and the filtrate was concentrated under reduced pressure to obtain crude N-methyl-2,7-diazaspiro[3.5]nonane-2-carboxamide (15C) as light yellow solid (150 mg, yield 100%), and used directly in the next reaction.

MS m/z=184.3 [M+H]+.

Step 3: tert-butyl N-[(1R)-1-benzyl-2-[[(1R)-1-benzyl-2-[[(1R)-1-[[(1R)-5-(tert-butoxycarbonylamino)-1-[2-(methylcarbamoyl)-2,7-diazaspiro[3.5]nonane-7-carbonyl]pentyl]carbamoyl]-3-methyl-butyl]amino]-2-oxo-ethyl]amino]-2-oxo-ethyl]carbamate (15D)

Tert-butyl N-[(1R)-1-benzyl-2-[[(1R)-1-benzyl-2-[[(1R)-1-[[(1R)-5-(tert-butoxycarbonylamino)-1-[2-(methylcarbamoyl)-2,7-diazaspiro[3.5]nonane-7-carbonyl]pentyl]carbamoyl]-3-methyl-butyl]amino]-2-oxo-ethyl]amino]-2-oxo-ethyl]carbamate (15D) (480 mg, 0.52 mmol) and dichloromethane (10 mL) were added in a 50 mL reaction flask, and trifluoroacetic acid (3 mL) was added dropwise at

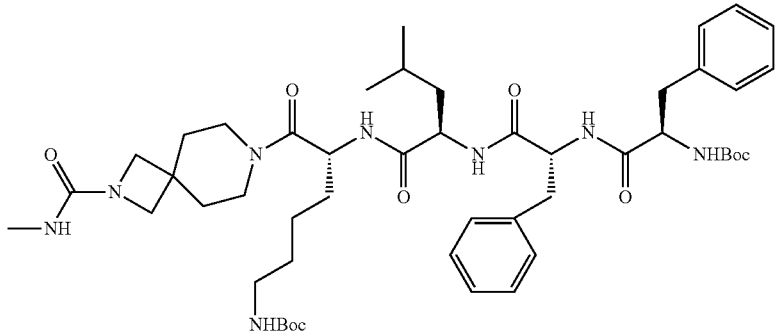 [SMILES: CNC(=O)N1CC2(CCN(C(=O)[C@@H](CCCCNC(=O)OC(C)(C)C)NC(=O)[C@@H](CC(C)C)NC(=O)[C@@H](Cc3ccccc3)NC(=O)[C@@H](Cc3ccccc3)NC(=O)OC(C)(C)C)CC2)C1]

Crude N-methyl-2,7-diazaspiro[3.5]nonane-2-carboxamide (15C) (150 mg, 0.82 mmol), 1-(3-dimethylaminopropyl)-3-ethylcarbodiimide hydrochloride (374 mg, 1.95 mmol), 1-hydroxybenzotriazole (110 mg, 0.81 mmol), intermediate 1 (565 mg, 0.75 mmol) and dichloromethane (30 mL) were added sequentially in a 50 mL reaction flask. After the addition, the system was allowed to react at room temperature for 5 h. The reaction solution was concentrated under reduced pressure and the residue was separated and purified by silica gel column chromatography (dichloromethane:methanol (v:v)=40:1) to obtain tert-butylN-[(1R)-1-benzyl-2-[[(1R)-1-benzyl-2-[[(1R)-1-[[(1R)-5-(tert-butoxycarbonylamino)-1-[2-(methylcarbamoyl)-2,7-diazaspiro[3.5]nonane-7-carbonyl]pentyl]carbamoyl]-3-methyl-butyl]amino]-2-oxo-ethyl]amino]-2-oxo-ethyl]carbamate (15D) as light yellow solid (480 mg, yield 63%).

Step 4: 7-[(2R)-6-amino-2-[[(2R)-2-[[(2R)-2-[[(2R)-2-amino-3-phenyl-propanoyl]amino]-3-phenyl-propanoyl]amino]-4-methyl-pentanoyl]amino]hexanoyl]-N-methyl-2,7-diazaspiro[3.5]nonane-2-carboxamide; di-trifluoroacetic acid (compound 15)

room temperature. After the addition, the system was allowed to react for 2 h. The reaction solution was concentrated under reduced pressure, and the residue was separated and purified by preparative liquid chromatography (preparation conditions: instrument: Gilson GX-281; column: Xbridge C18, 150×30 mm I.D., 5 μm; mobile phase: A for ACN and B for H₂O; isocratic: A 65%; flow rate: 30 mL/min; back pressure: 1000 PSI; column temperature: 30° C.; wavelength: 210 nm; period: 18 min; sample preparation: the compound dissolved in 12 mL methanol; injection: 0.9 mL/needle). The preparation was concentrated under reduced pressure to remove most of the solvent, and lyophilized to obtain 7-[(2R)-6-amino-2-[[(2R)-2-[[(2R)-2-[[(2R)-2-amino-3-phenyl-propanoyl]amino]-3-phenyl-propanoyl]amino]-4-methyl-pentanoyl]amino]hexanoyl]-N-methyl-2,7-diazaspiro[3.5]nonane-2-carboxamide; di-trifluoroacetic acid (compound 15) as white solid (260 mg, yield 53%).

MS m/z=360.3 [M+2H]$^+$/2;

$^1$HNMR (400 MHz, D$_2$O) δ 7.43-7.28 (m, 6H), 7.27-7.21 (m, 4H), 4.66 (t, 1H), 4.30 (t, 1H), 4.21 (t, 1H), 3.74 (s, 2H), 3.70 (s, 2H), 3.69-3.59 (m, 2H), 3.55-3.43 (m, 1H), 3.41-3.31 (m, 1H), 3.24-3.12 (m, 2H), 3.11-2.92 (m, 4H), 2.69 (s, 3H), 1.94-1.27 (m, 14H), 0.93 (dd, 6H).

Compound 15

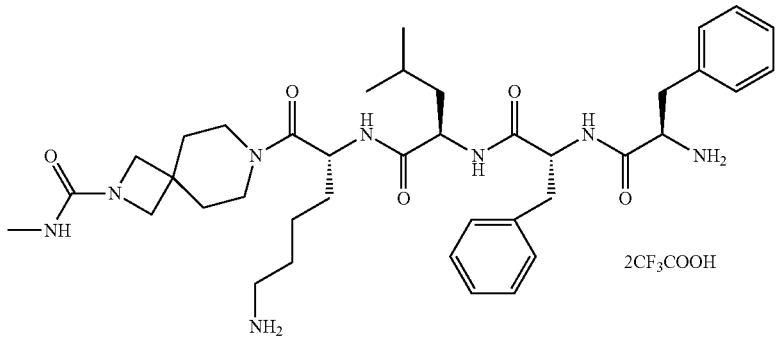

2CF₃COOH

Example 14: (2R)—N-[(1R)-5-amino-1-(5,5-difluoro-2-methylsulfonyl-2,7-diazaspiro[3.5]nonane-7-carbonyl)pentyl]-2-[[(2R)-2-[[(2R)-2-amino-3-phenyl-propanoyl]amino]-3-phenyl-propanoyl]amino]-4-methyl-pentanamide;2,2,2-trifluoroacetic acid (compound 16)
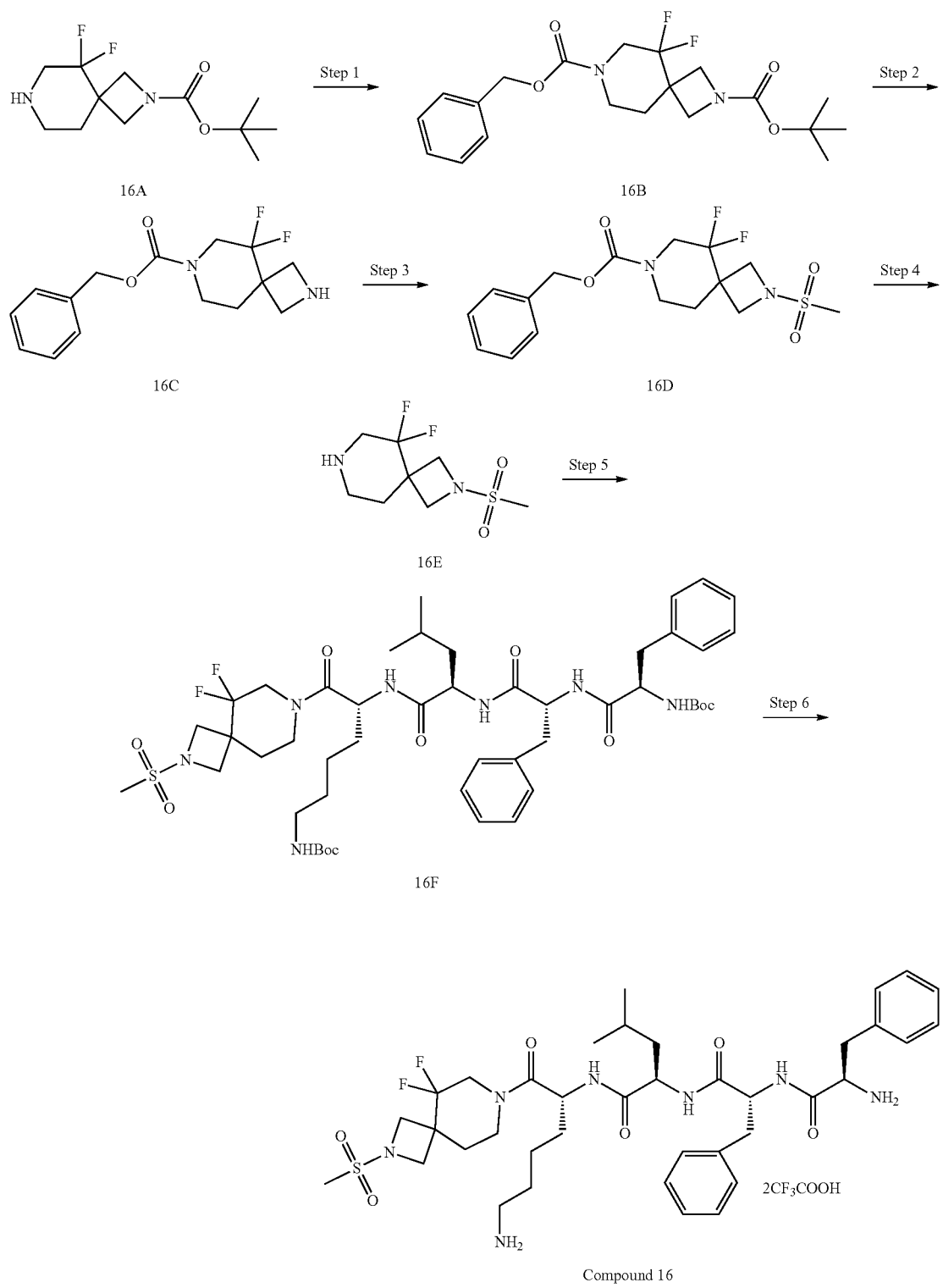

Step 1: O7-benzyl O2-tert-butyl 5,5-difluoro-2,7-diazaspiro[3.5]nonane-2,7-dicarboxylate (16B)

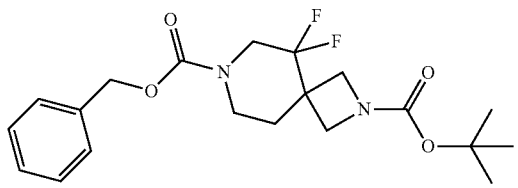 [SMILES: CC(C)(C)OC(=O)N1CC2(CCN(C(=O)OCc3ccccc3)CC2(F)F)C1]

Triethylamine (0.85 mL, 8.4 mmol), 5,5-difluoro-2,7-diazaspiro[3.5]nonane-2-tert-butyl carboxylate (16A) (2.1 g, 8.0 mmol) and tetrahydrofuran (15 mL) were added sequentially in a 50 mL single-necked flask. The reaction solution was cooled to 0° C., and then benzyl chloroformate (1.5 g, 8.8 mmol) was slowly added dropwise. After the addition, the reaction was maintained at 0° C. for 10 minutes, and then the temperature was raised to room temperature again and continued to stir for 5 h. The reaction solution was filtered, and the filtrate was concentrated under reduced pressure to obtain O7-benzyl O2-tert-butyl 5,5-difluoro-2,7-diazaspiro[3.5]nonane-2,7-dicarboxylate (16B) as light yellow oily product (3.5 g, yield 100%).

MS m/z=419.3 [M+Na]+;

Step 2: benzyl 5,5-difluoro-2,7-diazaspiro[3.5]nonane-7-carboxylate (16C)

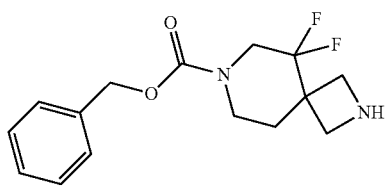 [SMILES: O=C(OCc1ccccc1)N1CCC2(CNC2)C(F)(F)C1]

O7-benzyl O2-tert-butyl 5,5-difluoro-2,7-diazaspiro[3.5]nonane-2,7-dicarboxylate (16B) (3.17 g, 8.0 mmol) and dichloromethane (30 mL) were added in a 50 mL reaction flask, and trifluoroacetic acid (6.0 mL) were added dropwise at room temperature. After the addition, the system was allowed to react at room temperature for 3 h. The reaction solution was adjusted to a pH of about 13 with ammonia water, and then the mixture was subjected to a liquid separation process. The organic phases were dried over anhydrous sodium sulfate, filtered, and the filtrate was concentrated under reduced pressure to obtain benzyl 5,5-difluoro-2,7-diazaspiro[3.5]nonane-7-carboxylate (16C) as yellow oily liquid (2.43 g, yield 100%), and used directly in the next reaction.

MS m/z=297.1 [M+H]+;

Step 3: benzyl 5,5-difluoro-2-methylsulfonyl-2,7-diazaspiro[3.5]nonane-7-carboxylate (16D)

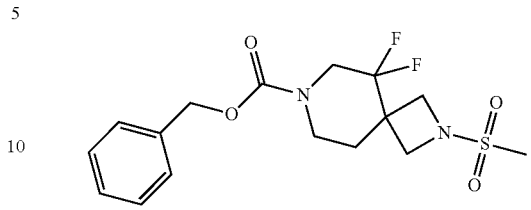

Benzyl 5,5-difluoro-2,7-diazaspiro[3.5]nonane-7-carboxylate (16C) (310 mg, 1.05 mmol), triethylamine (318 mg, 3.14 mmol) and dichloromethane (20 mL) were added in a 50 mL reaction flask, and dissolved under stirring. After cooling to −10° C., methanesulfonyl chloride (156 mg, 1.36 mmol) was added dropwise and the system was allowed to react for 4 h. Then the temperature was raised to room temperature, and the reaction solution was sequentially washed with saturated aqueous sodium bicarbonate solution (60 mL), 3M aqueous hydrochloric acid solution (60 mL), and separated. The organic phases were dried over anhydrous sodium sulfate, filtered, and the filtrate was concentrated under reduced pressure. The residue was separated and purified by silica gel column chromatography (dichloromethane:methanol (v:v)=60:1) to obtain benzyl 5,5-difluoro-2-methylsulfonyl-2,7-diazaspiro[3.5]nonane-7-carboxylate (16D) as white solid (233 mg, yield 59%).

MS m/z=397.2[M+Na]+;

1HNMR (400 MHz, CDCl3) δ 7.42-7.29 (m, 5H), 5.15 (s, 2H), 4.09 (d, 2H), 3.78-3.59 (m, 4H), 3.51 (t, 2H), 2.89 (s, 3H), 2.08 (s, 2H).

Step 4: 5,5-difluoro-2-methylsulfonyl-2,7-diazaspiro[3.5]nonane (16E)

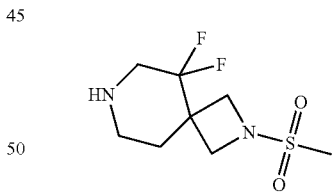

Benzyl 5,5-difluoro-2-methylsulfonyl-2,7-diazaspiro[3.5]nonane-7-carboxylate (16D) (230 mg, 0.5 mmol), palladium/carbon (40 mg, 20 wt %) and isopropanol (20 mL) were added in a 50 mL reaction flask. The atmosphere was replaced with hydrogen 3 times, and the reaction was heated to 100° C. in the oil bath and reacted for 8 h under a hydrogen (balloon) atmosphere. The reaction solution was then filtered through diatomite, and the filtrate was concentrated under reduced pressure to obtain 5,5-difluoro-2-methylsulfonyl-2,7-diazaspiro[3.5]nonane (16E) as light yellow solid (155 mg, yield 100%), and used directly in the next reaction.

MS m/z=241.1 [M+H]+;

Step 5: tert-butylN-[(1R)-1-benzyl-2-[[(1R)-1-benzyl-2-[[(1R)-1-[[(1R)-5-(tert-butoxycarbonylamino)-1-(5,5-difluoro-2-methylsulfonyl-2,7-diazaspiro[3.5]nonane-7-carbonyl)pentyl]carbamoyl]-3-methyl-butyl]amino]-2-oxo-ethyl]amino]-2-oxo-ethyl] carbamate (16F)

Step 6: (2R)—N-[(1R)-5-amino-1-(5,5-difluoro-2-methylsulfonyl-2,7-diazaspiro[3.5]nonane-7-carbonyl)pentyl]-2-[[(2R)-2-[[(2R)-2-amino-3-phenyl-propanoyl]amino]-3-phenyl-propanoyl]amino]-4-methyl-pentanamide;2,2,2-trifluoroacetic acid (compound 16)

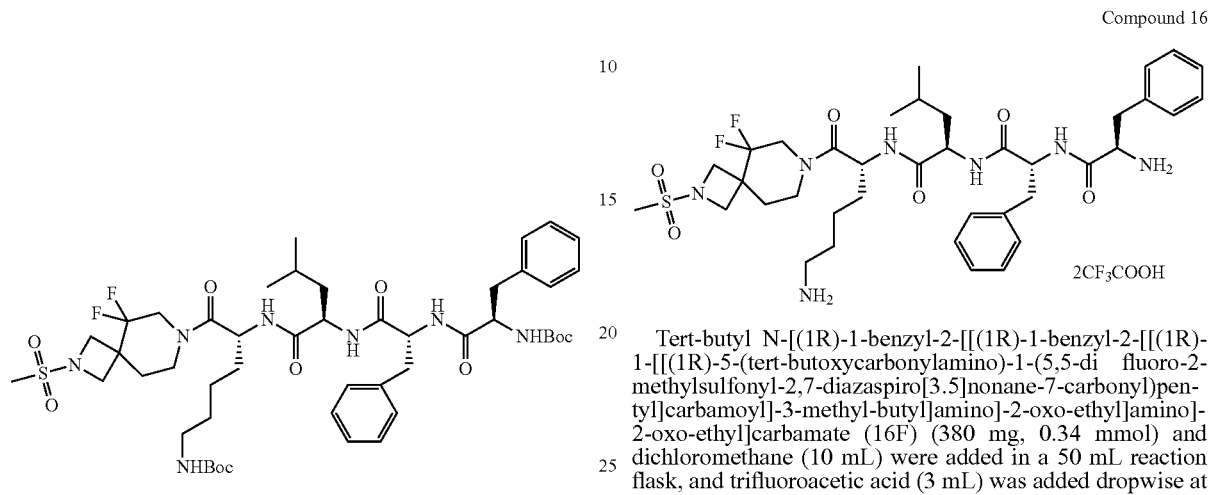

5,5-difluoro-2-methylsulfonyl-2,7-diazaspiro[3.5]nonane (16E) (155 mg, 0.5 mmol), 1-(3-dimethylaminopropyl)-3-ethylcarbodiimide hydrochloride (300 mg, 2.0 mmol), 1-hydroxybenzotriazole (115 mg, 0.85 mmol), intermediate 1 (377 mg, 0.5 mmol) and dichloromethane (30 mL) were added in a 50 mL reaction flask, and the system was allowed to react at room temperature for 5 h. Then the reaction solution was concentrated under reduced pressure, and the residue was separated and purified by silica gel column chromatography (dichloromethane:methanol (v:v)=40:1) to obtain tert-butyl N-[(1R)-1-benzyl-2-[[(1R)-1-benzyl-2-[[(1R)-1-[[(1R)-5-(tert-butoxycarbonylamino)-1-(5,5-di fluoro-2-methylsulfonyl-2,7-diazaspiro[3.5]nonane-7-carbonyl)pentyl]carbamoyl]-3-methyl-butyl]amino]-2-oxo-ethyl]amino]-2-oxo-ethyl]carbamate (16F) as white solid (380 mg, yield 78%).

Tert-butyl N-[(1R)-1-benzyl-2-[[(1R)-1-benzyl-2-[[(1R)-1-[[(1R)-5-(tert-butoxycarbonylamino)-1-(5,5-di fluoro-2-methylsulfonyl-2,7-diazaspiro[3.5]nonane-7-carbonyl)pentyl]carbamoyl]-3-methyl-butyl]amino]-2-oxo-ethyl]amino]-2-oxo-ethyl]carbamate (16F) (380 mg, 0.34 mmol) and dichloromethane (10 mL) were added in a 50 mL reaction flask, and trifluoroacetic acid (3 mL) was added dropwise at room temperature. After the addition, the system was allowed to react for 2 h. Then the reaction solution was concentrated under reduced pressure, and the residue was separated and purified by preparative liquid chromatography (preparation conditions: instrument: Gilson GX-281; column: Xbridge C18, 150×30 mm I.D., 5 μm; mobile phase: A for ACN and B for H₂O; isocratic: A 65%; flow rate: 30 mL/min; back pressure: 1000 PSI; column temperature: 30° C.; wavelength: 210 nm; period: 18 min; sample preparation: the compound dissolved in 12 mL methanol; injection: 0.9 mL/needle). The preparation was concentrated under reduced pressure to remove most of the solvent, and lyophilized to obtain (2R)—N-[(1R)-5-amino-1-(5,5-difluoro-2-methylsulfonyl-2,7-diazaspiro[3.5]nonane-7-carbonyl)pentyl]-2-[[(2R)-2-[[(2R)-2-amino-3-phenyl-propanoyl]amino]-3-phenyl-propanoyl]amino]-4-methyl-pentanamide; di-trifluoroacetic acid (compound 16) as white powder (270 mg, yield 71%).

MS m/z=388.8 [M+2H]⁺/2;

¹HNMR (400 MHz, D₂O) δ 7.44-7.17 (m, 10H), 4.66 (t, 1H), 4.42-4.13 (m, 4H), 4.13-3.49 (m, 7H), 3.25-2.92 (m, 9H), 2.30-2.00 (m, 2H), 1.91-1.26 (m, 9H), 0.93 (q, 6H).

Example 15: (2R)—N-[(1R)-5-amino-1-[2-[(2R)-2-aminopropanoyl]-2,7-diazaspiro[3.5]nonane-7-carbonyl]pentyl]-2-[[(2R)-2-[[(2R)-2-amino-3-phenyl-propanoyl]amino]-3-phenyl-propanoyl]amino]-4-methyl-pentanamide; tri-trifluoroacetic acid (compound 17)

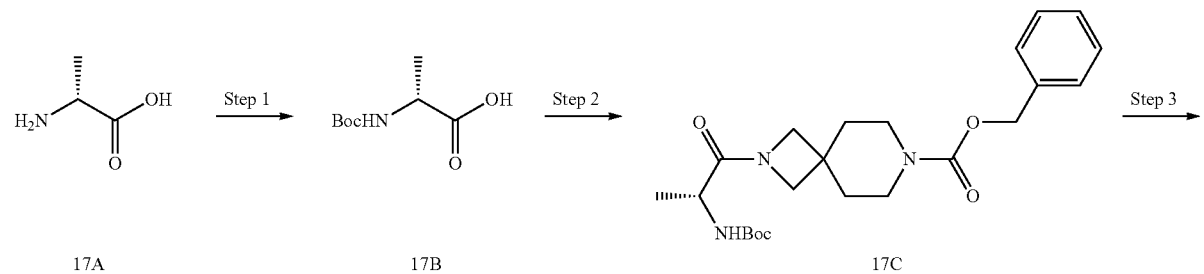

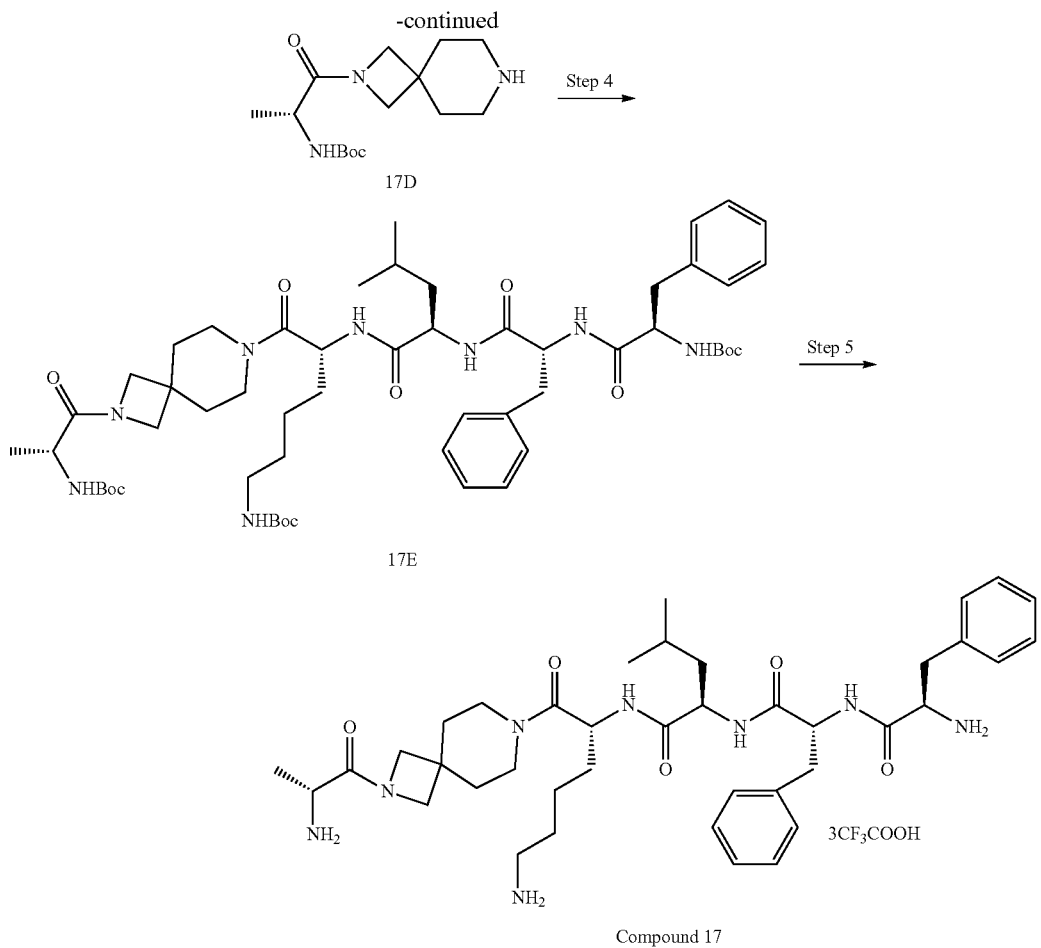

Compound 17

Step 1: (2R-2-(tert-butoxycarbonylamino)propanoic acid (17B)

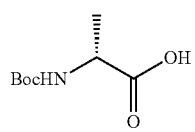

D-alanine (17A) (10 g, 112.24 mmol) and water (56 mL) were added in a 250 mL reaction flask, and the reaction solution was cooled to 0° C. and then sodium hydroxide (6.73 g, 168.36 mmol) was added. After the addition, the reaction was held at 0° C. for 10 minutes, and then a solution of di-tert-butyl dicarbonate (31.85 g, 145.91 mmol) in tetrahydrofuran (50 mL) was added dropwise. After the addition, the temperature was raised to room temperature and stirred overnight. The reaction solution was extracted with petroleum ether (100 mL×2) and the organic phase was discarded. The aqueous phase was acidified with 4 M hydrochloric acid solution to a pH of about 1, and then extracted with ethyl acetate (100 mL×4). The organic phases were combined and dried over anhydrous sodium sulfate, filtered, and the filtrate was concentrated under reduced pressure to obtain (2R)-2-(tert-butoxycarbonylamino)propanoic acid (17B) as colorless oily substance (21.2 g, yield: 100%).

MS m/z=212.1 [M+Na]$^+$;
$^1$HNMR (400 MHz, DMSO-d$_6$) δ 12.34 (br, 1H), 7.05 (d, 1H), 3.98-3.87 (m, 1H), 1.38 (s, 9H), 1.22 (d, 3H).

Step 2: benzyl 2-[(2R)-2-(tert-butoxycarbonylamino)propanoyl]-2,7-diazaspiro[3.5]nonane-7-carboxylate (17C)

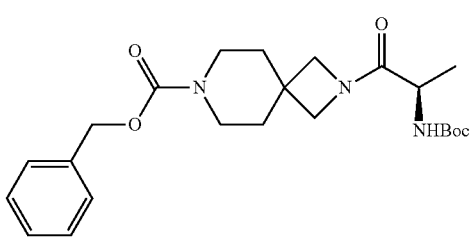 [SMILES: C[C@@H](NC(=O)OC(C)(C)C)C(=O)N1CC2(CCN(C(=O)OCc3ccccc3)CC2)C1]

Benzyl 2,7-diazaspiro[3.5]nonane-7-carboxylate (6C) (335 mg, 1.3 mmol), 1-(3-dimethylaminopropyl)-3-ethylcarbodiimide hydrochloride (748 mg, 3.9 mmol), 1-hydroxybenzotriazole (211 mg, 1.56 mmol), (2R)-2-(tert-butoxycarbonylamino)propanoic acid (17B) (246 mg, 1.3 mmol) and dichloromethane (30 mL) was added in a 50 mL reaction flask, and the system was allowed to react at room temperature for 5 h. Then the reaction solution was concentrated under reduced pressure and the residue was separated and purified by silica gel column chromatography (petroleum ether:ethyl acetate (v:v)=3:1) to obtain benzyl 2-[(2R)-2-(tert-butoxycarbonylamino)propanoyl]-2,7-diazaspiro[3.5]nonane-7-carboxylate (17C) as white solid (510 mg, yield 91%).

MS m/Z=454.3 [M+Na]⁺;

Step 3: tert-butylN-[(1R)-2-(2,7-diazaspiro[3.5]nonan-2-yl)-1-methyl-2-oxo-ethyl]carbamate (17D)

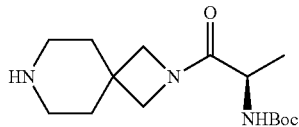

Benzyl 2-[(2R)-2-(tert-butoxycarbonylamino)propanoyl]-2,7-diazaspiro[3.5]nonane-7-carboxylate (17C)

(460 mg, 1.1 mmol), palladium hydroxide/carbon (92 mg, 20 wt %) and isopropanol (20 mL) were added in a 50 mL reaction flask. The atmosphere was replaced with hydrogen 3 times, and the reaction was heated to 100° C. in the oil bath for 8 h under a hydrogen (balloon) atmosphere. Then it was cooled to room temperature, the reaction solution was filtered through diatomite, and the filtrate was concentrated under reduced pressure to obtain crude tert-butyl N-[(1R)-2-(2,7-diazaspiro[3.5]nonan-2-yl)-1-methyl-2-oxo-ethyl]carbamate (17D) as light yellow solid (252 mg, yield 77%), and used directly in the next reaction.

MS m/z=298.3 [M+H]⁺;

Step 4: tert-butyl N-[(1R)-1-benzyl-2-[[(1R)-1-benzyl-2-[[(1R)-1-[[(1R)-5-(tert-butoxycarbonylamino)-1-[2-[(2R)-2-(tert-butoxycarbonylamino)propanoyl]-2,7-diazaspiro[3.5]nonane-7-carbonyl]pentyl]carbamoyl]-3-methyl-butyl]amino]-2-oxo-ethyl]amino]-2-oxo-ethyl]carbamate (17E)

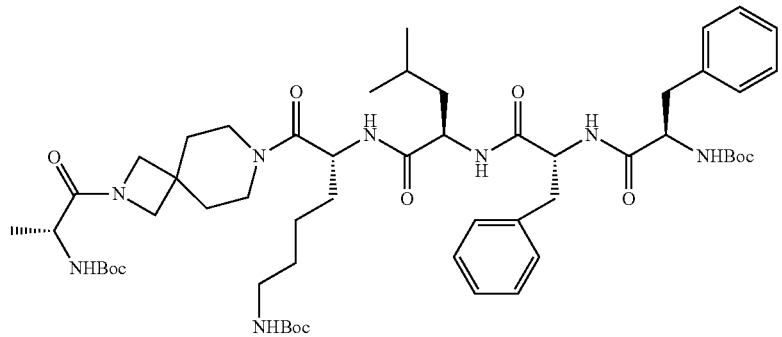 [SMILES: CC(C)C[C@@H](NC(=O)[C@@H](Cc1ccccc1)NC(=O)[C@@H](Cc1ccccc1)NC(=O)OC(C)(C)C)C(=O)N[C@H](CCCCNC(=O)OC(C)(C)C)C(=O)N1CCC2(CC1)CN(C(=O)[C@@H](C)NC(=O)OC(C)(C)C)C2]

Crude tert-butyl N-[(1R)-2-(2,7-diazaspiro[3.5]nonan-2-yl)-1-methyl-2-oxo-ethyl]carbamate (17D) (223 mg, 0.75 mmol), 1-(3-dimethylaminopropyl)-3-ethylcarbodiimide hydrochloride (374 mg, 1.95 mmol), 1-hydroxybenzotriazole (110 mg, 0.81 mmol), intermediate 1 (565 mg, 0.75 mmol) and dichloromethane (30 mL) were added sequentially in a 50 mL reaction flask, and the system was allowed to react at room temperature for 5 h. Then the reaction solution was concentrated under reduced pressure, and the residue was separated and purified by silica gel column chromatography (dichloromethane:methanol (v:v)=40:1) to obtain tert-butyl N-[(1R)-1-benzyl-2-[[(1R)-1-benzyl-2-[[(1R)-1-[[(1R)-5-(tert-butoxycarbonylamino)-1-[2-[(2R)-2-(tert-butoxycarbonylamino)propanoyl]-2,7-diazaspiro[3.5]nonane-7-carbonyl]pentyl]carbamoyl]-3-methyl-butyl]amino]-2-oxo-ethyl]amino]-2-oxo-ethyl]carbamate (17E) as light yellow solid (560 mg, yield 69%).

Step 5: (2R)—N-[(1R)-5-amino-1-[2-[(2R)-2-aminopropanoyl]-2,7-diazaspiro[3.5]nonane-7-carbonyl]pentyl]-2-[[(2R)-2-[[(2R)-2-amino-3-phenyl-propanoyl]amino]-3-phenyl-propanoyl]amino]-4-methyl-pentanamide; tri-trifluoroacetic acid (compound 17)

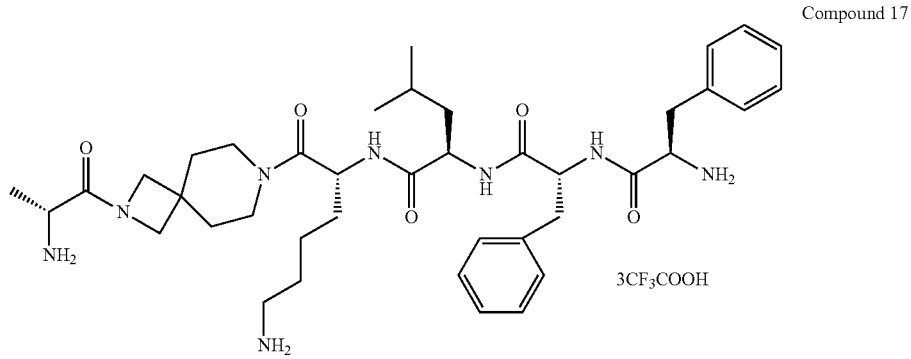 [SMILES: CC(C)C[C@@H](NC(=O)[C@@H](Cc1ccccc1)NC(=O)[C@H](N)Cc1ccccc1)C(=O)N[C@H](CCCCN)C(=O)N1CCC2(CC1)CN(C(=O)[C@@H](C)N)C2]

Compound 17

3CF₃COOH

Tert-butyl N-[(1R)-1-benzyl-2-[[(1R)-1-benzyl-2-[[(1R)-1-[[(1R)-5-(tert-butoxycarbonylamino)-1-[2-[(2R)-2-(tert-butoxycarbonylamino)propanoyl]-2,7-diazaspiro[3.5]nonane-7-carbonyl]pentyl]carbamoyl]-3-methyl-butyl]amino]-2-oxo-ethyl]amino]-2-oxo-ethyl]carbamate (17E) (560 mg, 0.52 mmol) and dichloromethane (10 mL) were added in a 50 mL reaction flask, and trifluoroacetic acid (3 mL) were added dropwise at room temperature. After the addition, the system was allowed to react at room temperature for 2 h. Then the reaction solution was concentrated under reduced pressure, and the residue was separated and purified by preparative liquid chromatography (preparation conditions: instrument: Gilson GX-281; column: Xbridge C18, 150×30 mm I.D., 5 μm; mobile phase: A for ACN and B for H₂O; isocratic: A 65%; flow rate: 30 mL/min; back pressure: 1000 PSI; column temperature: 30° C.; wavelength: 210 nm; period: 18 min; sample preparation: the compound dissolved in 12 mL methanol; injection: 0.9 mL/needle). The preparation was concentrated under reduced pressure to remove most of the solvent, and lyophilized to obtain (2R)—N-[(1R)-5-amino-1-[2-[(2R)-2-aminopropanoyl]-2,7-diazaspiro[3.5]nonane-7-carbonyl]pentyl]-2-[[(2R)-2-[[(2R)-2-amino-3-phenyl-propanoyl]amino]-3-phenyl-propanoyl]amino]-4-m ethyl-pentanamide; tri-trifluoroacetic acid (compound 17) as white powder (310 mg, yield 45%).

MS m/z=367.3 [M+2H]⁺/2;

¹HNMR (400 MHz, D₂O) δ 7.44-7.28 (m, 6H), 7.26-7.20 (m, 4H), 4.65 (t, 2H), 4.33-4.21 (m, 2H), 4.19-4.01 (m, 3H), 3.96-3.78 (m, 2H), 3.75-3.59 (m, 2H), 3.56-3.42 (m, 1H), 3.42-3.30 (m, 1H), 3.24-3.12 (m, 2H), 3.10-2.92 (m, 4H), 1.99-1.79 (m, 3H), 1.80-1.63 (m, 5H), 1.53 (d, 3H), 1.50-1.30 (m, 5H), 0.92 (dd, 6H).

Example 16: (2R)—N-[(1R)-5-amino-1-[7-[(2R)-2-aminopropanoyl]-2,7-diazaspiro[3.5]nonane-2-carbonyl]pentyl]-2-[[(2R)-2-[[(2R)-2-amino-3-phenyl-propanoyl]amino]-3-phenyl-propanoyl]amino]-4-methyl-pentanamide tri-trifluoroacetic acid (compound 18)

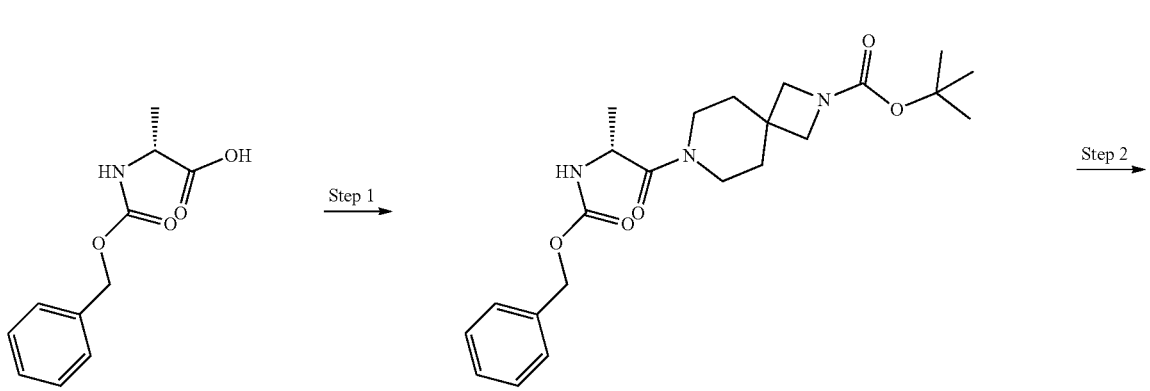

18A

Step 1 →

18B

Step 2 →

-continued
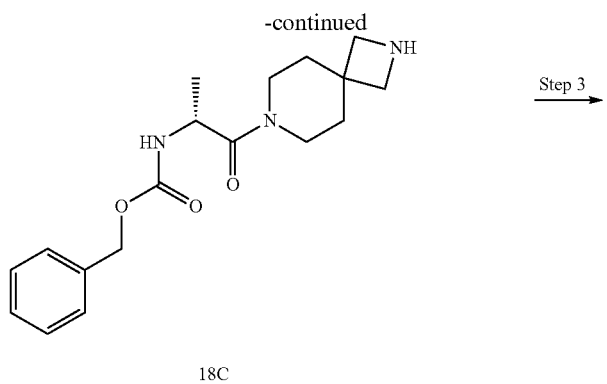
18C
Step 3
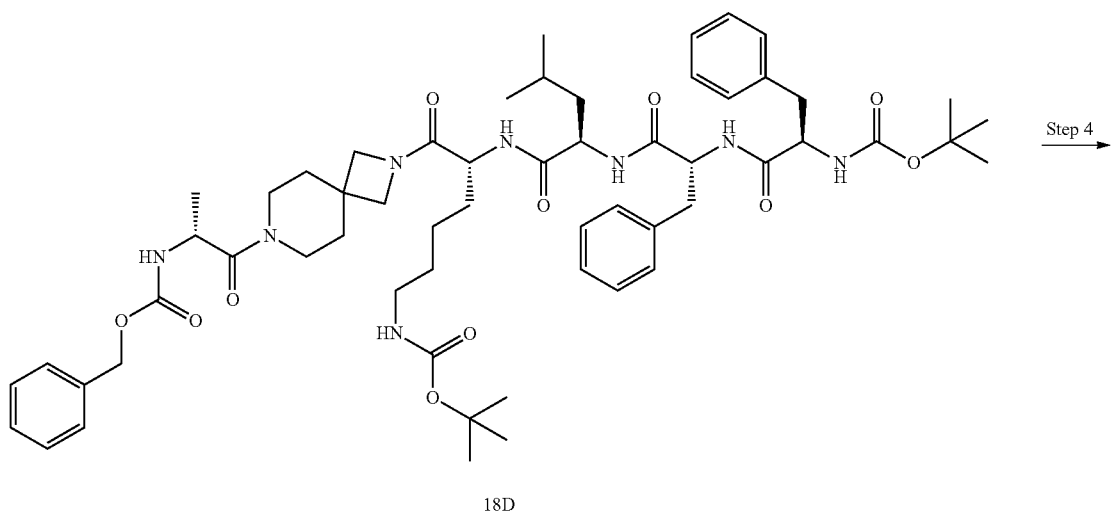
18D
Step 4
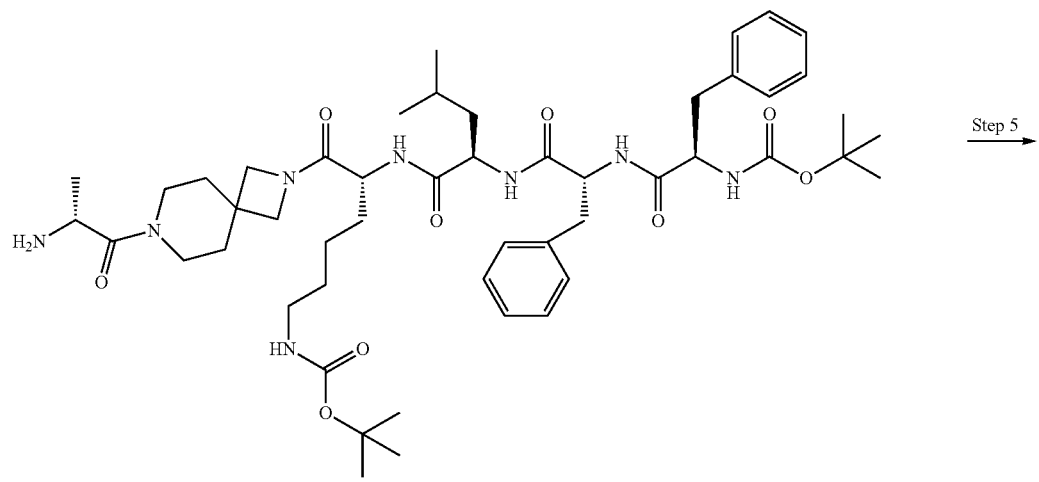
18E
Step 5

-continued

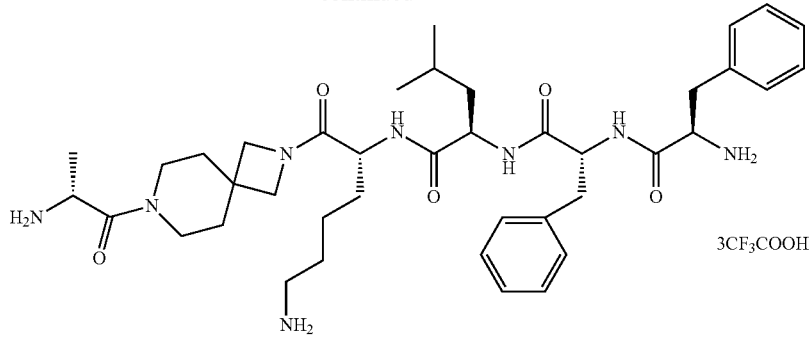

Compound 18

Step 1: benzyl N-[(1R)-2-(2,7-diazaspiro[3.5]nonan-7-yl)-1-methyl-2-oxo-ethyl]carbamate (18B)

Step 2: benzyl N-[(1R)-2-(2,7-diazaspiro[3.5]nonan-7-yl)-1-methyl-2-oxo-ethyl]carbamate (18C)

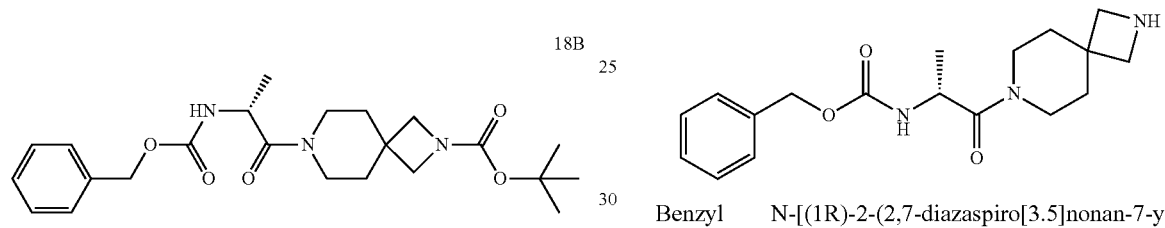

Tert-butyl 2,7-diazaspiro[3.5]nonane-2-carboxylate (6A) (0.45 g, 2 mmol), 1-(3-dimethylaminopropyl)-3-ethylcarbodiimide hydrochloride (780 mg, 4.1 mmol), 1-hydroxybenzotriazole (340 mg, 2.5 mmol), (2R)-2-(benzyloxycarbonylamino)propanoic acid (446 mg, 2.0 mmol) and dichloromethane (30 mL) were added in a 50 mL reaction flask, and the system was allowed to react at room temperature for 5 h. Then the reaction solution was concentrated under reduced pressure, and the residue was separated and purified by silica gel column chromatography (dichloromethane:methanol (v:v)=50:1) to obtain benzyl N-[(1R)-2-(2,7-diazaspiro[3.5]nonan-7-yl)-1-methyl-2-oxo-ethyl] carbamate (18B) as white solid (860 mg, yield 99%).

MS m/Z=454.2 [M+Na]⁺.

Benzyl N-[(1R)-2-(2,7-diazaspiro[3.5]nonan-7-yl)-1-methyl-2-oxo-ethyl]carbamate (18B) (0.86 g, 2 mmol) and dichloromethane (20 mL) were added in a 50 mL reaction flask, and trifluoroacetic acid (2 mL) was added dropwise at room temperature. After the addition, the system was allowed to react at room temperature for 3 h. The reaction solution was directly concentrated under reduced pressure to obtain crude benzyl N-[(1R)-2-(2,7-diazaspiro[3.5]nonan-7-yl)-1-methyl-2-oxo-ethyl]carbamate (18C) as yellow oily liquid (660 mg, yield 100%), and used directly in the next reaction.

MS m/z=332.2 [M+H]⁺;

Step 3: tert-butyl N-[(1R)-1-benzyl-2-[[(1R)-1-benzyl-2-[[(1R)-1-[[(1R)-1-[7-[(2R)-2-(benzyloxycarbonylamino)propanoyl]-2,7-diazaspiro[3.5]nonane-2-carbonyl]-5-(tert-butoxycarbonylamino)pentyl]carbamoyl]-3-meth yl-butyl]amino]-2-oxo-ethyl]amino-2-oxo-ethyl]carbamate (18D)

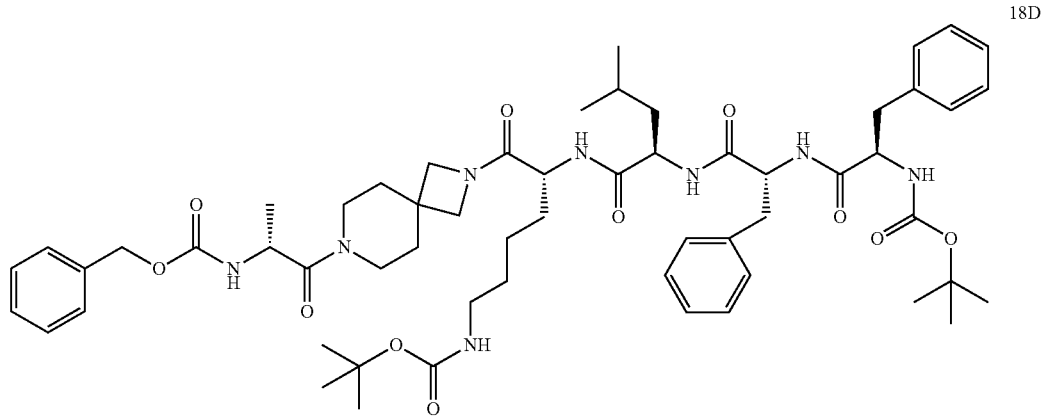 [SMILES: CC(C)C[C@@H](NC(=O)[C@@H](Cc1ccccc1)NC(=O)[C@@H](Cc1ccccc1)NC(=O)OC(C)(C)C)C(=O)N[C@H](CCCCNC(=O)OC(C)(C)C)C(=O)N1CC2(CCN(C(=O)[C@@H](C)NC(=O)OCc3ccccc3)CC2)C1]

Benzyl N-[(1R)-2-(2,7-diazaspiro[3.5]nonan-7-yl)-1-methyl-2-oxo-ethyl]carbamate (18C) (243 mg, 0.7 mmol), 1-(3-dimethylaminopropyl)-3-ethylcarbodiimide hydrochloride (300 mg, 2.0 mmol), 1-hydroxybenzotriazole (200 mg, 1.0 mmol), intermediate 1 (500 mg, 0.7 mmol) and dichloromethane (50 mL) were added in a 100 mL reaction flask, and the system was allowed to react at room temperature for 5 h. The reaction solution was concentrated under reduced pressure, and the residue was separated and purified by silica gel column chromatography (dichloromethane: methanol (v:v)=30:1) to obtain tert-butyl N-[(1R)-1-benzyl-2-[[(1R)-1-benzyl-2-[[(1R)-1-[[(1R)-1-[7-[(2R)-2-(benzyloxycarbonylamino)propanoyl]-2,7-diazaspiro[3.5]nonane-2-carbonyl]-5-(tert-butoxycarbonylamino)pentyl]carbamoyl]-3-methyl-butyl]amino]-2-oxo-ethyl]amino]-2-oxo-ethyl]carbamate (18D) as light yellow solid (740 mg, yield 99%).

Step 4: tert-butyl N-[(1R)-2-[[(1R)-2-[[(1R)-1-[[(1R)-1-[7-[(2R)-2-aminopropanoyl]-2,7-diazaspiro[3.5]nonane-2-carbonyl]-5-(tert-butoxycarbonylamino)pentyl]carbamoyl]-3-methyl-butyl]amino]-1-benzyl-2-oxo-ethyl]amino]-1-benzyl-2-oxo-ethyl]carbamate (18E)

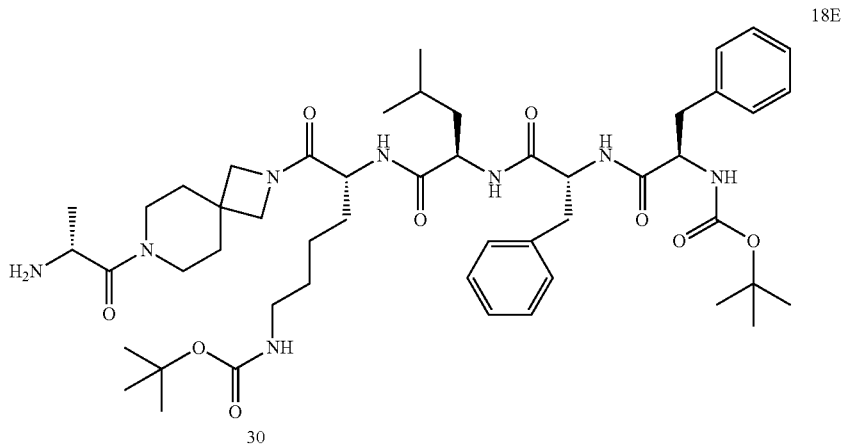

18E

Tert-butyl N-[(1R)-1-benzyl-2-[[(1R)-1-benzyl-2-[[(1R)-1-[[(1R)-1-[7-[(2R)-2-(benzyloxycarbonylamino)propanoyl]-2,7-diazaspiro[3.5]nonane-2-carbonyl]-5-(tert-butoxycarbonylamino)pentyl]carbamoyl]-3-methyl-butyl]amino]-2-oxo-ethyl]amino]-2-oxo-ethyl]carbamate (18D) (700 mg, 0.7 mmol), palladium on carbon (140 mg, 20 wt %) and methanol (15 mL) were added in a 50 mL reaction flask. The atmosphere was replaced with hydrogen 3 times, and the mixture reacted at room temperature for 8 h under a hydrogen atmosphere. The reaction solution was then filtered through diatomite, and the filtrate was concentrated under reduced pressure to obtain crude tert-butyl (1R)-2-[[(1R)-2-[[(1R)-1-[[(1R)-1-[7-[(2R)-2-aminopropanoyl]-1,7-diazaspiro[3.5]nonane-2-carbonyl]-5-(tert-butoxycarbonyl)pentyl]carbamoyl]-3-methyl-butyl]amino]-1-benzyl-2-oxo-ethyl]amino]-1-benzyl-2-oxo-ethyl]carbamate (18E) as light yellow oily substance (650 mg, yield 99%), and used directly in the next reaction.

Step 5: (2R)—N-[(1R)-5-amino-1-[7-[(2R)-2-aminopropanoyl]-2,7-diazaspiro[3.5]nonane-2-carbonyl]pentyl]-2-[[(2R)-2-[[(2R)-2-amino-3-phenyl-propanoyl]amino]-3-phenyl-propanoyl]amino]-4-methyl-pentanamide; tri-trifluoroacetic acid (compound 18)

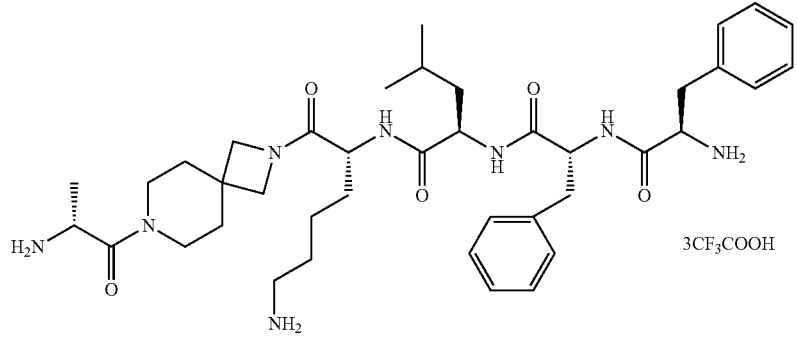 [SMILES: CC(C)C[C@@H](NC(=O)[C@@H](Cc1ccccc1)NC(=O)[C@H](N)Cc1ccccc1)C(=O)N[C@H](CCCCN)C(=O)N1CC2(CCN(C(=O)[C@@H](C)N)CC2)C1]

3CF₃COOH

Crude tert-butyl (1R)-2-[[(1R)-2-[[(1R)-1-[[(1R)-1-[7-[(2R)-2-aminopropanoyl]-1,7-diazaspiro[3.5]nonane-2-carbonyl]-5-(tert-butoxycarbonyl)pentyl]carbamoyl]-3-methyl-butyl]amino]-1-benzyl-2-oxo-ethyl]amino]-1-benzyl-2-oxo-ethyl]carbamate (18E) (650 mg, 0.7 mmol) and trifluoroacetic acid (2 mL) were added in a 50 mL reaction flask, and the system was allowed to react at room temperature for 2 h. Then the reaction solution was concentrated under reduced pressure, and the residue was separated and purified by preparative liquid chromatography (preparation conditions: instrument: Gilson GX-281; column: Xbridge C18, 150×30 mm I.D., 5 μm; mobile phase: A for ACN and B for H₂O; isocratic: A 65%; flow rate: 30 mL/min; back pressure: 1000 PSI; column temperature: 30° C.; wavelength: 210 nm; period: 18 min; sample preparation: the compound dissolved in 12 mL methanol; injection: 0.9 mL/needle). The preparation was concentrated under reduced pressure to remove most of the solvent, and lyophilized to obtain (2R)—N-[(1R)-5-amino-1-[7-[(2R)-2-aminopropanoyl]-2,7-diazaspiro[3.5]nonane-2-carbonyl]pentyl]-2-[[(2R)-2-[[(2R)-2-amino-3-phenyl-propanoyl]amino]-3-phenyl-propanoyl]amino]-4-m ethyl-pentanamide; tri-trifluoroacetic acid (compound 18) as white powder (170 mg, yield 19%).

MS m/z=733.5 [M+H]⁺;

¹HNMR (400 MHz, D₂O) δ 7.44-7.28 (m, 6H), 7.27-7.20 (m, 4H), 4.64 (t, 1H), 4.55-4.46 (m, 1H), 4.32-4.23 (m, 2H), 4.21-4.05 (m, 3H), 3.86-3.71 (m, 2H), 3.63-3.40 (m, 4H), 3.25-3.10 (m, 2H), 3.10-2.90 (m, 4H), 2.00-1.60 (m, 8H), 1.60-1.29 (m, 8H), 0.92 (dd, 6H).

Example 17: (2R)—N-[(1R)-5-amino-1-[7-[(2R)-2-aminopropanoyl]-5,5-difluoro-2,7-diazaspiro[3.5]nonane-2-carbonyl]pentyl]-2-[[(2R)-2-[[(2R)-2-amino-3-phenyl-propanoyl]amino]-3-phenyl-propanoyl]amino]-4-methyl-pentanamide; tri-trifluoroacetic acid (compound 19)

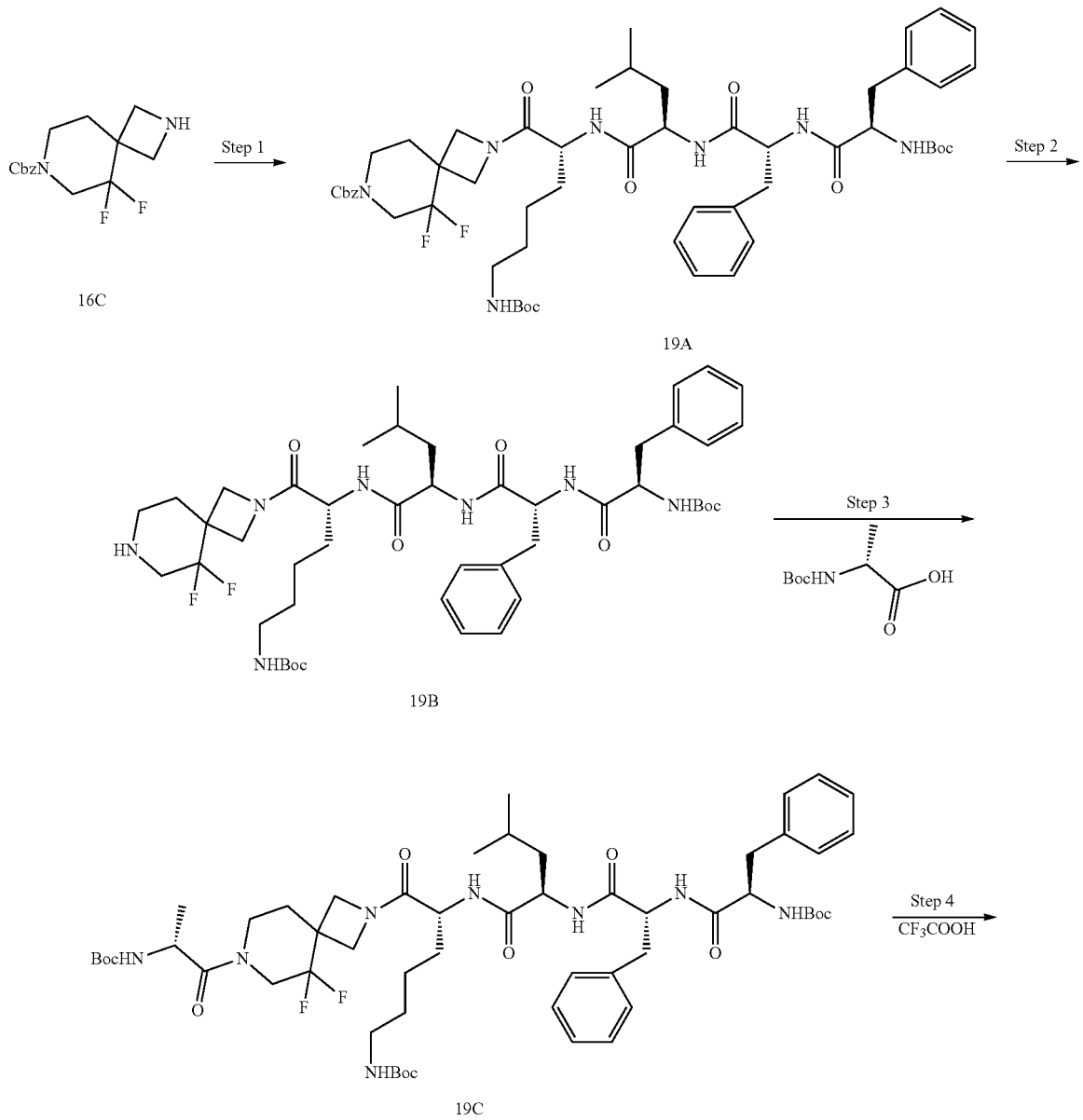

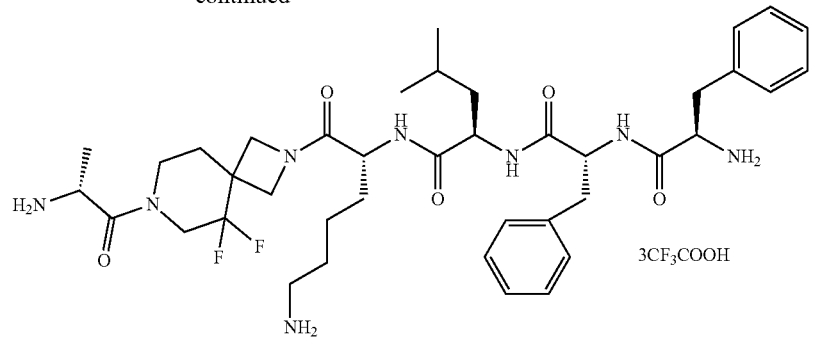

Compound 19

Step 1: benzyl2-[(2R)-6-(tert-butoxycarbonylamino)-2-[[(2R)-2-[[(2R)-2-[[(2R)-2-(tert-butoxycarbonylamino)-3-phenyl-propanoyl]amino]-3-phenyl-propanoyl]amino]-4-methyl-pentanoyl]amino]hexanoyl]-5,5-difluoro-2,7-diazaspiro[3.5]nonane-7-carboxylate (19A)

Step 2: tert-butyl N-[(1R)-1-benzyl-2-[[(1R)-1-benzyl-2-[[(1R)-1-[[(1R)-5-(tert-butoxycarbonylamino)-1-(5,5-di fluoro-2,7-diazaspiro[3.5]nonane-2-carbonyl)pentyl]carbamoyl]-3-methyl-butyl]amino]-2-oxo-ethyl]amino]-2-oxo-ethyl]carbamate (19B)

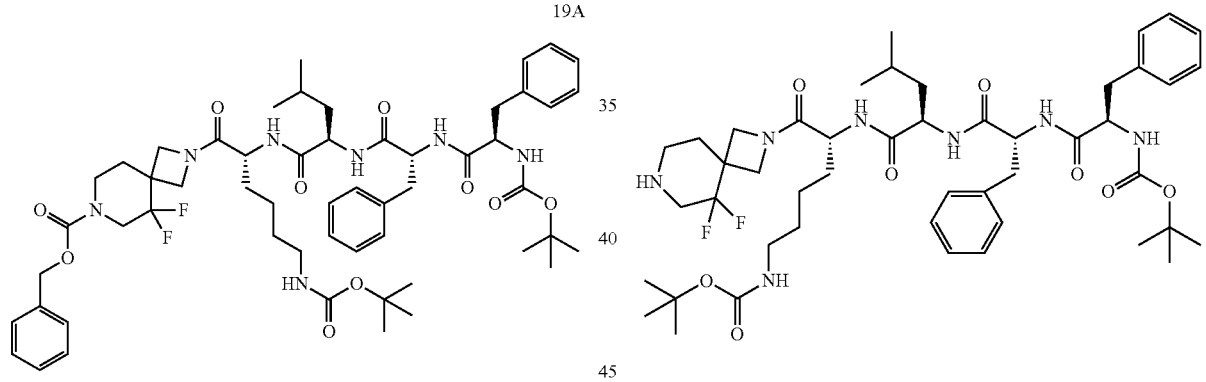

Benzyl 5,5-difluoro-2,7-diazaspiro[3.5]nonane-7-carboxylate (16C) (797 mg, 2.69 mmol), 1-(3-dimethylaminopropyl)-3-ethylcarbodiimide hydrochloride (1.04 g, 5.4 mmol), 1-hydroxybenzotriazole (400 mg, 3 mmol), intermediate 1 (2.03 g, 2.69 mmol) and dichloromethane (50 mL) were added in a 100 mL reaction flask, and the system was allowed to react at room temperature for 5 h. The reaction solution was concentrated under reduced pressure, and the residue was separated and purified by silica gel column chromatography (dichloromethane:methanol (v:v)=30:1) to obtain benzyl 2-[(2R)-6-(tert-butoxycarbonylamino)-2-[[(2R)-2-[[(2R)-2-[[(2R)-2-(tert-butoxycarbonylamino)-3-phenyl-propanoyl]amino]-3-phenyl-propanoyl]amino]-4-methyl-pentanoyl]amino]hexanoyl]-5,5-difluoro-2,7-diazaspiro[3.5]nonane-7-carboxylate (19A) as light yellow solid (2.49 g, yield 89.6%).

Benzyl 2-[(2R)-6-(tert-butoxycarbonylamino)-2-[[(2R)-2-[[(2R)-2-[[(2R)-2-(tert-butoxycarbonylamino)-3-phenyl-propanoyl]amino]-3-phenyl-propanoyl]amino]-4-methyl-pentanoyl]amino]hexanoyl]-5,5-difluoro-2,7-diazaspiro[3.5]nonane-7-carboxylate (19A) (2.49 g, 2.41 mmol), palladium on carbon (500 mg, 20 wt %) and methanol (25 mL) were added in a 50 mL reaction flask. The atmosphere was replaced with hydrogen 3 times, and the mixture reacted at room temperature for 4 h under a hydrogen (balloon) atmosphere. The reaction solution was then filtered through diatomite, and the filtrate was concentrated under reduced pressure to obtain crude tert-butyl N-[(1R)-1-benzyl-2-[[(1R)-1-benzyl-2-[[(1R)-1-[[(1R)-5-(tert-butoxycarbonylamino)-1-(5,5-di fluoro-2,7-diazaspiro[3.5]nonane-2-carbonyl)pentyl]carbamoyl]-3-methyl-butyl]amino]-2-oxo-ethyl]amino]-2-oxo-ethyl]carbamate (19B) as light yellow oily solid (2.16 g, yield 99%), and used directly in the next reaction.

MS m/z=899.5 [M+H]$^+$;

Step 3: tert-butyl N-(1R)-1-benzyl-2-[[(1R)-1-benzyl-2-[[(1R)-1-[[(1R)-5-(tert-butoxycarbonylamino)-1-[7-[(2R)-2-(tert-butoxycarbonylamino)propanoyl]-5,5-difluoro-2,7-diazaspiro[3.5]nonane-2-carbonyl]pentyl]carbamoyl]-3-methyl-butyl]amino]-2-oxo-ethyl]amino]-2-oxo-ethyl]carbamate (19C)

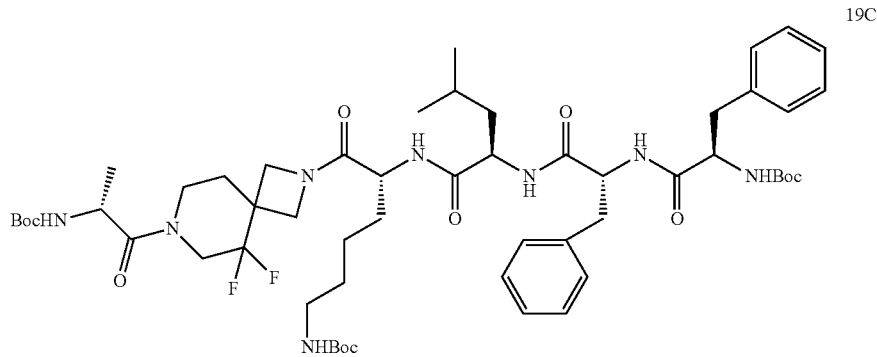 [SMILES: CC(C)C[C@@H](NC(=O)[C@@H](Cc1ccccc1)NC(=O)[C@@H](Cc1ccccc1)NC(=O)OC(C)(C)C)C(=O)N[C@H](CCCCNC(=O)OC(C)(C)C)C(=O)N1CC2(CCN(C(=O)[C@@H](C)NC(=O)OC(C)(C)C)CC2(F)F)C1]

Crude tert-butyl N-[(1R)-1-benzyl-2-[[(1R)-1-benzyl-2-[[(1R)-1-[[(1R)-5-(tert-butoxycarbonylamino)-1-(5,5-difluoro-2,7-diazaspiro[3.5]nonane-2-carbonyl)pentyl]carbamoyl]-3-methyl-butyl]amino]-2-oxo-ethyl]amino]-2-oxo-ethyl]carbamate (19B) (400 mg, 0.4 mmol), 1-(3-dimethylaminopropyl)-3-ethylcarbodiimide hydrochloride (0.23 g, 1.2 mmol), 1-hydroxybenzotriazole (70 mg, 0.5 mmol), Boc-D-alanine (78 mg, 0.41 mmol) and dichloromethane (50 mL) were added in a 50 mL reaction flask, and the system was allowed to react at room temperature for 5 h. The reaction solution was concentrated under reduced pressure, and the residue was separated and purified by silica gel column chromatography (dichloromethane:methanol (v:v) =30:1) to obtain tert-butyl N-(1R)-1-benzyl-2-[[(1R)-1-benzyl-2-[[(1R)-1-[[(1R)-5-(tert-butoxycarbonylamino)-1-[7-[(2R)-2-(tert-butoxycarbonylamino)propanoyl]-5,5-difluoro-2,7-diazaspiro[3.5]nonane-2-carbonyl]pentyl]carbamoyl]-3-methyl-butyl]amino]-2-oxo-ethyl]amino]-2-oxo-ethyl]carbamate (19C) as light yellow solid (340 mg, yield 79%).

Step 4: (2R)—N-[(1R)-5-amino-1-[7-[(2R)-2-aminopropanoyl]-5,5-difluoro-2,7-diazaspiro[3.5]nonane-2-carbonyl]pentyl]-2-[[(2R)-2-[[(2R)-2-amino-3-phenyl-propanoyl]amino]-3-phenyl-propanoyl]amino]-4-methyl-pentanamide; tri-trifluoroacetic acid (compound 19)

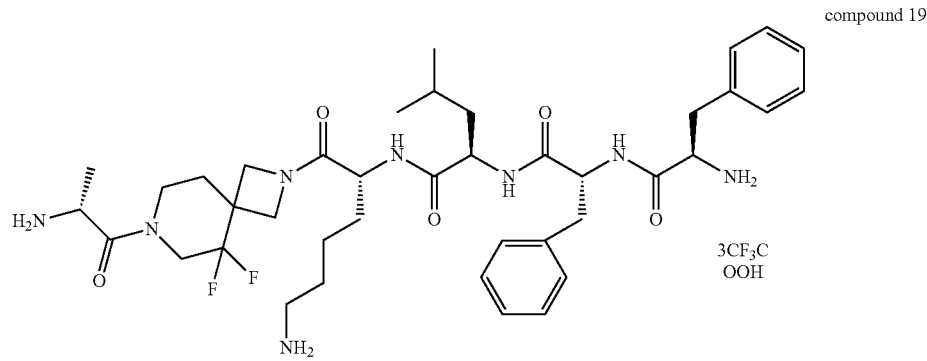 [SMILES: CC(C)C[C@@H](NC(=O)[C@@H](Cc1ccccc1)NC(=O)[C@H](N)Cc1ccccc1)C(=O)N[C@H](CCCCN)C(=O)N1CC2(CCN(C(=O)[C@@H](C)N)CC2(F)F)C1]

Tert-butyl N-(1R)-1-benzyl-2-[[(1R)-1-benzyl-2-[[(1R)-1-[[(1R)-5-(tert-butoxycarbonylamino)-1-[7-[(2R)-2-(tert-butoxycarbonylamino)propanoyl]-5,5-difluoro-2,7-diazaspiro[3.5]nonane-2-carbonyl]pentyl]carbamoyl]-3-methyl-butyl]amino]-2-oxo-ethyl]amino]-2-oxo-ethyl]carbamate (19C) (340 mg, 0.32 mmol) and trifluoroacetic acid (2 mL) were added in a 50 mL reaction flask, and the system was allowed to react at room temperature for 2 h. Then the reaction solution was concentrated under reduced pressure, and the residue was separated and purified by preparative liquid chromatography (preparation conditions: instrument: Gilson GX-281; column: Xbridge C18, 150×30 mm I.D., 5 μm; mobile phase: A for ACN and B for H$_2$O; isocratic: A 65%; flow rate: 30 mL/min; back pressure: 1000 PSI; column temperature: 30° C.; wavelength: 210 nm; period: 18 min; sample preparation: the compound dissolved in 12 mL methanol; injection: 0.9 mL/needle). The preparation was concentrated under reduced pressure to remove most of the solvent, and lyophilized to obtain (2R)—N-[(1R)-5-amino-1-[7-[(2R)-2-aminopropanoyl]-5,5-difluoro-2,7-diazaspiro[3.5]nonane-2-carbonyl]pentyl]-2-[[(2R)-2-[[(2R)-2-amino-3-phenyl-propanoyl]amino]-3-phenyl-propanoyl]amino]-4-methyl-pentanamide; tri-trifluoroacetic acid (compound 19) as white powder (170 mg, yield 48%).

MS m/z (ESI): 385.3[M+2H]$^+$/2;

$^1$H NMR (400 MHz, D$_2$O) δ 7.43-7.29 (m, 6H), 7.27-7.21 (m, 4H), 4.67-4.47 (m, 3H), 4.31-4.09 (m, 5H), 4.09-3.76 (m, 3H), 3.74-3.46 (m, 2H), 3.18 (d, 2H), 3.10-2.91 (m, 4H), 2.33-1.97 (m, 2H), 1.84-1.61 (m, 4H), 1.61-1.26 (m, 8H), 0.92 (dd, 6H).

Example 18: (2R)—N-[(1R)-1-(7-acetyl-2,7-diazaspiro[3.5]nonane-2-carbonyl)-5-amino-pentyl]-2-[[(2R)-2-[[(2R)-2-amino-3-phenyl-propanoyl]amino]-3-phenyl-propanoyl]amino]-4-methyl-pentanamide; di-trifluoroacetic acid (compound 20)

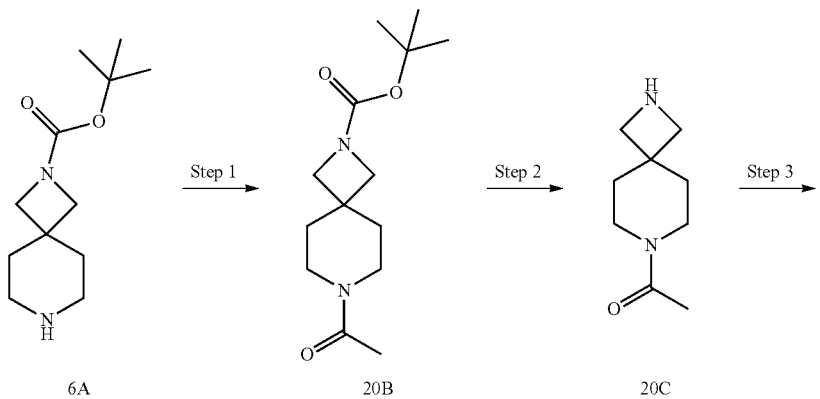

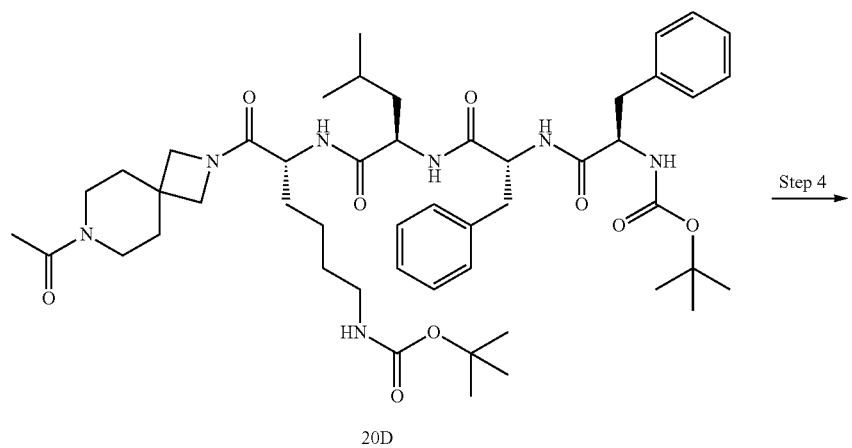

20D

-continued

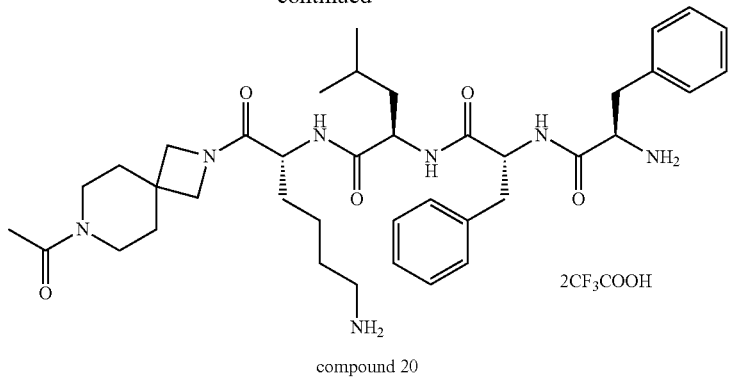

compound 20

Step 1: tert-butyl 7-acetyl-2,7-diazaspiro[3.5]nonane-2-carboxylate (20B)

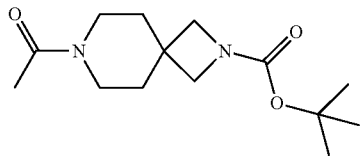 [SMILES: CC(=O)N1CCC2(CC1)CN(C(=O)OC(C)(C)C)C2]

Tert-butyl 2,7-diazaspiro[3.5]nonane-2-carboxylate (6A) (450 mg, 2.0 mmol) was dissolved in dichloromethane (5 mL) in a 50 mL reaction flask under nitrogen protection, and triethylamine (606 mg, 6.0 mmol) was added under stirring. Then the temperature was dropped to −20° C., and acetyl chloride (310 mg, 4.0 mmol) was added dropwise. After the addition, the temperature was naturally raised to room temperature and the system was stirred for 2 h. Subsequently, a 0.5 M diluted hydrochloric acid aqueous solution (20 mL) was added to the reaction, and the layers were separated by stirring and the mixture was subjected to a liquid separation process. The aqueous layer was extracted with dichloromethane (20 mL×2), and the organic phases were combined. The organic phases were dried over anhydrous sodium sulfate, filtered, and the filtrate was concentrated under reduced pressure, The residue was separated and purified by silica gel column chromatography (pure ethyl acetate), to obtain tert-butyl 7-acetyl-2,7-diazaspiro[3.5]nonane-2-carboxylate (20B) as light yellow oily liquid (520 mg, yield 97.0%).

Step 2: 1-(2,7-diazaspiro[3.5]nonan-7-yl)ethanone (20C)

1-(2,7-diazaspiro[3.5]nonan-7-yl)ethanone

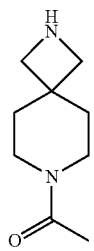

Tert-butyl 7-acetyl-2,7-diazaspiro[3.5]nonane-2-carboxylate (20B) (520 mg, 1.9 mmol) and dichloromethane (6 mL) were added in a 50 mL reaction flask, and trifluoroacetic acid (3 mL) was added dropwise at room temperature. After the addition, the system was allowed to react at room temperature for 3 h. The reaction solution was directly concentrated under reduced pressure, and 4 mL of concentrated ammonia water was added to the residue, followed by drying with anhydrous sodium sulfate, washing with methanol (20 mL), and concentrating the washing solution to obtain crude 1-(2,7-diazaspiro[3.5]nonan-7-yl)ethanone (20C) as yellow oily liquid (250 mg, yield 77%), and used directly in the next reaction.

Step 3: N-(1R)-2-[[(1R)-2-[[(1R)-1-[[(1R)-1-(7-acetyl-2,7-diazaspiro[3.5]nonane-2-carbonyl)-5-(tert-butoxycarbonylamino)pentyl]carbamoyl]-3-methyl-butyl]amino]-1-benzyl-2-oxo-ethyl]amino]-1-benzyl-2-oxo-ethyl carbamate (20D)

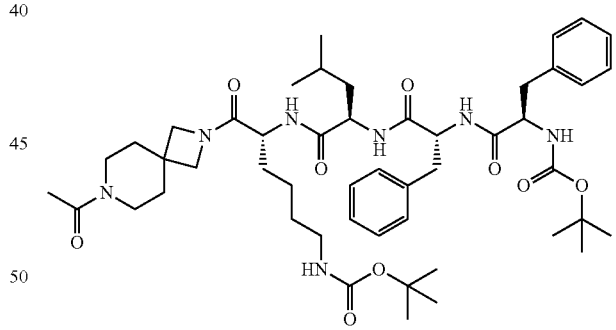

1-(2,7-diazaspiro[3.5]nonan-7-yl)ethanone (20C) (250 mg, 1.49 mmol) was added in the ethyl acetate (10 mL) in a 50 mL reaction flask under nitrogen protection. It was cooled to 0° C. in an ice bath, and intermediate 1 (800 mg, 1.06 mmol), 1-(3-dimethylaminopropyl)-3-ethylcarbodiimide hydrochloride (305 mg, 1.6 mmol), 1-hydroxybenzotriazole (172 mg, 1.27 mmol) were added. After the addition, the reaction was allowed to proceed at room temperature for 1.5 h. Subsequently, a 1M aqueous hydrochloric acid solution (15 mL) was added to the reaction solution, and the mixture was stirred and then subjected to a liquid separation process. A saturated aqueous sodium carbonate solution (15 mL) was added to the organic phase, and the mixture was stirred for 30 minutes and then subjected to a liquid separation process. The organic phase was washed with a saturated aqueous sodium chloride solution (15 mL), dried over anhydrous sodium sulfate, filtered, and the filtrate was concentrated under reduced pressure to obtain crude N-(1R)-2-[[(1R)-2-[[(1R)-1-[[(1R)-1-(7-acetyl-2,7-diazaspiro[3.5]nonane-2-carbonyl)-5-(tert-butoxycarbonylamino)pentyl]carbamoyl]- 3-methyl-butyl]amino]-1-benzyl-2-oxo-ethyl]amino]-1-benzyl-2-oxo-ethyl]carbamate (20D) as light yellow foamy solid (0.85 g, yield 88%), and used directly in the next reaction.

Step 4: (2R)—N-[(1R)-1-(7-acetyl-2,7-diazaspiro[3.5]nonane-2-carbonyl)-5-amino-pentyl]-2-[[(2R)-2-[[(2R)-2-amino-3-phenyl-propanoyl]amino]-3-phenyl-propanoyl]amino]-4-methyl-pentanamide; di-trifluoroacetic acid (compound 20)

Compound 20

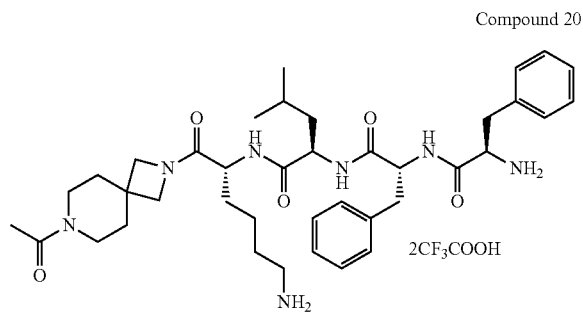 [SMILES: CC(=O)N1CCC2(CC1)CN(C(=O)[C@@H](CCCCN)NC(=O)[C@@H](CC(C)C)NC(=O)[C@@H](Cc1ccccc1)NC(=O)[C@H](N)Cc1ccccc1)C2]

2CF₃COOH

Crude N-(1R)-2-[[(1R)-2-[[(1R)-1-[[(1R)-1-(7-acetyl-2,7-diazaspiro[3.5]nonane-2-carbonyl)-5-(tert-butoxycarbonylamino)pentyl]carbamoyl]- 3-methyl-butyl]amino]-1-benzyl-2-oxo-ethyl]amino]-1-benzyl-2-oxo-ethyl] carbamate (20D) (0.85 g, 0.94 mmol) was dissolved in dichloromethane (7.5 mL), and trifluoroacetic acid (3.5 mL) was added. The system was stirred at room temperature for 1 h. Subsequently, the reaction solution was concentrated under reduced pressure. After the residue was separated and purified by preparative liquid chromatography (preparation conditions: instrument: Gilson GX-281; column: Xbridge C18, 150×30 mm I.D., 5 μm; mobile phase: A for ACN and B for H₂O; isocratic: A 65%; flow rate: 30 mL/min; back pressure: 1000 PSI; column temperature: 30° C.; wavelength: 210 nm; period: 18 min; sample preparation: the compound dissolved in 12 mL methanol; injection: 0.9 mL/needle), the preparation was concentrated under reduced pressure to remove most of the solvent, and lyophilized to obtain ((2R)—N-[(1R)-1-(7-acetyl-2,7-diazaspiro[3.5]nonane-2-carbonyl)-5-amino-pentyl]-2-[[(2R)-2-[[(2R)-2-amino-3-phenyl-propanoyl]amino]-3-phenyl-propanoyl]amino]-4-methyl-pentanamide; di-trifluoroacetic acid (compound 20) as white solid (310 mg, yield 40.0%).

MS m/z (ESI): 352.8[M+2H]⁺/2;

¹H NMR (400 MHz, D₂O) δ 7.46-7.17 (m, 10H), 4.64 (t, 1H), 4.29-4.05 (m, 5H), 3.83-3.74 (m, 2H), 3.57-3.35 (m, 4H), 3.24-3.11 (m, 2H), 3.09-2.93 (m, 4H), 2.17-1.29 (m, 16H), 0.92 (dd, 6H).

Example 19: (2R)—N-[(1R)-5-amino-1-[2-(1,1-dioxo-1,4-thiazinan-4-yl)-7-azaspiro[3.5]nonane-7-carbonyl]pentyl]-2-[[(2R)-2-[[(2R)-2-amino-3-phenyl-propanoyl]amino]-3-phenyl-propanoyl]amino]-4-methyl-pentanamide tri-trifluoroacetic acid (compound 21)

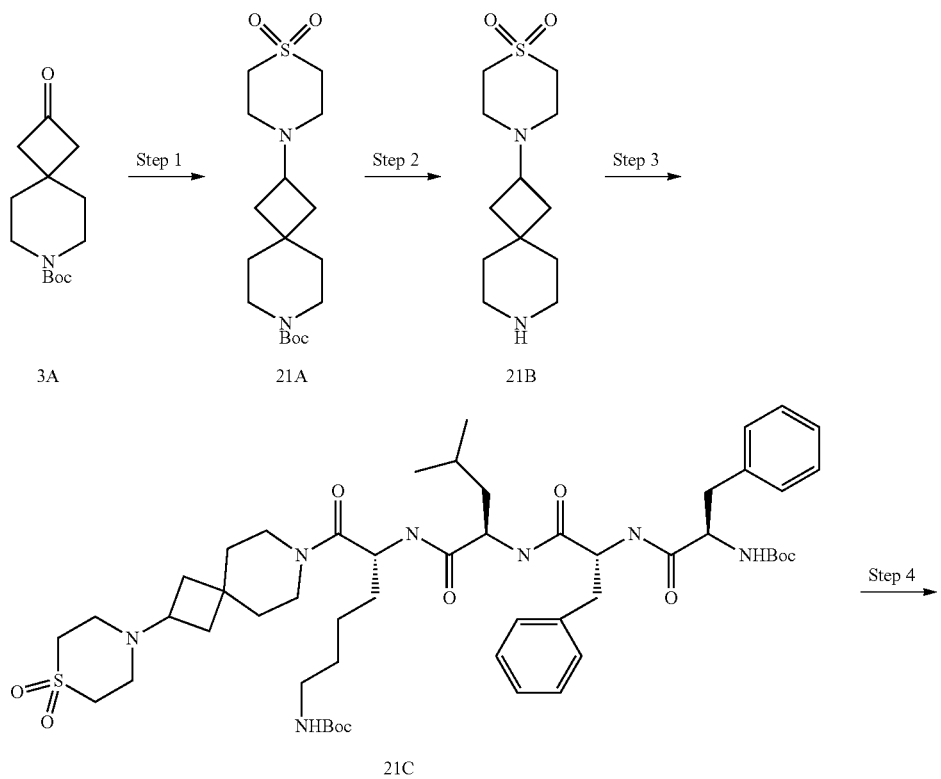

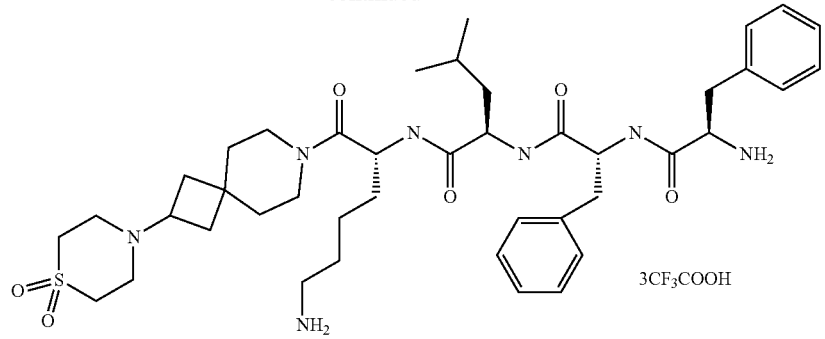

Compound 21

Step 1: tert-butyl 2-(1,1-dioxo-1,4-thiazinan-4-yl)-7-azaspiro[3.5]nonane-7-carboxylate (21A)

Step 2: 4-(7-azaspiro[3.5]nonan-2-yl)-1,4-thiazinane 1,1-dioxide (21B)

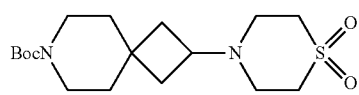

21A

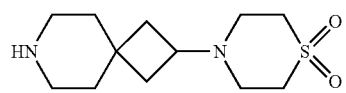

21B

Tert-butyl 2-oxo-7-azaspiro[3.5]nonane-7-carboxylate (3A) (129 mg, 0.54 mmol), acetic acid (65 mg, 1.08 mmol), 1,4-thiazinan 1,1-dioxide (72 mg, 0.54 mmol), sodium triacetoxyborohydride (229 m g, 1.08 mmol) and dichloromethane (20 mL) were added sequentially in a 50 mL reaction flask. After the addition, the reaction was allowed to proceed at room temperature for 16 h. The reaction solution was suction filtered, and the filtrate was washed with a saturated sodium bicarbonate solution (50 mL). After separation, the organic layer was dried over anhydrous sodium sulfate, suction filtered, and the filtrate was concentrated under reduced pressure, to obtain tert-butyl (1,1-dioxo-1,4-thiazinan-4-yl)-7-azaspiro[3.5]nonane-7-carboxylate (21A) as white powder (147 mg, yield 76%).

Tert-butyl (1,1-dioxo-1,4-thiazinan-4-yl)-7-azaspiro[3.5]nonane-7-carboxylate (21A)(147 mg, 0.41 mmol) and dichloromethane (10 mL) were added in a 50 mL reaction flask, and trifluoroacetic acid (2 mL) was added dropwise at room temperature. After the addition, the system was allowed to react at room temperature for 3 h. The reaction solution was directly concentrated under reduced pressure to obtain crude 4-(7-azaspiro[3.5]nonan-2-yl)-1,4-thiazinan-1,1-dioxide (21B) as yellow oily liquid (106 mg, yield 100%), and used directly in the next reaction.

Step 3: tert-butylN-[(1R)-1-benzyl-2-[[(1R)-1-benzyl-2-[[(1R)-1-[[(1R)-5-(tert-butoxycarbonylamino)-1-[2-(1,1-dioxo-1,4-thiazinan-4-yl)-7-azaspiro[3.5]nonane-7-carbonyl]pentyl]carbamoyl]-3-methylbutyl]amino]-2-oxo-ethyl]amino]-2-oxo-ethyl]carbamate (21C)

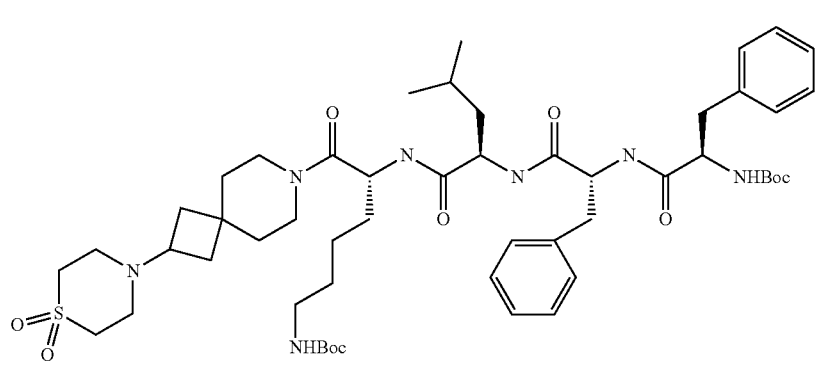

21C

Crude 4-(7-azaspiro[3.5]nonan-2-yl)-1,4-thiazinan-1,1-dioxide (21B) (106 mg, 0.41 mmol), 1-(3-dimethylaminopropyl)-3-ethylcarbodiimide hydrochloride (94 mg, 0.49 mmol), 1-hydroxybenzotriazole (66 mg, 0.49 mmol), intermediate 1 (309 mg, 0.41 mmol) and dichloromethane (50 mL) were added in a 50 mL single-necked flask, the system was allowed to react at room temperature for 5 h. The reaction solution was concentrated under reduced pressure, and the residue was separated and purified by silica gel column chromatography (dichloromethane:methanol (v:v)= 50:1), to obtain tert-butyl (1R)-1-benzyl-2-[[(1R)-1-benzyl-2-[[(1R)-1-[[(1R)-5-(tert-butoxycarbonylamino)-1-[2-(1,1-di oxo-1,4-thiazinan-4-yl)-7-azaspiro[3.5]nonane-7-carbonyl]pentyl]carbamoyl]-3-methyl-butyl]amino]-2-oxo-ethyl]amino]-2-oxo-ethyl]carbamate (21C) as white solid (367 mg, yield 90%).

Step 4: (2R)—N-[(1R)-5-amino-1-[2-(1,1-dioxo-1,4-thiazinan-4-yl)-7-azaspiro[3.5]nonane-7-carbonyl]pentyl]-2-[[(2R)-2-[[(2R)- 2-amino-3-phenyl-propanoyl]amino]-3-phenyl-propanoyl]amino]-4-methyl-pentanamide; tri-trifluoroacetic acid (compound 21)

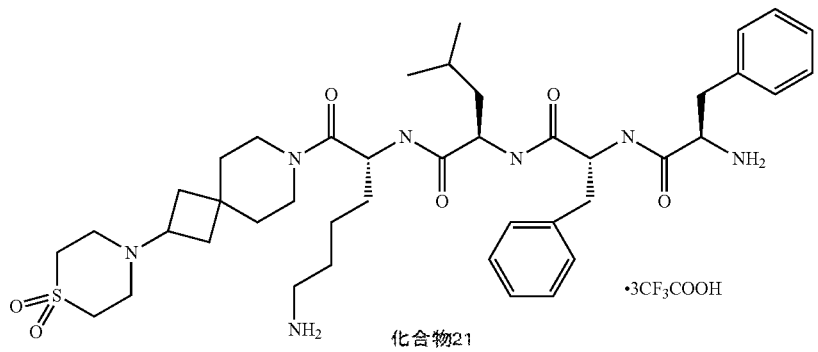 [SMILES: CC(C)C[C@@H](NC(=O)[C@@H](Cc1ccccc1)NC(=O)[C@H](N)Cc1ccccc1)C(=O)N[C@H](CCCCN)C(=O)N1CCC2(CC1)CC(N1CCS(=O)(=O)CC1)C2]

化合物21

Tert-butyl(1R)-1-benzyl-2-[[(1R)-1-benzyl-2-[[(1R)-1-[[(1R)-5-(tert-butoxycarbonylamino)-1-[2-(1,1-dioxo-1,4-thiazinan-4-yl)-7-azaspiro[3.5]nonane-7-carbonyl]pentyl] carbamoyl]-3-methyl-butyl]amino]-2-oxo-ethyl]amino]-2-oxo-ethyl]carbamate (21C) (367 mg, 0.37 mmol) and trifluoroacetic acid (2 mL) were added in a 50 mL reaction flask, and the system was allowed to react at room temperature for 2 h. Then the reaction solution was concentrated under reduced pressure, and the residue was separated and purified by preparative liquid chromatography (preparation conditions: instrument: Gilson GX-281; column: Xbridge C18, 150×30 mm I.D., 5 μm; mobile phase: A for ACN and B for H$_2$O; isocratic: A 65%; flow rate: 30 mL/min; back pressure: 1000 PSI; column temperature: 30° C.; wavelength: 210 nm; period: 18 min; sample preparation: the compound dissolved in 12 mL methanol; injection: 0.9 mL/needle). The preparation was concentrated under reduced pressure to remove most of the solvent, and lyophilized to obtain (2R)—N-[(1R)-5-amino-1-[2-(1,1-dioxo-1,4-thiazinan-4-yl)-7-azaspiro[3.5]nonane-7-carbonyl]pentyl]-2-[[(2R)-2-[[(2R)-2-amino-3-phenyl-propanoyl]amino]-3-phenyl-propanoyl]amino]-4-methyl-pentanamide; tri-trifluoroacetic acid (compound 21) as white powder (295 mg, yield 70%).

MS m/z=397.9 [M+2H]$^+$/2;

$^1$H NMR (400 MHz, D$_2$O) δ 7.36-7.19 (m, 10H), 4.63-4.60 (m, 1H), 4.32-4.16 (m, 3H), 3.92-3.78 (m, 1H), 3.63 (d, 9H), 3.53-3.22 (m, 3H), 3.15 (d, 2H), 3.01-2.91 (m, 4H), 2.48-2.32 (m, 2H), 1.98-2.06 (m, 2H), 1.75-1.23 (m, 13H), 0.89 (dd, 6H).

Example 20: 7-[(2R)-6-amino-2-[[(2R)-2-[[(2R)-2-[[(2R)-2-amino-3-phenyl-propanoyl]amino]-3-phenyl-propanoyl]amino]-4-methyl-pentanoyl]amino]hexanoyl]-N-methyl-2,7-diazaspiro[4.4]nonane-2-carboxamide; di-trifluoroacetic acid (compound 22)
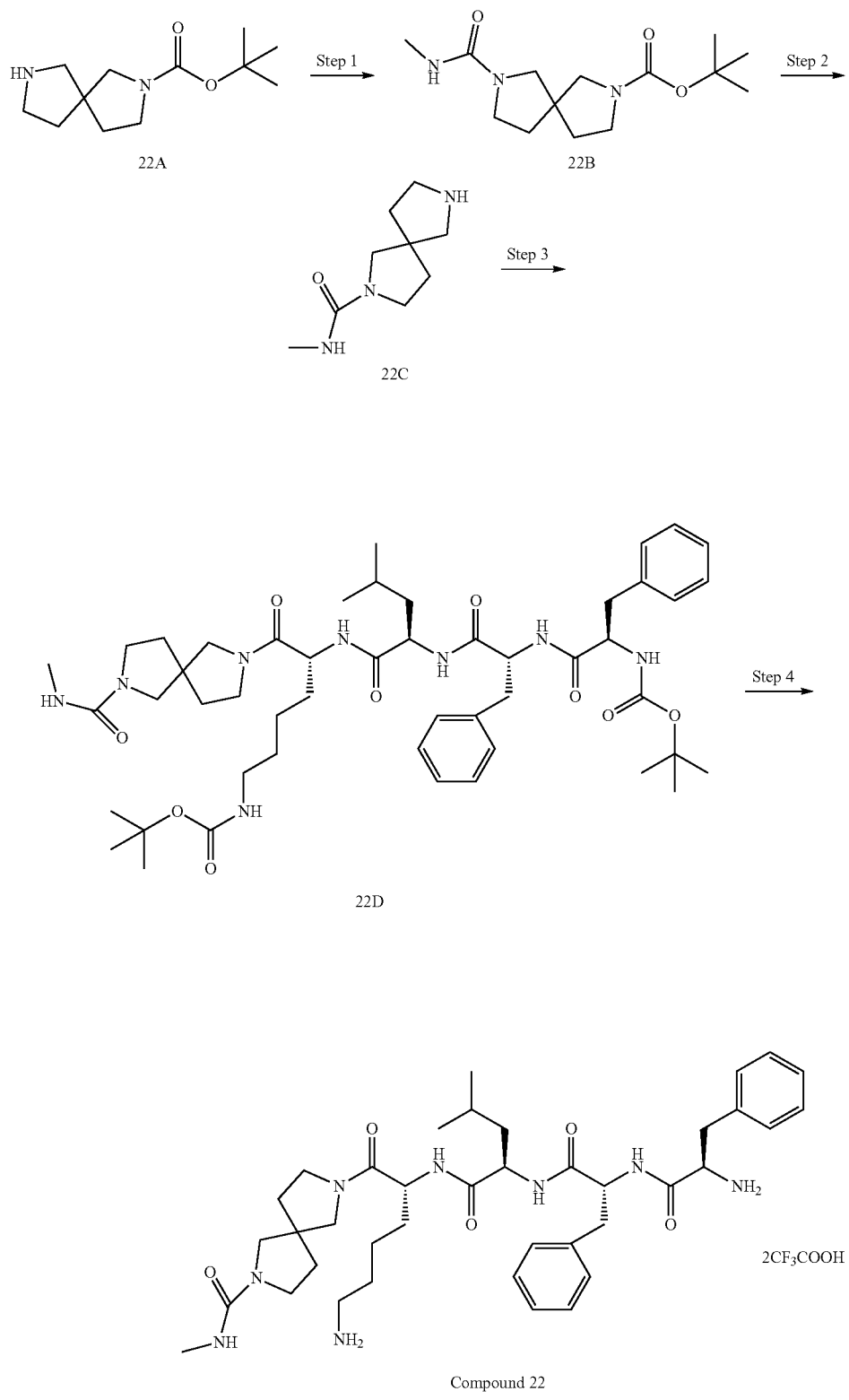
Compound 22

Step 1: tert-butyl 7-(methylcarbamoyl)-2,7-diazaspiro[4.4]nonane-2-carboxylate (22B)

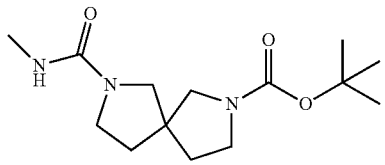

22B

2-Boc-2,7-diazaspiro[4.4]nonane (22A) (452 mg, 2.0 mmol), triethylamine (400 mg, 4.0 mmol) and dichloromethane (15 mL) were added in a 50 mL reaction flask, and dissolved under stirring. After cooling to −10° C., methyl amino formyl chloride (188 mg, 2.01 mmol) was added dropwise. After the addition, the reaction was allowed to proceed at room temperature for 3 h. 3 M diluted hydrochloric acid (50 mL) was added to the reaction solution, and then extract with dichloromethane (60 mL×2). The organic phases were dried over anhydrous sodium sulfate, filtered, and the filtrate was concentrated under reduced pressure to obtain tert-butyl 7-(methylcarbamoyl)-2,7-diazaspiro[4.4]nonane-2-carboxylate (22B) as white solid (570 mg, yield 65.5%).

$^1$H NMR (400 MHz, CDCl$_3$) δ 3.51-3.16 (m, 8H), 2.82 (s, 3H), 1.98-1.74 (m, 4H), 1.46 (s, 9H).

Step 2: N-methyl-2,7-diazaspiro[4.4]nonane-2-carboxamide (22C)

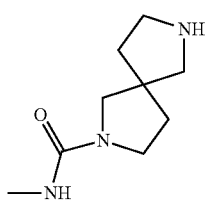

22C

Tert-butyl 7-(methylcarbamoyl)-2,7-diazaspiro[4.4]nonane-2-carboxylate (22B) (161 mg, 0.568 mmol), dichloromethane (10 mL) and trifluoroacetic acid (1.2 mL) were added in a 50 mL reaction flask, and the system was allowed to react at room temperature for 2 h. Then the reaction solution was concentrated under reduced pressure to obtain crude N-methyl-2,7-diazaspiro[4.4]nonane-2-carboxamide (22C) as light yellow oily substance, and used directly in the next reaction.

Step 3: tert-butyl N-[(1R)-1-benzyl-2-[[(1R)-1-benzyl-2-[[(1R)-1-[[(1R)-5-(tert-butoxycarbonylamino)-1-[2-(methylcarbamoyl)-2,7-diazaspiro[4.4]nonane-7-carbonyl]pentyl]carbamoyl]-3-methyl-butyl]amino]-2-oxo-ethyl]amino]-2-oxo-ethyl]carbamate (22D)

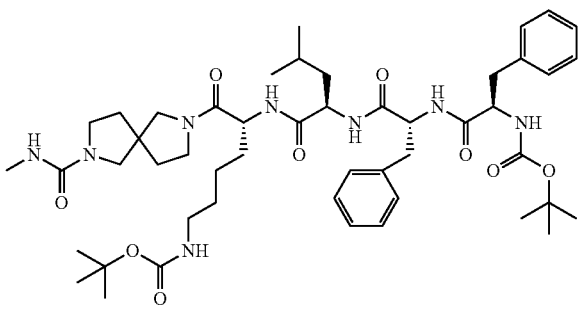

22D

Crude N-methyl-2,7-diazaspiro[4.4]nonane-2-carboxamide (22C) (81 mg, 0.44 mmol), 1-(3-dimethylaminopropyl)-3-ethylcarbodiimide hydrochloride (0.288 g, 1.5 mmol), 1-hydroxybenzotriazole (81 mg, 0.6 mmol), intermediate 1 (330 mg, 0.44 mmol) and dichloromethane (50 mL) were added sequentially in a 50 mL reaction flask, and the system was allowed to react at room temperature for 5 h. The reaction solution was concentrated under reduced pressure, and the residue was separated and purified by silica gel column chromatography (dichloromethane:methanol (v:v) =30:1) to obtain tert-butyl N-[(1R)-1-benzyl-2-[[(1R)-1-benzyl-2-[[(1R)-1-[[(1R)-5-(tert-butoxycarbonylamino)-1-[2-(methylcarbamoyl)-2,7-diazaspiro[4.4]nonane-7-carbonyl]pentyl]carbamoyl]-3-methyl-butyl]amino]-2-oxo-ethyl]amino]-2-oxo-ethyl]carbamate (22D) as light yellow solid (420 mg, yield 98%).

Step 4: 7-[(2R)-6-amino-2-[[(2R)-2-[[(2R)-2-[[(2R)-2-amino-3-phenyl-propanoyl]amino]-3-phenyl-propanoyl]amino]-4-methyl-pentanoyl]amino] hexanoyl]-N-methyl-2,7-diazaspiro[4.4]nonane-2-carboxamide; di-trifluoroacetic acid (compound 22)

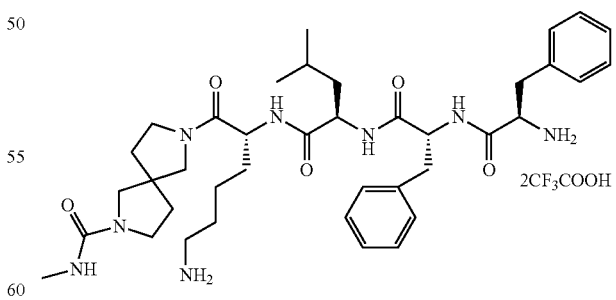

Tert-butyl N-[(1R)-1-benzyl-2-[[(1R)-1-benzyl-2-[[(1R)-1-[[(1R)-5-(tert-butoxycarbonylamino)-1-[2-(methylcarbamoyl)-2,7-diazaspiro[4.4]nonane-7-carbonyl]pentyl]carbamoyl]-3-methyl-butyl]amino]-2-oxo-ethyl]amino]-2-oxo-ethyl]carbamate (22D) (400 mg, 0.44 mmol) and trifluoroacetic acid (2 mL) were added in a 50 mL reaction flask, and the system was allowed to react at room temperature for 2 h. Then the reaction solution was concentrated under reduced pressure, and the residue was separated and purified by preparative liquid chromatography (preparation conditions: instrument: Gilson GX-281; column: Xbridge C18, 150×30 mm I.D., 5 μm; mobile phase: A for ACN and B for $H_2O$; isocratic: A 65%; flow rate: 30 mL/min; back pressure: 1000 PSI; column temperature: 30° C.; wavelength: 210 nm; period: 18 min; sample preparation: the compound dissolved in 12 mL methanol; injection: 0.9 mL/needle). The preparation was concentrated under reduced pressure to remove most of the solvent, and lyophilized to obtain 7-[(2R)-6-amino-2-[[(2R)-2-[[(2R)-2-amino-3-phenyl-propanoyl]amino]-3-phenyl-propanoyl]amino]-4-methyl-pentanoyl]amino]hexanoyl]-N- methyl-2,7-diazaspiro[4.4]nonane-2-carboxamide; di-trifluoroacetic acid (compound 22) as white powder (130 mg, yield 31.5%).

MS m/z (ESI): 360.3[M+2H]$^+$/2;

$^1$H NMR (400 MHz, $D_2O$) δ 7.43-7.19 (m, 10H), 4.68-4.60 (m, 1H), 4.50-4.19 (m, 3H), 3.93-3.62 (m, 2H), 3.55-3.27 (m, 5H), 3.24 (s, 1H), 3.18 (d, 2H), 3.09-2.94 (m, 4H), 2.74-2.66 (m, 3H), 2.10-1.85 (m, 4H), 1.84-1.62 (m, 4H), 1.59-1.43 (m, 4H), 1.43-1.29 (m, 1H), 0.92 (dd, 6H).

Example 21: (2R)-2-[[(2R)-2-[[(2R)-2-amino-3-phenyl-propanoyl]amino]-3-phenyl-propanoyl]amino]-N-[(1R)-5-amino-1-[2-(1-piperidinyl)-7-azaspiro[3.5]nonane-7-carbonyl]pentyl]-4-methyl-pentanamide; tri-trifluoroacetic acid (compound 23)

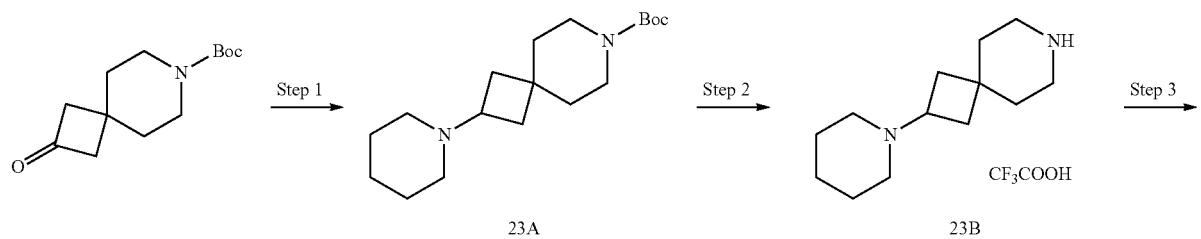

23A      23B

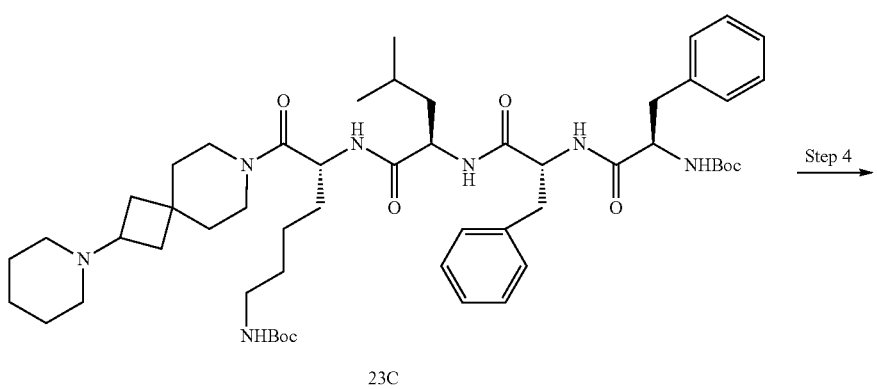

23C

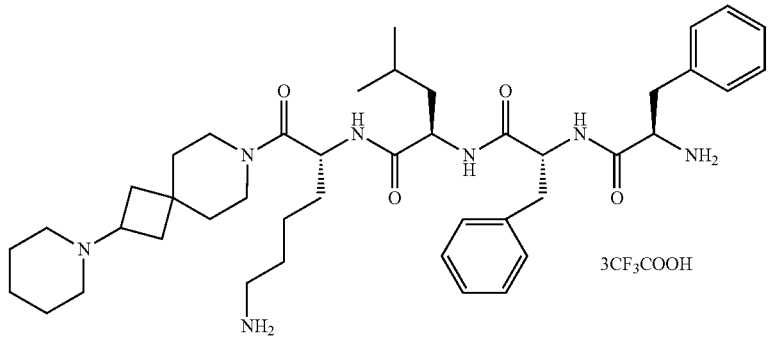

Compound 23

Step 1: tert-butyl 2-(1-piperidinyl)-7-azaspiro[3.5]nonane-7-carboxylate (23A)

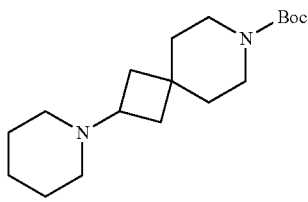 [SMILES: CC(C)(C)OC(=O)N1CCC2(CC1)CC(N1CCCCC1)C2]

2-oxo-7-azaspiro[3.5]nonane-7-tert-butyl carboxylate (0.48 g, 2 mmol), piperidine (0.25 g, 3 mmol) and dichloromethane (10 mL) were added to a reaction flask, stirred for 30 minutes, cooled to 0-5° C., and sodium cyanoborohydride (0.13 g, 4 mmol) was added. After the addition, the system was allowed to react at room temperature for 4 h, and TLC was used to monitor the completion of the reaction for completion. Dichloromethane (10 mL) and water (10 mL) were added and stirred for 5 min. The layers were allowed to stand still, and the organic layer was dried over anhydrous sodium sulfate, filtered, concentrated under reduced pressure to obtain crude tert-butyl 2-(1-piperidinyl)-7-azaspiro[3.5]nonane-7-carboxylate (23A) as light yellow solid (0.53 g, yield 86%), and used directly in the next step.

Step 2: 2-(1-piperidinyl)-7-azaspiro[3.5]nonane;2,2,2-trifluoroacetic acid (23B)

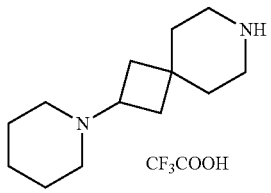 [SMILES: C1CCN(C2CC3(CCNCC3)C2)CC1 ; "CF3COOH"]

Tert-butyl 2-(1-piperidinyl)-7-azaspiro[3.5]nonane-7-carboxylate (23A, 0.53 g, 1.7 mmol) was added to dichloromethane (5 mL) in a 50 mL reaction flask under nitrogen protection, and trifluoroacetic acid (2 mL) was added under stirring. After the addition, the system was allowed to react at room temperature for 2 h. TLC was used to monitor the completion of the reaction and the reaction was concentrated to dryness under reduced pressure to obtain 2-(1-piperidinyl)-7-azaspiro[3.5]nonane; trifluoroacetic acid (23B) as light yellow oily substance (0.50 g, yield 90%), and used directly in the next step.

Step 3: tert-butylN-[(1R)-1-benzyl-2-[[(1R)-1-benzyl-2-[[(1R)-1-[[(1R)-5-(tert-butoxycarbonylamino)-1-[2-(1-piperidinyl)-7-azaspiro[3.5]nonane-7-carbonyl]pentyl]carbamoyl]-3-methyl-butyl]amino]-2-oxo-ethyl]amino]-2-oxo-ethyl]carbamate (23C)

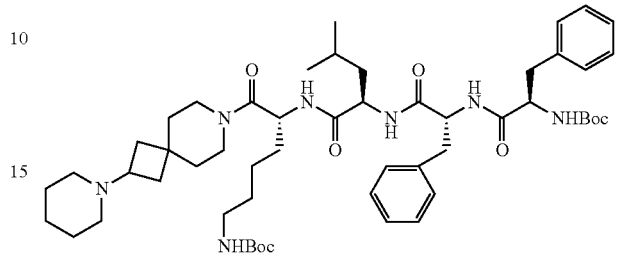

2-(1-piperidinyl)-7-azaspiro[3.5]nonane trifluoroacetic acid (23B, 0.50 g, 1.60 mmol) was added to dichloromethane (10 mL) in a 50 mL reaction flask under nitrogen protection. It was cooled to 0° C. in an ice bath, and intermediate 1 (0.50 g, 0.66 mmol), 1-(3-dimethylaminopropyl)-3-ethylcarbodiimide hydrochloride (190 mg, 0.99 mmol), 1-hydroxybenzotriazole (110 mg, 0.81 mmol) were added. After the addition, the system was allowed to react at room temperature for 3 h. Subsequently, a 1M aqueous hydrochloric acid solution (15 mL) was added to the reaction solution, and the mixture was stirred and then subjected to a liquid separation process. A saturated aqueous sodium carbonate solution (15 mL) was added to the organic phase, and the mixture was stirred for 30 minutes and then subjected to a liquid separation process. The organic phase was washed with a saturated aqueous sodium chloride solution (15 mL), dried over anhydrous sodium sulfate, filtered, and the filtrate was concentrated under reduced pressure to obtain crude tert-butyl N-[(1R)-1-benzyl-2-[[(1R)-1-benzyl-2-[[(1R)-1-[[(1R)-5-(tert-butoxycarbonylamino)-1-[2-(1-piperidinyl)-7-azaspiro[3.5]nonane-7-carbonyl]pentyl]carbamoyl]-3-methyl-butyl]amino]-2-oxo-ethyl]amino]-2-oxo-ethyl]carbamate (23C) as light yellow foamy solid (0.45 g, yield 72%), and used directly in the next reaction.

Step 4: (2R)-2-[[(2R)-2-[[(2R)-2-amino-3-phenyl-propanoyl]amino]-3-phenyl-propanoyl]amino]-N-[(1R)-5-amino-1-[2-(1-piperidinyl)-7-azaspiro[3.5]nonane-7-carbonyl]pentyl]-4-methyl-pentanamide; tri-trifluoroacetic acid (compound 23)

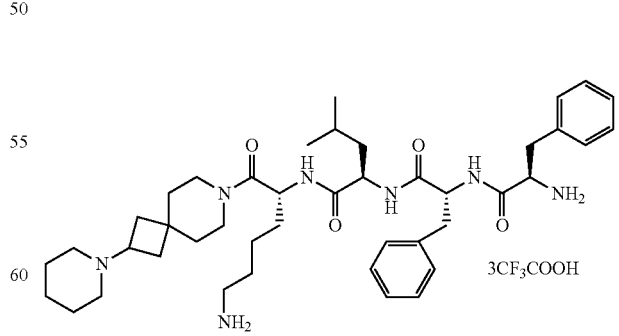

compound 23

Crude tert-butyl N-[(1R)-1-benzyl-2-[[(1R)-1-benzyl-2-[[(1R)-1-[[(1R)-5-(tert-butoxycarbonylamino)-1-[2-(1-piperidinyl)-7-azaspiro[3.5]nonane-7-carbonyl]pentyl]carbamoyl]-3-methyl-butyl]amino]-2-oxo-ethyl]amino]-2-oxo-ethyl]carbamate (23C) (0.45 g, 0.48 mmol) was dissolved in dichloromethane (7.5 mL), and trifluoroacetic acid (3.5 mL) was added, and the system was stirred at room temperature for 1 h. Subsequently, the reaction solution was concentrated under reduced pressure. After the residue was separated and purified by preparative liquid chromatography (preparation conditions: instrument: Gilson GX-281; column: Xbridge C18, 150×30 mm I.D., 5 μm; mobile phase: A for ACN and B for H₂O; isocratic: A 65%; flow rate: 30 mL/min; back pressure: 1000 PSI; column temperature: 30° C.; wavelength: 210 nm; period: 18 min; sample preparation: the compound dissolved in 12 mL methanol; injection: 0.9 mL/needle), the preparation was concentrated under reduced pressure to remove most of the solvent, and lyophilized to obtain (2R)-2-[[(2R)-2-[[(2R)-2-amino-3-phenyl-propanoyl]amino]-3-phenyl-propanoyl]amino]-N-[(1R)-5-amino-1-[2-(1-piperidinyl)-7-azaspiro[3.5]nonane-7-carbonyl]pentyl]-4-methylpentanamide; tri-trifluoroacetic acid (compound 23) as white solid (260 mg, yield 56%).

MS m/z (ESI): 372.9[M+2H]⁺/2;

¹H NMR (400 MHz, D₂O) δ7.48-7.09 (m, 10H), 4.68-4.60 (m, 1H), 4.34-4.17 (m, 2H), 3.73-3.52 (m, 3H), 3.52-2.92 (m, 10H), 2.80-2.64 (m, 2H), 2.47-2.24 (m, 2H), 2.05-1.88 (m, 4H), 1.88-1.20 (m, 18H), 1.00-0.81 (m, 6H).

Example 22: (2R)-2-[[(2R)-2-[[(2R)-2-amino-3-phenyl-propanoyl]amino]-3-phenyl-propanoyl]amino]-N-[(1R)-5-amino-1-(7-tetrahydropyran-4-yl-2,7-diazaspiro[3.5]nonane-2-carbonyl)pentyl]-4-methyl-pentanamide tri-trifluoroacetic acid (compound 24)

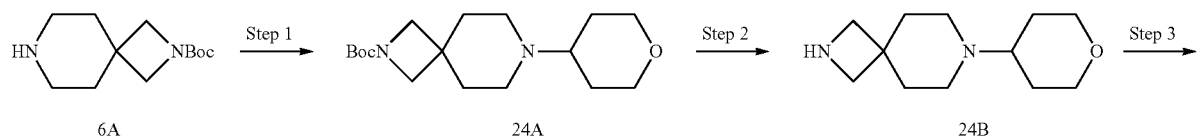

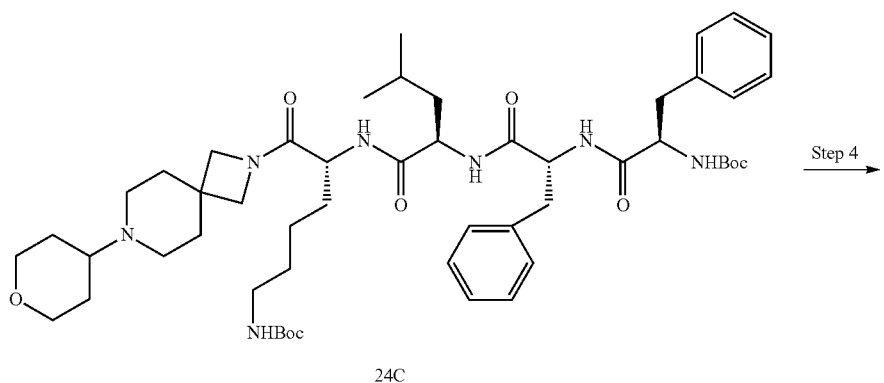

24C

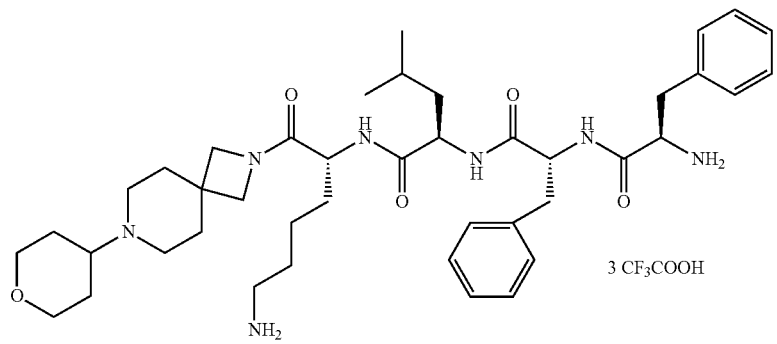

Compound 24

Step 1: tert-butyl 7-tetrahydropyran-4-yl-2,7-diazaspiro[3.5]nonane-2-carboxylate (24A)

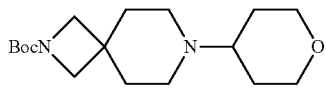 [SMILES: CC(C)(C)OC(=O)N1CC2(CCN(C3CCOCC3)CC2)C1]

Tert-butyl 2,7-diazaspiro[3.4]nonane-2-carboxylate (6A) (0.452 g, 2 mmol), tetrahydropyrone (200 mg, 2 mmol), acetic acid (120 mg, 2.0 mmol) and dichloroethane (7 mL) were added in a 50 mL reaction flask, and stirred for 0.5 h. Sodium triacetoxyborohydride (0.636 g, 3 mmol) was added, and the system was allowed to react for 5 h. The reaction solution was then quenched with water (10 mL), extracted with ethyl acetate (5 mL×3), and the organic phases were combined, dried over anhydrous sodium sulfate, filtered, and the filtrate was concentrated under reduced pressure. The residue was separated and purified by silica gel column chromatography (petroleum ether:ethyl acetate (v:v)=4:1) to obtain tert-butyl 7-tetrahydropyran-4-yl-2,7-diazaspiro[3.5]nonane-2-carboxylate (24A) as light yellow oily substance (500 mg, yield 80.64%).

MS m/z=311.2[M+H]⁺.

Step 2: 7-tetrahydropyran-4-yl-2,7-diazaspiro[3.5]nonane (24B)

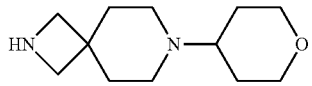

Tert-butyl 7-tetrahydropyran-4-yl-2,7-diazaspiro[3.5]nonane-2-carboxylate (24A) (0.5 g, 1.61 mmol) and dichloromethane (7 mL) were added in a 50 mL reaction flask, and trifluoroacetic acid (1 mL) was added dropwise at room temperature. After the addition, the system was allowed to react at room temperature for 3 h. The reaction solution was directly concentrated under reduced pressure to obtain crude 7-tetrahydropyran-4-yl-2,7-diazaspiro[3.5]nonane (24B) as light yellow oily liquid (338 mg, yield 100%), and used directly in the next reaction.

Step 3: tert-butylN-[(1R)-1-benzyl-2-[[(1R)-1-benzyl-2-[[(1R)-1-[[(1R)-5-(tert-butoxycarbonylamino)-1-(7-tetrahydropyran-4-yl-2,7-diazaspiro[3.5]nonane-2-carbonyl)pentyl]carbamoyl]-3-methyl-butyl]amino]-2-oxo-ethyl]amino]-2-oxo-ethyl]carbamate (24C)

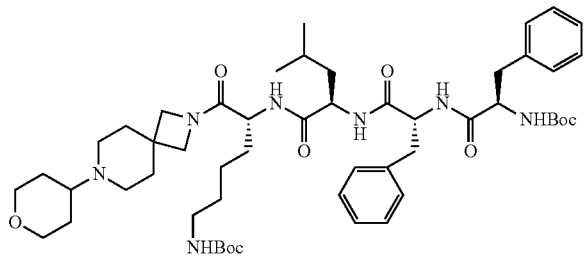 [SMILES: CC(C)C[C@@H](NC(=O)[C@@H](Cc1ccccc1)NC(=O)[C@@H](Cc1ccccc1)NC(=O)OC(C)(C)C)C(=O)N[C@H](CCCCNC(=O)OC(C)(C)C)C(=O)N1CC2(CCN(C3CCOCC3)CC2)C1]

Crude 7-tetrahydropyran-4-yl-2,7-diazaspiro[3.5]nonane (24B)(338 mg, 1.61 mmol), 1-(3-dimethylaminopropyl)-3-ethylcarbodiimide hydrochloride (384 mg, 2 mmol), 1-hydroxybenzotriazole (270 mg, 2 mmol), intermediate 1 (400 mg, 0.53 mmol) and dichloromethane (30 mL) were added in a 50 mL single-necked flask, and the system was allowed to react at room temperature for 5 h. Then the reaction solution was concentrated under reduced pressure, and the residue was separated and purified by silica gel column chromatography (petroleum ether:ethyl acetate (v:v)=1:2) to obtain tert-butyl N-[(1R)-1-benzyl-2-[[(1R)-1-benzyl-2-[[(1R)-1-[[(1R)-5-(tert-butoxycarbonylamino)-1-(7-tetrahydropyran-4-yl-2,7-diazaspiro[3.5]nonane-2-carbonyl)pentyl]carbamoyl]-3-methyl-butyl]amino]-2-oxo-ethyl]amino]-2oxo-ethyl]carbamate (24C) as white solid (200 mg, yield 39.93%) Step 4: (2R)-2-[[(2R)-2-[[(2R)-2-amino-3-phenyl-propanoyl]amino]-3-phenyl-propanoyl]amino]-N-[(1R)-5-amino-1-(2-piperazin-1-yl-7-azaspiro[3.5]nonane-7-carbonyl)pentyl]-4-methyl-pentanamide tri-trifluoroacetic acid (compound 24)

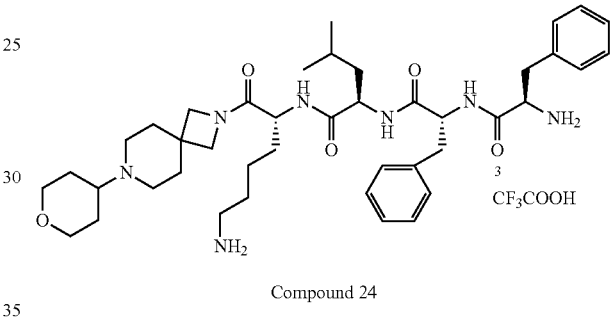

Compound 24

Tert-butyl N-[(1R)-1-benzyl-2-[[(1R)-1-benzyl-2-[[(1R)-1-[[(1R)-5-(tert-butoxycarbonylamino)-1-(7-tetrahydropyran-4-yl-2,7-diazaspiro[3.5]nonane-2-carbonyl)pentyl]carbamoyl]-3-methyl-butyl]amino]-2-oxo-ethyl]amino]-2oxo-ethyl]carbamate (24C) (200 mg, 0.21 mmol) and trifluoroacetic acid (2 mL) were added in a 50 mL reaction flask, and the system was allowed to react at room temperature for 2 h. Then the reaction solution was concentrated under reduced pressure, and the residue was separated and purified by preparative liquid chromatography (preparation conditions: instrument: Gilson GX-281; column: Xbridge C18, 150×30 mm I.D., 5 μm; mobile phase: A for ACN and B for H₂O; isocratic: A 65%; flow rate: 30 mL/min; back pressure: 1000 PSI; column temperature: 30° C.; wavelength: 210 nm; period: 18 min; sample preparation: the compound dissolved in 12 mL methanol; injection: 0.9 mL/needle). The preparation was concentrated under reduced pressure to remove most of the solvent, and lyophilized to obtain (2R)-2-[[(2R)-2-[[(2R)-2-amino-3-phenyl-propanoyl]amino]-3-phenyl-propanoyl]amino]-N-[(1R)-5-amino-1-(7-tetrahydropyran-4-yl-2,7-diazaspiro[3.5]nonane2-carbonyl)pentyl]-4-methyl-pentanamide; tri-trifluoroacetic acid (compound 24) as white powder (135 mg, yield 86.1%).

MS m/z=373.9[M+2H]+/2;

¹H NMR (400 MHz, D₂O) δ 7.46-7.29 (m, 10H), 4.71 (t, 1H), 4.27-4.16 (m, 7H), 3.93-3.86 (m, 2H), 3.66-3.53 (m, 5H), 3.25-3.05 (m, 8H), 2.34-2.13 (m, 6H), 1.79-1.43 (m, 11H), 1.02-0.95 (m, 6H).

Example 23: (2R)-2-[[(2R)-2-[[(2R)-2-amino-3-phenyl-propanoyl]amino]-3-phenyl-propanoyl]amino]-N-[(1R)-5-amino-1-(2-pyrrolidin-1-yl-7-azaspiro[3.5]nonane-7-carbonyl)pentyl]-4-methyl-pentanamide tri-trifluoroacetic acid (compound 25)

addition, the reaction was allowed to proceed at room temperature for 6 h. The reaction solution was suction-filtered, and the filtrate was washed with a saturated sodium bicarbonate solution (30 mL). After the liquid separation, the organic layer was dried over anhydrous sodium sulfate, suction-filtered, and the filtrate was concentrated under

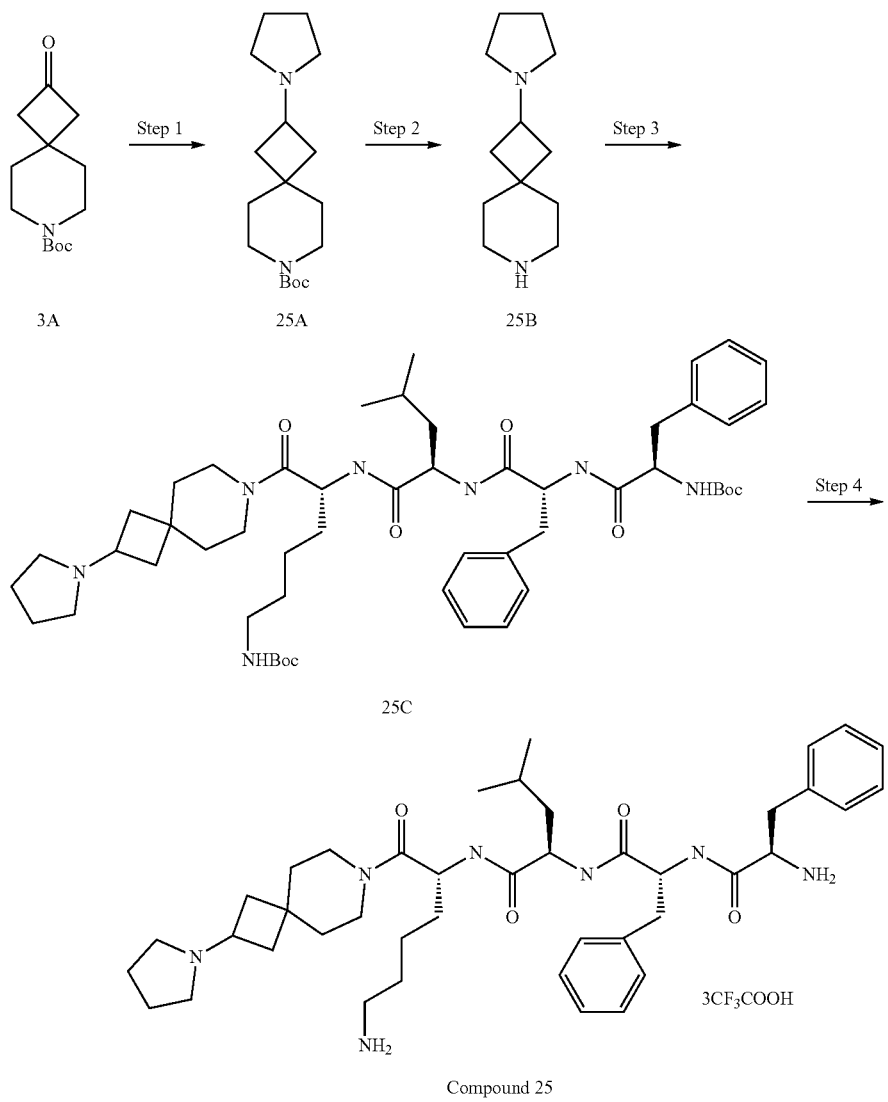

Step 1: tert-butyl 2-pyrrolidin-1-yl-7-azaspiro[3.5]nonane-7-carboxylate (25A)

25A

Tert-butyl 2-oxo-7-azaspiro[3.5]nonane-7-carboxylate (3A) (131 mg, 0.55 mmol), acetic acid (66 mg, 1.1 mmol), pyrrolidin (39 mg, 0.55 mmol), sodium triacetoxyborohydride (233 mg, 1.1 mmol) and dichloromethane (20 mL) were added sequentially in a 50 mL reaction flask. After the reduced pressure to obtain tert-butyl 2-pyrrolidin-1-yl-7-azaspiro[3.5]nonane-7-carboxylate (25A)) as white powder (120 mg, yield 75%).

Step 2: 2-pyrrolidin-1-yl-7-azaspiro[3.5]nonane (25B)

25B

Tert-butyl (2-pyrrolidin-1-yl-7-azaspiro[3.5]nonane-7-carboxylate (25A) (120 mg, 0.41 mmol) and dichloromethane (10 mL) were added in a 50 mL reaction flask, and trifluoroacetic acid (2 mL) was added dropwise at room temperature. After the addition, the system was allowed to react at room temperature for 3 h. The reaction solution was directly concentrated under reduced pressure to obtain crude 2-pyrrolidin-1-yl-7-azaspiro[3.5]nonane (25B) as yellow oily liquid (80 mg, yield 100%), and used directly in the next reaction.

Step 3: tert-butyl N-[(1R)-1-benzyl-2-[[(1R)-1-benzyl-2-[[(1R)-1-[[(1R)-5-(tert-butoxycarbonylamino)-1-(2-pyrrolidin-1-yl-7-azaspiro[3.5]nonane-7-carbonyl)pentyl]carbamoyl]-3-methyl-butyl]amino]-2-oxo-ethyl]amino]-2-oxo-ethyl]carbamate (25C)

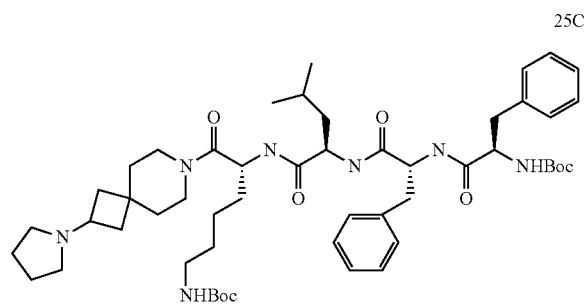 [SMILES: CC(C)C[C@@H](NC(=O)[C@@H](Cc1ccccc1)NC(=O)[C@@H](Cc1ccccc1)NC(=O)OC(C)(C)C)C(=O)N[C@H](CCCCNC(=O)OC(C)(C)C)C(=O)N1CCC2(CC1)CC(N1CCCC1)C2]

25C

Crude 2-pyrrolidin-1-yl-7-azaspiro[3.5]nonane (25B) (80 mg, 0.41 mmol), 1-(3-dimethylaminopropyl)-3-ethylcarbodiimide hydrochloride (96 mg, 0.5 mmol), 1-hydroxybenzotriazole (67.5 mg, 0.5 mmol), intermediate 1 (309 mg, 0.41 mmol) and dichloromethane (20 mL) were added in a 50 mL single-necked flask, and the system was allowed to react at room temperature for 5 h. The reaction solution was concentrated under reduced pressure, and the residue was separated and purified by silica gel column chromatography (dichloromethane:methanol (v:v)=50:1) to obtain tert-butyl (1R)-1-benzyl-2-[[(1R)-1-benzyl-2-[[(1R)-1-[[(1R)-5-(tert-butoxycarbonylamino)-1-(2-pyrrolidin-1-yl-7-azaspiro[3.5]nonane-7-carbonyl)pentyl]carbamoyl]-3-methyl-butyl]amino]-2-oxo-ethyl]amino]-2-oxo-ethyl]carbamate (25C) as light yellow solid (344 mg, yield 90%).

Step 4: (2R)-2-[[(2R)-2-[[(2R)-2-amino-3-phenyl-propanoyl]amino]-3-phenyl-propanoyl]amino]-N-[(1R)-5-amino-1-(2-pyrrolidin-1-yl-7-azaspiro[3.5]nonane-7-carbonyl)pentyl]-4-methyl-pentanamide tri-trifluoroacetic acid (compound 25)

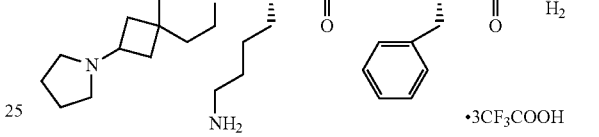

Compound 25

Tert-butyl (1R)-1-benzyl-2-[[(1R)-1-benzyl-2-[[(1R)-1-[[(1R)-5-(tert-butoxycarbonylamino)-1-(2-pyrrolidin-1-yl-7-azaspiro[3.5]nonane-7-carbonyl)pentyl]carbamoyl]-3-methyl-butyl]amino]-2-oxo-ethyl]amino]-2-oxo-ethyl] carbamate (25C) (344 mg, 0.37 mmol) and trifluoroacetic acid (2 mL) was added in a 50 mL reaction flask, and the system was allowed to react at room temperature for 2 h. Then the reaction solution was concentrated under reduced pressure, and the residue was separated and purified by preparative liquid chromatography (preparation conditions: instrument: Gilson GX-281; column: Xbridge C18, 150×30 mm I.D., 5 μm; mobile phase: A for ACN and B for $H_2O$; isocratic: A 65%; flow rate: 30 mL/min; back pressure: 1000 PSI; column temperature: 30° C.; wavelength: 210 nm; period: 18 min; sample preparation: the compound dissolved in 12 mL methanol; injection: 0.9 mL/needle). The preparation was concentrated under reduced pressure to remove most of the solvent, and lyophilized to obtain ((2R)-2-[[(2R)-2-[[(2R)-2-amino-3-phenyl-propanoyl)amino]-3-phenyl-propanoyl]amino]-N-[(1R)-5-amino-1-(2-pyrrolidin-1-yl-7-azaspiro[3.5]nonane-7-carbonyl)pentyl]-4-methyl-pentanamide; tri-trifluoroacetic acid (compound 25) as white powder (249 mg, yield 70%).

MS m/z=365.8 $[M+2H]^+/2$;

$^1H$ NMR (400 MHz, $D_2O$) δ 7.43-7.13 (m, 10H), 4.71-4.70 (m, 1H), 4.62 (t, 1H), 4.30-4.17 (m, 2H), 3.82-3.74 (m, 1H), 3.68-3.39 (m, 5H), 3.38-3.21 (m, 1H), 3.15 (d, 2H), 3.06-2.90 (m, 6H), 2.43-2.25 (m, 2H), 2.16-1.89 (m, 6H), 1.78-1.27 (m, 13H), 0.89 (dd, 6H).

Example 24: (2R)-1-[7-[(2R)-6-amino-2-[[(2R)-2-[[(2R)-2-[[(2R)-2-amino-3-phenyl-propanoyl]amino]-3-phenyl-propanoyl]amino]-4-methyl-pentanoyl]amino]hexanoyl]-7-azaspiro[3.5]nonan-2-yl]pyrrolidin-2-carboxylic acid tri-trifluoroacetic acid (compound 26)
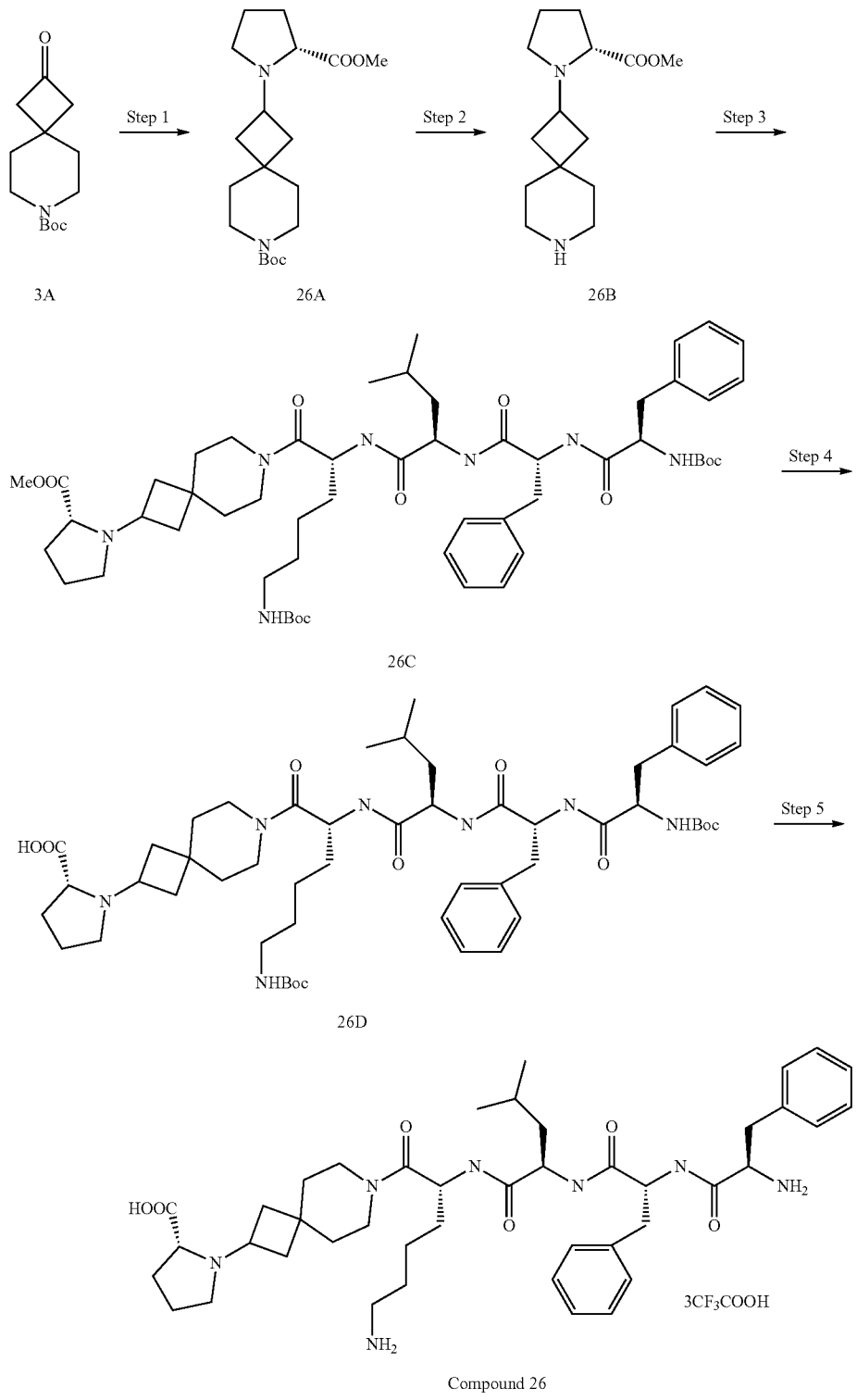
Compound 26

Step 1: tert-butyl2-[(2R)-2-methoxycarbonylpyrrolidin-1-yl]-7-azaspiro[3.5]nonane-7-carboxylat

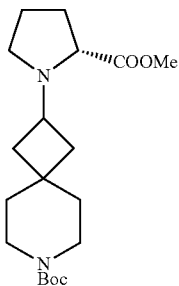

26A

Step 2: methyl (2R)-1-(7-azaspiro[3.5]nonan-2-yl)pyrrolidin-2-carboxylate (26B)

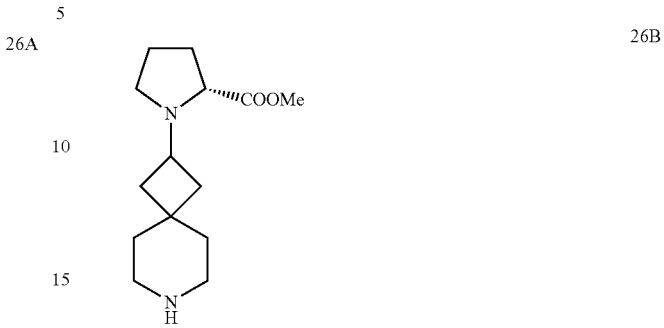

Boc Tert-butyl 2-oxo-7-azaspiro[3.5]nonane-7-carboxylate (3A) (287 mg, 1.2 mmol), acetic acid (144 mg, 2.4 mmol), D-proline methyl ester (154 mg, 1.2 mmol), sodium triacetoxyborohydride (233 mg, 2.4 mmol) and dichloromethane (30 mL) were added sequentially in a 50 mL reaction flask. After the addition, the reaction was allowed to proceed at room temperature for 6 h. The reaction solution was suction-filtered, and the filtrate was washed with a saturated sodium bicarbonate solution (50 mL). After the liquid separation, the organic layer was dried over anhydrous sodium sulfate, suction-filtered, and the filtrate was concentrated under reduced pressure to obtain tert-butyl 2-pyrrolidin-1-yl-7-azaspiro[3.5]nonane-7-carboxylate (26A)) as white powder (275 mg, yield 65%).

Tert-butyl 2-[(2R)-2-methoxycarbonylpyrrolidin-1-yl]-7-azaspiro[3.5]nonane-7-carboxylate (26A)(275 mg, 0.78 mmol) and dichloromethane (10 mL) were added in a 50 mL reaction flask, and trifluoroacetic acid (2 mL) was added dropwise at room temperature. After the addition, the system was allowed to react at room temperature for 3 h. The reaction solution was directly concentrated under reduced pressure to obtain methyl (2R)-1-(7-azaspiro[3.5]nonan-2-yl)pyrrolidin-2-carboxylate (26B) as yellow oily liquid (196 mg, yield 100%), and used directly in the next reaction.

Step 3: Methyl (2R)-1-[7-[(2R)-6-(tert-butoxycarbonylamino)-2-[[(2R)-2-[[(2R)-2-[[(2R)-2-(tert-butoxycarbonylamino)-3-phenyl-propanoyl]amino]-3-phenyl-propanoyl]amino]-4-methyl-pentanoyl]amino]hexanoyl]-7-azaspiro[3.5]nonan-2-yl]pyrrolidin-2-carboxylate (26C)

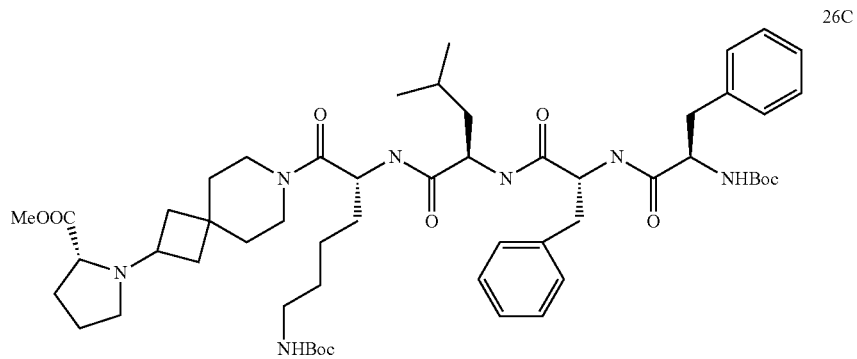 [SMILES: COC(=O)[C@H]1CCCN1C1CC2(CCN(C(=O)[C@@H](CCCCNC(=O)OC(C)(C)C)NC(=O)[C@@H](CC(C)C)NC(=O)[C@@H](Cc3ccccc3)NC(=O)[C@@H](Cc3ccccc3)NC(=O)OC(C)(C)C)CC2)C1]

Methyl (2R)-1-(7-azaspiro[3.5]nonan-2-yl)pyrrolidin-2-carboxylate (26B) (196 mg, 0.78 mmol), 1-(3-dimethylaminopropyl)-3-ethylcarbodiimide hydrochloride (180 mg, 0.94 mmol), 1-hydroxybenzotriazole (127 mg, 0.94 mmol), intermediate 1 (587 mg, 0.78 mmol) and dichloromethane (20 mL) were added in a 50 mL single-necked flask, and the system was allowed to react at room temperature for 5 h. The reaction solution was concentrated under reduced pressure, and the residue was separated and purified by silica gel column chromatography (dichloromethane:methanol (v:v) =50:1) to obtain methyl (2R)-1-[7-[(2R)-6-(tert-butoxycarbonylamino)-2-[[(2R)-2-[[(2R)-2-[[tert-butoxycarbonylamino)-3-phenyl-propanoyl)amino)-3-phenyl-propanoyl]amino]-4-methyl-pentanoyl]amino]hexanoyl]-7-azaspiro[3.5]nonan-2-yl]pyrrolidin-2-carboxylate (26C) as white solid (385 mg, yield 50%).

Step 4: (2R)-1-[7-[(2R)-6-(tert-butoxycarbonylamino)-2-[[(2R)-2-[[(2R)-2-[[(2R)-2-(tert-butoxycarbonylamino)-3-phenyl-propanoyl]amino]-3-phenyl-propanoyl]amino]-4-methyl-pentanoyl]amino]hexanoyl]-7-azaspiro[3.5]nonan-2-yl]pyrrolidin-2-carboxylic acid (26D)

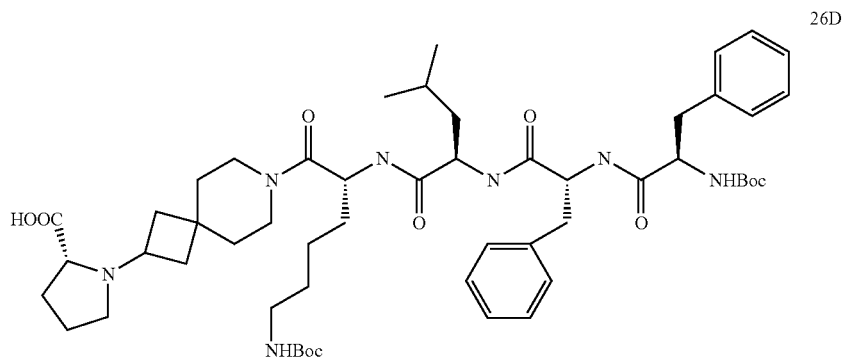 [SMILES: CC(C)C[C@@H](NC(=O)[C@@H](Cc1ccccc1)NC(=O)[C@@H](Cc1ccccc1)NC(=O)OC(C)(C)C)C(=O)N[C@H](CCCCNC(=O)OC(C)(C)C)C(=O)N1CCC2(CC1)CC(N1CCC[C@@H]1C(=O)O)C2]

Methyl (2R)-1-[7-[(2R)-6-(tert-butoxycarbonylamino)-2-[[(2R)-2-[[(2R)-2-[[tert-butoxycarbonylamino)-3-phenyl-propanoyl)amino]-3-phenyl-propanoyl]amino]-4-methyl-pentanoyl]amino]hexanoyl]-7-azaspiro[3.5]nonan-2-yl]pyrrolidin-2-carboxylate (26C) (385 mg, 0.39 mmol) was dissolved in methanol (5 mL) at room temperature, and an aqueous sodium hydroxide (16 mg, 0.4 mmol) solution (10 mL) was added to the reaction solution. The system was allowed to react at room temperature for 5 h. The reaction solution was adjusted to pH<4 with a 1M aqueous hydrochloric acid solution, extracted with ethyl acetate (20 mL), and the mixture was subjected to a liquid separation process The organic phases were dried over anhydrous sodium sulfate, filtered, and the filtrate was concentrated under reduced pressure to obtain methyl (2R)-1-[7-[(2R)-6-(tert-butoxycarbonylamino)-2-[[(2R)-2-[[(2R)-2-[[(2R)-2-(tert-butoxycarbonylamino)-3-phenyl-propanoyl)amino]-3-phenyl-propanoyl]amino]-4-methyl-pentanoyl]amino]hexanoyl]-7-azaspiro[3.5]nonan-2-yl]pyrrolidin-2-carboxylate (26D) as white solid (345 mg, yield 93%).

Step 5: (2R)-1-[7-[(2R)-6-amino-2-[[(2R)-2-[[(2R)-2-[[(2R)-2-amino-3-phenyl-propanoyl]amino]-3-phenyl-propanoyl]amino]-4-methyl-pentanoyl]amino]hexanoyl]-7-azaspiro[3.5]nonan-2-yl]pyrrolidin-2-carboxylic acid; tri-trifluoroacetic acid (compound 26)

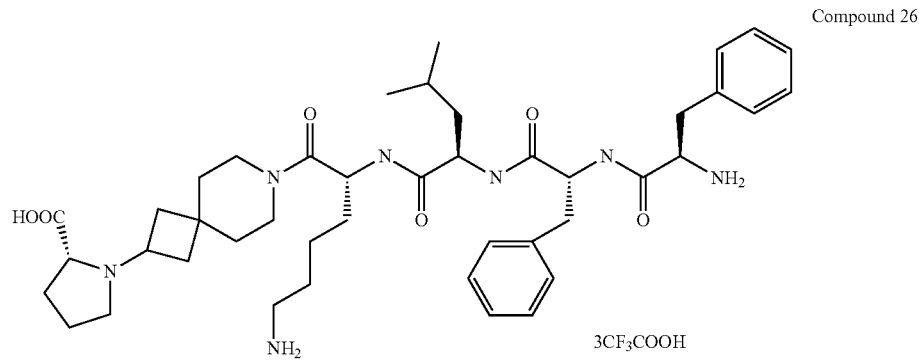 [SMILES: CC(C)C[C@@H](NC(=O)[C@@H](Cc1ccccc1)NC(=O)[C@H](N)Cc1ccccc1)C(=O)N[C@H](CCCCN)C(=O)N1CCC2(CC1)CC(N1CCC[C@@H]1C(=O)O)C2]

(2R)-1-[7-[(2R)-6-(tert-butoxycarbonylamino)-2-[[(2R)-2-[[(2R)-2-[[(2R)-2-(tert-butoxycarbonylamino)-3-phenyl-propanoyl]amino)-3-phenyl-propanoyl]amino]-4-methyl-pentanoyl]amino]hexanoyl]-7-azaspiro[3.5]nonan-2-yl]pyrrolidin-2-carboxylic acid (26D) (345 mg, 0.36 mmol) and trifluoroacetic acid (2 mL) were added in a 50 mL reaction flask, and the system was allowed to react at room temperature for 2 h. Then the reaction solution was concentrated under reduced pressure, and the residue was separated and purified by preparative liquid chromatography (preparation conditions: instrument: Gilson GX-281; column: Xbridge C18, 150×30 mm I.D., 5 μm; mobile phase: A for ACN and B for H₂O; isocratic: A 65%; flow rate: 30 mL/min; back pressure: 1000 PSI; column temperature: 30° C.; wavelength: 210 nm; period: 18 min; sample preparation: the compound dissolved in 12 mL methanol; injection: 0.9 mL/needle), The preparation was concentrated under reduced pressure to remove most of the solvent, and lyophilized to obtain (2R)-1-[7-[(2R)-6-amino-2-[[(2R)-2-[[(2R)-2-[[(2R)-2-amino-3-phenyl propanoyl]amino]-3-phenyl-propanoyl]amino]-4-methyl-pentanoyl]amino]hexanoyl]-7-azaspiro[3.5]nonan-2-yl]pyrrolidin-2-carboxylic acid; tri-trifluoroacetic acid (compound 26) as white powder (240 mg, yield 60%).

MS m/z=387.8 [M+2H]$^+$/2;

1H NMR (400 MHz, D₂O) δ 7.44-7.09 (m, 10H), 4.27-4.19 (m, 3H), 3.96-3.84 (m, 2H), 3.67-3.50 (m, 3H), 3.48-3.21 (m, 3H), 3.19-2.89 (m, 7H), 2.50-2.22 (m, 3H), 2.18-1.91 (m, 5H), 1.78-1.24 (m, 13H), 0.88 (dd, 6H).

Example 25: 2-[(2R)-6-amino-2-[[(2R)-2-[[(2R)-2-[[(2R)-2-amino-3-phenyl-propanoyl]amino]-3-phenyl-propanoyl]amino]-4-methyl-pentanoyl]amino]hexanoyl]-N-methyl-2,7-diazaspiro[3.5]nonane-7-carboxamide; di-trifloroacetic acid (compound 27)

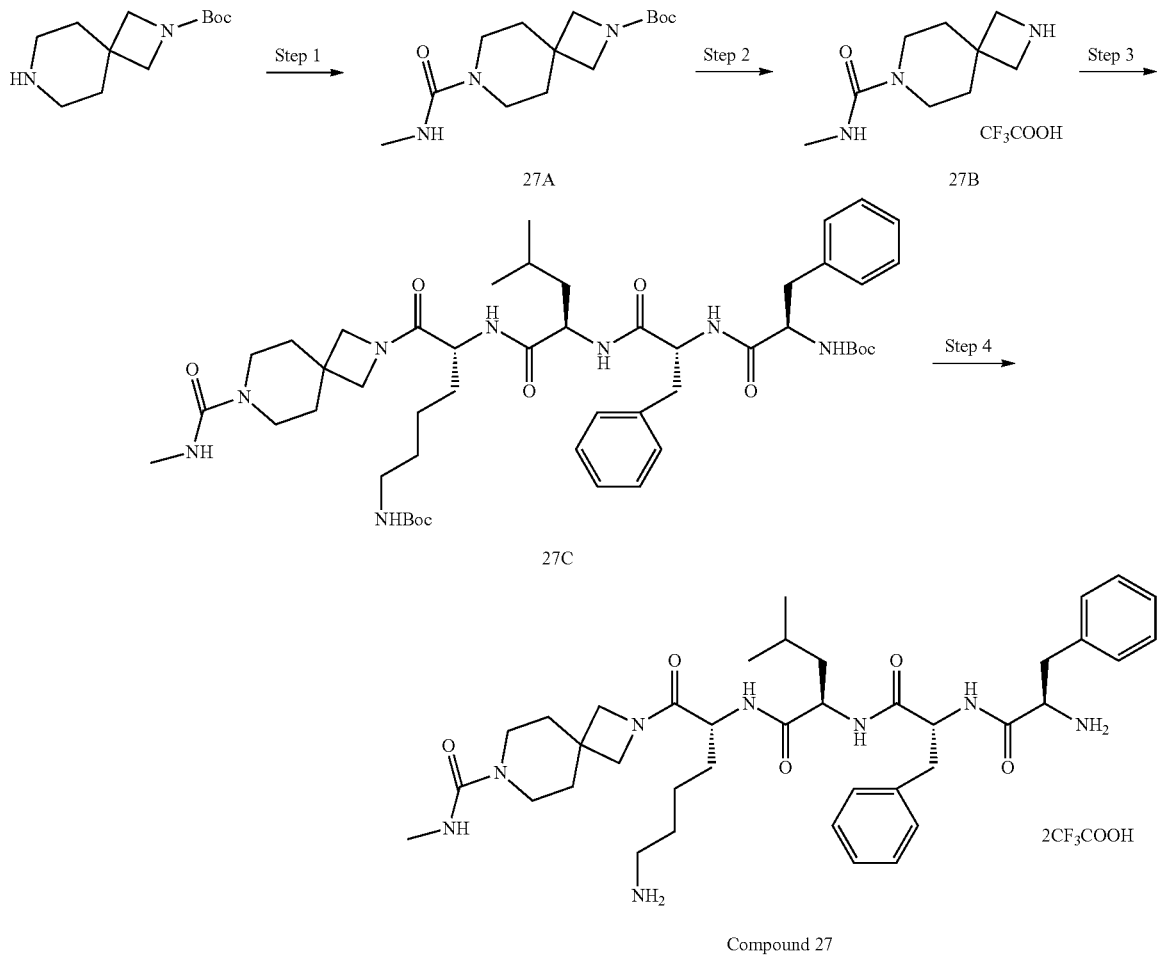

Compound 27

Step 1: tert-butyl 7-(methylcarbamoyl)-2,7-diazaspiro[3.5]nonane-2-carboxylate (27A)

2-tert-butoxygencarbonyl-2,7-diazaspiro[3.5]nonane (0.45 g, 2 mmol), dichloromethane (10 mL) and triethylamine (0.30 g, 3 mmol) were added to a reaction flask under nitrogen protection; It was cooled to 0-5° C., and methylaminoformyl chloride (0.20 g, 2.2 mmol) was added. After the addition, cooling was removed, and the temperature was raised to room temperature and reacted for 1 h. TLC was used to monitor the completion of the reaction. Dichloromethane (10 mL) and water (10 mL) were added, and after stirring for 5 minutes, the layers were left to separate; the organic layer was dried over anhydrous sodium sulfate, filtered, and concentrated under reduced pressure. The residue was separated and purified by silica gel column chromatography (dichloromethane/methanol=(v/v) 20/1) to obtain tert-butyl 7-(methylcarbamoyl)-2,7-diazaspiro-[3.5] nonane-2-carboxylate (27A) as light yellow oily substance (0.48 g, yield 85%).

Step 2: N-methyl-2,7-diazaspiro[3.5]nonane-7-carboxamide;2,2,2-trifluoroacetic acid (27B)

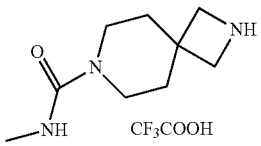

Tert-butyl 7-(methylcarbamoyl)-2,7-diazaspiro-[3.5] nonane-2-carboxylate (27A, 0.48 g, 1.7 mmol) was added to dichloromethane (5 mL) in a 50 mL reaction flask under nitrogen protection, and trifluoroacetic acid (2 mL) was added under stirring. After the addition, the system was allowed to react at room temperature for 2 h. TLC was used to monitor the completion of the reaction, and the reaction was concentrated to dryness under reduced pressure to obtain N-methyl-2,7-diazaspiro[3.5]nonane-7-carboxamide; trifluoroacetic acid (27B) as light yellow oily substance (0.49 g, yield 97%), and used directly in the next step.

Step 3: tert-butylN-[(1R)-1-benzyl-2-[[(1R)-1-benzyl-2-[[(1R)-1-[[(1R)-5-(tert-butoxycarbonylamino)-1-[7-(methylcarbamoyl)-2,7-diazaspiro[3.5]nonane-2-carbonyl]pentyl]carbamoyl]-3-methyl-butyl]amino]-2-oxo-ethyl]amino]-2-oxo-ethyl]carbamate (27C)

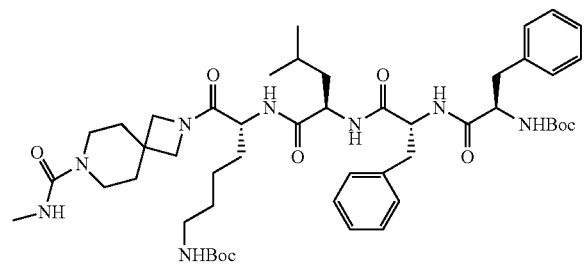 [SMILES: CNC(=O)N1CCC2(CC1)CN(C(=O)[C@@H](CCCCNC(=O)OC(C)(C)C)NC(=O)[C@@H](CC(C)C)NC(=O)[C@@H](Cc1ccccc1)NC(=O)[C@@H](Cc1ccccc1)NC(=O)OC(C)(C)C)C2]

Crude N-methyl-2,7-diazaspiro[3.5]nonane-7-carboxamide; trifluoroacetic acid (27B) (0.48 g, 2.60 mmol) was added in dichloromethane (10 mL) in a 50 mL reaction flask under nitrogen protection. It was cooled to 0° C. in an ice bath, and intermediate 1 (0.50 g, 0.66 mmol), 1-(3-dimethylaminopropyl)-3-ethylcarbodiimide hydrochloride (200 mg, 1.73 mmol), 1-hydroxybenzotriazole (125 mg, 0.93 mmol) were added. After the addition, the system was allowed to react at room temperature for 3 h. Subsequently, a 1M aqueous hydrochloric acid solution (15 mL) was added to the reaction solution, and the mixture was stirred and then subjected to a liquid separation process. A saturated aqueous sodium carbonate solution (15 mL) was added to the organic phase, and the mixture was stirred for 30 minutes and then subjected to a liquid separation process. The organic phase was washed with a saturated aqueous sodium chloride solution (15 mL), dried over anhydrous sodium sulfate, filtered, and the filtrate was concentrated under reduced pressure to obtain crude tert-butyl N-[(1R)-1-benzyl-2-[[(1R)-1-benzyl-2-[[(1R)-1-[[(1R)-5-(tert-butoxycarbonylamino)-1-[7-(methylcarbamoyl)-2,7-diazaspiro[3.5]nonane-2-carbonyl]pentyl]carbamoyl]-3-methyl-butyl]amino]-2-oxo-ethyl]amino]-2-oxo-ethyl]carbamate (27C) as light yellow foamy solid (0.5 g, yield 80%), and used directly in the next reaction.

Step 4: 2-[(2R)-6-amino-2-[[(2R)-2-[[(2R)-2-[[(2R)-2-amino-3-phenyl-propanoyl]amino]-3-phenyl-propanoyl]amino]-4-methyl-pentanoyl]amino]hexanoyl]-N-methyl-2,7-diazaspiro[3.5]nonane-7-carboxamide; di-trifluoroacetic acid (compound 27)

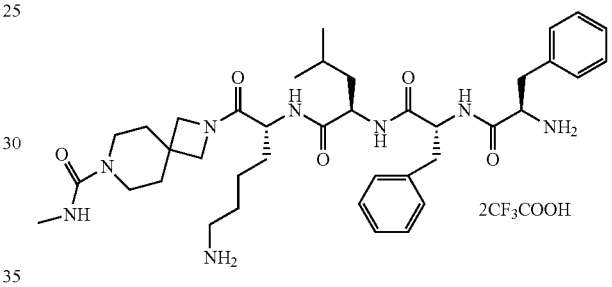

Crude tert-butyl N-[(1R)-1-benzyl-2-[[(1R)-1-benzyl-2-[[(1R)-1-[[(1R)-5-(tert-butoxycarbonylamino)-1-[7-(methylcarbamoyl)-2,7-diazaspiro[3.5]nonane-2-carbonyl]pentyl]carbamoyl]-3-methyl-butyl]amino]-2-oxo-ethyl]amino]-2-oxo-ethyl]carbamate (27C) (0.5 g, 0.5 mmol) was dissolved in dichloromethane (7.5 mL), and trifluoroacetic acid (3.5 mL) was added. The system was stirred at room temperature for 1 h. Subsequently, the reaction solution was concentrated under reduced pressure, and the residue was separated and purified by preparative liquid chromatography (preparation conditions: instrument: Gilson GX-281; column: Xbridge C18, 150×30 mm I.D., 5 μm; mobile phase: A for ACN and B for H$_2$O; isocratic: A 65%; flow rate: 30 mL/min; back pressure: 1000 PSI; column temperature: 30° C.; wavelength: 210 nm; period: 18 min; sample preparation: the compound dissolved in 12 mL methanol; injection: 0.9 mL/needle). The preparation was concentrated under reduced pressure to remove most of the solvent, and lyophilized to obtain 2-[(2R)-6-amino-2-[[(2R)-2-[[(2R)-2-[[(2R)-2-amino-3-phenyl-propanoyl]amino]-3-phenyl-propanoyl]amino]-4-methylpentanoyl]amino]hexanoyl]-N-methyl-2,7-diazaspiro[3.5]nonane-7-carboxamide; di-trifluoroacetic acid (compound 27) as white solid (220 mg, yield 40%).

MS m/z (ESI): 360.3[M+1H]$^+$/2;

$^1$H NMR (400 MHz, D$_2$O) δ 7.45-7.16 (m, 10H), 4.66-4.57 (m, 1H), 4.32-4.19 (m, 2H), 4.19-3.99 (m, 3H), 3.83-3.66 (m, 2H), 3.40-3.22 (m, 4H), 3.22-3.12 (m, 2H), 3.06-2.99 (m, 4H), 2.69 (s, 3H), 1.80-1.62 (m, 8H), 1.58-1.27 (m, 5H), 1.03-0.79 (m, 6H).

Example 26: 7-[(2R)-6-amino-2-[[(2R)-2-[[(2R)-2-[[(2R)-2-amino-3-phenyl-propanoyl]amino]-3-phenyl-propanoyl]amino]-4-methyl-pentanoyl]amino]hexanoyl]-5,5-difluoro-N-methyl-2,7-diazaspiro[3.5]nonane-2-carboxamide; di-trifluoroacetic acid (compound 28)

After cooling to −10° C., methylaminoformyl chloride (104 mg, 1.11 mmol) was added dropwise. After the addition, the reaction was allowed to proceed at room temperature for 3 h. A 3 M diluted hydrochloric acid (50 mL) was added to the reaction solution, and the mixture was extracted with dichloromethane (60 mL×2). The organic phases were dried over anhydrous sodium sulfate, filtered, and the filtrate was

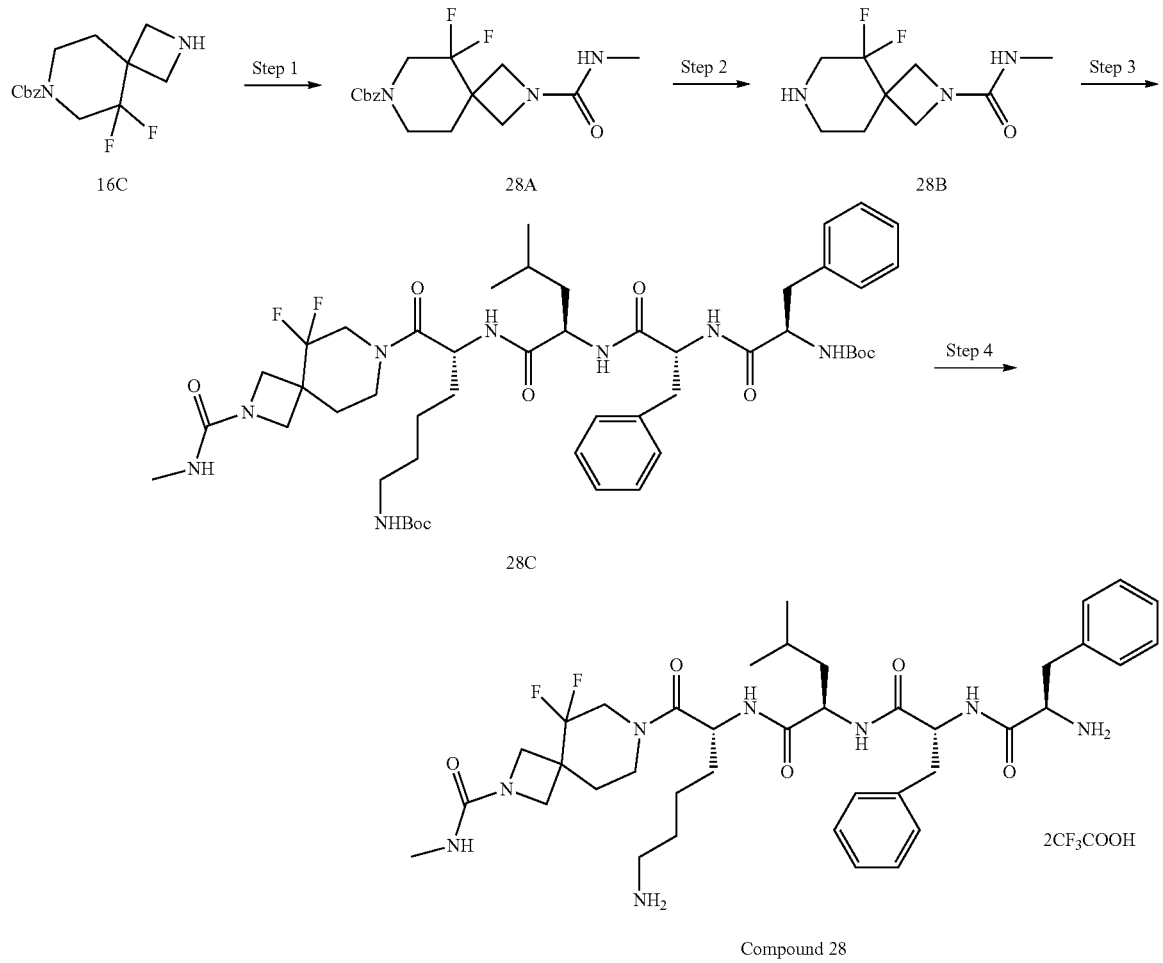

Step 1: benzyl 5,5-difluoro-2-(methylcarbamoyl)-2,7-diazaspiro[3.5]nonane-7-carboxylate (28A)

concentrated under reduced pressure to obtain benzyl 5,5-difluoro-2-(methylcarbamoyl)-2,7-diazaspiro[3.5]nonane-7-carboxylate (28A) as white solid (268 mg, yield 68.6%).
MS m/z (ESI): 354.1[M+H]$^+$;
$^1$H NMR (400 MHz, CDCl3) δ 7.41-7.28 (m, 5H), 5.14 (s, 2H), 4.09 (d, 2H), 3.65 (dd, 4H), 3.51-3.44 (m, 2H), 2.79 (s, 3H), 2.01 (s, 2H).

Step 2: 5,5-difluoro-N-methyl-2,7-diazaspiro[3.5]nonane-2-carboxamide (28B)

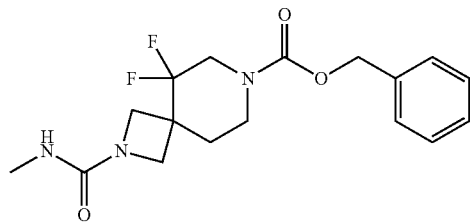

Benzyl 5,5-difluoro-2,7-diazaspiro[3.5]nonane-7-carboxylate (16C) (330 mg, 1.11 mmol), triethylamine (364 mg, 3.6 mmol) and dichloromethane (20 mL) were added in a 50 mL reaction flask, and it was dissolved under stirring.

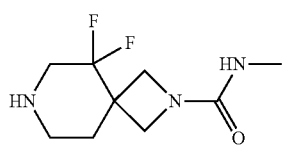

Benzyl 5,5-difluoro-2-(methylcarbamoyl)-2,7-diazaspiro[3.5]nonane-7-carboxylate (28A) (269 mg, 0.76 mmol), palladium on carbon (54 mg, 20 wt %) and methanol (5 mL) were added in a 50 mL reaction flask. The atmosphere was replaced with hydrogen 3 times, and the mixture reacted under a hydrogen (balloon) atmosphere at room temperature for 3 h. The reaction solution was then filtered through diatomite, and the filtrate was concentrated under reduced pressure to obtain crude 5,5-difluoro-N-methyl-2,7-diazaspiro[3.5]nonane-2-carboxamide (28B) as light yellow oily substance (164 mg, yield 98.55%), and used directly in the next reaction.

MS m/z (ESI): 220.2[M+H]⁺;

Step 3: tert-butyl N-[(1R)-1-benzyl-2-[[(1R)-1-benzyl-2-[[(1R)-1-[[(1R)-5-(tert-butoxy carbonylamino)-1-[5,5-difluoro-2-(methylcarbamoyl)-2,7-diazaspiro[3.5]nonane-7-carbonyl]pentyl]carbamoyl]-3-methyl-butyl]amino]-2-oxo-ethyl]amino]-2-oxo- ethyl]carbamate (28C)

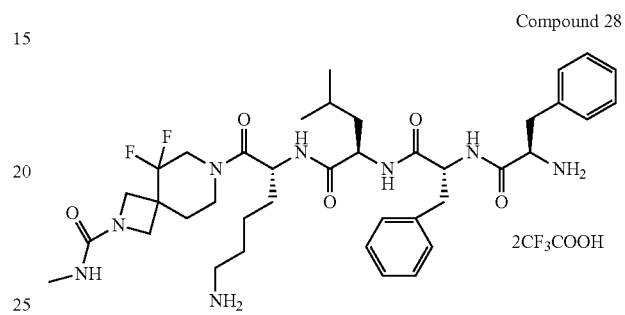

28C

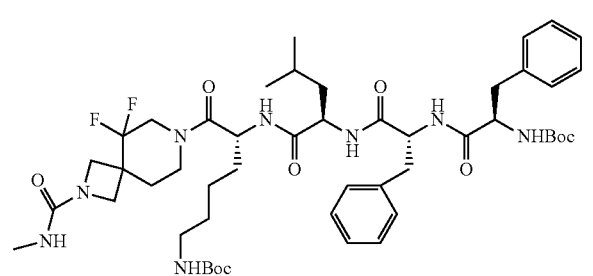

Crude 5,5-difluoro-N-methyl-2,7-diazaspiro[3.5]nonane-2-carboxamide (28B) (164 mg, 0.75 mmol), 1-(3-dimethylaminopropyl)-3-ethylcarbodiimide hydrochloride (0.374 g, 1.95 mmol), 1-hydroxybenzotriazole (110 mg, 0.81 mmol), intermediate 1 (565 mg, 0.75 mmol) and dichloromethane (50 mL) were added sequentially in a 50 mL reaction flask, and the system was allowed to react at room temperature for 5 h. The reaction solution was concentrated under reduced pressure, and the residue was separated and purified by silica gel column chromatography (dichloromethane:methanol (v:v)=50:1) to obtain tert-butyl N-[(1R)-1-benzyl-2-[[(1R)-1-benzyl-2-[[(1R)-1-[[(1R)-5-(tert-butoxycarbonylamino)-1-[5,5-di fluoro-2-(methylcarbamoyl)-2,7-diazaspiro[3.5]nonane-7-carbonyl]pentyl]carbamoyl]-3-methy 1-butyl]amino]-2-oxo-ethyl]amino]-2-oxo-ethyl]carbamate (28C) as light yellow solid (600 mg, yield 84%).

Step 4: 7-[(2R)-6-amino-2-[[(2R)-2-[[(2R)-2-[[(2R)-2-amino-3-phenyl-propanoyl]amino]-3-phenyl-propanoyl]amino]-4-methyl-pentanoyl]amino]hexanoyl]-5,5-difluoro-N-methyl-2,7-diazaspiro[3.5]nonane-2-carboxamide; ditrifluoroacetic acid (compound 28)

Tert-butyl N-[(1R)-1-benzyl-2-[[(1R)-1-benzyl-2-[[(1R)-1-[[(1R)-5-(tert-butoxycarbonylamino)-1-[5,5-di fluoro-2-(methylcarbamoyl)-2,7-diazaspiro[3.5]nonane-7-carbonyl]pentyl]carbamoyl]-3-methy 1-butyl]amino]-2-oxo-ethyl]amino]-2-oxo-ethyl]carbamate (28C) (600 mg, 0.6 mmol) and trifluoroacetic acid (3 mL) were added in a 50 mL reaction flask, and the system was allowed to react at room temperature for 2 h. Then the reaction solution was concentrated under reduced pressure, and the residue was separated and purified by preparative liquid chromatography (preparation conditions: instrument: Gilson GX-281; column: Xbridge C18, 150×30 mm I.D., 5 μm; mobile phase: A for ACN and B for H₂O; isocratic: A 65%; flow rate: 30 mL/min; back pressure: 1000 PSI; column temperature: 30° C.; wavelength: 210 nm; period: 18 min; sample preparation: the compound dissolved in 12 mL methanol; injection: 0.9 mL/needle). The preparation was concentrated under reduced pressure to remove most of the solvent, and lyophilized to obtain 7-[(2R)-6-amino-2-[[(2R)-2-[[(2R)-2-[[(2R)-2-amino-3-phenyl-propanoyl]amino]-3-phenyl-propanoyl]amino]-4-methyl-pentanoyl]amino]hexanoyl]-5,5-difluoro-N-methyl-2,7-diazaspiro[3.5]nonane-2-carboxamide; di-trifluoroacetic acid (compound 28) as white powder (100 mg, yield 13%).

MS m/z (ESI): 755.5[M+H]⁺;

¹H NMR (400 MHz, D₂O) δ 7.43-7.18 (m, 10H), 4.86-4.75 (m, 1H), 4.65 (t, 1H), 4.39-4.17 (m, 2H), 4.15-4.05 (m, 2H), 4.04-3.45 (m, 6H), 3.24-3.10 (m, 2H), 3.10-2.90 (m, 4H), 2.77-2.60 (m, 3H), 2.06 (d, 2H), 1.85-1.61 (m, 4H), 1.60-1.46 (m, 3H), 1.45-1.27 (m, 2H), 0.92 (dt, 6H).

Example 27: 2-[(2R)-6-amino-2-[[(2R)-2-[[(2R)-2-[[(2R)-2-amino-3-phenyl-propanoyl]amino]-3-phenyl-propanoyl]amino]-4-methyl-pentanoyl]amino]hexanoyl]-5,5-difluoro-N-methyl-2,7-diazaspiro[3.5]nonane-7-carboxamide; ditrifluoroacetic acid (compound 29)

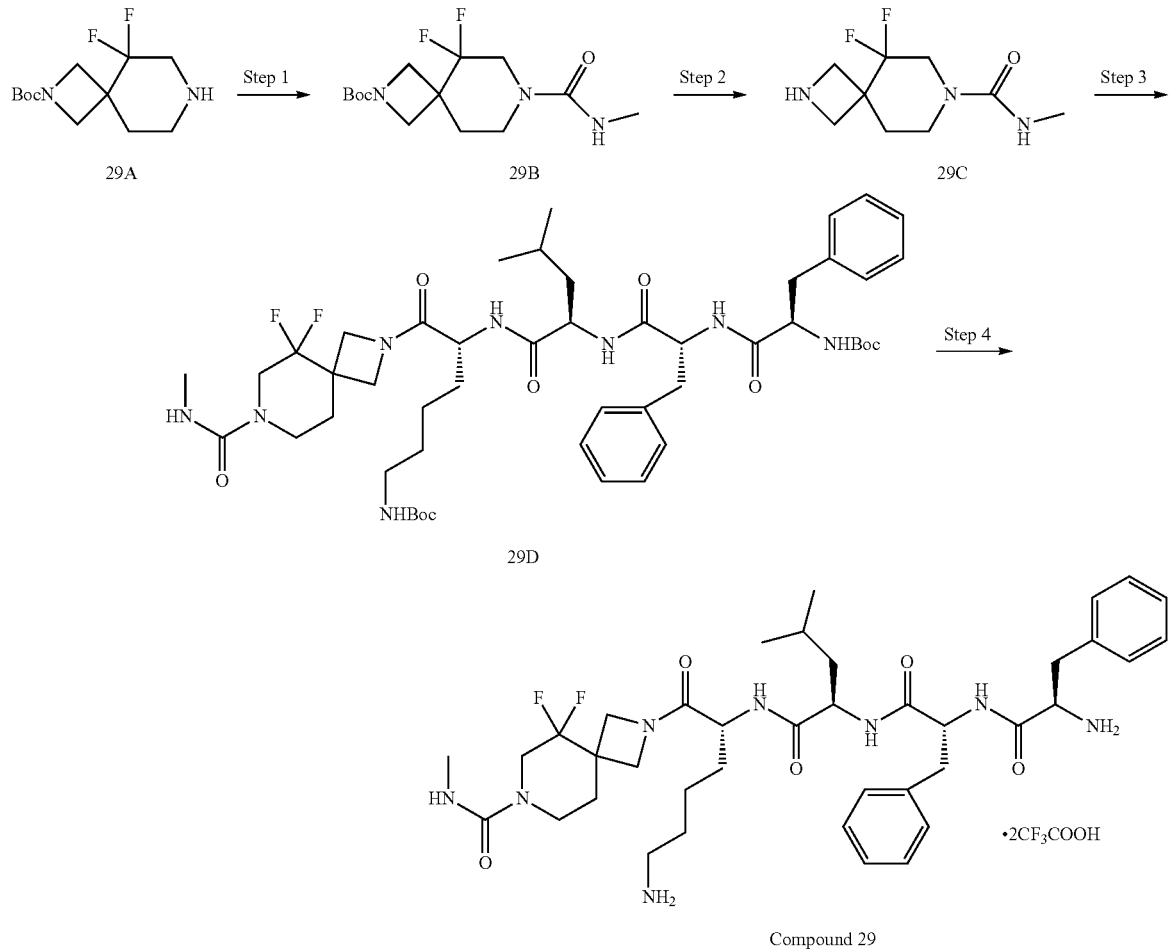

Step 1: tert-butyl 5,5-difluoro-7-(methylcarbamoyl)-2,7-diazaspiro[3.5]nonane-2-carboxylate (29B)

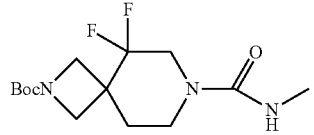

Benzyl 5,5-difluoro-2,7-diazaspiro[3.5]nonane-7-carboxylate (16C) (113 mg, 0.43 mmol), triethylamine (43 mg, 0.43 mmol) and dichloromethane (10 mL) were added in a 50 mL reaction flask, and it was dissolved under stirring. After cooling to −10° C., methylaminoformyl chloride (42 mg, 0.45 mmol) was added dropwise. After the addition, the reaction was allowed to proceed at room temperature for 3 h. A 0.3 M diluted hydrochloric acid (10 mL) was added to the reaction solution, and the mixture was extracted with dichloromethane (5 mL×2). The organic phases were dried over anhydrous sodium sulfate, filtered, and the filtrate was concentrated under reduced pressure to obtain tert-butyl 5,5-difluoro-7-(methylcarbamoyl)-2,7-diazaspiro[3.5]nonane-2-carboxylate (29B) as white solid (96 mg, yield 70%).

Step 2: 5,5-difluoro-N-methyl-2,7-diazaspiro[3.5]nonane-7-carboxamide (29C)

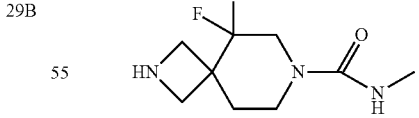

Tert-butyl 5,5-difluoro-7-(methylcarbamoyl)-2,7-diazaspiro[3.5]nonane-2-carboxylate (29B) (96 mg, 0.3 mmol) and dichloromethane (8 mL) were added in a 50 mL reaction flask, and trifluoroacetic acid (2 mL) was added dropwise at room temperature. After the addition, the system was allowed to react at room temperature for 3 h. The reaction solution was directly concentrated under reduced pressure to obtain 5,5-difluoro-N-methyl-2,7-diazaspiro[3.5]nonane-7-carboxamide (29C), as yellow oily liquid (66 mg, yield 100%), and used directly in the next reaction.

Step 3: tert-butylN-[(1R)-1-benzyl-2-[[(1R)-1-benzyl-2-[[(1R)-1-[[(1R)-5-(tert-butoxycarbonylamino)-1-[5,5-difluoro-7-(methylcarbamoyl)-2,7-diazaspiro[3.5]nonane-2-carbonyl]pentyl]carbamoyl]-3-methyl-butyl]amino]-2-oxo-ethyl]amino]-2-oxo-ethyl]carbamate (29D)

Step 4: 2-[(2R)-6-amino-2-[[(2R)-2-[[(2R)-2-[[(2R)-2-amino-3-phenyl-propanoyl]amino]-3-phenyl-propanoyl]amino]-4-methyl-pentanoyl]amino]hexanoyl]-5,5-difluoro-N-methyl-2,7-diazaspiro[3.5]nonane-7-carboxamide ditrifluoroacetic acid (compound 29)

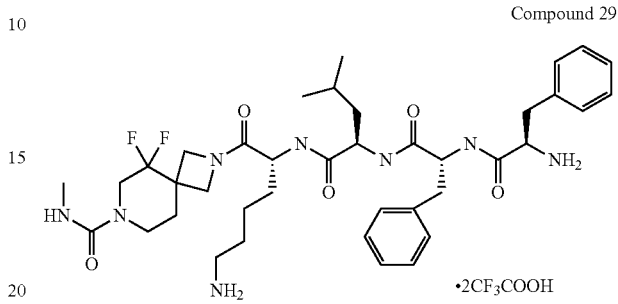

Compound 29

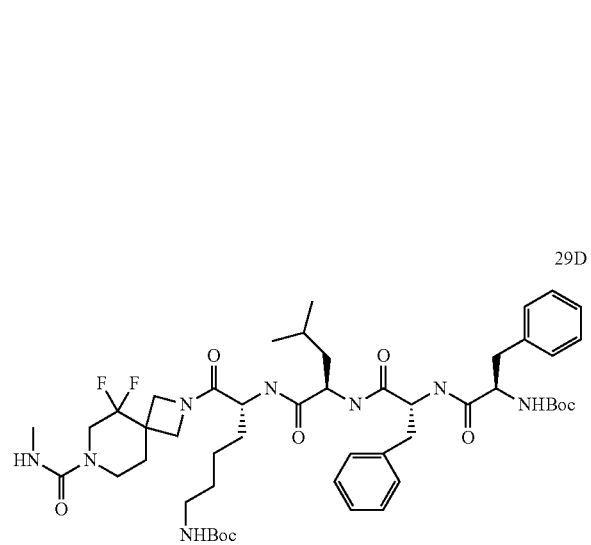 [SMILES: CNC(=O)N1CCC2(CN(C(=O)[C@@H](CCCCNC(=O)OC(C)(C)C)NC(=O)[C@@H](CC(C)C)NC(=O)[C@@H](Cc3ccccc3)NC(=O)[C@@H](Cc3ccccc3)NC(=O)OC(C)(C)C)C2)C(F)(F)C1]

29D 5,5-difluoro-N-methyl-2,7-diazaspiro[3.5]nonane-7-carboxamide (29C) (66 mg, 0.3 mmol), 1-(3-dimethylaminopropyl)-3-ethylcarbodiimide hydrochloride (239 mg, 0.36 mmol), 1-hydroxybenzotriazole (49 mg, 0.36 mmol), intermediate 1 (226 mg, 0.3 mmol) and dichloromethane (30 mL) were added in a 50 mL single-necked flask, and the system was allowed to react at room temperature for 5 h. The reaction solution was concentrated under reduced pressure, and the residue was separated and purified by silica gel column chromatography (dichloromethane:methanol (v:v) =50:1) to obtain tert-butyl (1R)-1-benzyl-2-[[(1R)-1-benzyl-2-[[(1R)-1-[[(1R)-5-(tert-butoxycarbonylamino)-1-[5,5-difluoro-7-(methylcarbamoyl)-2,7-diazaspiro[3.5]nonane-2-carbonyl]pentyl]carbamoyl]-3-methyl-butyl]amino]-2-oxo-ethyl]amino]-2-oxo-ethyl]carbamate (29D) as white solid (286 mg, yield 90%).

Tert-butyl(1R)-1-benzyl-2-[[(1R)-1-benzyl-2-[[(1R)-1-[[(1R)-5-(tert-butoxycarbonylamino)-1-[5,5-difluoro-7-(methylcarbamoyl)-2,7-diazaspiro[3.5]nonane-2-carbonyl]pentyl]carbamoyl]-3-methyl-butyl]amino]-2-oxo-ethyl]amino]-2-oxo-ethyl]carbamate (29D) (286 mg, 0.3 mmol) and trifluoroacetic acid (2 mL) were added in a 50 mL reaction flask, and the system was allowed to react at room temperature for 2 h. Then the reaction solution was concentrated under reduced pressure, and the residue was separated and purified by preparative liquid chromatography (preparation conditions: instrument: Gilson GX-281; column: Xbridge C18, 150×30 mm I.D., 5 μm; mobile phase: A for ACN and B for H₂O; isocratic: A 65%; flow rate: 30 mL/min; back pressure: 1000 PSI; column temperature: 30° C.; wavelength: 210 nm; period: 18 min; sample preparation: the compound dissolved in 12 mL methanol; injection: 0.9 mL/needle). The preparation was concentrated under reduced pressure to remove most of the solvent, and lyophilized to obtain 2-[(2R)-6-amino-2-[[(2R)-2-[[(2R)-2-[[(2R)-2-amino-3-phenyl-propanoyl]amino]-3-phenyl-propanoyl]amino]-4-methyl-pentanoyl]amino]hexanoyl]-5,5-difluoro-N-methyl-2,7-diazaspiro[3.5]nonane-7-carboxamide; di-trifluoroacetic acid (compound 29) as white powder (192 mg, yield 65%).

MS m/z=378.3 [M+2H]$^+$/2;

$^1$H NMR (400 MHz, D$_2$O) δ 7.46-7.12 (m, 10H), 4.64-4.58 (m, 1H), 4.53-4.43 (m, 1H), 4.26-4.19 (m, 2H), 4.17-4.02 (m, 3H), 3.80-3.76 (m, 1H), 3.72-3.57 (m, 2H), 3.36 (s, 2H), 3.19-3.11 (m, 2H), 3.03-2.95 (m, 4H), 2.68 (s, 3H), 2.03-1.99 (m, 2H), 1.75-1.63 (m, 4H), 1.54-1.26 (m, 5H), 0.89 (dd, 6H).

Example 28: (2R)—N-[(1R)-1-(7-acetyl-2,7-diazaspiro[3.4]octane-2-carbonyl)-5-amino-pentyl]-2-[[(2R)-2-[[(2R)-2-amino-3-phenyl-propanoyl]amino]-3-phenyl-propanoyl]amino]-4-methyl-pentanamide; di-trifluoroacetic acid (compound 30)

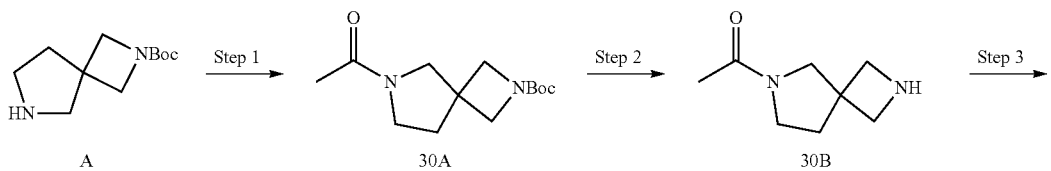

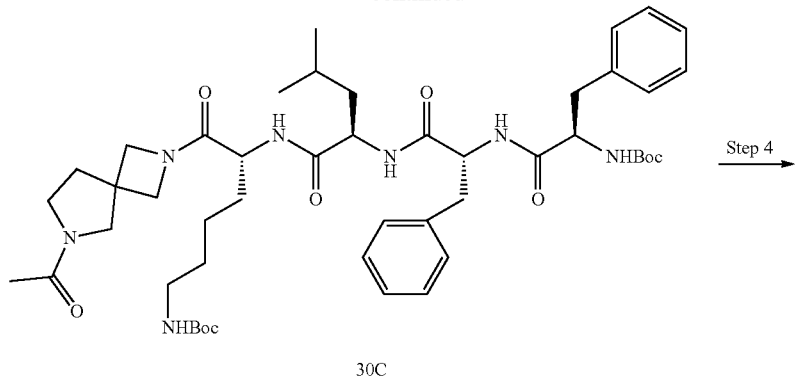

30C

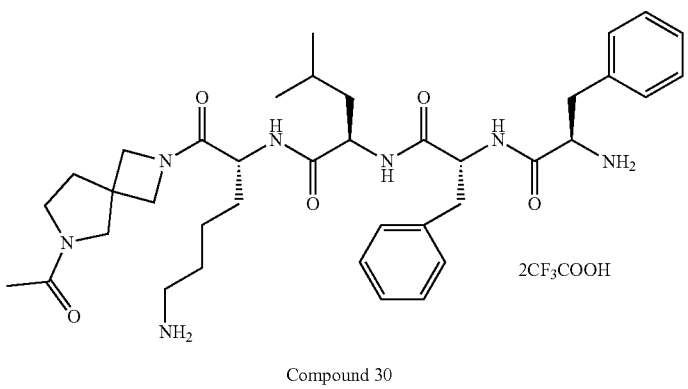

Compound 30

Step 1: tert-butyl 7-acetyl-2,7-diazaspiro[3.4]oc-tane-2-carboxylate (30A)

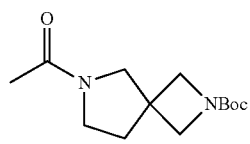 [SMILES: CC(=O)N1CCC2(C1)CN(C(=O)OC(C)(C)C)C2]

Tert-butyl 2,7-diazaspiro[3.4]octane-2-carboxylate (A) (0.414 g, 2 mmol), triethylamine (420 mg, 4.0 mmol) and dichloromethane (7 mL) were added in a 50 mL reaction flask, and it was dissolved under stirring. After cooling to −10° C., acetyl chloride (188 mg, 2.4 mmol) was added and the resultant reacted for 10 min. Then the temperature was raised to room temperature and the system was stirred for 3 h. The reaction was then quenched with a saturated aqueous sodium bicarbonate solution (10 mL) and extracted with ethyl acetate (5 mL×3), and the organic phases were combined. The organic phases were dried over anhydrous sodium sulfate, filtered, and the filtrate was concentrated under reduced pressure. The residue was separated and purified by silica gel column chromatography (petroleum ether:ethyl acetate (v:v)=4:1) to obtain tert-butyl 7-acetyl-2,7-diazaspiro[3.4]octane-2-carboxylate (30A) as light yellow oily substance (411 mg, yield 81%).

MS m/z=255.2[M+H]$^+$.

Step 2: 7-acetyl-2,7-diazaspiro[3.4]octane (30B)

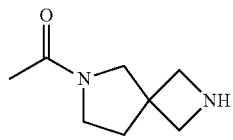

Tert-butyl 7-acetyl-2,7-diazaspiro[3.4]octane-2-carboxylate (30A) (0.41 g, 1.62 mmol) and dichloromethane (7 mL) were added in a 50 mL reaction flask, and trifluoroacetic acid (1 mL) was added dropwise at room temperature. After the addition, the system was allowed to react at room temperature for 3 h. The reaction solution was directly concentrated under reduced pressure to obtain crude 7-acetyl-2,7-diazaspiro[3.4]octane (30B) as light yellow oily liquid (249 mg, yield 100%), and used directly in the next reaction.

Step 3: tert-butyl N-[(1R)-2-[[(1R)-2-[[(1R)-1-[[(1R)-1-(7-acetyl-2,7-diazaspiro[3.4]octane-2-carbonyl)-5-(tert-butoxycarbonylamino)pentyl]carbamoyl]-3-methyl-butyl]amino]-1-benzyl-2-oxo-ethyl]amino]-1-benzyl-2-oxo-ethyl]carbamate (30C)

Step 4: (2R)—N-[(1R)-1-(7-acetyl-2,7-diazaspiro[3.4]octane-2-carbonyl)-5-amino-pentyl]-2-[[(2R)-2-[[(2R)-2-amino-3-phenyl-propanoyl]amino]-3-phenyl-propanoyl]amino]-4-methyl-pentanamide; di-trifluoroacetic acid (compound 30)

Compound 30

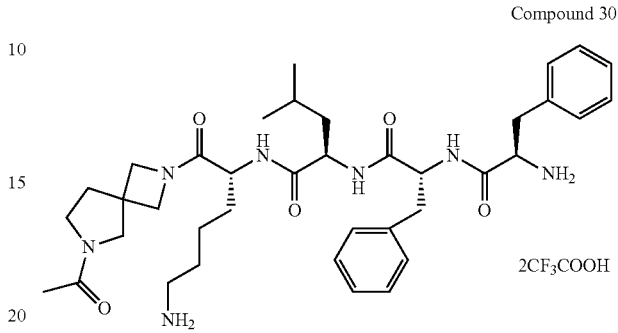

2CF₃COOH

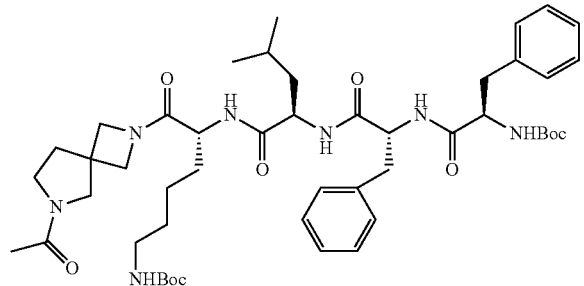 [SMILES: CC(=O)N1CCC2(C1)CN(C(=O)[C@@H](CCCCNC(=O)OC(C)(C)C)NC(=O)[C@@H](CC(C)C)NC(=O)[C@@H](Cc1ccccc1)NC(=O)[C@@H](Cc1ccccc1)NC(=O)OC(C)(C)C)C2]

Tert-butyl N-[(1R)-2-[[(1R)-1-[[(1R)-1-(7-acetyl-2,7-diazaspiro[3.4]octane-2-carbonyl)-5(tert-butoxycarbonylamino)pentyl]carbamoyl]-3-methyl-butyl]amino]-1-benzyl-2-oxo-ethyl]amino]-1-benzyl-2 oxo-ethyl]carbamate (30C) (200 mg, 0.22 mmol) and trifluoroacetic acid (2 mL) were added in a 50 mL reaction flask, and the system was allowed to react at room temperature for 2 h. Then the reaction solution was concentrated under reduced pressure, and the residue was separated and purified by preparative liquid chromatography (preparation conditions: instrument: Gilson GX-281; column: Xbridge C18, 150×30 mm I.D., 5 µm; mobile phase: A for ACN and B for H₂O; isocratic: A 65%; flow rate: 30 mL/min; back pressure: 1000 PSI; column temperature: 30° C.; wavelength: 210 nm; period: 18 min; sample preparation: the compound dissolved in 12 mL methanol; injection: 0.9 mL/needle). The preparation was concentrated under reduced pressure to remove most of the solvent, and lyophilized to obtain (2R)—N-[(1R)-1-(7-acetyl-2,7-diazaspiro[3.4]octane-2-carbonyl)-5-amino-pentyl]-2-[[(2R)-2-[[(2R)-2-amino-3-phenyl-propanoyl]amino]-3-phenyl-propanoyl]amino]-4-methyl-pentanamide; di-trifluoroacetic acid (compound 30) as white powder (120 mg, yield 79.1%).

MS m/z=345.9[M+2H]⁺/2;

¹H NMR (400 MHz, D₂O) δ 7.45-7.29 (m, 10H), 4.71 (t, 1H), 4.37-4.2 (m, 5H), 4.05-4.00 (m, 2H), 3.82-3.52 (m, 4H), 3.26-3.05 (m, 6H), 2.32-2.11 (m, 5H), 1.8-1.76 (m, 4H), 1.61-1.45 (m, 5H), 1.02-0.96 (dd, 6H).

Crude 7-acetyl-2,7-diazaspiro[3.4]octane (30B) (249 mg, 1.62 mmol), 1-(3-dimethylaminopropyl)-3-ethylcarbodiimide hydrochloride (384 mg, 2 mmol), 1-hydroxybenzotriazole (270 mg, 2 mmol), intermediate 1 (400 mg, 0.53 mmol) and dichloromethane (30 mL) were added in a 50 mL single-necked flask, and the system was allowed to react at room temperature for 5 h. Then the reaction solution was concentrated under reduced pressure, and the residue was separated and purified by silica gel column chromatography (petroleum ether:ethyl acetate (v:v)=1:2) to obtain tert-butylN-[(1R)-2-[[(1R)-1-[[(1R)-1-(7-acetyl-2,7-diazaspiro[3.4]octane-2-carbonyl)-5(tert-butoxycarbonylamino)pentyl]carbamoyl]-3-methyl-butyl]amino]-1-benzyl-2-oxo-ethyl]amino]-1-benzyl-2oxo-ethyl]carbamate (30C) as white solid (200 mg, yield 42.3%).

Example 29: (2R)—N-[(1R)-1-(7-acetyl-2,7-diazaspiro[4.4]nonane-2-carbonyl)-5-amino-pentyl]-2-[[(2R)-2-[[(2R)-2-amino-3-phenyl-propanoyl]amino]-3-phenyl-propanoyl]amino]-4-methyl-pentanamide; di-trifluoroacetic acid (compound 31)

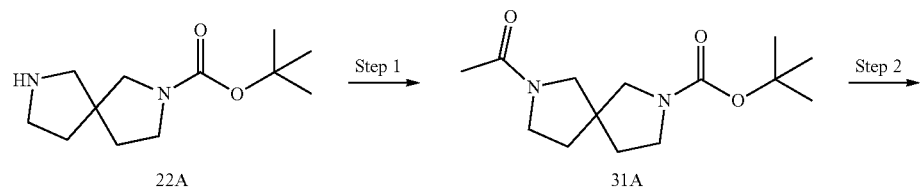

22A → Step 1 → 31A → Step 2

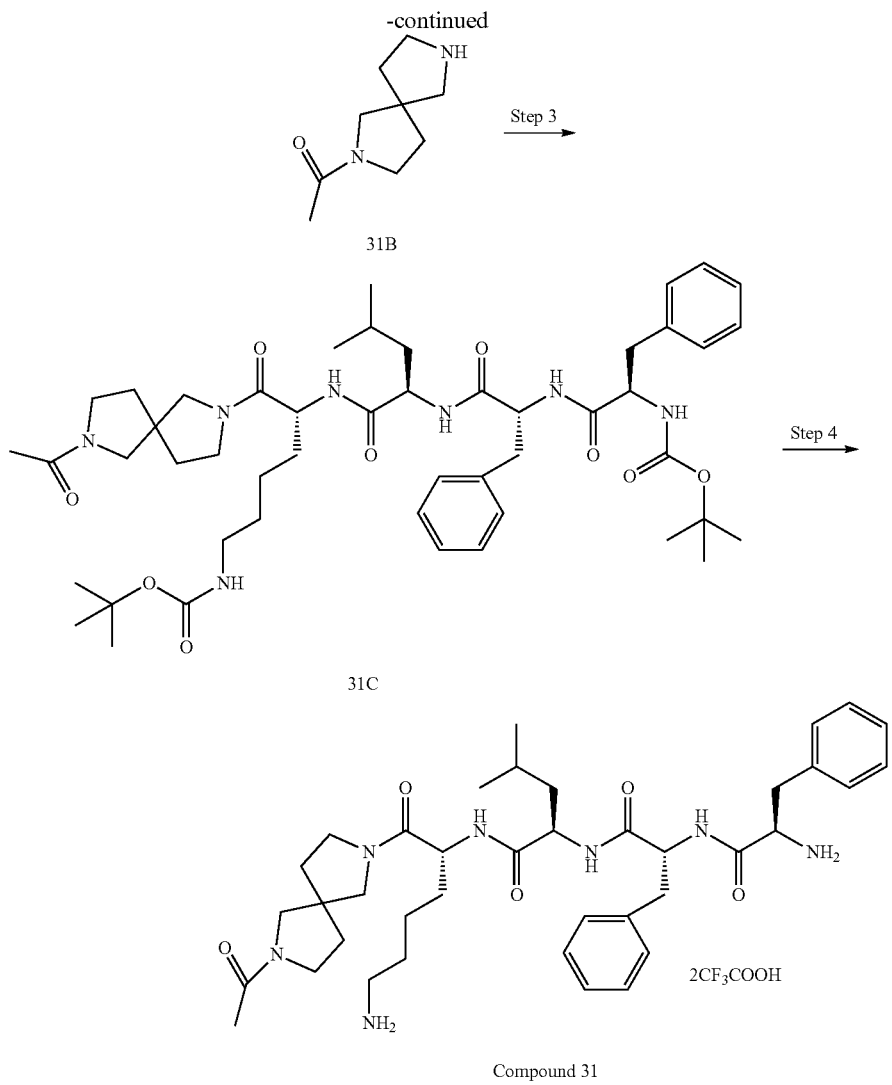

Compound 31

Step 1: tert-butyl 7-acetyl-2,7-diazaspiro[4.4]nonane-2-carboxylate (31A)

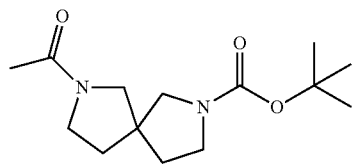

2-Boc-2,7-diazaspiro[4.4]nonane (22A) (452 mg, 2.0 mmol), triethylamine (400 mg, 4.0 mmol) and dichloromethane (15 mL) were added in a 50 mL reaction flask, and it was dissolved under stirring. After cooling to −10° C., acetyl chloride (160 mg, 2.0 mmol) was added dropwise. After the addition, the reaction was allowed to proceed at room temperature for 4 h. Then a 1 M dilute hydrochloric acid (50 mL) was added to the reaction solution, and the mixture was extracted with dichloromethane (60 mL×2). The organic phases were dried over anhydrous sodium sulfate, filtered, and the filtrate was concentrated under reduced pressure to obtain tert-butyl 7-acetyl-2,7-diazaspiro[4.4]nonane-2-carboxylate (31A) as light yellow oily substance (392 mg, yield 73%).

MS m/z=291.2[M+Na]$^+$.

Step 2: 1-(2,7-diazaspiro[4.4]nonan-2-yl)ethanone (31B)

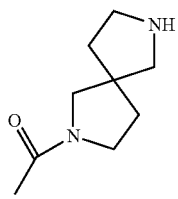

Tert-butyl 7-acetyl-2,7-diazaspiro[4.4]nonane-2-carboxylate (31A) (161 mg, 0.6 mmol), dichloromethane (10 mL) and trifluoroacetic acid (2 mL) were added in a 50 mL reaction flask, and the system was allowed to react at room temperature for 2 h. The reaction solution was concentrated under reduced pressure to obtain crude 1-(2,7-diazaspiro[4.4]nonane-2-yl)ethanone (31B) as light yellow oily substance (100 mg, yield 99%).

Step 3: tert-butyl N-[(1R)-2-[[(1R)-2-[[(1R)-1-[[(1R)-1-(7-acetyl-2,7-diazaspiro[4.4]nonane-2-carbonyl)-5-(tert-butoxycarbonylamino)pentyl]carbamoyl]-3-methyl-butyl]amino]-1-benzyl-2-oxo-ethyl]amino]-1-benzyl-2-oxo-ethyl]carbamate (31C)

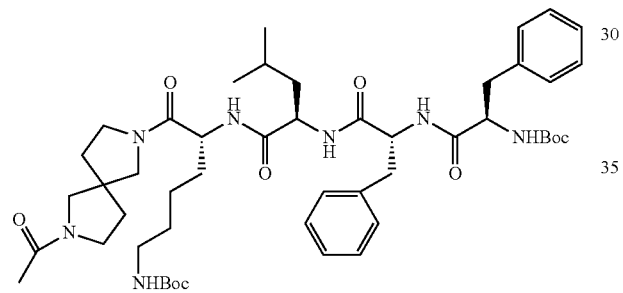

31C

Crude 1-(2,7-diazaspiro[4.4]nonane-2-yl)ethanone (31B) (100 mg, 0.6 mmol), 1-(3-dimethylaminopropyl)-3-ethyl-carbodiimide hydrochloride (0.288 g, 1.5 mmol), 1-hydroxybenzotriazole (81 mg, 0.6 mmol), intermediate 1 (400 mg, 0.5 mmol) and dichloromethane (50 mL) were added sequentially in a 50 mL reaction flask, and the system was allowed to react at room temperature for 5 h. The reaction solution was concentrated under reduced pressure, and the residue was separated and purified by silica gel column chromatography (dichloromethane:methanol (v:v)=30:1) to obtain tert-butyl N-[(1R)-2-[[(1R)-2-[[(1R)-1-[[(1R)-1-(7-acetyl-2,7-diazaspiro[4.4]nonane-2-carbonyl)-5-(tert-butoxycarbonylamino)pentyl]carbamoyl]-3-methyl-butyl]amino]-1-benzyl-2-oxo-ethyl]amino]-1-benzyl-2-oxo-ethyl]carbamate (31C) as light yellow solid (120 mg, yield 22%).

Step 4: (2R)—N-[(1R)-1-(7-acetyl-2,7-diazaspiro[4.4]nonane-2-carbonyl)-5-amino-pentyl]-2-[[(2R)-2-[[(2R)-2-amino-3-phenyl-propanoyl]amino]-3-phenyl-propanoyl]amino]-4-methyl-pentanamide; di-trifluoroacetic acid (compound 31)

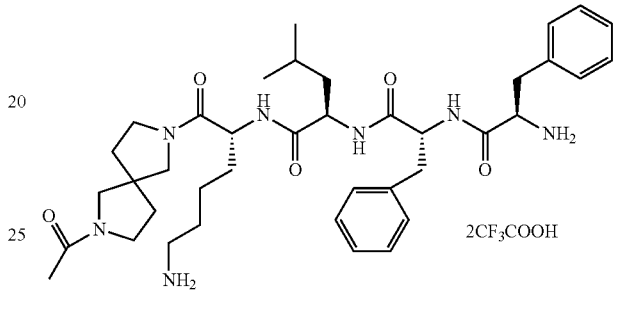

Compound 31

Tert-butyl N-[(1R)-2-[[(1R)-2-[[(1R)-1-[[(1R)-1-(7-acetyl-2,7-diazaspiro[4.4]nonane-2-carbonyl)-5-(tert-butoxycarbonylamino)pentyl]carbamoyl]-3-methyl-butyl]amino]-1-benzyl-2-oxo-ethyl]amino]-1-benzyl-2-oxo-ethyl]carbamate (31C) (120 mg, 0.22 mmol) and trifluoroacetic acid (2 mL) were added in a 50 mL reaction flask, and the system was allowed to react at room temperature for 2 h. Then the reaction solution was concentrated under reduced pressure, and the residue was separated and purified by preparative liquid chromatography (preparation conditions: instrument: Gilson GX-281; column: Xbridge C18, 150×30 mm I.D., 5 μm; mobile phase: A for ACN and B for H$_2$O; isocratic: A 65%; flow rate: 30 mL/min; back pressure: 1000 PSI; column temperature: 30° C.; wavelength: 210 nm; period: 18 min; sample preparation: the compound dissolved in 12 mL methanol; injection: 0.9 mL/needle). The preparation was concentrated under reduced pressure to remove most of the solvent, and lyophilized to obtain (2R)—N-[(1R)-1-(7-acetyl-2,7-diazaspiro[4.4]nonane-2-carbonyl)-5-amino-pentyl]-2-[[(2R)-2-[[(2R)-2-amino-3-phenyl-propanoyl]amino]-3-phenyl-propanoyl]amino]-4-methyl-pentanamide; di-trifluoroacetic acid (compound 31) as white powder (77 mg, yield 85%).

MS m/z (ESI): 352.7[M+2H]$^+$/2;

$^1$H NMR (400 MHz, D$_2$O) δ 7.43-7.18 (m, 10H), 4.68-4.60 (m, 1H), 4.47-4.19 (m, 3H), 3.91-3.27 (m, 8H), 3.18 (d, 2H), 3.08-2.92 (m, 4H), 2.13-1.86 (m, 7H), 1.85-1.63 (m, 4H), 1.62-1.27 (m, 5H), 0.92 (dd, 6H).

Example 30: (2R)—N-[(1R)-1-(7-acetyl-5,5-difluoro-2,7-diazaspiro[3.5]nonane-2-carbonyl)-5-amino-pentyl]-2-[[(2R)-2-[[(2R)-2-amino-3-phenyl-propanoyl]amino]-3-phenyl-propanoyl]amino]-4-methyl-pentanamide; di-trifluoroacetic acid (compound 32)
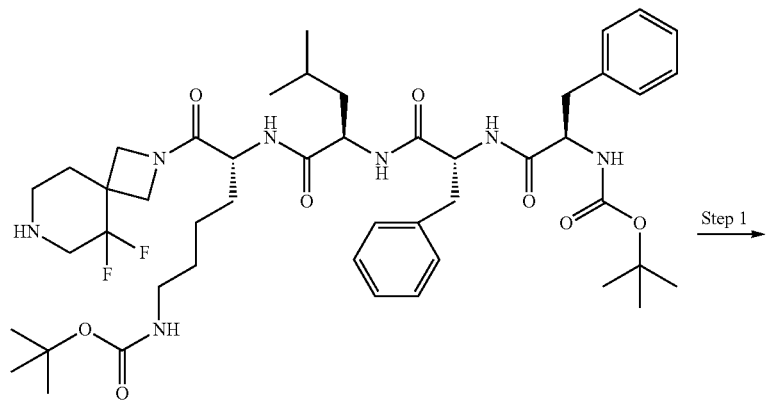
19B
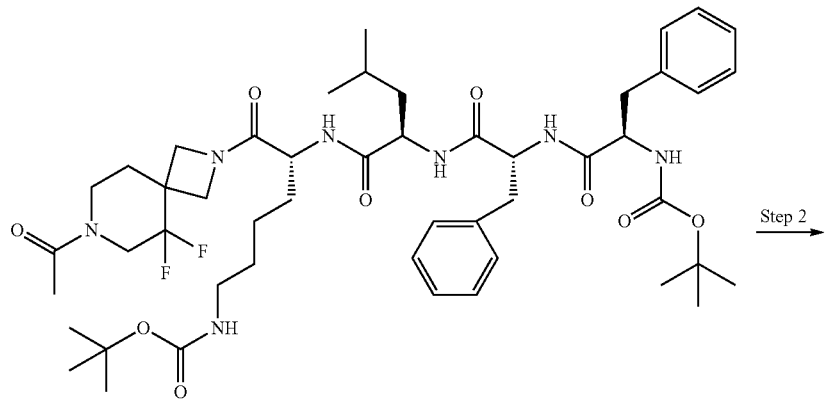
32A
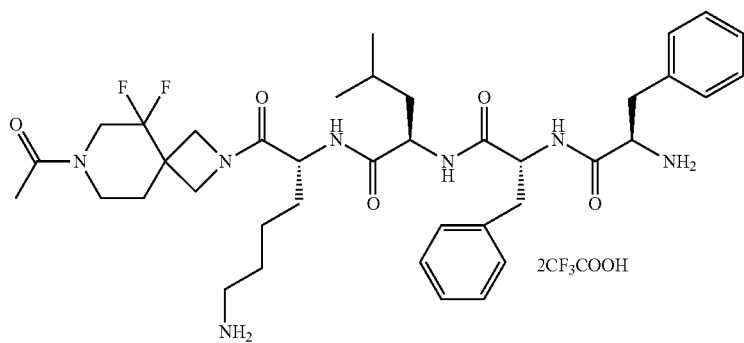
Compound 32

187

Step 1: tert-butyl N-[(1R)-2-[[(1R)-2-[[(1R)-1-[[(1R)-1-(7-acetyl-5,5-difluoro-2,7-diazaspiro[3.5]nonane-2-carbonyl)-5-(tert-butoxycarbonylamino)pentyl]carbamoyl]-3-methyl-butyl]amino]-1-benzyl-2-oxo-ethyl]amino]-1-benzyl-2-oxo-ethyl]carbamate (32A)

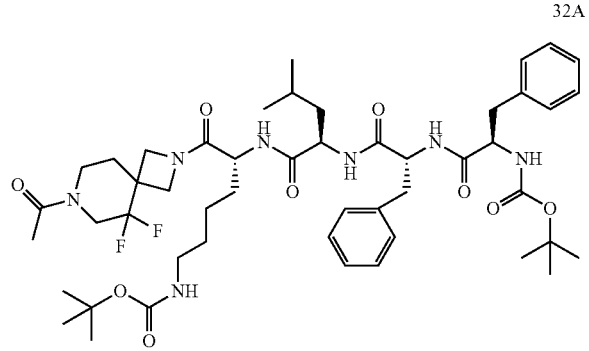 [SMILES: CC(=O)N1CCC2(CN(C(=O)[C@@H](CCCCNC(=O)OC(C)(C)C)NC(=O)[C@@H](CC(C)C)NC(=O)[C@@H](Cc3ccccc3)NC(=O)[C@@H](Cc3ccccc3)NC(=O)OC(C)(C)C)C2)C(F)(F)C1]

Tert-butyl N-[(1R)-1-benzyl-2-[[(1R)-1-benzyl-2-[[(1R)-1-[[(1R)-5-(tert-butoxycarbonylamino)-1-(5,5-di fluoro-2,7-diazaspiro[3.5]nonane-2-carbonyl)pentyl]carbamoyl]-3-methyl-butyl]amino]-2-oxo-ethyl]amino]-2-oxo-ethyl]carbamate (19B) (430 mg, 0.48 mmol), 1-(3-dimethylaminopropyl)-3-ethylcarbodiimide hydrochloride (0.18 g, 0.94 mmol), 1-hydroxybenzotriazole (71 mg, 0.53 mmol), acetic acid (28.8 mg, 0.48 mmol) and dichloromethane (20 mL) were added sequentially in a 50 mL reaction flask, and the system was allowed to react at room temperature for 3 h. The reaction solution was concentrated under reduced pressure, and the residue was separated and purified by silica gel column chromatography (dichloromethane:methanol (v:v)=50:1) to obtain tert-butyl N-[(1R)-2-[[(1R)-2-[[(1R)-1-[[(1R)-1-(7-acetyl-5,5-difluoro-2,7-diazaspiro[3.5]nonane-2-carbonyl)-5-(tert- butoxycarbonylamino)pentyl]carbamoyl]-3-methyl-butyl]amino]-1-benzyl-2-oxo-ethyl]amino]-1-benzyl-2-oxo-ethyl]carbamate (32A) as white solid (430 mg, yield 95%).

Step 2: (2R)—N-[(1R)-1-(7-acetyl-5,5-difluoro-2,7-diazaspiro[3.5]nonane-2-carbonyl)-5-amino-pentyl]-2-[[(2R)-2-[[(2R)-2-amino-3-phenyl-propanoyl]amino]-3-phenyl-propanoyl]amino]-4-methyl-pentanamide; di-trifluoroacetic acid (compound 32)

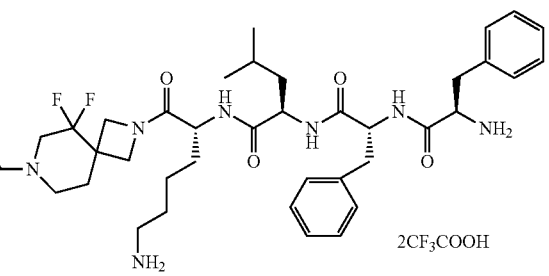

Compound 32

Tert-butyl N-[(1R)-2-[[(1R)-2-[[(1R)-1-[[(1R)-1-(7-acetyl-5,5-difluoro-2,7-diazaspiro[3.5]nonane-2-carbonyl)-5-(tert- butoxycarbonylamino)pentyl]carbamoyl]-3-methyl-butyl]amino]-1-benzyl-2-oxo-ethyl]amino]-1-benzyl-2-oxo-ethyl]carbamate (32A) (430 mg, 0.46 mmol) and trifluoroacetic acid (2 mL) were added in a 50 mL reaction flask, and the system was allowed to react at room temperature for 2 h. Then the reaction solution was concentrated under reduced pressure, and the residue was separated and purified by preparative liquid chromatography (preparation conditions: instrument: Gilson GX-281; column: Xbridge C18, 150×30 mm I.D., 5 μm; mobile phase: A for ACN and B for H$_2$O; isocratic: A 65%; flow rate: 30 mL/min; back pressure: 1000 PSI; column temperature: 30° C.; wavelength: 210 nm; period: 18 min; sample preparation: the compound dissolved in 12 mL methanol; injection: 0.9 mL/needle). The preparation was concentrated under reduced pressure to remove most of the solvent, and lyophilized to obtain (2R)—N-[(1R)-1-(7-acetyl-5,5-difluoro-2,7-diazaspiro[3.5]nonane-2-carbonyl)-5-amino-pentyl]-2-[[(2R)-2-[[(2R)-2-amino-3-phenyl-propanoyl]amino]-3-phenyl-propanoyl]amino]-4-methyl-pentanamide; di-trifluoroacetic acid (compound 32) as white powder (273 mg, yield 61%).

MS m/z (ESI): 370.8[M+2H]$^+$/2;

$^1$H NMR (400 MHz, D$_2$O) δ 7.43-7.19 (m, 10H), 4.67-4.60 (m, 1H), 4.58-4.47 (m, 1H), 4.31-4.08 (m, 5H), 3.98-3.70 (m, 3H), 3.70-3.43 (m, 2H), 3.18 (d, 2H), 3.06-2.94 (m, 4H), 2.23-1.94 (m, 5H), 1.80-1.63 (m, 4H), 1.56-1.29 (m, 5H), 0.91 (dd, 6H).

Example 31: (2R)—N-[(1R)-5-amino-1-[7-(oxetan-3-yl)-2,7-diazaspiro[3.5]nonane-2-carbonyl]pentyl]-2-[[(2R)-2-[[(2R)-2-amino-3-phenyl-propanoyl]amino]-3-phenyl-propanoyl]amino]-4-methyl-pentanamide; tri-trifluoroacetic acid (compound 33)

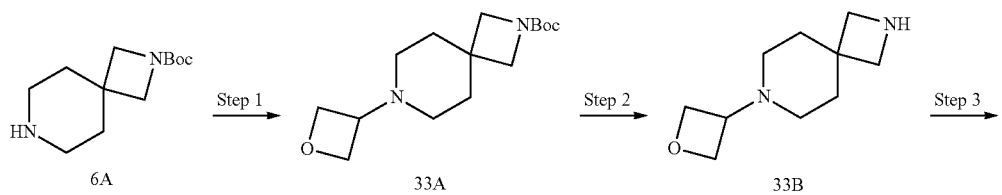

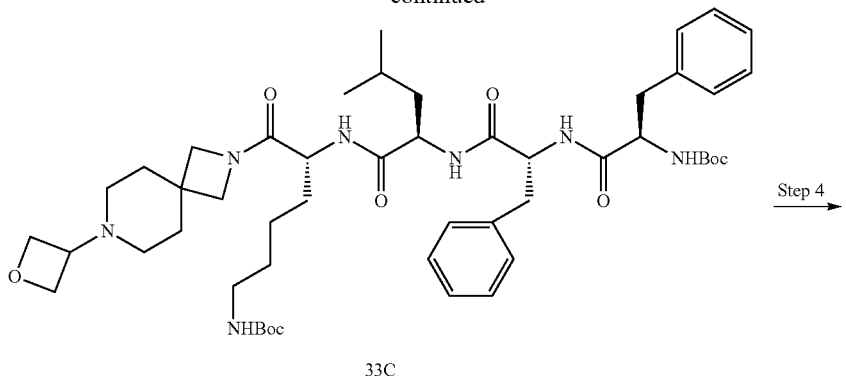

33C

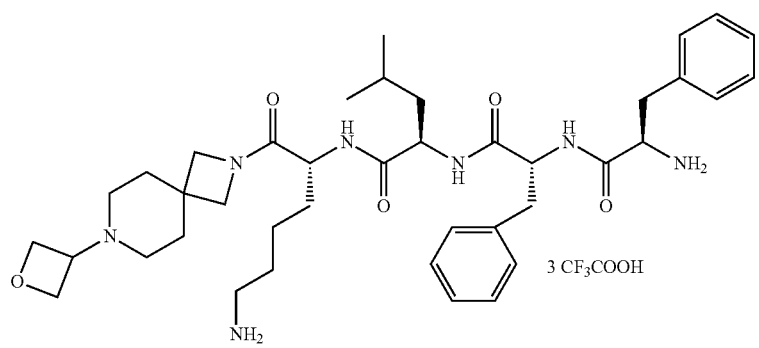

Compound 33

Step 1: tert-butyl 7-(oxetan-3-yl)-2,7-diazaspiro[3.5]nonane-2-carboxylate (33A)

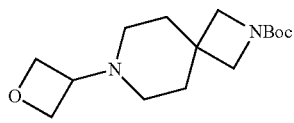

33A

Tert-butyl 2,7-diazaspiro[3.5]nonane-2-carboxylate (6A) (0.452 g, 2.0 mmol), acetic acid (0.24 g, 4.0 mmol), 3-oxetanone (0.288 g, 4.0 mmol), sodium triacetoxyborohydride (1.48 g, 6.98 mmol) and dichloromethane (20 mL) were added sequentially in a 50 mL reaction flask. After the addition, the reaction was allowed to proceed at room temperature for 16 h. The reaction solution was filtered, and the filtrate was washed with a saturated sodium bicarbonate solution (50 mL). After the liquid separation, the organic layer was dried over anhydrous sodium sulfate, filtered, and the filtrate was concentrated under reduced pressure to obtain tert-butyl 7-(oxetan-3-yl)-2,7-diazaspiro[3.5]nonane-2-carboxylate (33A) as white powder (432 mg, yield 76%).

$^1$H NMR (400 MHz, CDCl$_3$) δ 4.67-4.55 (m, 4H), 3.61 (s, 4H), 3.41 (p, 1H), 2.19 (s, 4H), 1.78 (t, 4H), 1.44 (s, 9H).

Step 2: 7-(oxetan-3-yl)-2,7-diazaspiro[3.5]nonane (33B)

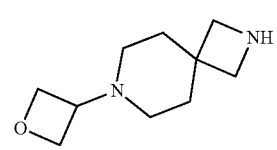

33B

Tert-butyl 7-(oxetan-3-yl)-2,7-diazaspiro[3.5]nonane-2-carboxylate (33A)(0.14 g, 0.5 mmol) and dichloromethane (5 mL) were added in a 50 mL reaction flask, and trifluoroacetic acid (57 mg, 0.5 mmol) was added dropwise at room temperature. After the addition, the system was allowed to react at room temperature for 3 h. The reaction solution was directly concentrated under reduced pressure to obtain crude 7-(oxetan-3-yl)-2,7-diazaspiro[3.5]nonane (33B) as yellow oily liquid (70.5 mg, yield 88%), and used directly in the next reaction.

Step 3: tert-butyl N-[(1R)-1-benzyl-2-[[(1R)-1-benzyl-2-[[(1R)-1-[[(1R)-5-(tert-butoxycarbonylamino)-1-[7-(oxetan-3-yl)-2,7-diazaspiro[3.5]nonane-2-carbonyl]pentyl]carbamoyl]-3-methyl-butyl]amino]-2-oxo-ethyl]amino]-2-oxo-ethyl]carbamate (33C)

Step 4: (2R)—N-[(1R)-5-amino-1-[7-(oxetan-3-yl)-2,7-diazaspiro[3.5]nonane-2-carbonyl]pentyl]-2-[[(2R)-2-[[(2R)-2-amino-3-phenyl-propanoyl]amino]-3-phenyl-propanoyl]amino]-4-methyl-pentanamide; tri-trifluoroacetic acid (compound 33)

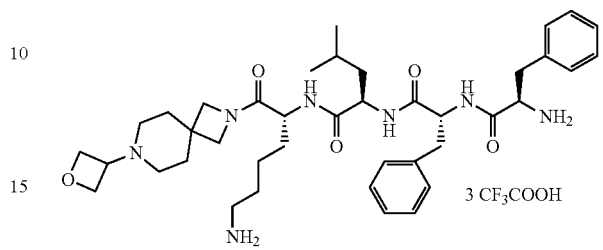

Compound 33

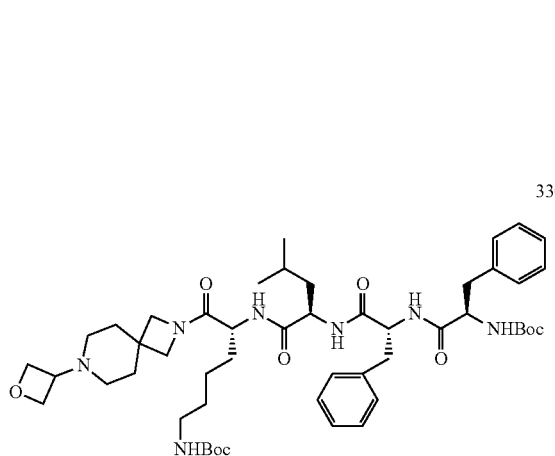

33C

Crude 7-(oxetan-3-yl)-2,7-diazaspiro[3.5]nonane (33B) (70.5 mg, 0.44 mmol), 1-(3-dimethylaminopropyl)-3-ethyl-carbodiimide hydrochloride (288 mg, 1.5 mmol), 1-hydroxybenzotriazole (81 mg, 0.60 mmol), intermediate 1 (330 mg, 0.44 mmol) and dichloromethane (50 mL) were added in a 100 mL reaction flask, and the system was allowed to react at room temperature for 5 h. The reaction solution was concentrated under reduced pressure, and the residue was separated and purified by silica gel column chromatography (dichloromethane:methanol (v:v)=50:1) to obtain tert-butyl N-[(1R)-1-benzyl-2-[[(1R)-1-benzyl-2-[[(1R)-1-[[(1R)-5-(tert-butoxycarbonylamino)-1-[7-(oxetan-3-yl)-2,7-diazaspiro[3.5]nonane-2-carbonyl]pentyl]carbamoyl]-3-methyl-butyl]amino]-2-oxo-ethyl]amino]-2-oxo-ethyl]carbamate (33C) as light yellow solid (400 mg, yield 99%).

Tert-butyl N-[(1R)-1-benzyl-2-[[(1R)-1-benzyl-2-[[(1R)-1-[[(1R)-5-(tert-butoxycarbonylamino)-1-[7-(oxetan-3-yl)-2,7-diazaspiro[3.5]nonane-2-carbonyl]pentyl]carbamoyl]-3-methyl-yl]amino]-2-oxo-ethyl]amino]-2-oxo-ethyl] carbamate (33C) (400 mg, 0.40 mmol) and trifluoroacetic acid (2 mL) were added in a 50 mL reaction flask, and the system was allowed to react at room temperature for 2 h. Then the reaction solution was concentrated under reduced pressure, and the residue was separated and purified by preparative liquid chromatography (preparation conditions: instrument: Gilson GX-281; column: Xbridge C18, 150×30 mm I.D., 5 μm; mobile phase: A for ACN and B for H$_2$O; isocratic: A 65%; flow rate: 30 mL/min; back pressure: 1000 PSI; column temperature: 30° C.; wavelength: 210 nm; period: 18 min; sample preparation: the compound dissolved in 12 mL methanol; injection: 0.9 mL/needle). The preparation was concentrated under reduced pressure to remove most of the solvent, and lyophilized to obtain (2R)—N-[(1R)-5-amino-1-[7-(oxetan-3-yl)-2,7-diazaspiro[3.5] nonane-2-carbonyl]pentyl]-2-[[(2R)-2-[[(2R)-2-amino-3-phenyl-propanoyl]amino]-3-phenyl-propanoyl]amino]-4-methyl-pentanamide tri-trifluoroacetic acid (compound 33) as white powder (160 mg, yield 56%).

MS m/z (ESI): 359.8[M+2H]$^+$/2;

$^1$H NMR (400 MHz, D$_2$O) δ 7.42-7.20 (m, 10H), 4.96 (t, 2H), 4.85 (dd, 2H), 4.66-4.56 (m, 2H), 4.48-4.35 (m, 2H), 4.30-4.10 (m, 5H), 3.84 (s, 2H), 3.43 (br, 1H), 3.17 (d, 2H), 3.14 (s, 1H), 3.07-2.93 (m, 4H), 2.12 (br, 4H), 1.80-1.60 (m, 4H), 1.58-1.29 (m, 5H), 0.91 (dd, 6H).

Example 32: (2R)—N-[(1R)-5-amino-1-[7-(dimethylsulfamoyl)-2,7-diazaspiro[3.5]nonane-2-carbonyl]pentyl]-2-[[(2R)-2-[[(2R)-2-amino-3-phenyl-propanoyl]amino]-3-phenyl-propanoyl]amino]-4-m ethyl-pentanamide; di-trifluoroacetic acid (compound 34)

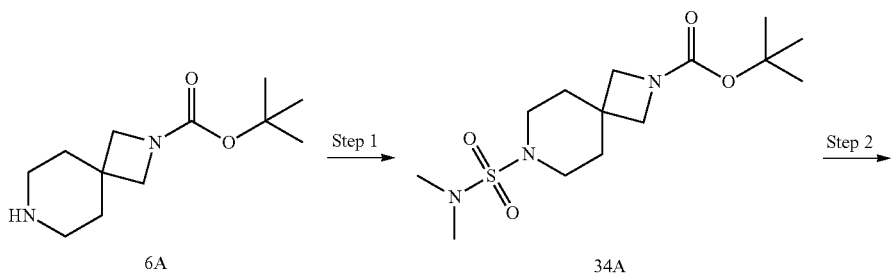

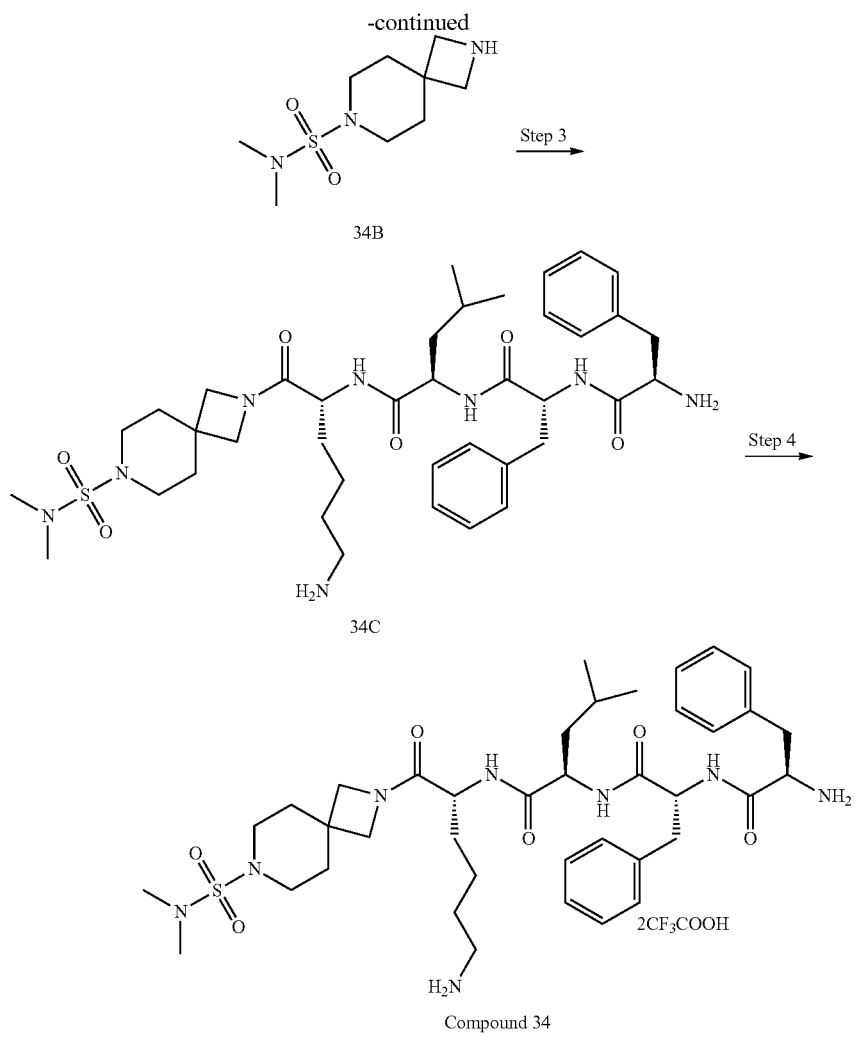

Step 1: tert-butyl 7-(dimethylsulfamoyl)-2,7-diazaspiro[3.5]nonane-2-carboxylate (34A)

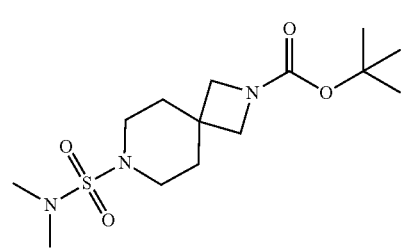

Tert-butyl 2,7-diazaspiro[3.5]nonane-2-carboxylate (6A) (0.452 g, 2 mmol), triethylamine (400 mg, 4.0 mmol) and dichloromethane (15 mL) were added in a 50 mL reaction flask, and it was dissolved under stirring. After cooling to −10° C., dimethylaminosulfonyl chloride (287 mg, 2.0 mmol) was added dropwise. After the addition, the reaction was allowed to proceed at room temperature for 3 h. A 3M dilute hydrochloric acid (50 mL) was added to the reaction solution, followed by extraction with dichloromethane (60 mL×2). The organic phases were dried over anhydrous sodium sulfate, filtered, and the filtrate was concentrated under reduced pressure to obtain crude tert-butyl 7-(dimethylsulfamoyl)-2,7-diazaspiro[3.5]nonane-2-carboxylate (34A) as light yellow solid (440 mg, yield 66%).

Step 2: N,N-dimethyl-2,7-diazaspiro[3.5]nonane-7-sulfonamide (34B)

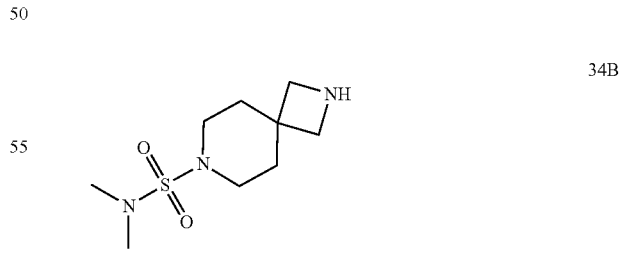

Crude tert-butyl 7-(dimethylsulfamoyl)-2,7-diazaspiro[3.5]nonane-2-carboxylate (34A) (0.22 g, 0.66 mmol) and dichloromethane (5 mL) were added in a 50 mL reaction flask, and trifluoroacetic acid (2 mL) was added dropwise at room temperature. After the addition, the system was allowed to react at room temperature for 3 h. The reaction solution was directly concentrated under reduced pressure to obtain crude N,N-dimethyl-2,7-diazaspiro[3.5]nonane-7-sulfonamide (34B) as yellow oily liquid (103 mg, yield 76%), and used directly in the next reaction.

Step 3: tert-butyl N-[(1R)-1-benzyl-2-[[(1R)-1-benzyl-2-[[(1R)-1-[[(1R)-5-(tert-butoxy carbonylamino)-1-[7-(dimethylsulfamoyl)-2,7-diazaspiro[3.5]nonane-2-carbonyl]pentyl]carbamoyl]-3-methyl-butyl]amino]-2-oxo-ethyl]amino]-2-oxo-ethyl]carbamate (34C)

Step 4: (2R)—N-[(1R)-5-amino-1-[7-(dimethylsulfamoyl)-2,7-diazaspiro[3.5]nonane-2-carbonyl]pentyl]-2-[[(2R)-2-[[(2R)-2-amino-3-phenyl-propanoyl]amino]-3-phenyl-propanoyl]amino]-4-methyl-pentanamide; di-trifluoroacetic acid (compound 34)

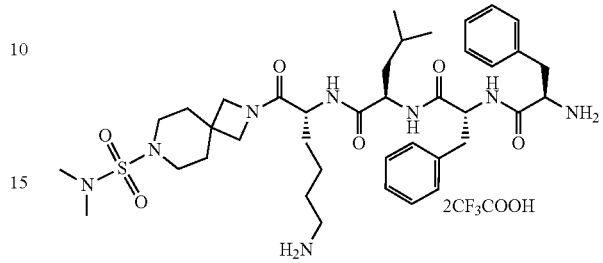

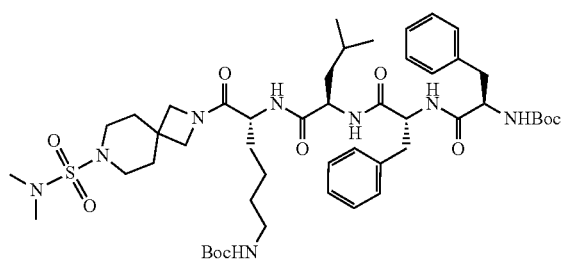

Crude N, N-dimethyl-2,7-diazaspiro[3.5]nonane-7-sulfonamide (34B) (103 mg, 0.44 mmol), 1-(3-dimethylaminopropyl)-3-ethylcarbodiimide hydrochloride (288 mg, 1.5 mmol), 1-hydroxybenzotriazole (81 mg, 0.60 mmol), intermediate 1 (330 mg, 0.44 mmol) and dichloromethane (50 mL) were added in a 100 mL reaction flask, and the system was allowed to react at room temperature for 5 h. The reaction solution was concentrated under reduced pressure, and the residue was separated and purified by silica gel column chromatography (dichloromethane:methanol (v:v)= 50:1) to obtain tert-butyl N-[(1R)-1-benzyl-2-[[(1R)-1-benzyl-2-[[(1R)-1-[[(1R)-5-(tert-butoxycarbonylamino)-1-[7-(di methylsulfamoyl)-2,7-diazaspiro[3.5]nonane-2-carbonyl]pentyl]carbamoyl]-3-methyl-butyl]amino]-2-oxo-ethyl] amino]-2-oxo-ethyl]carbamate (34C) as light yellow solid (240 mg, yield 56%).

Tert-butyl N-[(1R)-1-benzyl-2-[[(1R)-1-benzyl-2-[[(1R)-1-[[(1R)-5-(tert-butoxycarbonylamino)-1-[7-(di methylsulfamoyl)-2,7-diazaspiro[3.5]nonane-2-carbonyl]pentyl]carbamoyl]-3-methyl-butyl]amino]-2-oxo-ethyl]amino]-2-oxo-ethyl]carbamate (34C) (400 mg, 0.4 mmol) and trifluoroacetic acid (2 mL) were added in a 50 mL reaction flask, and the system was allowed to react at room temperature for 2 h. The reaction solution was concentrated under reduced pressure, and the residue was separated and purified by preparative liquid chromatography (preparation conditions: instrument: Gilson GX-281; column: Xbridge C18, 150×30 mm I.D., 5 μm; mobile phase: A for ACN and B for $H_2O$; isocratic: A 65%; flow rate: 30 mL/min; back pressure: 1000 PSI; column temperature: 30° C.; wavelength: 210 nm; period: 18 min; sample preparation: the compound dissolved in 12 mL methanol; injection: 0.9 mL/needle). The preparation was concentrated under reduced pressure to remove most of the solvent, and lyophilized to obtain (2R)—N-[(1R)-5-amino-1-[7-(dimethylsulfamoyl)-2,7-diazaspiro[3.5]nonane-2-carbonyl]pentyl]-2-[[(2R)-2-[[(2R)-2-amino-3-phenyl-propanoyl]amino]-3-phenyl-propanoyl]amino]-4-methyl-pentanamide di-trifluoroacetic acid (compound 34) as white powder (130 mg, yield 29%).

MS m/z (ESI): 385.3 [M+2H]$^+$/2;

$^1$H NMR (400 MHz, $D_2O$) δ 7.46-7.29 (m, 6H), 7.29-7.18 (m, 4H), 4.65 (t, 1H), 4.32-3.99 (m, 5H), 3.85-3.68 (m, 2H), 3.35-3.11 (m, 6H), 3.11-2.92 (m, 4H), 2.81 (d, 6H), 1.96-1.79 (m, 4H), 1.71 (dd, 4H), 1.60-1.32 (m, 5H), 0.93 (dd, 6H).

Example 33: (2R)—N-[(1R)-5-amino-1-[7-(dimethylsulfamoyl)-2,7-diazaspiro[3.4]octane-2-carbonyl] pentyl]-2-[[(2R)-2-[[(2R)-2-amino-3-phenyl-propanoyl]amino]-3-phenyl-propanoyl]amino]-4-methyl-pentanamide; di-trifluoroacetic acid (compound 35)

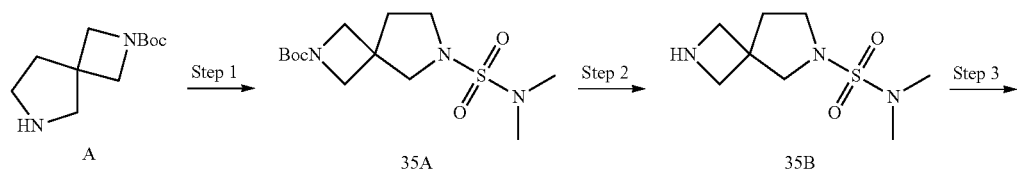

-continued

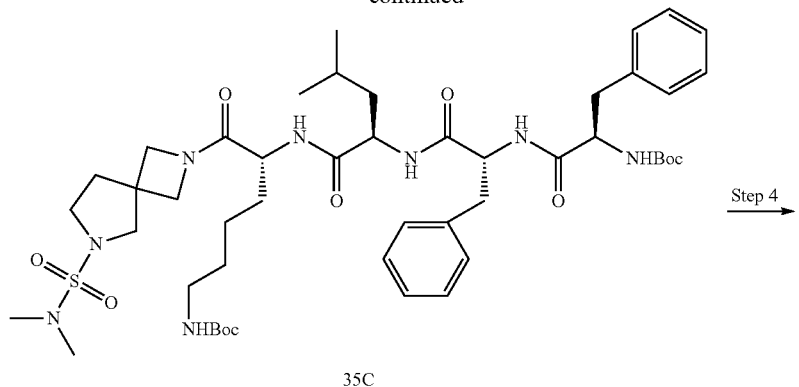

35C

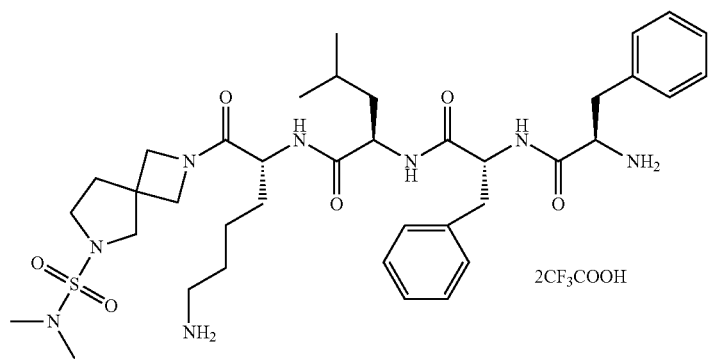

Compound 35

Step 1: tert-butyl 7-(dimethylsulfamoyl)-2,7-diazaspiro[3.4]octane-2-carboxylate (35A)

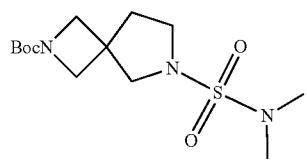 [SMILES: CN(C)S(=O)(=O)N1CCC2(CN(C(=O)OC(C)(C)C)C2)C1]

Tert-butyl 2,7-diazaspiro[3.4]octane-2-carboxylate (A) (0.414 g, 2 mmol), triethylamine (420 mg, 4.0 mmol) and dichloromethane (7 mL) were added in a 50 mL reaction flask, and it was dissolved under stirring. After cooling to −10° C., dimethylsulfamoyl chloride (343 mg, 2.4 mmol) was added dropwise, and the reaction was allowed to proceed for 10 minutes. Then the temperature was raised to room temperature and stirred for 3 h. The reaction solution was quenched with a saturated aqueous sodium bicarbonate solution (10 mL), extracted with ethyl acetate (5 mL×3), and the organic phases were combined. The organic phases were dried over anhydrous sodium sulfate, filtered, and the filtrate was concentrated under reduced pressure. The residue was separated and purified by silica gel column chromatography (petroleum ether:ethyl acetate (v:v)=4:1) to obtain tert-butyl 7-(dimethylsulfamoyl)-2,7-diazaspiro[3.4]octane-2-carboxylate (35A) as light yellow oily substance (414 mg, yield 0.65%).

MS m/z=320.2[M+H]$^+$;

Step 2: 7-(dimethylsulfamoyl)-2,7-diazaspiro[3.4]octane (35B)

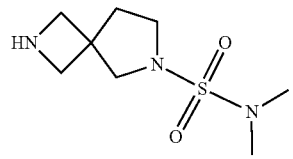

Tert-butyl 7-(dimethylsulfamoyl)-2,7-diazaspiro[3.4]octane-2-carboxylate (35A) (0.41 g, 1.3 mmol) and dichloromethane (7 mL) were added in a 50 mL reaction flask, and trifluoroacetic acid (1 mL) was added dropwise at room temperature. After the addition, the system was allowed to react at room temperature for 3 h. The reaction solution was directly concentrated under reduced pressure to obtain crude 7-(dimethylsulfamoyl)-2,7-diazaspiro[3.4]octane (35B) as light yellow oily liquid (284 mg, yield 100%), and used directly in the next reaction.

Step 3: tert-butyl N-[(1R)-2-[[(1R)-2-[[(1R)-1-[[(1R)-1-(7-dimethylsulfamoyl-2,7-diazaspiro[3.4]octane-2-carbonyl)-5-(tert-butoxycarbonylamino)pentyl]carbamoyl]-3-methyl-butyl]amino]-1-benzyl-2-oxo-ethyl]amino]-1-benzyl-2-oxo-ethyl]carbamate (35C)

Step 4: (2R)—N-[(1R)-5-amino-1-[7-(dimethylsulfamoyl)-2,7-diazaspiro[3.4]octane-2-carbonyl]pentyl]-2-[[(2R)-2-[[(2R)-2-amino-3-phenyl-propanoyl]amino]-3-phenyl-propanoyl]amino]-4-methyl-pentanamide; di-trifluoroacetic acid (compound 35)

Compound 35

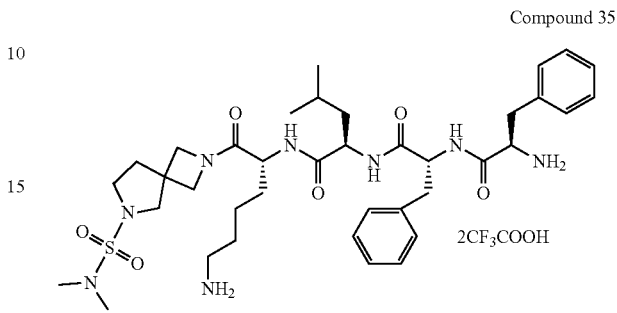

2CF₃COOH

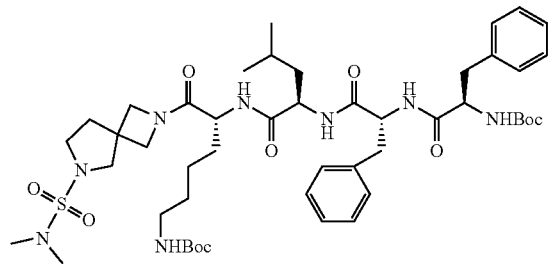 [SMILES: CC(C)C[C@@H](NC(=O)[C@@H](Cc1ccccc1)NC(=O)[C@@H](Cc1ccccc1)NC(=O)OC(C)(C)C)C(=O)N[C@H](CCCCNC(=O)OC(C)(C)C)C(=O)N1CC2(CCN(S(=O)(=O)N(C)C)C2)C1]

Crude 7-(dimethylsulfamoyl)-2,7-diazaspiro[3.4]octane (35B) (284 mg, 1.3 mmol), 1-(3-dimethylaminopropyl)-3-ethylcarbodiimide hydrochloride (384 mg, 2 mmol), 1-hydroxybenzotriazole (270 mg, 2 mmol), intermediate 1 (400 mg, 0.53 mmol) and dichloromethane (30 mL) were added in a 50 mL single-necked flask, and the system was allowed to react at room temperature for 5 h. The reaction solution was concentrated under reduced pressure, and the residue was separated and purified by silica gel column chromatography (petroleum ether:ethyl acetate (v:v)=1:2) to obtain tert-butyl N-[(1R)-2-[[(1R)-1-[[(1R)-1-(7-acetyl-2,7-diazaspiro[3.4]octane-2-carbonyl)-5(tert-butoxycarbonylamino)pentyl]carbamoyl]-3-methyl-butyl]amino]-1-benzyl-2-oxo-ethyl]amino]-1-benzyl-2 oxo-ethyl]carbamate (35C) as white solid (201 mg, yield 39.7%).

Tert-butyl N-[(1R)-2-[[(1R)-1-[[(1R)-1-(7-acetyl-2,7-diazaspiro[3.4]octane-2-carbonyl)-5(tert-butoxycarbonylamino)pentyl]carbamoyl]-3-methyl-butyl]amino]-1-benzyl-2-oxo-ethyl]amino]-1-benzyl-2 oxo-ethyl]carbamate (35C) (201 mg, 0.17 mmol) and trifluoroacetic acid (2 mL) were added in a 50 mL reaction flask, and the system was allowed to react at room temperature for 2 h. The reaction solution was concentrated under reduced pressure, and the residue was separated and purified by preparative liquid chromatography (preparation conditions: instrument: Gilson GX-281; column: Xbridge C18, 150×30 mm I.D., 5 μm; mobile phase: A for ACN and B for H₂O; isocratic: A 65%; flow rate: 30 mL/min; back pressure: 1000 PSI; column temperature: 30° C.; wavelength: 210 nm; period: 18 min; sample preparation: the compound dissolved in 12 mL methanol; injection: 0.9 mL/needle). The preparation was concentrated under reduced pressure to remove most of the solvent, and lyophilized to obtain (2R)—N-[(1R)-5-amino-1-(7-(dimethylsulfamoyl)-2,7-diazaspiro[3.4]octane-2-carbonyl]pentyl]-2-[[(2R)-2-[[(2R)-2-amino-3-phenyl-propanoyl]amino]-3-phenyl-propanoyl]amino]-4-methyl-pentanamide di-trifluoroacetic acid (compound 35) as white powder (115 mg, yield 89.7%).

MS m/z=378.3 [M+2H]⁺/2;

¹H NMR (400 MHz, D₂O) δ 7.46-7.29 (m, 10H), 4.71 (t, 1H), 4.38-4.21 (m, 5H), 4.07-4.05 (m, 2H), 3.60-3.46 (m, 4H), 3.23-3.05 (m, 6H), 2.9-2.89 (d, 6H), 2.32-2.26 (m, 2H) 1.8-1.59 (m, 9H), 1.02-0.96 (dd, 6H).

Example 34: (2R)-2-[[(2R)-2-[[(2R)-2-amino-3-phenyl-propanoyl]amino]-3-phenyl-propanoyl]amino]-N-[(1R)-5-amino-1-(2-piperazin-1-yl-7-azaspiro[3.5]nonane-7-carbonyl)pentyl]-4-methyl-pentanamide; tetra-trifluoroacetic acid (compound 36)

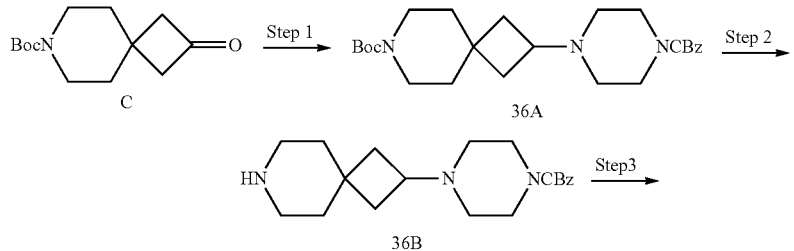

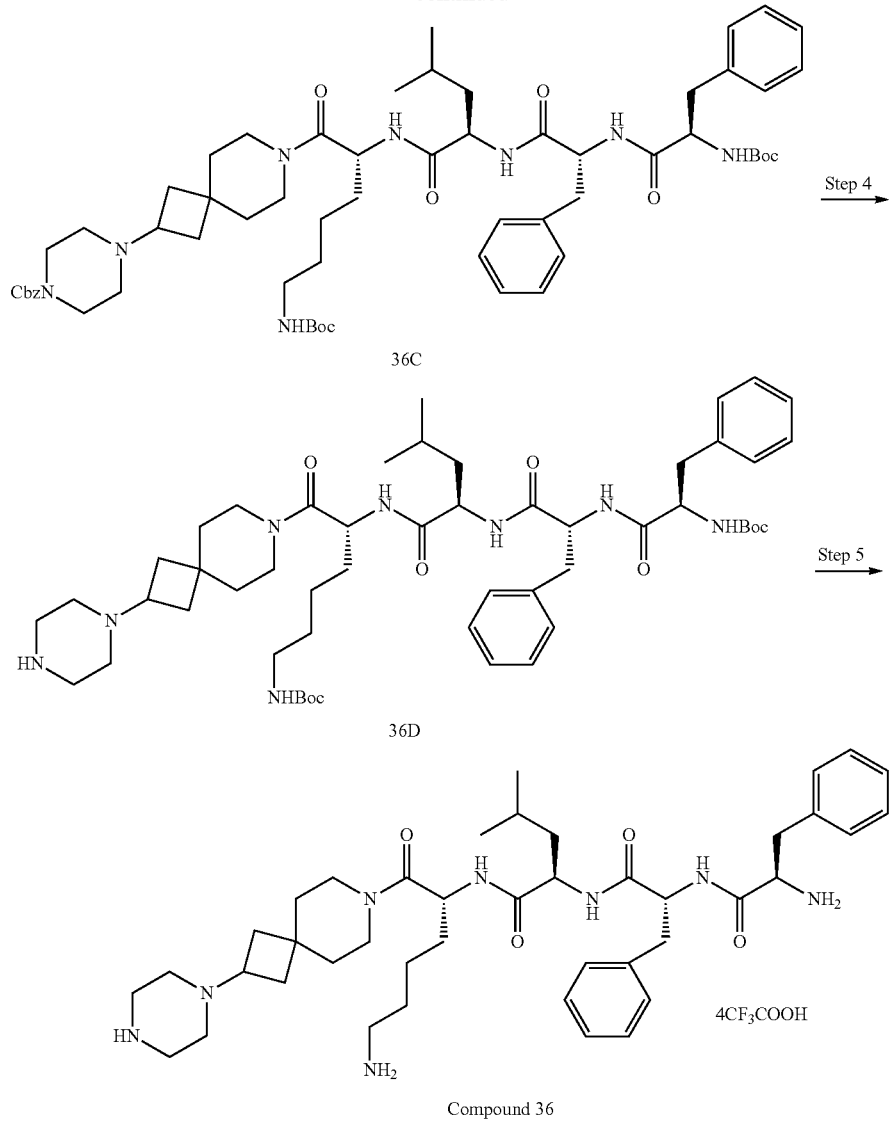

Compound 36

Step 1: tert-butyl2-(4-benzyloxycarbonylpiperazin-1-yl)-7-azaspiro[3.5]nonane-7-carboxylate (36A)

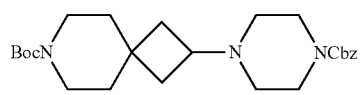 [SMILES: CC(C)(C)OC(=O)N1CCC2(CC1)CC(N1CCN(C(=O)OCc3ccccc3)CC1)C2]

Tert-butyl 2-oxo-7-azaspiro[3.5]nonane-7-carboxylate (C) (0.478 g, 2 mmol), benzyl-1-piperazine carbonate (440 mg, 2 mmol), acetic acid (120 mg, 2.0 mmol) and dichloroethane (7 mL) were added in a 50 mL reaction flask, and the system was stirred for half an hour. Sodium triacetoxyborohydride (0.636 g, 3 mmol) was added and the resultant reacted for 5 h. The reaction system was quenched with water (10 mL), extracted with ethyl acetate (5 mL×3), and the organic phases were combined. The organic phases were dried over anhydrous sodium sulfate, filtered, and the filtrate was concentrated under reduced pressure. The residue was separated and purified by silica gel column chromatography (petroleum ether:ethyl acetate (v:v)=4:1) to obtain tert-butyl 2-(4-benzyloxycarbonylpiperazin-1-yl)-7-azaspiro[3.5]nonane-7-carboxylate (36A) as light yellow oily substance (450 mg, yield 50.79%).
MS m/z=444.2[M+H]$^+$;

Step 2: benzyl 4-(7-azaspiro[3.5]nonan-2-yl)piperazine-1-carboxylate (36B)

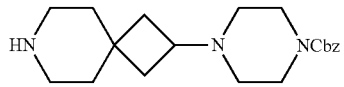 [SMILES: O=C(OCc1ccccc1)N1CCN(C2CC3(CCNCC3)C2)CC1]

Tert-butyl 2-(4-benzyloxycarbonylpiperazin-1-yl)-7-azaspiro[3.5]nonane-7-carboxylate (36A) (0.45 g, 1.20 mmol) and dichloromethane (7 mL) were added in a 50 mL reaction flask, and trifluoroacetic acid (1 mL) was added dropwise at room temperature. After the addition, the system was allowed to react at room temperature for 3 h. The reaction solution was directly concentrated under reduced pressure to obtain crude benzyl 4-(7-azaspiro[3.5]nonane-2-yl)piperazine-1-carboxylate (36B) as light yellow oily liquid (411 mg, yield 100%), and used directly in the next reaction.

Step 3: benzyl 4-[7-[(2R)-6-(tert-butoxycarbo-nylamino)-2-[[(2R)-2-[[(2R)-2-[[(2R)-2-(tert-butoxycarbonylamino)-3-phenyl-propanoyl]amino]-3-phenyl- propanoyl]amino]-4-methyl-pentanoyl]amino]hexanoyl]-7-azaspiro[3.5]nonan-2-yl]piperazine-1-carboxylate (36C)

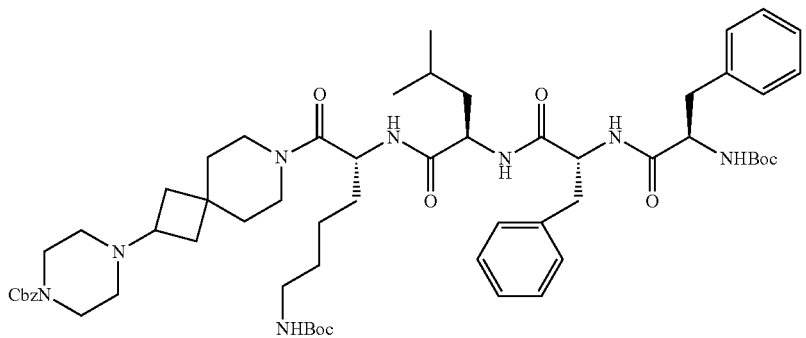 [SMILES: CC(C)C[C@@H](NC(=O)[C@@H](Cc1ccccc1)NC(=O)[C@@H](Cc1ccccc1)NC(=O)OC(C)(C)C)C(=O)N[C@H](CCCCNC(=O)OC(C)(C)C)C(=O)N1CCC2(CC1)CC(N1CCN(C(=O)OCc3ccccc3)CC1)C2]

Crude benzyl 4-(7-azaspiro[3.5]nonane-2-yl)piperazine-1-carboxylate (36B) (411 mg, 1.2 mmol), 1-(3-dimethylaminopropyl)-3-ethylcarbodiimide hydrochloride (384 mg, 2 mmol), 1-hydroxybenzotriazole (270 mg, 2 mmol), intermediate 1 (400 mg, 0.53 mmol) and dichloromethane (30 mL) were added in a 50 mL single-necked flask, and the system was allowed to react at room temperature for 5 h. The reaction solution was concentrated under reduced pressure, and the residue was separated and purified by silica gel column chromatography (petroleum ether:ethyl acetate (v:v) =1:2) to obtain benzyl4-[7-[(2R)-6-(tert-butoxycarbo-nylamino)-2-[[(2R)-2-[[(2R)-2-[[(2R)-2-(tert-butoxycarbo-nylamino)-3-phenyl-propanoyl]amino]-3-phenyl-propanoyl]amino]-4-methylpentanoyl]amino]hexanoyl]-7-azaspiro[3.5]nonane-2-yl]piperazine-1-carboxylate (36C) as white solid (300 mg, yield 52.4%).

Step 4: tert-butyl N-[(1R)-1-benzyl-2-[[(1R)-1-benzyl-2-[[(1R)-1-[[(1R)-5-(tert-butoxycarbonylamino)-1-(2-piperazin-1-yl-7-azaspiro[3.5]nonane-7-carbonyl)pentyl]carbamoyl]-3-methyl-butyl]amino]-2-oxo-ethyl]amino]-2-oxo-ethyl]carbamate (36D)

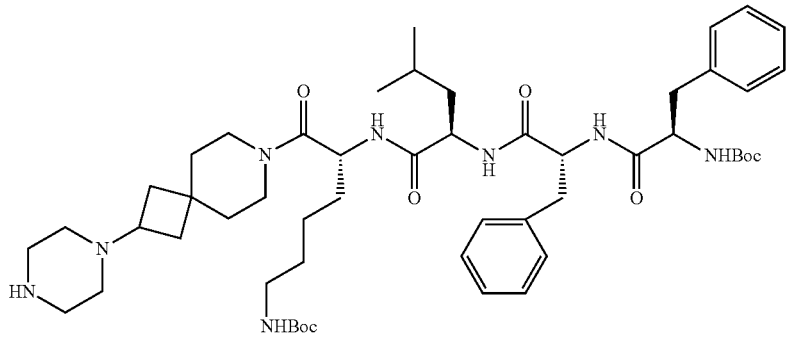 [SMILES: CC(C)C[C@@H](NC(=O)[C@@H](Cc1ccccc1)NC(=O)[C@@H](Cc1ccccc1)NC(=O)OC(C)(C)C)C(=O)N[C@H](CCCCNC(=O)OC(C)(C)C)C(=O)N1CCC2(CC1)CC(N1CCNCC1)C2]

Benzyl 4-[7-[(2R)-6-(tert-butoxycarbonylamino)-2-[[(2R)-2-[[(2R)-2-[[(2R)-2-(tert-butoxycarbonylamino)-3-phenyl-propanoyl]amino]-3-phenyl- propanoyl]amino]-4-methylpentanoyl]amino]hexanoyl]-7-azaspiro[3.5]nonane-2-yl]piperazine-1-carboxylate (36C) (300 mg, 0.27 mmol) and methanol (5 mL), and Pd/C (30 mg) were added in a 50 mL reaction flask, and the system was allowed to react at room temperature for 4 h under a hydrogen atmosphere. The reaction solution was filtered through diatomite, and concentrated under reduced pressure to obtain tert-butyl N-[(1R)-1-benzyl-2-[[(1R)-1-benzyl-2-[[(1R)-1-[[(1R)-5-(tert-butoxycarbonylamino)-1-(2-piperazine-1-yl-7-azaspiro[3.5]nonane-7-carbonyl)pentyl]carbamoyl]-3-methyl-butyl]amino]-2-oxo-ethyl]amino]-2-oxo-ethyl]carbamate (36D) (255 mg, 100%) and used directly in the next step.

Step 5: (2R)-2-[[(2R)-2-[[(2R)-2-amino-3-phenyl-propanoyl]amino]-3-phenyl-propanoyl]amino]-N-[(1R)-5-amino-1-(2-piperazin-1-yl-7-azaspiro[3.5]nonane-7-carbonyl)pentyl]-4-methyl-pentanamide tetra-trifluoroacetic acid (compound 36)

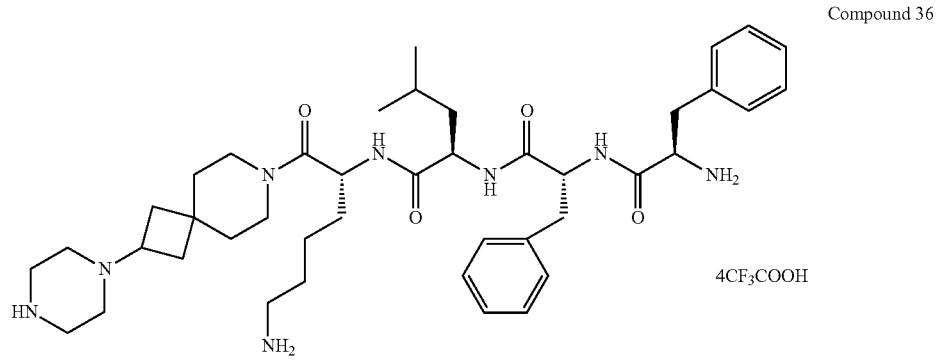 [SMILES: CC(C)C[C@@H](NC(=O)[C@@H](Cc1ccccc1)NC(=O)[C@H](N)Cc1ccccc1)C(=O)N[C@H](CCCCN)C(=O)N1CCC2(CC1)CC(N1CCNCC1)C2]

Compound 36

4CF₃COOH

Crude tert-butyl N-[(1R)-1-benzyl-2-[[(1R)-1-benzyl-2-[[(1R)-1-[[(1R)-5-(tert-butoxycarbonylamino)-1-(2-piperazine-1-yl-7-azaspiro[3.5]nonane-7-carbonyl)pentyl]carbamoyl]-3-methyl-butyl]amino]-2-oxo-ethyl]amino]-2-oxo-ethyl]carbamate (36D) (255 mg, 0.27 mmol) and trifluoroacetic acid (2 mL) were added in a 50 mL reaction flask, and the system was allowed to react at room temperature for 2 h. The reaction solution was concentrated under reduced pressure, and the residue was separated and purified by preparative liquid chromatography (preparation conditions: instrument: Gilson GX-281; column: Xbridge C18, 150×30 mm I.D., 5 μm; mobile phase: A for ACN and B for H₂O; isocratic: A 65%; flow rate: 30 mL/min; back pressure: 1000 PSI; column temperature: 30° C.; wavelength: 210 nm; period: 18 min; sample preparation: the compound dissolved in 12 mL methanol; injection: 0.9 mL/needle). The preparation was concentrated under reduced pressure to remove most of the solvent, and lyophilized to obtain (2R)-2-[[(2R)-2-[[(2R)-2-amino-3-phenyl-propanoyl]amino]-3-phenyl-propanoyl]amino]-N-[(1R)-5-amino-1-(2-piperazine-1-yl-7-azaspiro[3.5]nonane-7-carbonyl)pentyl]-4-methyl-pentanamidetetra-trifluoroacetic acid (compound 36) as white powder (160 mg, yield 77.6%).

MS m/z=373.4[M+2H]⁺/2;

¹H NMR (400 MHz, D₂O) δ 7.47-7.30 (m, 10H), 4.71 (t, 1H), 4.36-4.29 (m, 2H), 3.90-3.86 (m, 1H), 3.85-3.24 (m, 12H), 3.23-3.04 (m, 6H), 2.52-2.44 (m, 2H), 2.14-2.12 (m, 2H), 1.77-1.47 (m, 14H), 1.03-0.96 (dd, 6H).

Example 35: (2R)—N-[(1R)-5-amino-1-[7-[(2R)-2-amino-3-phenyl-propanoyl]-2,7-diazaspiro[3.5]nonane-2-carbonyl]pentyl]-2-[[(2R)-2-[[(2R)-2-amino-3-phenyl-propanoyl]amino]-3-phenyl-propanoyl]amino]-4-methyl-pentanamide; tri-trifluoroacetic acid (compound 37)

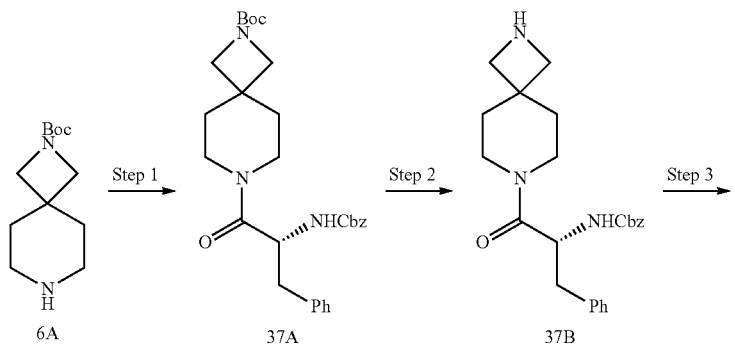

-continued
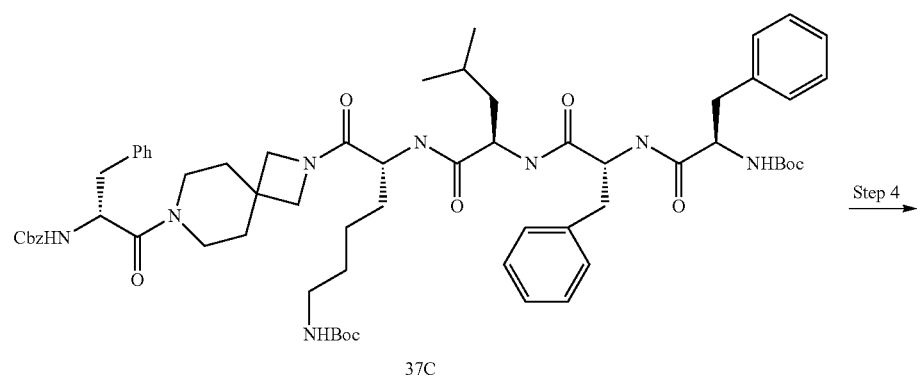
37C
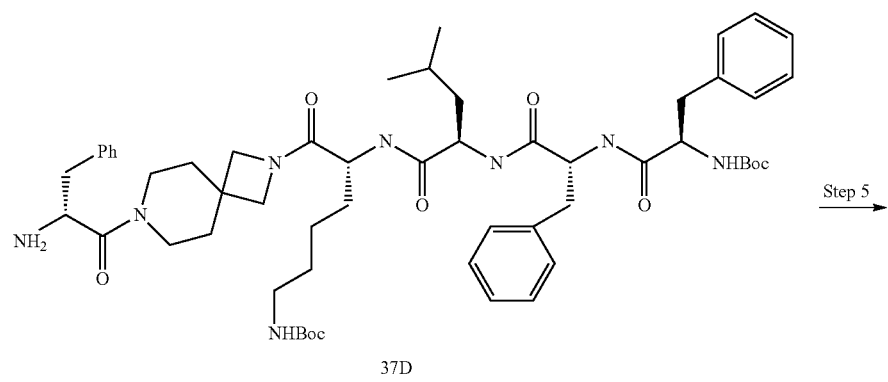
37D
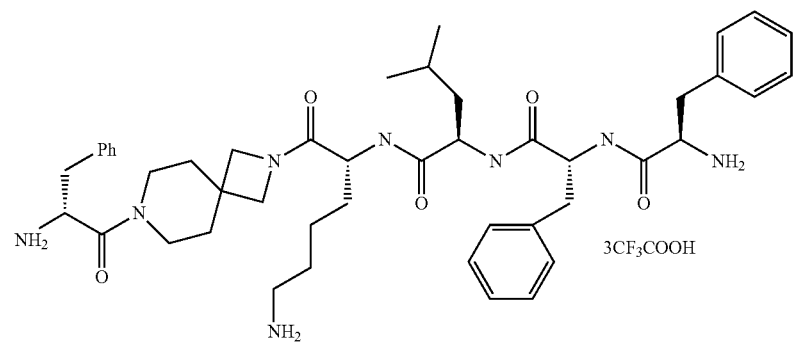
Compound 37

Step 1: tert-butyl 7-[(2R)-2-(benzyloxycarbonylamino)-3-phenyl-propanoyl]-2,7-diazaspiro[3.5]nonane-2-carboxylate (37A)

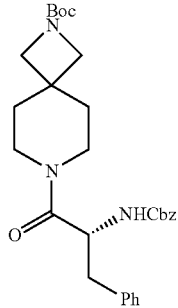

Tert-butyl 2,7-diazaspiro[3.5]nonane-2-carboxylate (6A) (83 mg, 0.35 mmol), 1-(3-dimethylaminopropyl)-3-ethylcarbodiimide hydrochloride (80 mg, 0.42 mmol), 1-hydroxybenzotriazole (57 mg, 0.42 mmol), (2R)-2-(benzyloxycarbonylamino)-3-phenyl-propanoic acid (105 mg, 0.35 mmol) and dichloromethane (30 mL) were added in a 50 mL reaction flask, and the system was allowed to react at room temperature for 5 h. The reaction solution was concentrated under reduced pressure, and the residue was separated and purified by silica gel column chromatography (dichloromethane:methanol (v:v)=50:1) to obtain tert-butyl 7-[(2R)-2-(benzyloxycarbonylamino)-3-phenyl-propanoyl]-2,7-diazaspiro[3.5]nonane-2-carboxylate (37A) as white solid (177 mg, yield 80%).

Step 2: Benzyl N-[(1R)-1-benzyl-2-(2,7-diazaspiro[3.5]nonan-7-yl)-2-oxo-ethyl]carbamate (37B)

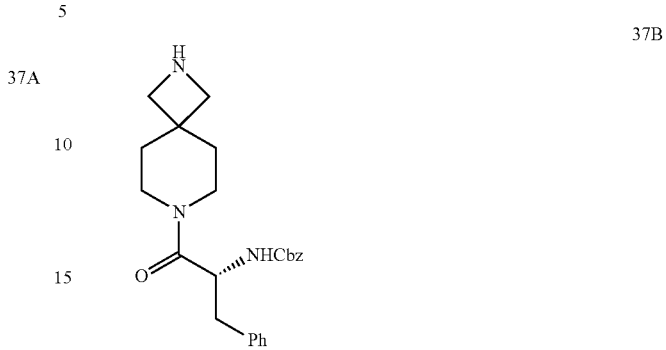

Tert-butyl 7-[(2R)-2-(benzyloxycarbonylamino)-3-phenyl-propanoyl]-2,7-diazaspiro[3.5]nonane-2-carboxylate (37A)(177 mg, 0.35 mmol) and dichloromethane (20 mL) were added in a 50 mL reaction flask, and trifluoroacetic acid (2 mL) was added dropwise at room temperature. After the addition, the system was allowed to react at room temperature for 3 h. The reaction solution was directly concentrated under reduced pressure to obtain benzyl N-[(1R)-1-benzyl-2-(2,7-diazaspiro[3.5]nonan-7-yl)-2-oxo-ethyl]carbamate (37B) as yellow oily liquid (143 mg, yield 100%), and used directly in the next reaction.

Step 3: tert-butyl N-[(1R)-1-benzyl-2-[[(1R)-1-benzyl-2-[[(1R)-1-[[(1R)-1-[7-[(2R)-2-(benzyloxycarbonylamino)-3-phenyl-propanoyl]-2,7-diazaspiro[3.5]nonane-2-carbonyl]-5-(tert-butoxycarbonylamino)pentyl]carbamoyl]-3-methyl-butyl]amino]-2-oxo-ethyl]amino]-2-oxo-ethyl]carbamate (37C)

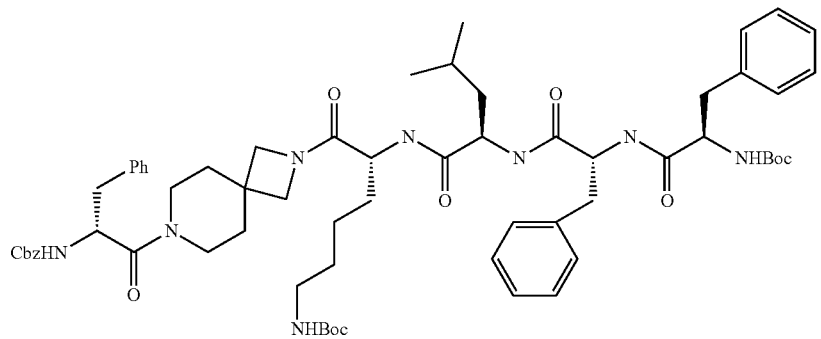 [SMILES: CC(C)C[C@@H](NC(=O)[C@@H](Cc1ccccc1)NC(=O)[C@@H](Cc1ccccc1)NC(=O)OC(C)(C)C)C(=O)N[C@H](CCCCNC(=O)OC(C)(C)C)C(=O)N1CC2(CCN(C(=O)[C@@H](Cc3ccccc3)NC(=O)OCc3ccccc3)CC2)C1]

Benzyl N-[(1R)-1-benzyl-2-(2,7-diazaspiro[3.5]nonan-7-yl)-2-oxo-ethyl]carbamate (37B) (143 mg, 0.35 mmol), 1-(3-dimethylaminopropyl)-3-ethylcarbodiimide hydrochloride (80 mg, 0.42 mmol), 1-hydroxybenzotriazole (57 mg, 0.42 mmol), intermediate 1 (264 mg, 0.35 mmol) and dichloromethane (30 mL) were added in a 50 mL single-necked flask, and the system was allowed to react at room temperature for 5 h. The reaction solution was concentrated under reduced pressure, and the residue was separated and purified by silica gel column chromatography (dichloromethane:methanol (v:v)=50:1) to obtain tert-butyl (1R)-1-benzyl-2-[[(1R)-1-benzyl-2-[[(1R)-1-[[(1R)-1-[7-[(2R)-2-(benzyloxycarbonylamino)-3-phenyl-propanoyl]-2,7-diazaspiro[3.5]nonane-2-carbonyl]-5-(tert-butoxycarbonylamino)pentyl]carbamoyl]-3-methyl-butyl]amino]-2-oxo-ethyl]amino]-2-oxo-ethyl]carbamate (37C) as white solid (400 mg, yield 99%).

Step 4: tert-butyl N-[(1R)-2-[[(1R)-2-[[(1R)-1-[[(1R)-1-[7-[(2R)-2-amino-3-phenyl-propanoyl]-2,7-diazaspiro[3.5]nonane-2-carbonyl]-5-(tert-butoxycarbonylamino)pentyl]carbamoyl]-3-methyl-butyl]amino]-1-benzyl-2-oxo-ethyl]amino]-1-benzyl-2-oxo-ethyl]carbamate (37D)

Step 5: (2R)—N-[(1R)-5-amino-1-[7-[(2R)-2-amino-3-phenyl-propanoyl]-2,7-diazaspiro[3.5]nonane-2-carbonyl]pentyl]-2-[[(2R)-2-[[(2R)-2-amino-3-phenyl-propanoyl]amino]-3-phenyl-propanoyl]amino]-4-methyl-pentanamide tri-trifluoroacetic acid (compound 37)

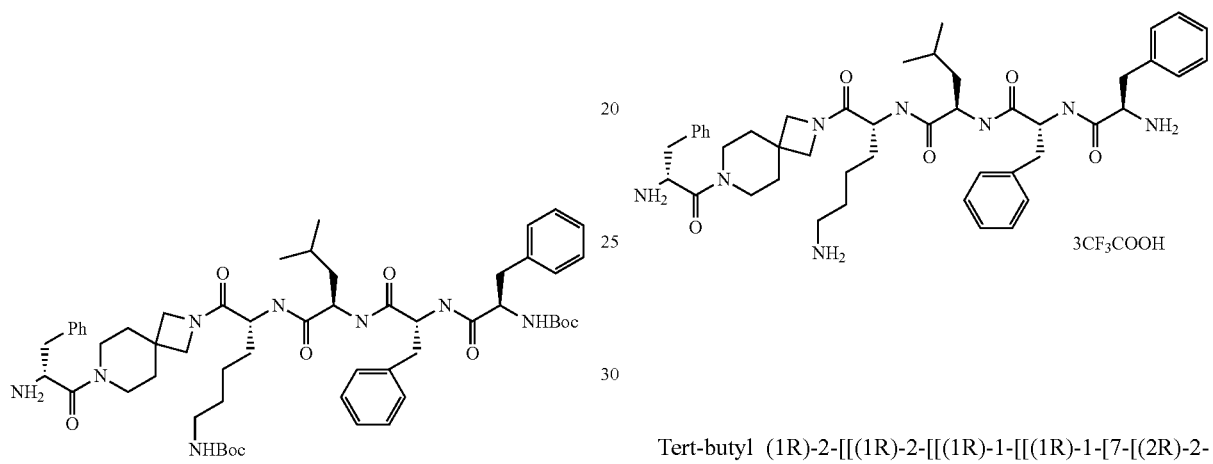

Compound 37

Tert-butyl(1R)-1-benzyl-2-[[(1R)-1-benzyl-2-[[(1R)-1-[[(1R)-1-[7-[(2R)-2-(benzyloxycarbonylamino)-3-phenyl-propanoyl]-2,7-diazaspiro[3.5]nonane-2-carbonyl]-5-(tert-butoxycarbonylamino)pentyl]carbamoyl]-3-methyl-butyl]amino]-2-oxo-ethyl]amino]-2-oxo-ethyl]carbamate (37C) (400 mg, 0.35 mmol), palladium on carbon (80 mg, 20 wt %1) and methanol (20 mL) were added in a 50 mL single-necked flask. The atmosphere was replaced with hydrogen 3 times, and the mixture reacted at room temperature for 3 h under a hydrogen (balloon) atmosphere. The reaction solution was filtered through diatomite, and the filtrate was concentrated under reduced pressure to obtain crude tert-butyl (1R)-2-[[(1R)-2-[[(1R)-1-[[(1R)-1-[7-[(2R)-2-amino-3-phenyl-propanoyl]-2,7-diazaspiro[3.5]nonane-2-carbonyl]-5-(tert-butoxycarbonylamino)pentyl]carbamoyl]-3-methyl-butyl]amino]-1-benzyl-2-oxo-ethyl]amino]-1-benzyl-2-oxo-ethyl]carbamate (37D) as light yellow solid (353 mg, yield 100%), and used directly in the next reaction.

Tert-butyl (1R)-2-[[(1R)-2-[[(1R)-1-[[(1R)-1-[7-[(2R)-2-amino-3-phenyl-propanoyl]-2,7-diazaspiro[3.5]nonane-2-carbonyl]-5-(tert-butoxycarbonyl)pentyl]carbamoyl]-3-methyl-butyl]amino]-1-benzyl-2-oxo-ethyl]amino]-1-benzyl-2-oxo-ethyl]carbamate (37D)(353 mg, 0.35 mmol) and trifluoroacetic acid (2 mL) were added in a 50 mL reaction flask, and the system was allowed to react at room temperature for 2 h. The reaction solution was concentrated under reduced pressure, and the residue was separated and purified by preparative liquid chromatography (preparation conditions: instrument: Gilson GX-281; column: Xbridge C18, 150×30 mm I.D., 5 μm; mobile phase: A for ACN and B for H$_2$O; isocratic: A 65%; flow rate: 30 mL/min; back pressure: 1000 PSI; column temperature: 30° C.; wavelength: 210 nm; period: 18 min; sample preparation: the compound dissolved in 12 mL methanol; injection: 0.9 mL/needle). The preparation was concentrated under reduced pressure to remove most of the solvent, and lyophilized to obtain (2R)—N-[(1R)-5-amino-1-[7-[(2R)-2-amino-3-phenyl-propanoyl]-2,7-diazaspiro[3.5]nonane-2-carbonyl]pentyl]-2-[[(2R)-2-[[(2R)-2-amino-3-phenyl-propanoyl]amino]-3-phenyl-propanoyl]amino]-4-methyl-pentanamide; tri-trifluoroacetic acid (compound 37) as white powder (282 mg, yield 70%).

MS m/z=405.3 [M+2H]$^+$/2;

1H NMR (400 MHz, D$_2$O) δ 7.52-7.09 (m, 15H), 4.78-4.74 (m, 1H), 4.64-4.58 (m, 1H), 4.26-4.19 (m, 2H), 4.15-3.96 (m, 3H), 3.83 (d, 1H), 3.71-3.63 (m, 1H), 3.59-3.50 (m, 1H) 3.43-2.90 (m, 11H), 1.90-1.18 (m, 13H), 0.98-0.80 (m, 6H).

Example 36: (2R)—N-[(1R)-5-amino-1-[7-[(2R)-2-amino-4-methyl-pentanoyl]-2,7-diazaspiro[3.5]nonane-2-carbonyl]pentyl]-2-[[(2R)-2-[[(2R)-2-amino-3-phenyl-propanoyl]amino]-3-phenyl-propanoyl]amino]-4-methyl-pentanamide; tri-trifluoroacetic acid (compound 38)
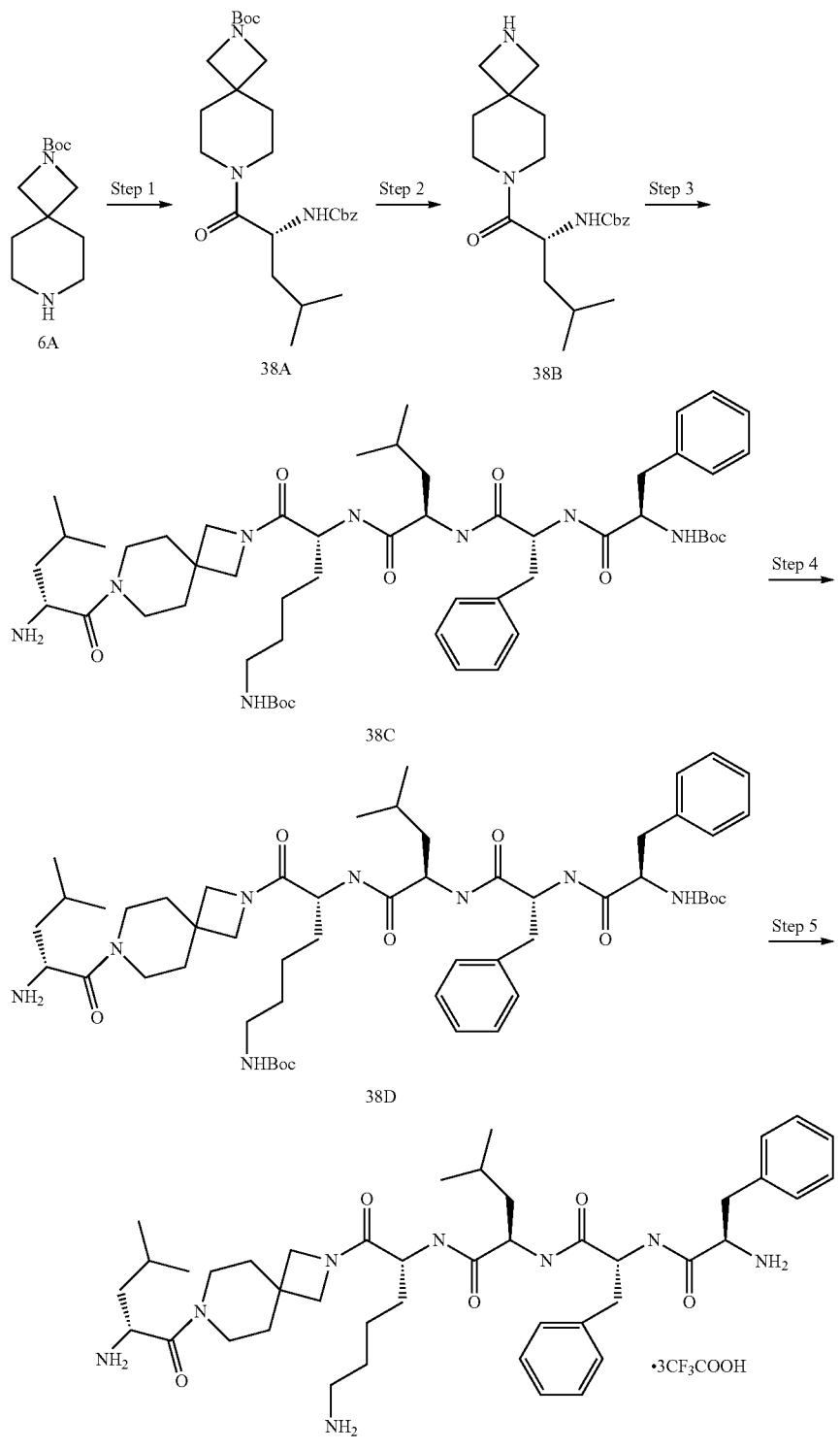
Compound 38

Step 1 tert-butyl 7-[(2R)-2-(benzyloxycarbonylamino)-4-methyl-pentanoyl]-2,7-diazaspiro[3.5]nonane-2-carboxylate (38A)

Step 2 benzyl N-[(1R)-1-(2,7-diazaspiro[3.5]nonane-7-carbonyl)-3-methyl-butyl]carbamate (38B)

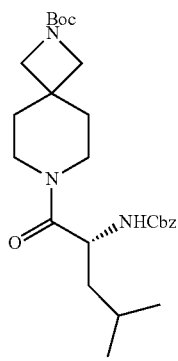

38A

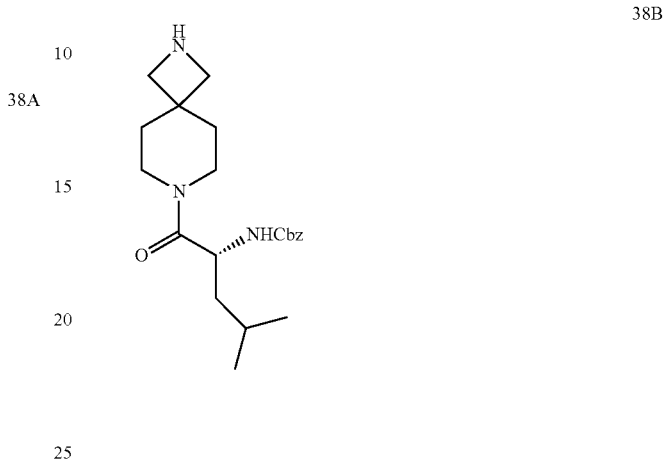

Tert-butyl 2,7-diazaspiro[3.5]nonane-2-carboxylate (6A) (93 mg, 0.41 mmol), 1-(3-dimethylaminopropyl)-3-ethyl-carbodiimide hydrochloride (94 mg, 0.49 mmol), 1-hydroxybenzotriazole (66 mg, 0.49 mmol), (2R)-2-(benzyloxycarbonylamino)propanoic acid (446 mg, 2.0 mmol) and dichloromethane (10 mL) were added in a 50 mL reaction flask, and the system was allowed to react at room temperature for 5 h. The reaction solution was concentrated under reduced pressure, and the residue was separated and purified by silica gel column chromatography (dichloromethane:methanol (v:v)=50:1) to obtain tert-butyl 7-[(2R)-2-(benzyloxycarbonylamino)-4-methyl-pentanoyl]-2,7-diazaspiro[3.5]nonane-2-carboxylate (38A) as white solid (175 mg, yield 90%).

Tert-butyl 7-[(2R)-2-(benzyloxycarbonylamino)-4-methyl-pentanoyl]-2,7-diazaspiro[3.5]nonane-2-carboxylate (38A)(175 mg, 0.37 mmol) and dichloromethane (20 mL) were added in a 50 mL reaction flask, and trifluoroacetic acid (2 mL) was added dropwise at room temperature. After the addition, the system was allowed to react at room temperature for 3 h. The reaction solution was directly concentrated under reduced pressure to obtain benzyl N-[(1R)-1-(2,7-diazaspiro[3.5]nonane-7-carbonyl)-3-methyl-butyl]carbamate (38B) as yellow oily liquid (138 mg, yield 100%), and used directly in the next reaction.

Step 3 tert-butyl N-[(1R)-1-benzyl-2-[[(1R)-1-benzyl-2-[[(1R)-1-[[(1R)-1-[7-[(2R)-2-(benzyloxycarbonylamino)-4-methyl-pentanoyl]-2,7-diazaspiro[3.5]nonane-2-carbonyl]-5-(tert-butoxycarbonylamino)pentyl]carbamoyl]-3-methyl-butyl]amino]-2-oxo-ethyl]amino]-2-oxo-ethyl]carbamate (38C)

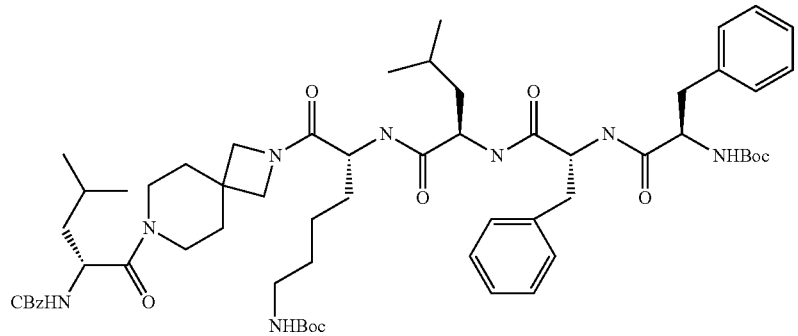

Benzyl N-[(1R)-1-(2,7-diazaspiro[3.5]nonane-7-carbonyl)-3-methyl-butyl]carbamate (38B) (138 mg, 0.37 mmol), 1-(3-dimethylaminopropyl)-3-ethylcarbodiimide hydrochloride (84 mg, 0.44 mmol), 1-hydroxybenzotriazole (59 mg, 0.44 mmol), intermediate 1 (279 mg, 0.37 mmol) and dichloromethane (30 mL) were added in a 50 mL single-necked flask, and the system was allowed to react at room temperature for 5 h. The reaction solution was concentrated under reduced pressure, and the residue was separated and purified by silica gel column chromatography (dichloromethane:methanol (v:v)=50:1) to obtain tert-butyl (1R)-1-benzyl-2-[[(1R)-1-benzyl-2-[[(1R)-1-[[(1R)-1-[7-[(2R)-2-(benzyloxycarbonylamino)-4-methyl-pentanoyl]-2,7-diazaspiro[3.5]nonane-2-carbonyl]-5-(tert-butoxycarbonylamino)pentyl]carbamoyl]-3-methyl-butyl]amino]-2-oxo-ethyl]amino]-2-oxo-ethyl]carbamate (38C) as white solid (366 mg, yield 90%).

Step 4: tert-butyl N-[(1R)-2-[[(1R)-2-[[(1R)-1-[[(1R)-1-[7-[(2R)-2-amino-4-methyl-pentanoyl]-2,7-diazaspiro[3.5]nonane-2-carbonyl]-5-(tert-butoxycarbonylamino)pentyl]carbamoyl]-3-methyl-butyl]amino]-1-benzyl-2-oxo-ethyl]amino]-1-benzyl-2-oxo-ethyl]carbamate (38D)

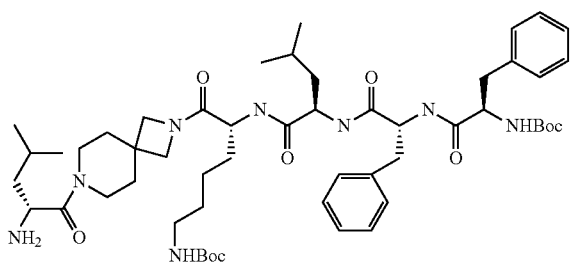 [SMILES: CC(C)C[C@@H](N)C(=O)N1CCC2(CC1)CN(C(=O)[C@@H](CCCCNC(=O)OC(C)(C)C)NC(=O)[C@@H](CC(C)C)NC(=O)[C@@H](Cc1ccccc1)NC(=O)[C@@H](Cc1ccccc1)NC(=O)OC(C)(C)C)C2]

Tert-butyl(1R)-1-benzyl-2-[[(1R)-1-benzyl-2-[[(1R)-1-[[(1R)-1-[7-[(2R)-2-(benzyloxycarbonylamino)-4-methyl-pentanoyl]-2,7-diazaspiro[3.5]nonane-2-carbonyl]-5-(tert-butoxycarbonylamino)pentyl]carbamoyl]-3-methyl-butyl]amino]-2-oxo-ethyl]amino]-2-oxo-ethyl]carbamate (38C) (366 mg, 0.33 mmol), palladium on carbon (73 mg, 20 wt % 1) and methanol (20 mL) were added in a 50 mL single-necked flask. The atmosphere was replaced with hydrogen 3 times, and the mixture reacted at room temperature for 3 h under a hydrogen atmosphere. The reaction solution was filtered through diatomite, and the filtrate was concentrated under reduced pressure to obtain crude (1R)-2-[(1R)-2-[[(1R)-1-[[(1R)-1-[7-[(2R)-2-amino-4-methyl-pentanoyl]-2,7-diazaspiro[3.5]nonane-2-carbonyl]-5-(tert-butoxycarbonyl)pentyl]carbamoyl]-3-methyl-butyl]amino]-1-benzyl-2-oxo-ethyl]amino]-1-benzyl-2-oxo-ethyl]tert-butyl carbamate (38D) as light yellow solid (322 mg, yield 100%), and used directly in the next reaction.

Step 5: (2R)—N-[(1R)-5-amino-1-[7-[(2R)-2-amino-4-methyl-pentanoyl]-2,7-diazaspiro[3.5]nonane-2-carbonyl]pentyl]-2-[[(2R)-2-[[(2R)-2-amino-3-phenyl-propanoyl]amino]-3-phenyl-propanoyl]amino]-4-methyl-pentanamide; tri-trifluoroacetic acid (compound 38)

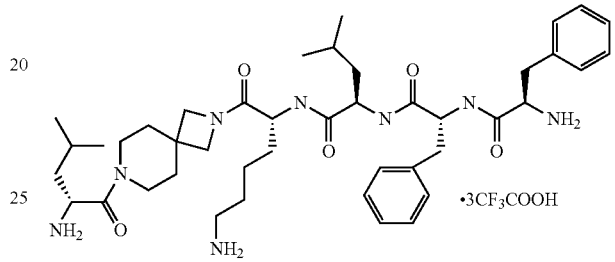

Compound 38

Tert-butyl(1R)-2-[(1R)-2-[[(1R)-1-[[(1R)-1-[7-[(2R)-2-amino-4-methyl-pentanoyl]-2,7-di azaspiro[3.5]nonane-2-carbonyl]-5-(tert-butoxycarbonyl)pentyl]carbamoyl]-3-methyl-butyl]amino]-1-benzyl-2-oxo-ethyl]amino]-1-benzyl-2-oxo-ethyl]carbamate (38D) (322 mg, 0.33 mmol) and trifluoroacetic acid (2 mL) were added in a 50 mL reaction flask, and the system was allowed to react at room temperature for 2 h. The reaction solution was concentrated under reduced pressure, and the residue was separated and purified by preparative liquid chromatography (preparation conditions: instrument: Gilson GX-281; column: Xbridge C18, 150×30 mm I.D., 5 μm; mobile phase: A for ACN and B for $H_2O$; isocratic: A 65%; flow rate: 30 mL/min; back pressure: 1000 PSI; column temperature: 30° C.; wavelength: 210 nm; period: 18 min; sample preparation: the compound dissolved in 12 mL methanol; injection: 0.9 mL/needle). The preparation was concentrated under reduced pressure to remove most of the solvent, and lyophilized to obtain (2R)—N-[(1R)-5-amino-1-[7-[(2R)-2-amino-4-methyl-pentanoyl]-2,7-diazaspiro[3.5]nonane-2-carbonyl]pentyl]-2-[[(2R)-2-[[(2R)-2-amino-3-phenyl-propanoyl]amino]-3-phenyl-propanoyl]amino]-4-methyl-pentanamide; tri-trifluoroacetic acid (compound 38) as white powder (240 mg, yield 65%).

MS m/z=388.3 $[M+2H]^+/2$;

$^1$H NMR (400 MHz, $D_2O$) δ 7.44-7.14 (m, 10H), 4.61 (t, 1H), 4.50-4.42 (m, 1H), 4.28-4.02 (m, 5H), 3.83-3.70 (m, 2H), 3.66-3.36 (m, 4H), 3.14 (t, 2H), 2.97 (t, 4H), 1.94-1.64 (m, 10H), 1.54-1.30 (m, 6H), 1.01-0.81 (m, 12H).

Example 37: (2R)—N-[(1R)-5-amino-1-[2-(cyclo-propanecarbonyl)-2,7-diazaspiro[3.5]nonane-7-carbonyl]pentyl]-2-[[(2R)-2-[[(2R)-2-amino-3-phenyl-propanoyl]amino]-3-phenyl-propanoyl]amino]-4-methyl-pentanamide; di-trifluoroacetic acid (compound 39)
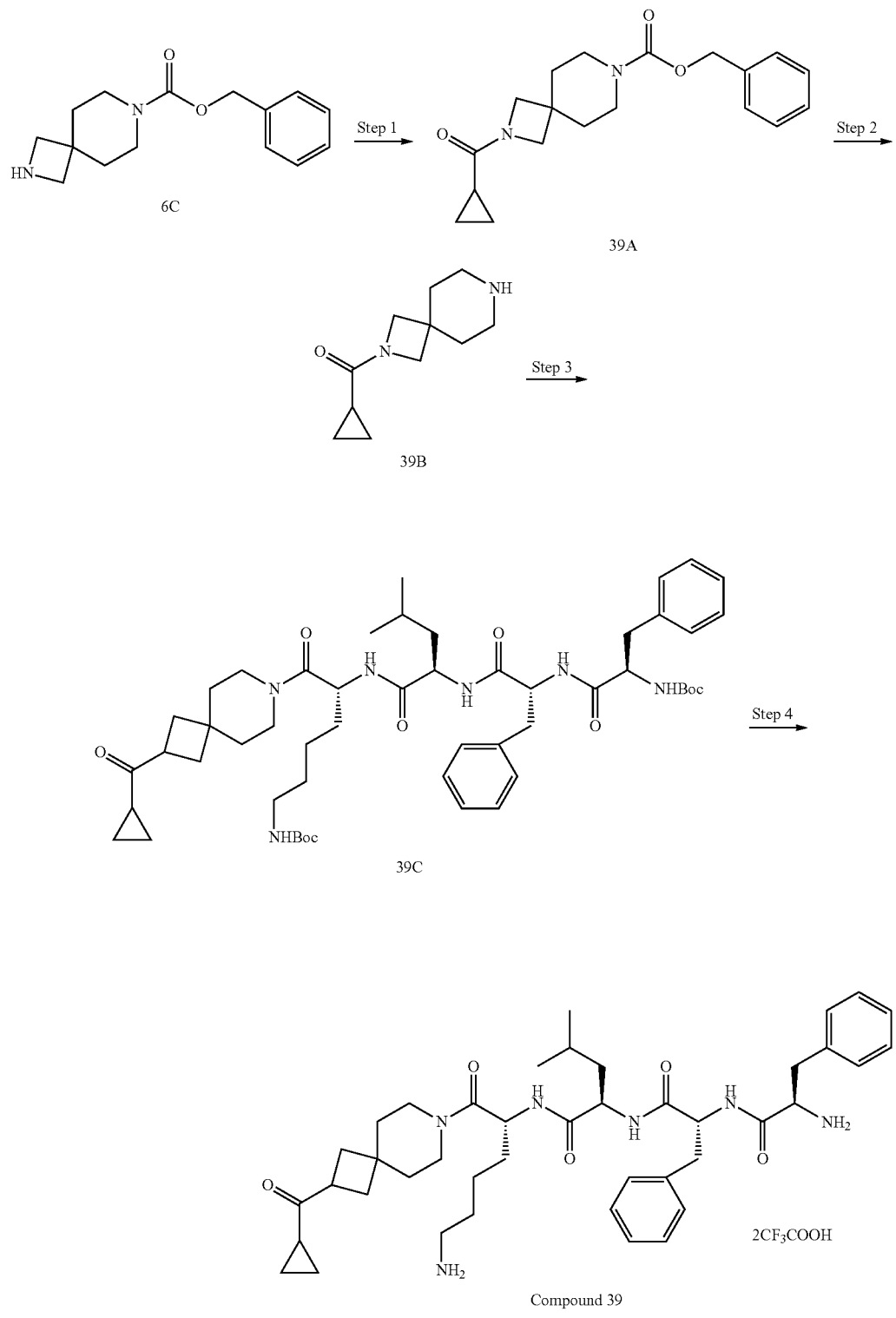

221

Step 1: benzyl 2-(cyclopropanecarbonyl)-2,7-diazaspiro[3.5]nonane-7-carboxylate (39A)

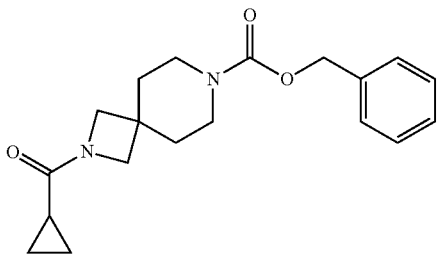

39A

Benzyl 2,7-diazaspiro[3.5]nonane-7-carboxylate (6C) (390 mg, 1.5 mmol), 1-(3-dimethylaminopropyl)-3-ethylcarbodiimide hydrochloride (760 mg, 4.9 mmol), 1-hydroxybenzotriazole (300 mg, 2.0 mmol), cyclopropylcarboxylic acid (172 mg, 2.0 mmol) and dichloromethane (50 mL) were added in a 50 mL single-necked flask, and the system was allowed to react at room temperature for 5 h. The reaction solution was concentrated under reduced pressure, and the residue was separated and purified by silica gel column chromatography (dichloromethane:methanol (v:v) =50:1) to obtain benzyl 2-(cyclopropanecarbonyl)-2,7-diazaspiro[3.5]nonane-7-carboxylate (39A) as light yellow oily substance (320 mg, yield 65%).

Step 2: cyclopropyl(2,7-diazaspiro[3.5]nonan-2-yl)methanone (39B)

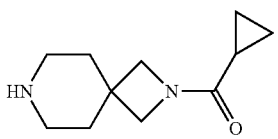

39B

Benzyl 2-(cyclopropanecarbonyl)-2,7-diazaspiro[3.5]nonane-7-carboxylate (39A) (320 mg, 0.97 mmol), palladium on carbon (64 mg, 20 wt % l) and methanol (10 mL) were added in a 50 mL single-necked flask. The atmosphere was replaced with hydrogen 3 times, and reacted at room temperature for 3 h under a hydrogen (balloon) atmosphere. The reaction solution was filtered through diatomite, and the filtrate was concentrated under reduced pressure to obtain crude cyclopropyl(2,7-diazaspiro[3.5]nonan-2-yl)methanone (39B) as light yellow solid (189 mg, yield 100%), and used directly in the next reaction.

222

Step 3: tert-butyl N-[(1R)-1-benzyl-2-[[(1R)-1-benzyl-2-[[(1R)-1-[[(1R)-5-(tert-butoxycarbonylamino)-1-[2-(cyclopropanecarbonyl)-2,7-diazaspiro[3.5]nonane-7-carbonyl]pentyl]carbamoyl]-3-methyl-butyl]amino]-2-oxo-ethyl]amino]-2-oxo-ethyl] carbamate (39C)

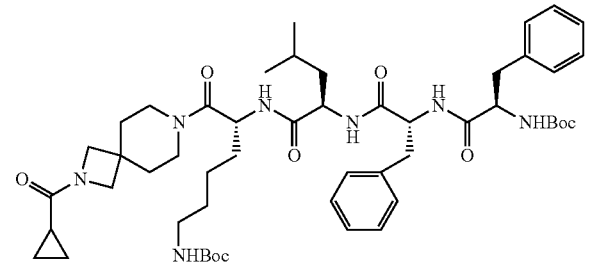

39C

Crude cyclopropyl(2,7-diazaspiro[3.5]nonan-2-yl)methanone (39B) (189 mg, 0.75 mmol), 1-(3-dimethylaminopropyl)-3-ethylcarbodiimide hydrochloride (216 mg, 1.13 mmol), 1-hydroxybenzotriazole (122 mg, 0.9 mmol), intermediate 1 (565 mg, 0.75 mmol) and dichloromethane (30 mL) were added in a 50 mL single-necked flask, and the system was allowed to react at room temperature for 5 h. The reaction solution was concentrated under reduced pressure, and the residue was separated and purified by silica gel column chromatography (petroleum ether:ethyl acetate (v:v) =1:2) to obtain tert-butyl N-[(1R)-1-benzyl-2-[[(1R)-1-benzyl-2-[[(1R)-1-[[(1R)-5-(tert-butoxycarbonylamino)-1-[2-(cyclopropanecarbonyl)-2,7-diazaspiro[3.5]nonane-7-carbonyl]pentyl]carbamoyl]-3-methyl-butyl]amino]-2-oxo-ethyl]amino]-2-oxo-ethyl]carbamate (39C) as light yellow solid (410 mg, yield 45%).

Step 4: (2R)—N-[(1R)-5-amino-1-[2-(cyclopropanecarbonyl)-2,7-diazaspiro[3.5]nonane-7-carbonyl]pentyl]-2-[[(2R)-2-[[(2R)-2-amino-3-phenyl-propanoyl]amino]-3-phenyl-propanoyl]amino]-4-methyl-pentanamide; di-trifluoroacetic acid (compound 39)

Compound 39

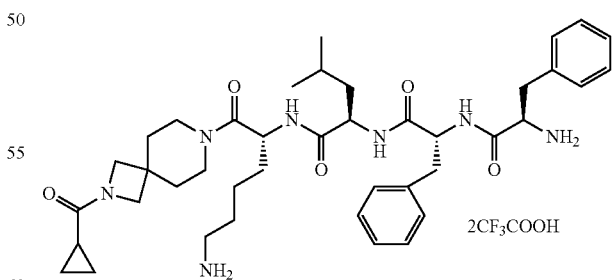

Tert-butyl N-[(1R)-1-benzyl-2-[[(1R)-1-benzyl-2-[[(1R)-1-[[(1R)-5-(tert-butoxycarbonylamino)-1-[2-(cyclopropanecarbonyl)-2,7-diazaspiro[3.5]nonane-7-carbonyl]pentyl]carbamoyl]-3-methyl-butyl]amino]-2-oxo-ethyl]amino]-2-oxo-ethyl]carbamate (39C) (410 mg, 0.44 mmol) and trifluoroacetic acid (2 mL) were added in a 50 mL reaction flask, and the system was allowed to react at room temperature for 2 h. The reaction solution was concentrated under reduced pressure, and the residue was separated and purified by preparative liquid chromatography (preparation conditions: instrument: Gilson GX-281; column: Xbridge C18, 150×30 mm I.D., 5 μm; mobile phase: A for ACN and B for H₂O; isocratic: A 65%; flow rate: 30 mL/min; back pressure: 1000 PSI; column temperature: 30° C.; wavelength: 210 nm; period: 18 min; sample preparation: the compound dissolved in 12 mL methanol; injection: 0.9 mL/needle). The preparation was concentrated under reduced pressure to remove most of the solvent, and lyophilized to obtain (2R)—N-[(1R)-5-amino-1-[2-(cyclopropanecarbonyl)-2,7-diazaspiro[3.5]nonane-7-carbonyl]pentyl]-2-[[(2R)-2-[[(2R)-2-amino-3-phenyl-propanoyl]amino]-3-phenyl-propanoyl]amino]-4-methyl-pentanamide; di-trifluoroacetic acid (compound 39) as white powder (330 mg, yield 78%).

MS m/z=365.8 [M+2H]⁺/2;

¹H NMR (400 MHz, D₂O) δ 7.45-7.18 (m, 10H), 4.66 (t, 1H), 4.26 (dt, 2H), 4.13 (d, 2H), 3.78 (d, 2H), 3.71-3.61 (m, 2H), 3.56-3.45 (m, 1H), 3.42-3.31 (m, 1H), 3.18 (d, 2H), 3.10-2.93 (m, 4H), 1.99-1.30 (m, 15H), 1.01-0.77 (m, 10H).

Example 38: (2R)—N-[(1R)-5-amino-1-[7-(cyclopropanecarbonyl)-2,7-diazaspiro[3.5]nonane-2-carbonyl]pentyl]-2-[[(2R)-2-[[(2R)-2-amino-3-phenyl-propanoyl]amino]-3-phenyl-propanoyl]amino]-4-methyl-pentanamide; di-trifluoroacetic acid (compound 40)

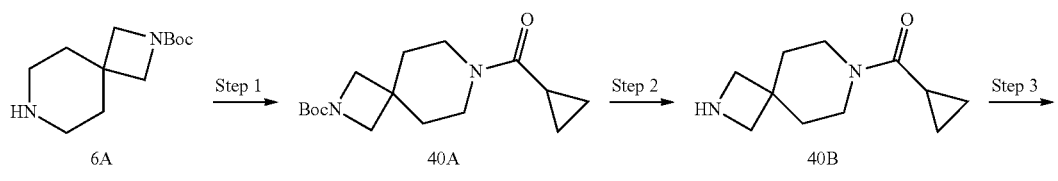

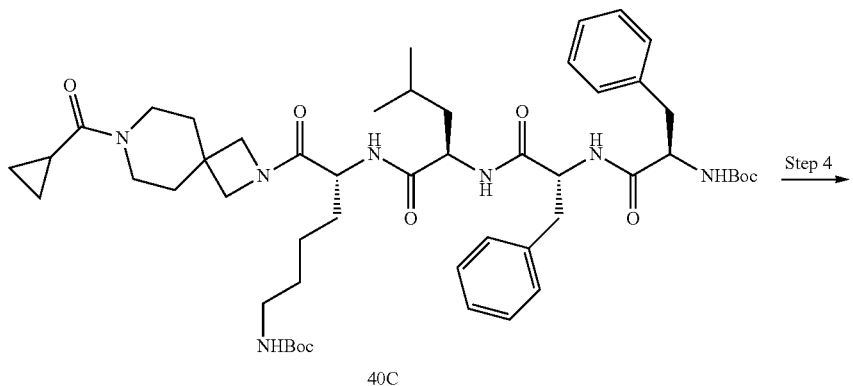

40C

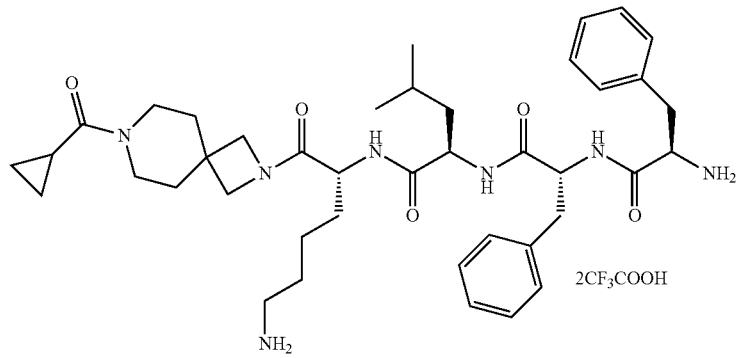

Compound 40

Step 1: tert-butyl 7-(cyclopropanecarbonyl)-2,7-diazaspiro[3.5]nonane-2-carboxylate (40A)

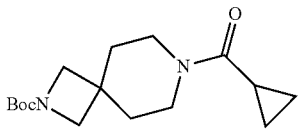

40A

Tert-butyl 2,7-diazaspiro[3.5]nonane-2-carboxylate (6A) (0.453 g, 2.0 mmol), 1-(3-dimethylaminopropyl)-3-ethylcarbodiimide hydrochloride (767 mg, 4.0 mmol), 1-hydroxybenzotriazole (324 mg, 2.4 mmol), cyclopropylcarboxylic acid (176 mg, 2.2 mmol) and dichloromethane (50 mL) were added in a 50 mL single-necked flask, and the system was allowed to react at room temperature for 5 h. The reaction solution was concentrated under reduced pressure, and the residue was separated and purified by silica gel column chromatography (dichloromethane:methanol (v:v)=50:1) to obtain tert-butyl 7-(cyclopropanecarbonyl)-2,7-diazaspiro[3.5]nonane-2-carboxylate (40A) as light yellow oily substance (590 mg, yield 96%).

$^1$H NMR (400 MHz, CDCl$_3$) δ 3.68 (s, 4H), 3.62-3.52 (m, 4H), 1.81-1.69 (m, 5H), 1.45 (s, 9H), 1.00-0.93 (m, 2H), 0.78-0.71 (m, 2H).

Step 2: cyclopropyl(2,7-diazaspiro[3.5]nonan-7-yl)methanone (40B)

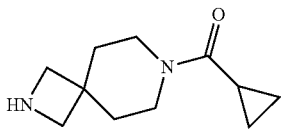

40B

Tert-butyl 7-(cyclopropanecarbonyl)-2,7-diazaspiro[3.5]nonane-2-carboxylate (40A) (0.25 g, 0.83 mmol) and dichloromethane (7 mL) were added in a 50 mL reaction flask, and trifluoroacetic acid (1 mL) was added dropwise at room temperature. After the addition, the system was allowed to react at room temperature for 3 h. The reaction solution was directly concentrated under reduced pressure to obtain crude cyclopropyl(2,7-diazaspiro[3.5]nonan-7-yl)methanone (40B) as yellow oily liquid (161 mg, yield 100%), and used directly in the next reaction.

Step 3: tert-butyl N-[(1R)-1-benzyl-2-[[(1R)-1-benzyl-2-[[(1R)-1-[[(1R)-5-(tert-butoxy carbonylamino)-1-[7-(cyclopropanecarbonyl)-2,7-diazaspiro[3.5]nonane-2-carbonyl]pentyl]carbamoyl]-3-methyl-butyl]amino]-2-oxo-ethyl]amino]-2-oxo-ethyl]carbamate (40C)

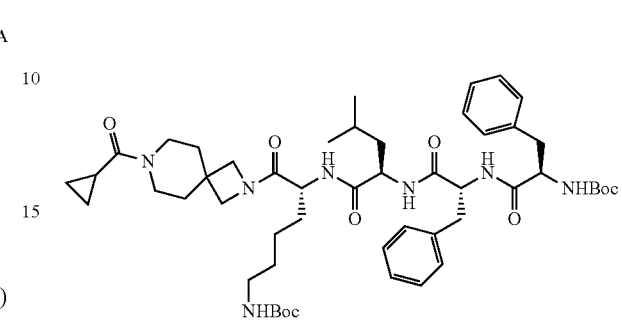

Crude (2,7-diazaspiro[3.5]nonan-7-yl)methanone (40B) (0.16 g, 0.83 mmol) 1-(3-dimethylaminopropyl)-3-ethylcarbodiimide hydrochloride (239 mg, 1.25 mmol), 1-hydroxybenzotriazole (135 mg, 1.0 mmol), intermediate 1 (625 mg, 0.83 mmol) and dichloromethane (50 mL) were added in a 50 mL single-necked flask, and the system was allowed to react at room temperature for 5 h. The reaction solution was concentrated under reduced pressure, and the residue was separated and purified by silica gel column chromatography (dichloromethane:methanol (v:v)=50:1) to obtain tert-butyl N-[(1R)-1-benzyl-2-[[(1R)-1-benzyl-2-[[(1R)-1-[[(1R)-5-(tert-butoxycarbonylamino)-1-[7-(cyclopropanecarbonyl)-2,7-diazaspiro[3.5]nonane-2-carbonyl]pentyl]carbamoyl]-3-methyl-butyl]amino]-2-oxo-ethyl]amino]-2-oxo-ethyl] carbamate (40C) as light yellow solid (700 mg, yield 90%).

Step 4: (2R)—N-[(1R)-5-amino-1-[7-(cyclopropanecarbonyl)-2,7-diazaspiro[3.5]nonane-2-carbonyl]pentyl]-2-[[(2R)-2-[[(2R)-2-amino-3-phenyl-propanoyl]amino]-3-phenyl-propanoyl]amino]-4-methyl-pentanamide; di-trifluoroacetic acid (compound 40)

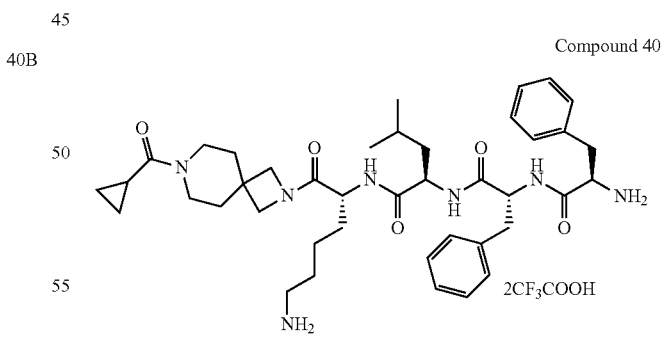

Compound 40

Tert-butyl N-[(1R)-1-benzyl-2-[[(1R)-1-benzyl-2-[[(1R)-1-[[(1R)-5-(tert-butoxycarbonylamino)-1-[7-(cyclopropanecarbonyl)-2,7-diazaspiro[3.5]nonane-2-carbonyl]pentyl]carbamoyl]-3-methyl-butyl]amino]-2-oxo-ethyl]amino]-2-oxo-ethyl]carbamate (40C) (700 mg, 0.75 mmol) and trifluoroacetic acid (3 mL) were added in a 50 mL reaction flask, and the system was allowed to react at room temperature for 2 h. The reaction solution was concentrated under reduced pressure, and the residue was separated and purified by preparative liquid chromatography (preparation conditions: instrument: Gilson GX-281; column: Xbridge C18, 150×30 mm I.D., 5 μm; mobile phase: A for ACN and B for H₂O; isocratic: A 65%; flow rate: 30 mL/min; back pressure: 1000 PSI; column temperature: 30° C.; wavelength: 210 nm; period: 18 min; sample preparation: the compound dissolved in 12 mL methanol; injection: 0.9 mL/needle). The preparation was concentrated under reduced pressure to remove most of the solvent, and lyophilized to obtain (2R)—N-[(1R)-5-amino-1-[7-(cyclopropanecarbonyl)-2,7-diazaspiro[3.5]nonane-2-carbonyl]pentyl]-2-[[(2R)-2-[[(2R)-2-amino-3-phenyl-propanoyl]amino]-3-phenyl-propanoyl]amino]-4-methyl-pentanamide di-trifluoroacetic acid (compound 40) as white powder (200 mg, yield 28%).

MS m/z=365.8 [M+2H]⁺/2;

¹H NMR (400 MHz, D₂O) δ 7.40-7.17 (m, 10H), 4.62 (t, 1H), 4.32-4.00 (m, 5H), 3.82-3.60 (m, 4H), 3.48 (br, 2H), 3.23-3.08 (m, 2H), 3.07-2.91 (m, 4H), 2.01-1.61 (m, 9H), 1.58-1.27 (m, 5H), 0.97-0.67 (m, 10H).

Example 39: (2R)—N-[(1R)-5-amino-1-[2-[(2R)-2-amino-3-phenyl-propanoyl]-2,7-diazaspiro[3.5]nonane-7-carbonyl]pentyl]-2-[[(2R)-2-[[(2R)-2-amino-3-phenyl-propanoyl]amino]-3-phenyl-propanoyl]amino]-4-methyl-pentanamide; tri-trifluoroacetic acid (compound 41)

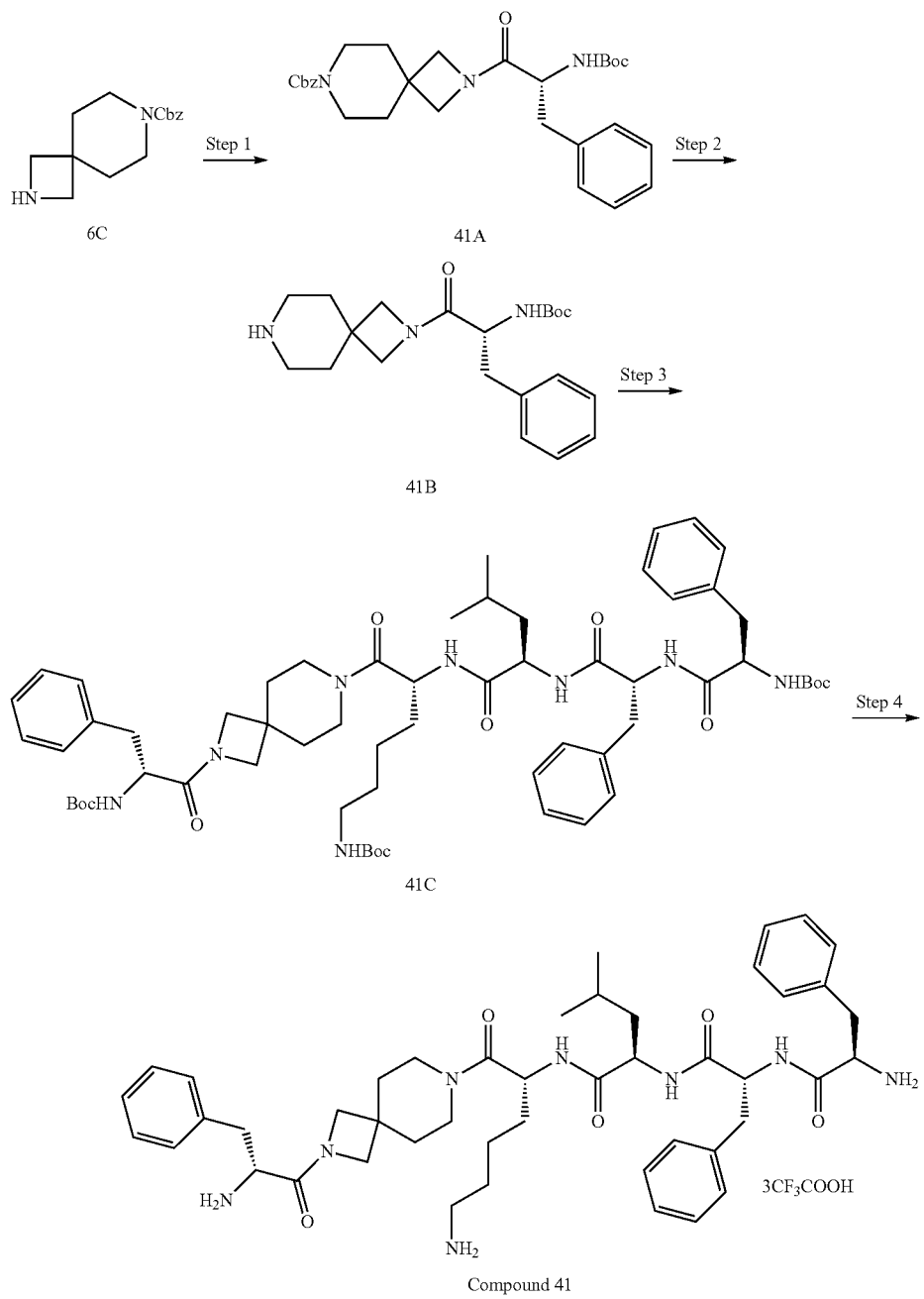

Compound 41

229

Step 1: benzyl 2-[(2R)-2-(tert-butoxycarbonylamino)-3-phenyl-propanoyl]-2,7-diazaspiro[3.5]nonane-7-carboxylate (41A)

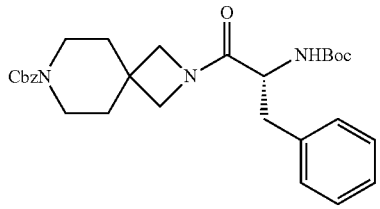

Benzyl 2,7-diazaspiro[3.5]nonane-7-carboxylate (6C) (390 mg, 1.5 mmol), 1-(3-dimethylaminopropyl)-3-ethylcarbodiimide hydrochloride (760 mg, 4.9 mmol), 1-hydroxybenzotriazole (300 mg, 2.0 mmol), Boc-D-Phenylalanine (530 mg, 2.0 mmol) and dichloromethane (50 mL) were added in a 50 mL single-necked flask, and the system was allowed to react at room temperature for 5 h. The reaction solution was concentrated under reduced pressure, and the residue was separated and purified by silica gel column chromatography (dichloromethane:methanol (v:v)=50:1) to obtain benzyl 2-[(2R)-2-(tert-butoxycarbonylamino)-3-phenyl-propanoyl]-2,7-diazaspiro[3.5]nonane-7-carboxylate (41A), as white solid (514 mg, yield 67%).

230

Step 2: tert-butyl N-[(1R)-1-benzyl-2-(2,7-diazaspiro[3.5]nonan-2-yl)-2-oxo-ethyl]carbamate (41B)

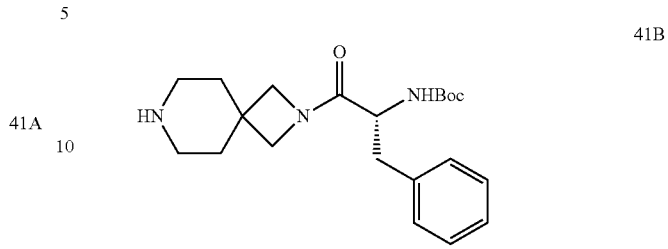

Benzyl 2-[(2R)-2-(tert-butoxycarbonylamino)-3-phenyl-propanoyl]-2,7-diazaspiro[3.5]nonane-7-carboxylate (41A) (514 mg, 1.01 mmol), palladium on carbon (100 mg, 20 wt %) and methanol (20 mL) were added in a 50 mL single-necked flask. The atmosphere was replaced with hydrogen 3 times, and the mixture reacted at room temperature for 3 h under a hydrogen (balloon) atmosphere. The reaction solution was filtered through diatomite, and the filtrate was concentrated under reduced pressure to obtain crude tert-butyl N-[(1R)-1-benzyl-2-(2,7-diazaspiro[3.5]nonan-2-yl)-2-oxo-ethyl]carbamate (41B) as light yellow solid (377 mg, yield 100%), and used directly in the next reaction.

Step 3: tert-butyl N-[(1R)-1-benzyl-2-[[(1R)-1-benzyl-2-[[(1R)-1-[[(1R)-5-(tert-butoxy carbonylamino)-1-[2-[(2R)-2-(tert-butoxycarbonylamino)-3-phenyl-propanoyl]-2,7-diazaspiro[3.5]nonane-7-carbonyl]pentyl]carbamoyl]-3-methyl-butyl]amino]-2-oxo-ethyl]amino]-2-oxo-ethyl]carbamate (41C)

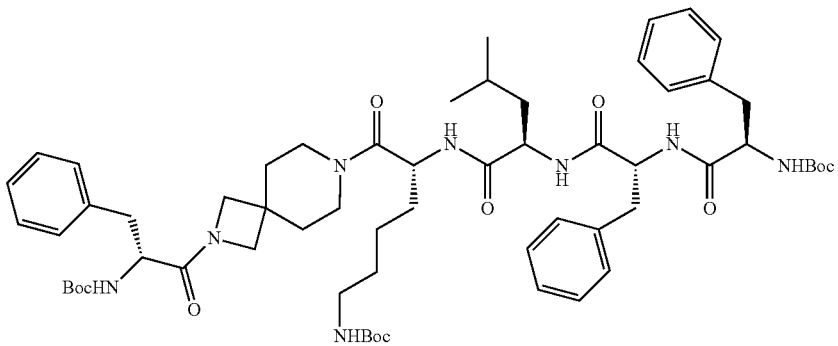 [SMILES: CC(C)C[C@@H](NC(=O)[C@@H](Cc1ccccc1)NC(=O)[C@@H](Cc1ccccc1)NC(=O)OC(C)(C)C)C(=O)N[C@H](CCCCNC(=O)OC(C)(C)C)C(=O)N1CCC2(CC1)CN(C(=O)[C@@H](Cc1ccccc1)NC(=O)OC(C)(C)C)C2]

Crude tert-butyl N-[(1R)-1-benzyl-2-(2,7-diazaspiro[3.5]nonan-2-yl)-2-oxo-ethyl]carbamate (41B) (377 mg, 1.01 mmol), 1-(3-dimethylaminopropyl)-3-ethylcarbodiimide hydrochloride (290 mg, 1.52 mmol), 1-hydroxybenzotriazole (164 mg, 1.21 mmol), intermediate 1 (761 mg, 1.01 mmol) and dichloromethane (30 mL) were added in a 50 mL single-necked flask, and the system was allowed to react at room temperature for 5 h. The reaction solution was concentrated under reduced pressure, and the residue was separated and purified by silica gel column chromatography (petroleum ether:ethyl acetate (v:v)=1:2) to obtain tert-butyl N-[(1R)-1-benzyl-2-[[(1R)-1-benzyl-2-[[(1R)-1-[[(1R)-5-(tert-butoxycarbonylamino)-1-[2-[(2R)-2-(tert-butoxycarbonylamino)-3-phenyl-propanoyl]-2,7-diazaspiro[3.5] nonane-7-carbonyl]pentyl]carbamoyl]-3-methyl-butyl] amino]-2-oxo-ethyl]amino]-2-oxo-ethyl]carbamate (41C), as light yellow solid (410 mg, yield 36.6%).

Step 4: (2R)—N-[(1R)-5-amino-1-[2-[(2R)-2-amino-3-phenyl-propanoyl]-2,7-diazaspiro[3.5]nonane-7-carbonyl]pentyl]-2-[[(2R)-2-[[(2R)-2-amino-3-phenyl-propanoyl]amino]-3-phenyl-propanoyl]amino]-4-methyl-pentanamide; tri-trifluoroacetic acid (compound 41)

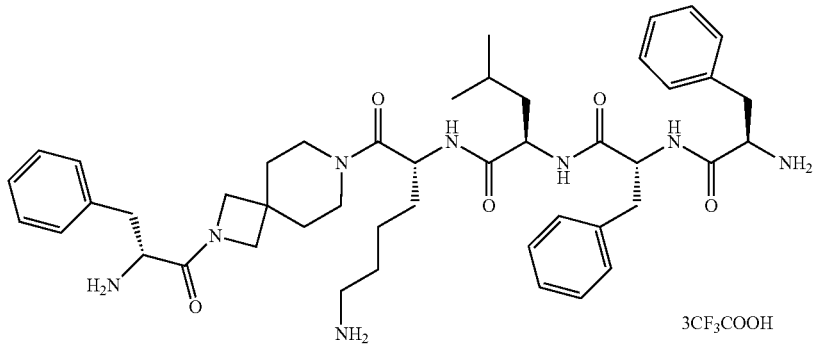

Compound 41

Tert-butyl N-[(1R)-1-benzyl-2-[[(1R)-1-benzyl-2-[[(1R)-1-[[(1R)-5-(tert-butoxycarbonylamino)-1-[2-[(2R)-2-(tert-butoxycarbonylamino)-3-phenyl-propanoyl]-2,7-diazaspiro[3.5]nonane-7-carbonyl]pentyl]carbamoyl]-3-methyl-butyl]amino]-2-oxo-ethyl]amino]-2-oxo-ethyl]carbamate (41C) (410 mg, 0.37 mmol) and trifluoroacetic acid (2 mL) were added in a 50 mL reaction flask, and the system was allowed to react at room temperature for 2 h. The reaction solution was concentrated under reduced pressure, and the residue was separated and purified by preparative liquid chromatography (preparation conditions: instrument: Gilson GX-281; column: Xbridge C18, 150×30 mm I.D., 5 μm; mobile phase: A for ACN and B for H$_2$O; isocratic: A 65%; flow rate: 30 mL/min; back pressure: 1000 PSI; column temperature: 30° C.; wavelength: 210 nm; period: 18 min; sample preparation: the compound dissolved in 12 mL methanol; injection: 0.9 mL/needle). The preparation was concentrated under reduced pressure to remove most of the solvent, and lyophilized to obtain (2R)—N-[(1R)-5-amino-1-[2-[(2R)-2-amino-3-phenyl-propanoyl]-2,7-diazaspiro[3.5]nonane-7-carbonyl]pentyl]-2-[[(2R)-2-[[(2R)-2-amino-3-phenyl-propanoyl]amino]-3-phenyl-propanoyl]amino]-4-methyl-pentanamide tri-trifluoroacetic acid (compound 41) as white powder (298 mg, yield 70%).

MS m/z=405.4 [M+2H]$^+$/2;

$^1$HNMR (400 MHz, D$_2$O) δ 7.52-7.28 (m, 11H), 7.28-7.20 (m, 4H), 4.67-4.62 (m, 1H), 4.32-4.15 (m, 3H), 3.85-3.38 (m, 6H), 3.37-3.22 (m, 2H), 3.22-3.13 (m, 2H), 3.12-2.90 (m, 6H), 2.65 (dd, 1H), 1.83-1.48 (m, 9H), 1.47-1.28 (m, 3H), 1.25-1.11 (m, 1H), 0.92 (dd, 6H).

Example 40: (2R)—N-[(1R)-5-amino-1-[2-(2-hydroxyacetyl)-2,7-diazaspiro[3.5]nonane-7-carbonyl]pentyl]-2-[[(2R)-2-[[(2R)-2-amino-3-phenyl-propanoyl]amino]-3-phenyl-propanoyl]amino]-4-methyl-pentanamide; di-trifluoroacetic acid (compound 42)

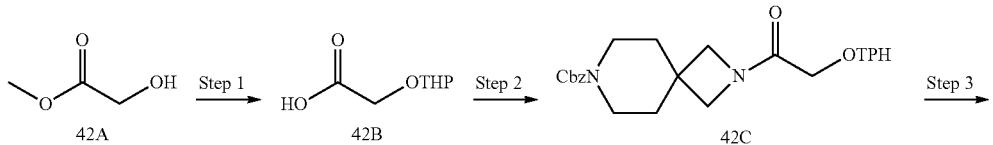

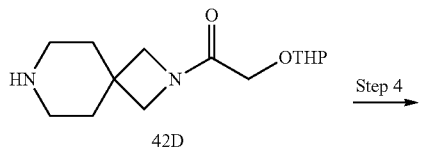

-continued

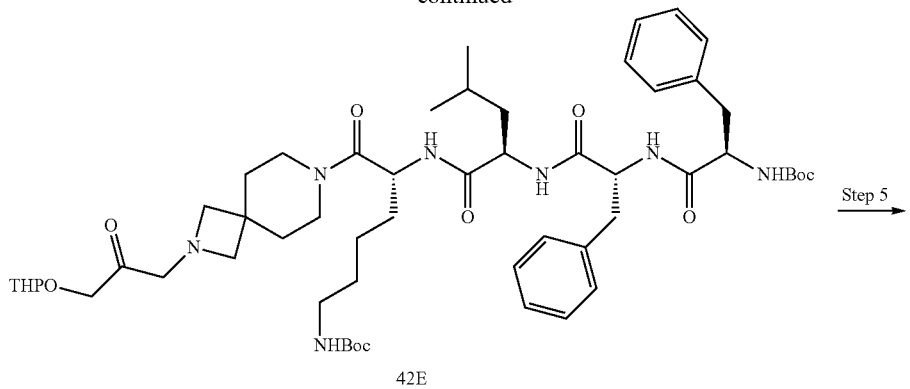

42E

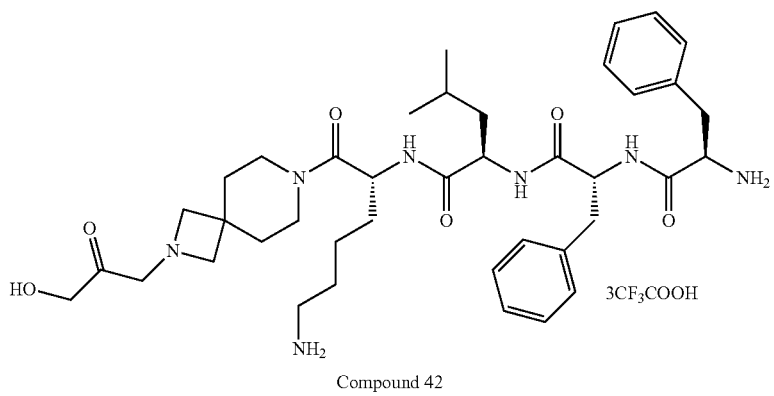

Compound 42

Step 1: 2-tetrahydropyran-2-yloxyacetic acid (42B)

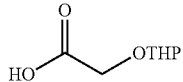

42B 3,4-dihydro-2H-pyran (840 mg, 10 mmol), methyl glycolate (42A) (900 mg, 10 mmol), p-toluenesulfonic acid monohydrate (100 mg, 0.5 mmol) and dichloromethane (100 mL) were added sequentially in a 250 mL single-necked flask. After the addition, the system was allowed to react at room temperature for 2 h. The reaction solution was concentrated under reduced pressure, and a lithium hydroxide solution (a mixed solution of 75 mL of methanol+25 mL of water) was added to the residue. After the addition, the reaction was allowed to proceed at room temperature overnight. 0.1 M diluted hydrochloric acid (12 mL) was added dropwise to the reaction solution, and the pH of the reaction solution was tested to be 2-3. The reaction solution was extracted with dichloromethane (100 mL×2), the organic layer was dried over anhydrous sodium sulfate, suction-filtered, and the filtrate was concentrated under reduced pressure to obtain 2-tetrahydropyran-2-yloxyacetic acid (42B) as light yellow oily substance (510 mg, yield 30%).

MS m/z=183.1 [M+Na]$^+$;

Step 2: benzyl 2-(2-tetrahydropyran-2-yloxyacetyl)-2,7-diazaspiro[3.5]nonane-7-carboxylate (42C)

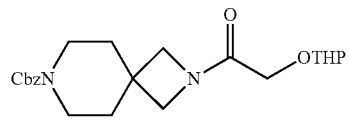

42C 2-tetrahydropyran-2-yloxyacetic acid (42B) (510 mg, 3.2 mmol), 1-(3-dimethylaminopropyl)-3-ethylcarbodiimide hydrochloride (1.2 g, 6.3 mmol), 1-hydroxybenzotriazole (516 mg, 3.82 mmol), benzyl 2,7-diazaspiro[3.5]nonane-7-carboxylate (6C) (830 mg, 3.2 mmol) and dichloromethane (50 mL) were added to in a 50 mL single-necked flask, and the system was allowed to react at room temperature for 5 h. The reaction solution was concentrated under reduced pressure, and the residue was separated and purified by silica gel column chromatography (dichloromethane:methanol (v:v)=50:1) to obtain benzyl 2-(2-tetrahydropyran-2-yloxy-acetyl)-2,7-diazaspiro[3.5]nonane-7-carboxylate (42C) as light yellow solid (580 mg, yield 45%).

Step 3: 1-(2,7-diazaspiro[3.5]nonan-2-yl)-2-tetrahydropyran-2-yloxy-ethanone (42D)

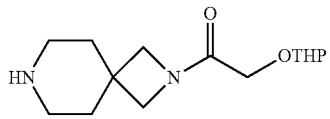

Benzyl 2-(2-tetrahydropyran-2-yloxyacetyl)-2,7-diazaspiro[3.5]nonane-7-carboxylate (42C) (580 mg, 1.4 mmol), palladium on carbon (120 mg, 20 wt % l) and methanol (20 mL) were added in a 50 mL single-necked flask. The atmosphere was replaced with hydrogen 3 times, and the mixture reacted at room temperature for 3 h under a hydrogen (balloon) atmosphere. The reaction solution was filtered through diatomite, and the filtrate was concentrated under reduced pressure to obtain crude 1-(2,7-diazaspiro[3.5]nonan-2-yl)-2-tetrahydropyran-2-yloxy-ethanone (42D) as light yellow solid (387 mg, yield 100%), and used directly in the next reaction.

Step 4: tert-butyl N-[(1R)-1-benzyl-2-[[(1R)-1-benzyl-2-[[(1R)-1-[[(1R)-5-(tert-butoxy carbonylamino)-1-[2-(2-tetrahydropyran-2-yloxyacetyl)-2,7-diazaspiro[3.5]nonane-7-carbonyl]pentyl]carbamoyl]-3-methyl-butyl]amino]-2-oxo-ethyl]amino]-2-oxo-ethyl]carbamate (42E)

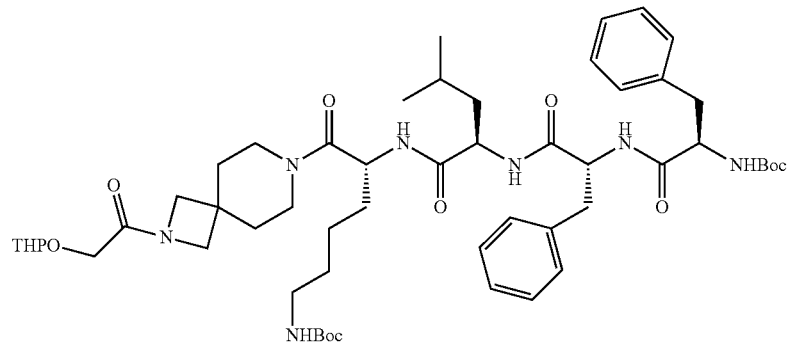

Crude 1-(2,7-diazaspiro[3.5]nonan-2-yl)-2-tetrahydropyran-2-yloxy-ethanone (42D) (387 mg, 1.4 mmol), 1-(3-dimethylaminopropyl)-3-ethylcarbodiimide hydrochloride (553 mg, 2.88 mmol), 1-hydroxybenzotriazole (233 mg, 1.72 mmol), intermediate 1 (1.09 g, 1.45 mmol) and dichloromethane (50 mL) were added in a 50 mL single-necked flask, and the system was allowed to react at room temperature for 5 h. The reaction solution was concentrated under reduced pressure, and the residue was separated and purified by silica gel column chromatography (dichloromethane:methanol (v:v)=50:1) to obtain tert-butyl N-[(1R)-1-benzyl-2-[[(1R)-1-benzyl-2-[[(1R)-1-[[(1R)-5-(tert-butoxycarbonylamino)-1-[2-(2-tetrahydropyran-2-yloxyacetyl)-2,7-diazaspiro[3.5]nonane-7-carbonyl]pentyl]carbamoyl]-3-methyl-butyl]amino]-2-oxo-ethyl]amino]-2-oxo-ethyl]carbamate (42E) as light yellow solid (590 mg, yield 41%).

Step 5: (2R)—N-[(1R)-5-amino-1-[2-(2-Hydroxy-ethyl)-2,7-diazaspiro[3.5]nonane-7-carbonyl]pentyl]-2-[[(2R)-2-[[(2R)-2-amino-3-phenyl-propanoyl]amino]-3-phenyl-propanoyl]amino]-4-methyl-pentanamide di-trifluoroacetic acid (compound 42)

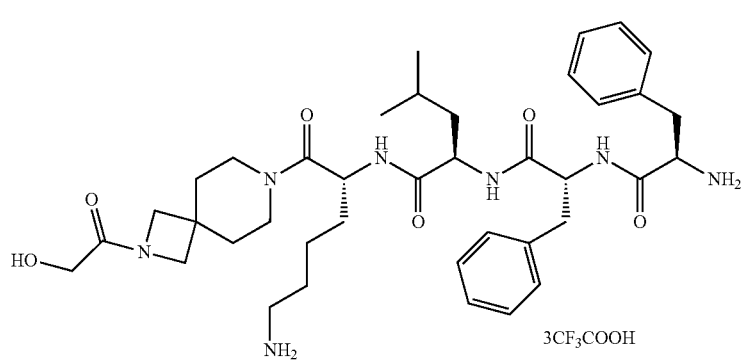

Compound 42

Tert-butyl N-[(1R)-1-benzyl-2-[[(1R)-1-benzyl-2-[[(1R)-1-[[(1R)-5-(tert-butoxycarbonylamino)-1-[2-(2-tetrahydropyran-2-yloxyacetyl)-2,7-diazaspiro[3.5]nonane-7-carbonyl]pentyl]carbamoyl]-3-methyl-butyl]amino]-2-oxo-ethyl]amino]-2-oxo-ethyl]carbamate (42E) (590 mg, 0.59 mmol) and trifluoroacetic acid (4 mL) were added in a 50 mL reaction flask, and the system was allowed to react at room temperature for 2 h. The reaction solution was concentrated under reduced pressure, and the residue was separated and purified by preparative liquid chromatography (preparation conditions: instrument: Gilson GX-281; column: Xbridge C18, 150×30 mm I.D., 5 μm; mobile phase: A for ACN and B for H$_2$O; isocratic: A 65%; flow rate: 30 mL/min; back pressure: 1000 PSI; column temperature: 30° C.; wavelength: 210 nm; period: 18 min; sample preparation: the compound dissolved in 12 mL methanol; injection: 0.9 mL/needle). The preparation was concentrated under reduced pressure to remove most of the solvent, and lyophilized to obtain (2R)—N-[(1R)-5-amino-1-[2-(2-Hydroxyethyl)-2,7-diazaspiro[3.5]nonane-7-carbonyl]pentyl]-2-[[(2R)-2-[[(2R)-2-amino-3-phenyl-propanoyl]amino]-3-phenyl-propanoyl]amino]-4-methyl-pentanamide di-trifluoroacetic acid (compound 42) as white powder (286 mg, yield 67%).

MS m/z=720.3 [M+H]$^+$;

$^1$H NMR (400 MHz, D$_2$O) δ 7.44-7.29 (m, 6H), 7.24 (d, 4H), 4.66 (t, 1H), 4.34-4.20 (m, 2H), 4.14 (d, 2H), 4.02 (d, 2H), 3.83 (d, 2H), 3.72-3.60 (m, 2H), 3.56-3.42 (m, 1H), 3.42-3.30 (m, 1H), 3.18 (d, 2H), 3.10-2.94 (m, 4H), 1.96-1.29 (m, 14H), 0.92 (dd, 6H).

Example 41: (2R)-2-[[(2R)-2-[[(2R)-2-amino-3-phenyl-propanoyl]amino]-3-phenyl-propanoyl]amino]-N-[(1R)-5-amino-1-(2-propanoyl-2,7-diazaspiro[3.5]nonane-7-carbonyl)pentyl]-4-methyl-pentanamide; di-trifluoroacetic acid (compound 43)

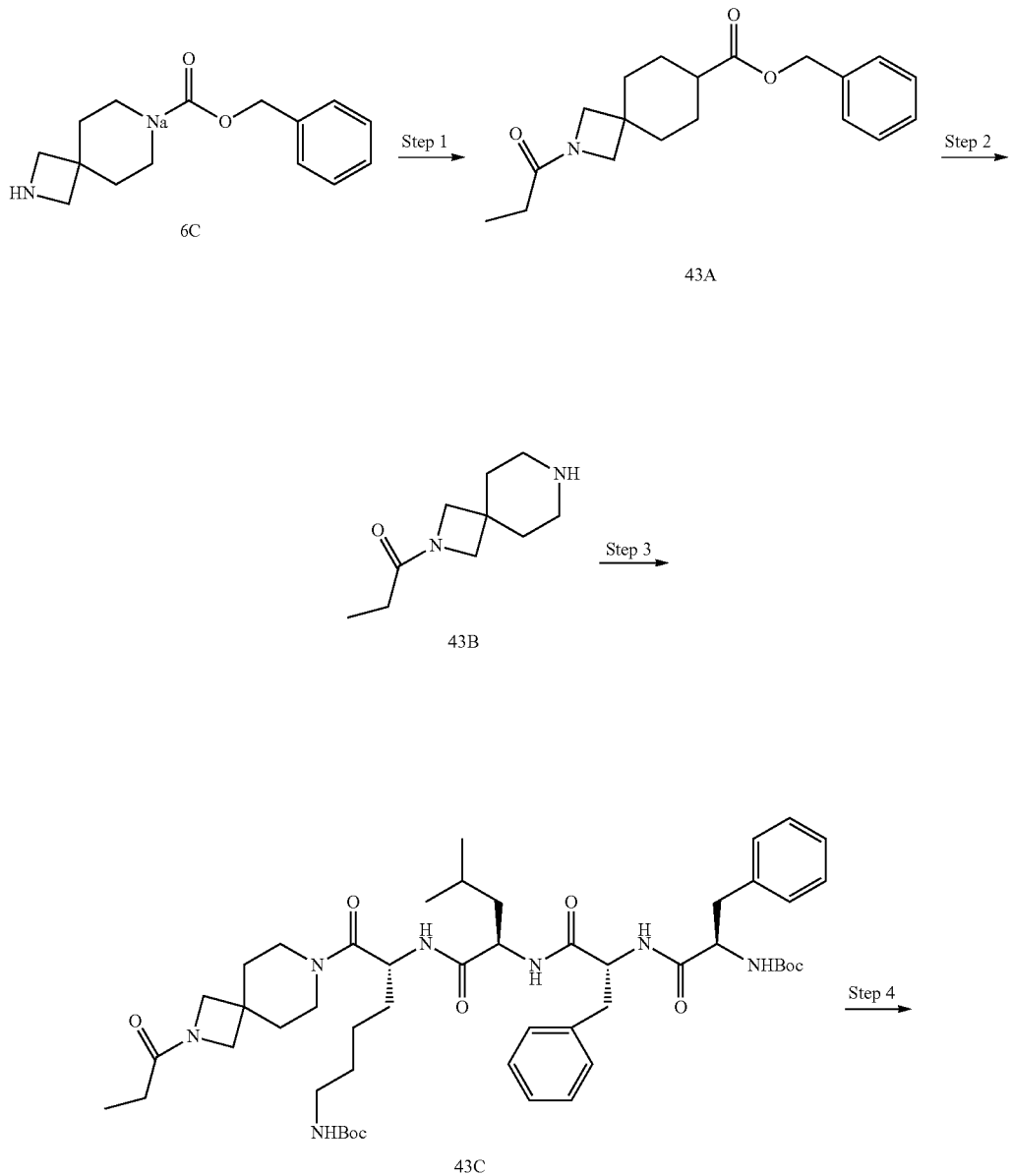

-continued

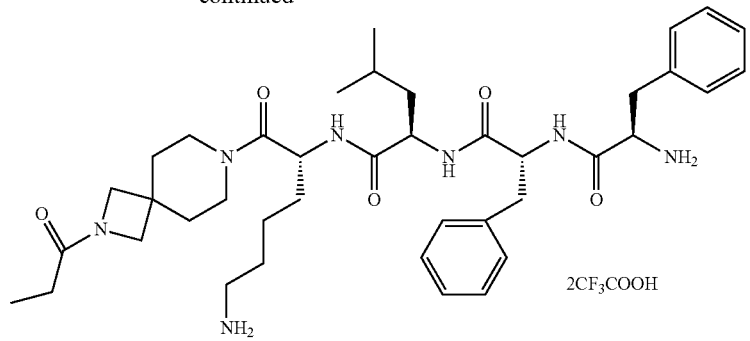

Compound 43

Step 1: benzyl 2-propanoyl-2,7-diazaspiro[3.5]nonane-7-carboxylate (43A)

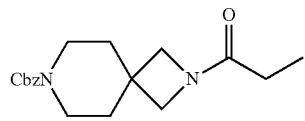

Benzyl 2,7-diazaspiro[3.5]nonane-7-carboxylate (6C) (390 mg, 1.5 mmol), 1-(3-dimethylaminopropyl)-3-ethylcarbodiimide hydrochloride (575 mg, 3.0 mmol), 1-hydroxybenzotriazole (243 mg, 1.80 mmol), propanoic acid (122 mg, 1.65 mmol) and dichloromethane (50 mL) were added in a 50 mL single-necked flask, and the system was allowed to react at room temperature for 5 h. The reaction solution was concentrated under reduced pressure, and the residue was separated and purified by silica gel column chromatography (dichloromethane:methanol (v:v)=50:1) to obtain benzyl 2-propanoyl-2,7-diazaspiro[3.5]nonane-7-carboxylate (43A) as light yellow solid (245 mg, yield 52%).

Step 2: 1-(2,7-diazaspiro[3.5]nonan-2-yl)propan-1-one (43B)

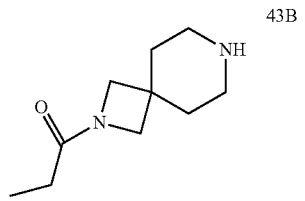

Benzyl 2-propanoyl-2,7-diazaspiro[3.5]nonane-7-carboxylate (43A) (245 mg, 0.775 mmol), palladium on carbon (49 mg, 20 wt % l) and methanol (20 mL) were added in a 50 mL single-necked flask. The atmosphere was replaced with hydrogen 3 times, and the mixture reacted at room temperature for 3 h under a hydrogen atmosphere. The reaction solution was filtered through diatomite, and the filtrate was concentrated under reduced pressure to obtain crude 1-(2,7-diazaspiro[3.5]nonan-2-yl)propan-1-one (43B) as light yellow solid (141 mg, yield 99.8%), and used directly in the next reaction.

Step 3: tert-butyl N-[(1R)-1-benzyl-2-[[(1R)-1-benzyl-2-[[(1R)-1-[[(1R)-5-(tert-butoxy carbonylamino)-1-(2-propanoyl-2,7-diazaspiro[3.5]nonane-7-carbonyl)pentyl]carbamoyl]-3-m ethyl-butyl]amino]-2-oxo-ethyl]amino]-2-oxo-ethyl]carbamate (43C)

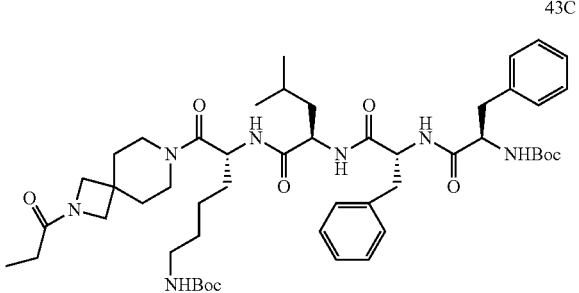 [SMILES: CCC(=O)N1CC2(CCN(C(=O)[C@@H](CCCCNC(=O)OC(C)(C)C)NC(=O)[C@@H](CC(C)C)NC(=O)[C@@H](Cc3ccccc3)NC(=O)[C@@H](Cc3ccccc3)NC(=O)OC(C)(C)C)CC2)C1]

Crude 1-(2,7-diazaspiro[3.5]nonan-2-yl)propan-1-one (43B) (141 mg, 0.774 mmol), 1-(3-dimethylaminopropyl)-3-ethylcarbodiimide hydrochloride (383 mg, 2.0 mmol), 1-hydroxybenzotriazole (135 mg, 1.0 mmol), intermediate 1 (0.565 g, 0.75 mmol) and dichloromethane (50 mL) were added in a 50 mL single-necked flask, and the system was allowed to react at room temperature for 5 h. The reaction solution was concentrated under reduced pressure, and the residue was separated and purified by silica gel column chromatography (dichloromethane:methanol (v:v)=50:1) to obtain tert-butyl N-[(1R)-1-benzyl-2-[[(1R)-1-benzyl-2-[[(1R)-1-[[(1R)-5-(tert-butoxycarbonylamino)-1-(2-propanoyl-2,7-diazaspiro[3.5]nonane-7-carbonyl)pentyl]carbamoyl]-3-methyl-butyl]amino]-2-oxo-ethyl]amino]-2-oxo-ethyl]carbamate (43C) as light yellow solid (500 mg, yield 72.7%).

Step 4: (2R)-2-[[(2R)-2-[[(2R)-2-amino-3-phenyl-propanoyl]amino]-3-phenyl-propanoyl]amino]-N-[(1R)-5-amino-1-(2-propanoyl-2,7-diazaspiro[3.5]nonane-7-carbonyl)pentyl]-4-methyl-pentanamide; di-trifluoroacetic acid (compound 43)

Compound 43

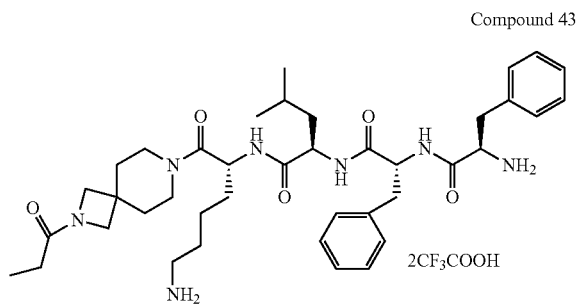 [SMILES: CCC(=O)N1CC2(CCN(C(=O)[C@@H](CCCCN)NC(=O)[C@@H](CC(C)C)NC(=O)[C@@H](Cc3ccccc3)NC(=O)[C@H](N)Cc3ccccc3)CC2)C1]

Tert-butyl N-[(1R)-1-benzyl-2-[[(1R)-1-benzyl-2-[[(1R)-1-[[(1R)-5-(tert-butoxycarbonylamino)-1-(2-propanoyl-2,7-diazaspiro[3.5]nonane-7-carbonyl)pentyl]carbamoyl]-3-methyl-butyl]amino]-2-oxo-ethyl]amino]-2-oxo-ethyl]carbamate (43C) (260 mg, 0.28 mmol) and trifluoroacetic acid (1.3 mL) were added in a 50 mL reaction flask, and the system was allowed to react at room temperature for 2 h. The reaction solution was concentrated under reduced pressure, and the residue was separated and purified by preparative liquid chromatography (preparation conditions: instrument: Gilson GX-281; column: Xbridge C18, 150×30 mm I.D., 5 μm; mobile phase: A for ACN and B for H₂O; isocratic: A 65%; flow rate: 30 mL/min; back pressure: 1000 PSI; column temperature: 30° C.; wavelength: 210 nm; period: 18 min; sample preparation: the compound dissolved in 12 mL methanol; injection: 0.9 mL/needle). The preparation was concentrated under reduced pressure to remove most of the solvent, and lyophilized to obtain (2R)-2-[[(2R)-2-[[(2R)-2-amino-3-phenyl-propanoyl]amino]-3-phenyl-propanoyl]amino]-N-[(1R)-5-amino-1-(2-propanoyl-2,7-diazaspiro[3.5]nonane-7-carbonyl)pentyl]-4-methyl-pentanamide di-trifluoroacetic acid (compound 43) as white powder (125 mg, yield 51%).

MS m/z=359.8 [M+2H]⁺/2;

¹H NMR (400 MHz, D₂O) δ 7.45-7.28 (m, 6H), 7.24 (d, 4H), 4.80-4.75 (m, 1H) 4.66 (t, 1H), 4.29 (t, 1H), 4.27 (t, 1H), 4.01 (d, 2H), 3.77 (d, 2H), 3.71-3.60 (m, 2H), 3.55-3.42 (m, 1H), 3.41-3.27 (m, 1H), 3.18 (dd, 2H), 3.11-2.93 (m, 4H), 2.19 (qd, 2H), 1.95-1.63 (m, 8H), 1.61-1.49 (m, 3H), 1.48-1.30 (m, 2H), 1.07 (td, 3H), 0.92 (dd, 6H).

Example 42: (2R)-2-[[(2R)-2-[[(2R)-2-amino-3-phenyl-propanoyl]amino]-3-phenyl-propanoyl]amino]-N-[(1R)-5-amino-1-[2-(2,2,2-trifluoroacetyl)-2,7-diazaspiro[3.5]nonane-7-carbonyl]pentyl]-4-methyl-pentanamide; di-trifluoroacetic acid (compound 44)

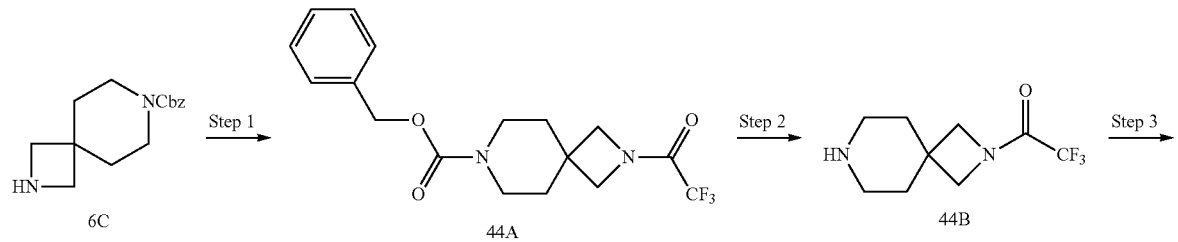

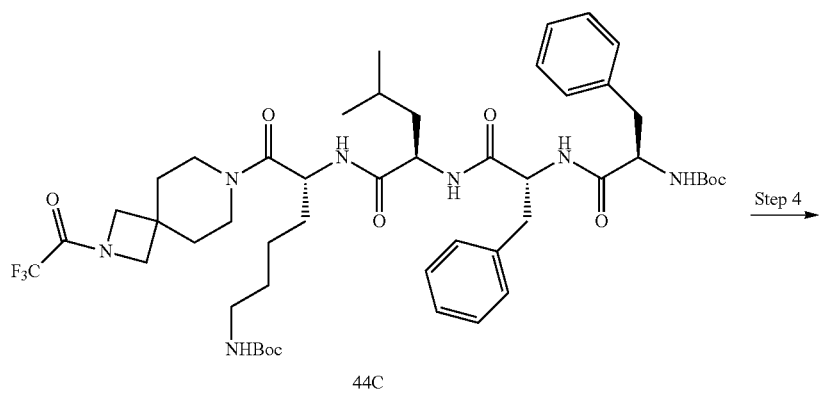

44C

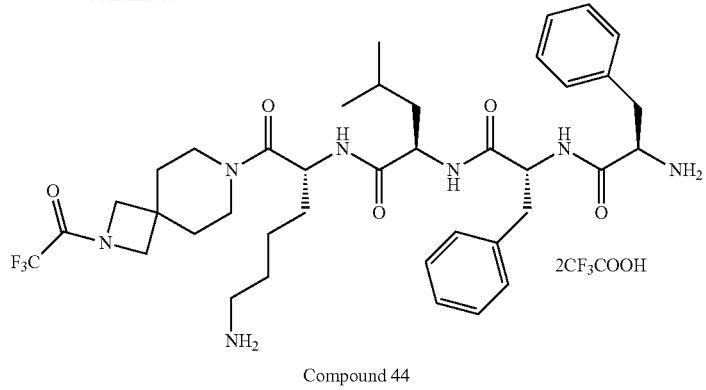

Compound 44

Step 1: benzyl 2-(2,2,2-trifluoroacetyl)-27-diazaspiro[35]nonane-7-carboxylate (44A)

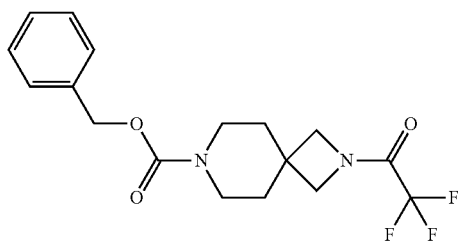

Benzyl 2,7-diazaspiro[3.5]nonane-7-carboxylate (6C) (390 mg, 1.5 mmol), 1-(3-dimethylaminopropyl)-3-ethylcarbodiimide hydrochloride (575 mg, 3.0 mmol), 1-hydroxybenzotriazole (243 mg, 1.80 mmol), trifluoroacetic acid (171 mg, 1.5 mmol) and dichloromethane (50 mL) were added in a 50 mL single-necked flask, and the system was allowed to react at room temperature for 5 h. The reaction solution was concentrated under reduced pressure, and the residue was separated and purified by silica gel column chromatography (dichloromethane:methanol (v:v)=50:1) to obtain benzyl 2-(2,2,2-trifluoroacetyl)-2,7-diazaspiro[3.5]nonane-7-carboxylate (44A) as light yellow solid (224 mg, yield 63%).

Step 2: 1-(2,7-diazaspiro[3.5]nonan-2-yl)-2,2,2-trifluoro-ethanone (44B)

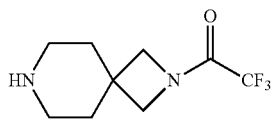

Benzyl 2-(2,2,2-trifluoroacetyl)-2,7-diazaspiro[3.5]nonane-7-carboxylate (44A) (223 mg, 0.63 mmol), palladium on carbon (46 mg, 20 wt % l) and methanol (20 mL) were added in a 50 mL single-necked flask. The atmosphere was replaced with hydrogen 3 times, and the mixture reacted at room temperature for 3 h under a hydrogen (balloon) atmosphere. The reaction solution was filtered through diatomite, and the filtrate was concentrated under reduced pressure to obtain crude 1-(2,7-diazaspiro[3.5]nonan-2-yl)-2,2,2-trifluoro-ethanone (44B) as light yellow solid (116 mg, yield 83%), and used directly in the next reaction.

Step 3: tert-butyl N-[(1R)-1-benzyl-2-[[(1R)-1-benzyl-2-[[(1R)-1-[[(1R)-5-(tert-butoxy carbonylamino)-1-[2-(2,2,2-trifluoroacetyl)-2,7-diazaspiro[3.5]nonane-7-carbonyl]pentyl]carbamoyl]-3-methyl-butyl]amino]-2-oxo-ethyl]amino]-2-oxo-ethyl]carbamate (44C)

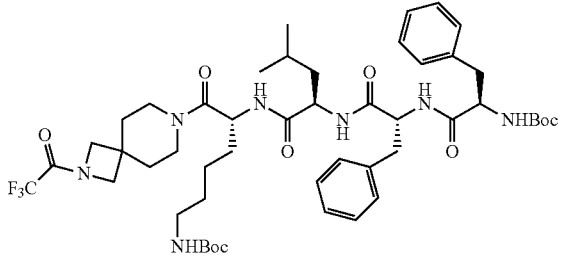 [SMILES: CC(C)C[C@@H](NC(=O)[C@@H](Cc1ccccc1)NC(=O)[C@@H](Cc1ccccc1)NC(=O)OC(C)(C)C)C(=O)N[C@H](CCCCNC(=O)OC(C)(C)C)C(=O)N1CCC2(CC1)CN(C(=O)C(F)(F)F)C2]

Crude 1-(2,7-diazaspiro[3.5]nonan-2-yl)-2,2,2-trifluoro-ethanone (44B) (116 mg, 0.52 mmol), 1-(3-dimethylaminopropyl)-3-ethylcarbodiimide hydrochloride (575 mg, 3.7 mmol), 1-hydroxybenzotriazole (240 mg, 1.3 mmol), intermediate 1 (0.47 g, 0.626 mmol) and dichloromethane (50 mL) were added in a 50 mL single-necked flask, and the system was allowed to react at room temperature for 5 h. The reaction solution was concentrated under reduced pressure, and the residue was separated and purified by silica gel column chromatography (dichloromethane:methanol (v:v)=50:1) to obtain tert-butyl N-[(1R)-1-benzyl-2-[[(1R)-1-benzyl-2-[[(1R)-1-[[(1R)-5-(tert-butoxycarbonylamino)-1-[2-(2,2,2-trifluoroacetyl)-2,7-diazaspiro[3.5]nonane-7-carbonyl]pentyl]carbamoyl]-3-methyl-butyl]amino]-2-oxo-ethyl]amino]-2-oxo-ethyl]carbamate (44C) as light yellow solid (216 mg, yield 42%).

Step 4: (2R)-2-[[(2R)-2-[[(2R)-2-amino-3-phenyl-propanoyl]amino]-3-phenyl-propanoyl]amino]-N-[(1R)-5-amino-1-[2-(2,2,2-trifluoroacetyl)-2,7-diaz-aspiro[3.5]nonane-7-carbonyl]pentyl]-4-methyl-pentanamide; di-trifluoroacetic acid (compound 44)

Compound 44

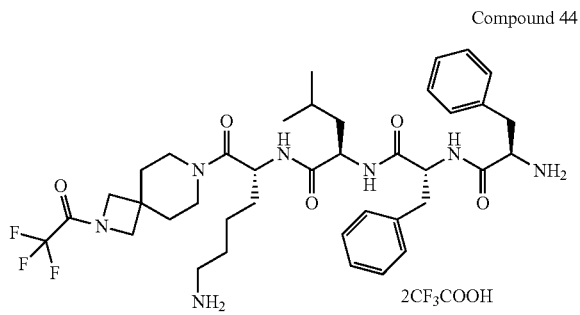 [SMILES: CC(C)C[C@@H](NC(=O)[C@@H](Cc1ccccc1)NC(=O)[C@H](N)Cc1ccccc1)C(=O)N[C@H](CCCCN)C(=O)N1CCC2(CC1)CN(C(=O)C(F)(F)F)C2]

2CF₃COOH

Tert-butyl N-[(1R)-1-benzyl-2-[[(1R)-1-benzyl-2-[[(1R)-1-[[(1R)-5-(tert-butoxycarbonylamino)-1-[2-(2,2,2-trifluoroacetyl)-2,7-diazaspiro[3.5]nonane-7-carbonyl]pentyl]carbamoyl]-3-methyl-butyl]amino]-2-oxo-ethyl]amino]-2-oxo-ethyl]carbamate (44C) (210 mg, 0.22 mmol) and trifluoroacetic acid (2 mL) were added in a 50 mL reaction flask, and the system was allowed to react at room temperature for 2 h. The reaction solution was concentrated under reduced pressure, and the residue was separated and purified by preparative liquid chromatography (preparation conditions: instrument: Gilson GX-281; column: Xbridge C18, 150×30 mm I.D., 5 μm; mobile phase: A for ACN and B for H₂O; isocratic: A 65%; flow rate: 30 mL/min; back pressure: 1000 PSI; column temperature: 30° C.; wavelength: 210 nm; period: 18 min; sample preparation: the compound dissolved in 12 mL methanol; injection: 0.9 mL/needle). The preparation was concentrated under reduced pressure to remove most of the solvent, and lyophilized to obtain (2R)-2-[[(2R)-2-[[(2R)-2-amino-3-phenyl-propanoyl]amino]-3-phenyl-propanoyl]amino]-N-[(1R)-5-amino-1-[2-(2,2,2-trifluoro-acetyl)-2,7-diazaspiro[3.5]nonane-7-carbonyl]pentyl]-4-methyl-pentanamide di-trifluoroacetic acid (compound 44) as white powder (111 mg, yield 51%).

MS m/z=758.3 [M+H]⁺;

¹H NMR (400 MHz, D₂O) δ 7.44-7.28 (m, 6H), 7.24 (d, 4H), 4.64 (t, 1H), 4.38-4.21 (m, 4H), 3.97 (d, 2H), 3.73-3.58 (m, 2H), 3.56-3.43 (m, 1H), 3.40-3.32 (m, 1H), 3.25-3.11 (m, 2H), 3.11-2.93 (m, 4H), 1.99-1.63 (m, 9H), 1.53 (d, 3H), 1.49-1.33 (m, 2H), 0.93 (dd, 6H).

Biological Test Examples

Test 1: Agonist Activity on Human κ-Opioid Receptors

Forskolin can stimulate the release of cAMP from a human κ-opioid receptor-overexpressing cell line, OPRK1 cells (DiscoveRx), and κ-opioid receptor agonists can inhibit the cAMP release stimulated by forskolin. By detecting the inhibitory effect of the test compound on the cAMP release stimulated by forskolin, the agonistic activity of the compound on the human κ-opioid receptor can be determined. First, a certain concentration of forskolin and different concentrations of the test compound were incubated with human κ-opioid receptor overexpressing cell lines. A cAMP immunoassay (LANCE®, PerkinElmer) based on time-resolved fluorescence resonance energy transfer (TR-FRET) was used to determine cAMP levels in the stimulated OPRK1 cells. The specific method is as follows:

OPRK1 cells (DiscoveRx) that highly express human κ-opioid receptors were cultured in McCoy's 5A (Gibco 16600-082) medium containing 10% FBS (Gibco 10099-141). On the day of the experiment, the cells in the exponential growth phase were washed and separated with PBS/5 mM EDTA, collected by centrifugation, resuspended with Stimulation Buffer and counted. The concentration of cells was adjusted to 3*10⁵ cells/ml. DMSO was used to dissolve Forskolin and the test compound respectively, so that the mother liquor concentration each was 10 mM, and then diluted Forskolin to 4 M with Stimulation Buffer, and different concentrations of the test compound (the concentrations were 80, 16, 3.2, 0.64, 0.128, 0.0256, 0.00512, 0.001024, 0 μM) was added, 5 μl per well was added to a 384-well plate. 5 μl of cell suspension was added to each well and incubated at room temperature for 30 min. Subsequently, 5 μl of 4×Eu-cAMP tracer working solution (50-fold dilution of Eu-cAMP stock solution with cAMP Detection Buffer) and 5 μl of 4×Ulight-anti-cAMP working solution (150-fold dilution of ULight-anti-cAMP stock solution with cAMP Detection Buffer) were added to each well, and incubated at room temperature for 1 hour. 384-well plates were assayed for cAMP levels using a microplate reader (Perkin Elmer, Envision) TR-FRET method. The obtained data were processed and fitted to EC50 using the origin 7.5 software. The human κ-opioid receptor agonistic activity of the compound of the present invention was measured through the above experiments, and the measured EC50 values are shown in Table 1.

Stimulation Buffer preparation method: 14 mL 1*HBSS (invitrogen, cat. #14025-092), 75 μL 1 M HEPES (Invitrogen, cat. #15630-080), 30 μL 250 mM IBMX was dissolved in DMSO (Sigma, cat. #17018) and mixed with 200 μL 7.5% BSA Stabilizer. pH of the solution was adjusted to 7.4 with 0.1 N NaOH and make up to 15 mL with 1*HBSS.

TABLE 1

Agonist activity of test compounds on human κ-opioid receptors

| Compound No. | EC$_{50}$(nM) |
|---|---|
| Compound 2 | 0.41 |
| Compound 4 | 0.0159 |
| Compound 8 | 0.0112 |
| Compound 12 | 0.067 |
| Compound 13 | 0.00682 |
| Compound 14 | 0.0155 |
| Compound 15 | 0.0117 |
| Compound 17 | 0.00919 |
| Compound 18 | 0.04 |
| Compound 19 | 0.044 |
| Compound 20 | 0.086 |
| Compound 22 | 0.0112 |
| Compound 23 | 0.023 |
| Compound 30 | 0.071 |
| Compound 31 | 0.0136 |
| Compound 33 | 0.05 |

Conclusion: The compounds of the invention have significant agonistic effects on human κ-opioid receptors.

Test 2: Mouse Hot Plate Experiment 18-22 g of female C57 mice were purchased from Chengdu Dashuo Experimental Animal Co., Ltd. The temperature of the hot plate instrument was set to 56° C., and after reaching 56° C., the temperature was stabilized for 30 minutes before experiment. The animals were placed in a hot plate test in order to observe the reaction of licking the hind feet, which was used as an indicator of pain response. The time from the entry of the animal to the hot plate to the heat-induced licking of the hind feet was recorded. Animals that meet the inclusion criteria (response time to lick the hind foot is less than 25s) are included in the group number. The animals were grouped by baseline threshold, with 10 in each group. Compounds of different concentrations were administered subcutaneously at 10 ml/kg, and a detection was carried out after 15 minutes of administration, with 30 seconds as the cut-off time, and the reaction time was recorded. The results were analyzed statistically, and the % MPE value was calculated according to the formula: % MPE=$(T_n-T_0)/(30-T_0)$, ($T_n$ is the time for the animal to lick the hind foot after administration, $T_0$ is the time for the animal to lick the foot before administration) The experimental results are shown in Table 2.

TABLE 2

| Compound No. | MPE(%) |
|---|---|
| Compound 2 | −17.20 |
| Compound 4 | −19.62 |
| Compound 8 | −18.61 |
| Compound 15 | −13.29 |

Conclusion: The analgesic effect of the compounds of the present invention is achieved via the peripheral κ-opioid receptors.

Test 3: Mouse Writhing Experiment

Intraperitoneal injection of acetic acid in mice can cause writhing in mice. Writhing response refers to mice that exhibit typical behavioral responses that are characteristic of contraction or extension of abdominal muscles. The analgesic activity of the compound can be reflected by detecting the inhibitory effect of the compound on the writhing behavior of mice caused by acetic acid. The specific method is as follows:

8-week-old ICR mice (purchased from Chengdu Dashuo Biotechnology Company, license number: SCXK (Sichuan) 2008-24 (NO: 51203500002150)). Mice were randomly divided into groups of 10 animals, half male and half female; fasting but freely accessible to water for 12 h before the experiment. On the day of the experiment, 1.0 mg/kg of the test compound was administered intravenously, and the control group was given a blank reagent. 15 minutes after the administration, a 0.6% (v/v) acetic acid solution was intraperitoneally injected at a dose of 0.4 mL/mouse. The number of mouse writhing in 15 min and 6 h after acetic acid injection was recorded respectively, and the percentage inhibition to acetic acid-caused writhing in mice by the compound was calculated respectively. The analysis results are shown in Table 3.

Percent inhibition %=(number of writhing in the control group−number of writhing in the administration group)/number of writhing in the control group.

TABLE 3

Inhibition percentage of test compounds to acetic acid-induced writhing behavior of mice

| Compound No. | 15 min_post inhibition percentage (%) | 6 h_post inhibition percentage (%) |
|---|---|---|
| Compound 2 | 98.07 | 80.58 |
| Compound 3 | 86.44 | NQ |
| Compound 4 | 95.76 | 81.27 |

TABLE 3-continued

Inhibition percentage of test compounds to acetic acid-induced writhing behavior of mice

| Compound No. | 15 min_post inhibition percentage (%) | 6 h_post inhibition percentage (%) |
|---|---|---|
| Compound 8 | 90.68 | 90.82 |
| Compound 9 | 81.92 | NQ |
| Compound 12 | 91.04 | NQ |
| Compound 13 | 88.98 | NQ |
| Compound 14 | 92.87 | NQ |
| Compound 15 | 94.50 | 87.14 |
| Compound 17 | 95.43 | 97.89 |
| Compound 18 | 99.37 | 95.69 |
| Compound 19 | 99.71 | 84.74 |
| Compound 20 | 97.47 | 83.41 |
| Compound 22 | 90.38 | 88.71 |
| Compound 23 | 88.46 | 87.93 |
| Compound 24 | 94.89 | 80.51 |
| Compound 25 | 98.08 | 85.03 |
| Compound 26 | 94.25 | 92.94 |
| Compound 27 | 94.00 | NQ |
| Compound 28 | 84.29 | NQ |
| Compound 30 | 97.36 | NQ |
| Compound 31 | 99.28 | 90.03 |
| Compound 33 | 89.42 | NQ |
| Compound 36 | 89.14 | 75.71 |
| Compound 37 | 95.85 | NQ |
| Compound 42 | 99.33 | 75.14 |
| Compound 43 | 98.00 | 76.57 |
| Compound 44 | 93.32 | NQ |
| Control | 61.11 | 28.96 |

NQ means no test.

The control is

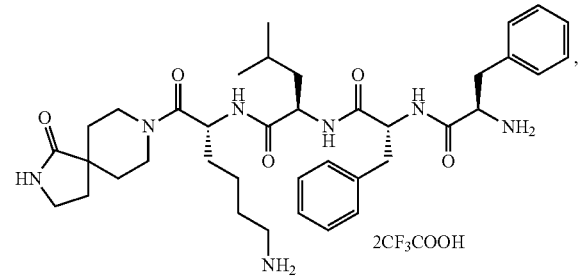 [SMILES: CC(C)C[C@@H](NC(=O)[C@@H](Cc1ccccc1)NC(=O)[C@H](N)Cc1ccccc1)C(=O)N[C@H](CCCCN)C(=O)N1CCC2(CCNC2=O)CC1]

the compound 25 disclosed in CN101627049A is its free base.

Conclusion: The compounds of the present invention have significant analgesic effects.

Some test compounds were further tested for a long-acting test on acetic acid-induced writhing behavior of mice. According to the same test method as described above, the administration method was intravenous injection, and the dosage was 3 mg/kg or 10 mg/kg. The number of times of mouse writhing within 18 h after the injection of acetic acid was recorded, and the percentage inhibition to acetic acid-induced writhing behavior of mice by test compounds was calculated respectively. The results are shown in Table 4.

TABLE 4

18 h-post inhibition percentage of test compounds to acetic acid-induced writhing behavior of mice

| Compound No. | Dosage | 18h-post inhibition percentage (%) |
| --- | --- | --- |
| Cr-845 | 10 mg/kg | 49.11 |
| Compound 8 | 3 mg/kg | 83.86 |
| Compound 10 | 3 mg/kg | 72.30 |
| Compound 17 | 10 mg/kg | 78.11 |
| Compound 18 | 3 mg/kg | 54.00 |
| Compound 23 | 10 mg/kg | 73.37 |
| Compound 25 | 10 mg/kg | 74.26 |
| Compound 26 | 10 g/kg | 69.82 |
| Compound 31 | 10 mg/kg | 75.44 |
| Compound 42 | 10 mg/kg | 61.69 |
| Compound 43 | 3 mg/kg | 70.19 |

Structure of CR845 is

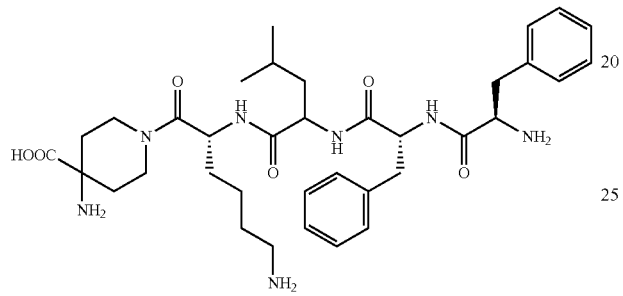

Conclusion: Some compounds of the present invention have significant analgesic effects and have the advantage of long-lasting effects.

4. Rat PK Test

| Test purposes | A single dose of the test substance was intravenously administrated to SD rats, the concentration of the test substance in the plasma of rats was measured, and the pharmacokinetic characteristics and bioavailability of the test substance in the rat were evaluated. |
| --- | --- |
| Administration method | Intravenous injection |
| Dosage | 1 mg/kg ((calculated in free form)) |
| Test animal | Male SD rats, about 180~220 g, 6~8 weeks old, 12 in total, divided into 2 groups, purchased from Chengdu Dashuo Experimental Animal Co., Ltd. |
| Test content | 0.20 ml of rat blood was taken from the orbit before and after administration and placed in ETDAK2 centrifuge tube. It was centrifuged at 5000 rpm and 4° C. for 10 min to collect plasma. IV blood collection time points: 0, 5, 15, 30 min, 1, 2, 4, 6, 8, 24 h. Prior to analysis, all plasma samples were stored at −80° C. |

TABLE 5

PK results of rat (1 mg/kg)

| compound No. | administration method | $t_{1/2}$ (h) | Cl (ml/kgmin) | Vdss (L/kg) | $AUC_{0-t}$ (ng/ml · h) |
| --- | --- | --- | --- | --- | --- |
| CR-845 | iv | 3.90 | 8.29 | 1.56 | 1959 |
| compound 2 | iv | 4.22 | 5.97 | 1.47 | 2664 |

5. Mouse PK Test

| Test purposes | A single dose of the test substance was intravenously administered to ICR mice, the concentration of the test substance in the plasma of the mice was measured, and the pharmacokinetic characteristics of the test substance in the mice were evaluated. |
| --- | --- |
| Administration method | Intravenous injection |
| Dosage | 1 mg/kg (calculated in free form) |
| Test animal | Male ICR mice, about 18~22 g, 6~8 weeks old, 6 mice in total, divided into 2 groups, purchased from Chengdu Dashuo Experimental Animal Co., Ltd. |
| Test content | 20 µl of blood was taken from the orbit of mice anesthetized with isoflurane before and after administration and placed in ETDAK2 anticoagulation tube. It was centrifuged at 5000 rpm and 4° C. for 10 min to collect plasma. IV blood collection time points: 0, 5, 15, 30 min, 1, 2, 4, 6, 8, 24 h. Prior to analysis, all plasma samples were stored at −80° C. |

TABLE 6

PK results of mouse (1 mg/kg)

| compound No. | administration method | $t_{1/2}$ (h) | $AUC_{0-t}$ (ng/ml · h) |
| --- | --- | --- | --- |
| CR-845 | iv | 0.388 | 1117 |
| compound 8 | iv | 5.77 | 1220 |
| compound 17 | iv | 3.88 | 2244 |

The invention claimed is:

1. A compound having formula (I) or a stereoisomer, or pharmaceutically acceptable salt thereof:

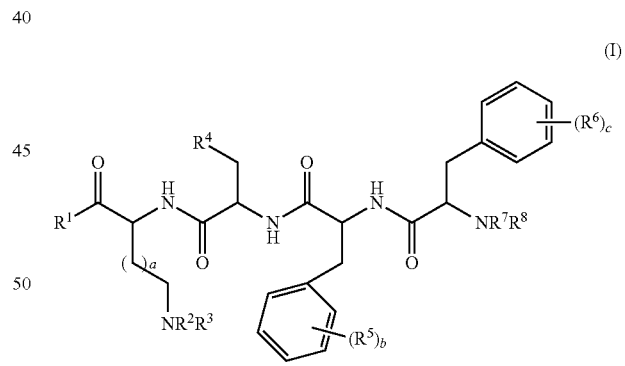

wherein
$R^1$ is

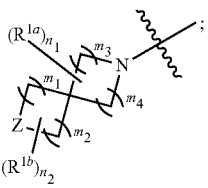

each of $m_1$, $m_2$ is independently selected from 1, 2, 3 or 4;

each of $m_3$, $m_4$ is independently selected from 0, 1, 2, 3 or 4; with the proviso that $m_3$ and $m_4$ are not 0 at the same time;

each of $n_1$, $n_2$ is independently selected from 0, 1, 2, 3 or 4;

Z is selected from $CR^{z1}R^{z2}$ or $NR^{z3}$;

each of $R^{z1}$, $R^{z2}$ is independently selected from H, F, Cl, Br, I, OH, $CF_3$, nitro, $C_{1-6}$ alkyl, $C_{1-6}$ alkoxy, $C_{2-6}$ alkenyl, $C_{2-6}$ alkynyl, —C(=O)—$C_{1-6}$ alkyl, —$(CH_2)_q$—C(=O)O—$C_{1-6}$ alkyl, —$(CH_2)_q$—$NR^{1e}R^{1f}$, —$(CH_2)_q$—COOH, —$(CH_2)_q$—$CONH_2$, $C_{3-8}$ carbocyclic group or 3 to 8 membered heterocyclic group, and the alkyl, alkoxy, alkenyl, alkynyl, carbocyclic or heterocyclic group is optionally further substituted with 0 to 5 substituents selected from the group consisting of F, Cl, Br, I, OH, $CF_3$, =O, carboxyl, nitro, cyano, amino, $C_{1-6}$ alkyl, $C_{1-6}$ alkoxy, $C_{2-6}$ alkenyl, $C_{2-6}$ alkynyl, $C_{3-8}$ carbocyclic group or 3 to 8 membered heterocyclic group, the heterocyclic group contains 1 to 3 heteroatoms optionally selected from N, O or S, and when the heteroatom is selected from S, it is optionally substituted with =O or (=O)$_2$;

each of $R^{1e}$, $R^{1f}$ is independently selected from H, $C_{1-6}$ alkyl, —C(=O)O—$C_{1-6}$ alkyl, —C(=O)O—$(CH_2)_q$—$C_{3-8}$ carbocyclic group or —C(=O)O—$(CH_2)_q$-3 to 8 membered heterocyclic group, the alkyl, carbocyclic or heterocyclic group is optionally further substituted with 0 to 5 substituents selected from the group consisting of F, Cl, Br, I, OH, $CF_3$, cyano, nitro, $C_{1-6}$ alkyl, $C_{1-6}$ alkoxy, $C_{2-6}$ alkenyl, $C_{2-6}$ alkynyl, $C_{3-8}$ carbocyclic group or 3 to 8 membered heterocyclic group, and the heterocyclic group contains 1 to 3 heteroatoms selected from N, O or S;

alternatively, $R^{z1}$ and $R^{z2}$ form a 3 to 10 membered nitrogen-containing heterocyclic ring with the carbon atom to which they are attached, and the ring is optionally further substituted with substituents selected from the group consisting of F, Cl, Br, I, OH, $CF_3$, cyano, nitro, =O, $C_{1-6}$ alkyl, $C_{1-6}$ alkoxy, $C_{2-6}$ alkenyl, $C_{2-6}$ alkynyl, $C_{3-8}$ carbocyclic group or 3 to 8 membered heterocyclic group;

each of $R^{1a}$, $R^{1b}$ is independently selected from F, $CF_3$, $C_{1-6}$ alkyl, $C_{2-6}$ alkenyl, $C_{2-6}$ alkynyl or 3 to 8 membered heterocyclic group, and the alkyl, alkenyl, alkynyl or heterocyclic group is optionally further substituted with 0 to 5 substituents selected from the group consisting of F, Cl, Br, I, OH, $CF_3$, nitro, cyano, $C_{1-6}$ alkyl, $C_{1-6}$ alkoxy, $C_{2-6}$ alkenyl, $C_{2-6}$ alkynyl, $C_{3-8}$ carbocyclic group or 3 to 8 membered heterocyclic group, and the heterocyclic group contains 1 to 3 heteroatoms optionally selected from N, O or S;

$R^{z3}$ is independently selected from H, —C(=O)—$C_{1-6}$ alkyl, —C(=O)O—$C_{1-6}$ alkyl, —C(=O)—$C_{3-8}$ carbocyclic group, —C(=O)O—$C_{3-8}$ carbocyclic group, —C(=O)O-(3 to 8 membered heterocyclic group), —S(=O)$_p$—$C_{1-6}$ alkyl, —S(=O)$_p$—$C_{3-8}$ carbocyclic group, —S(=O)$_p$-(3 to 8 membered heterocyclic group), —C(=O)$NR^{1g}R^{1h}$, —S(=O)$_p$—$NR^{1i}R^{1j}$ or 3 to 8 membered heterocyclic group, and the alkyl, carbocyclic or heterocyclic group is optionally further substituted with 0 to 5 substituents selected from the group consisting of F, Cl, Br, I, OH, $CF_3$, nitro, cyano, amino, $C_{1-6}$ alkyl, $C_{1-6}$ alkoxy, $C_{2-6}$ alkenyl, $C_{2-6}$ alkynyl, $C_{3-8}$ carbocyclic group or 3 to 8 membered heterocyclic group, and the heterocyclic group contains 1 to 3 heteroatoms optionally selected from N, O or S;

each of $R^{1g}$, $R^{1h}$, $R^{1i}$, $R^{1j}$ is independently selected from H or $C_{1-6}$ alkyl;

alternatively, $R^{1g}$, $R^{1h}$ form a 3 to 10 membered heterocyclic ring with the nitrogen atom to which they are attached, the ring is optionally further substituted with substituents selected from the group consisting of F, Cl, Br, I, OH, $CF_3$, cyano, nitro, $C_{1-6}$ alkyl, $C_{1-6}$ alkoxy, $C_{2-6}$ alkenyl, $C_{2-6}$ alkynyl or —S(=O)$_p$—$C_{1-6}$ alkyl, the heterocyclic group contains 1 to 3 heteroatoms selected from N, O or S;

q is 0, 1, 2, 3 or 4;

p is 0, 1 or 2;

a is 0, 1, 2 or 3;

$R^4$ is independently selected from H, $C_{1-6}$ alkyl, $C_{2-6}$ alkenyl, $C_{2-6}$ alkynyl or —$(CH_2)_q$—$C_{3-8}$ carbocyclic group, the alkyl, alkenyl, alkynyl or carbocyclic group is optionally further substituted with 0 to 5 substituents selected from the group consisting of F, Cl, Br, I, OH, CN, $CF_3$, $NO_2$, $C_{1-6}$ alkyl, $C_{1-6}$ alkoxy, $C_{2-6}$ alkenyl, $C_{2-6}$ alkynyl, $C_{3-8}$ carbocyclic group or 3 to 8 membered heterocyclic group, the heterocyclic group contains 1 to 3 heteroatoms selected from N, O or S;

each of $R^2$, $R^3$, $R^7$, $R^8$ is independently selected from H, $C_{1-6}$ alkyl, —C(=O)O—$C_{1-4}$ alkyl, —C(=O)O—$(CH_2)_q$—$C_{3-8}$ carbocyclic group, —C(=O)O—$(CH_2)_q$-3 to 8 membered heterocyclic group or

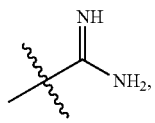 [SMILES: *C(=N)N]

and the alkyl, carbocyclic or heterocyclic group is optionally further substituted with 0 to 5 substituents selected from the group consisting of F, Cl, Br, I, OH, $CF_3$, nitro, cyano, $C_{1-6}$ alkyl, $C_{1-6}$ alkoxy, $C_{2-6}$ alkenyl, $C_{2-6}$ alkynyl, $C_{3-8}$ carbocyclic group or 3 to 8 membered heterocyclic group, and the heterocyclic group contains 1 to 3 heteroatoms optionally selected from N, O or S;

b is 0, 1, 2, 3, 4 or 5;

c is 0, 1, 2, 3, 4 or 5;

each of $R^5$, $R^6$ is independently selected from F, Cl, Br, I, $CF_3$, cyano, nitro, $C_{1-4}$ alkyl, —$OR^{5a}$, —C(O)$OR^{5b}$, —$SR^{5c}$, —S(O)$R^{5d}$, —S(O)$_2R^{5e}$ or —$NR^{5f}R^{5g}$;

each of $R^{5a}$, $R^{5b}$, $R^{5c}$, $R^{5d}$, $R^{5e}$, $R^{5f}$ and $R^{5g}$ is independently selected from H or $C_{1-4}$ alkyl;

alternatively, $R^{5f}$, $R^{5g}$ form a 5 to 6 membered heterocyclic ring with the nitrogen atom to which they are attached, and the heterocyclic group contains 1 to 3 heteroatoms optionally selected from N, O or S.

2. The compound or a stereoisomer, or pharmaceutically acceptable salt thereof according to claim 1, wherein each of $m_1$, $m_2$, $m_3$, $m_4$ is independently selected from 1 or 2;

each of $n_1$, $n_2$ is independently selected from 0, 1 or 2;

Z is $CR^{z1}R^{z2}$ or $NR^{z3}$;

each of $R^{z1}$, $R^{z2}$ is independently selected from H, $C_{1-4}$ alkyl, —$(CH_2)_q$—C(=O)O—$C_{1-4}$ alkyl, —$(CH_2)_q$—$NR^{1e}R^{1f}$, —$(CH_2)_q$—COOH, —$(CH_2)_q$—$CONH_2$, $C_{3-6}$ carbocyclic group or a 3 to 6 membered heterocyclic group, and the alkyl, carbocyclic or heterocyclic group is optionally further substituted with 0 to 5 substituents selected from the group consisting of F, Cl, Br, I, OH, $CF_3$, =O, carboxyl, nitro, cyano, amino, $C_{1-4}$ alkyl, $C_{1-4}$ alkoxy, $C_{2-4}$ alkenyl, $C_{2-4}$ alkynyl, $C_{3-6}$ carbocyclic group or a 3 to 6 membered heterocyclic group, and the heterocyclic group contains 1 to 3 heteroatoms optionally selected from N, O or S, and when the heteroatom is selected from S, it is optionally in form of S, S=O or $S(=O)_2$;

each of $R^{1e}$, $R^{1f}$ is independently selected from H, $C_{1-4}$ alkyl, —C(=O)O—$C_{1-4}$ alkyl or —C(=O)O—$(CH_2)_q$—$C_{3-6}$ carbocyclic group, the alkyl or carbocyclic group is optionally further substituted with 0 to 3 substituents selected from the group consisting of F, Cl, Br, I, OH, $CF_3$, nitro, cyano, methyl, ethyl, methoxy, ethoxy, phenyl;

alternatively, $R^{z1}$ and $R^{z2}$ optionally form a 4 to 6 membered nitrogen-containing heterocyclic ring with a carbon atom to which they are attached, and the ring is optionally further substituted with =O;

$R^{1a}$, $R^{1b}$ are independently selected from F, $CF_3$, methyl, ethyl, propanoyl or isopropyl;

$R^{z3}$ is each independently selected from H, —C(=O)—$C_{1-4}$ alkyl, —C(=O)—$C_{3-6}$ carbocyclic group, —C(=O)O—$C_{1-4}$ alkyl, —S(=O)$_p$—$C_{1-4}$ alkyl, —S(=O)$_p$—$C_{3-6}$ carbocyclic group, —C(=O)NR$^{1g}$R$^{1h}$, —S(=O)$_p$—NR$^{1i}$R$^{1j}$ or a 3 to 6 membered heterocyclic group, the alkyl, carbocyclic or heterocyclic group is optionally further substituted with 0 to 3 substituents selected from the group consisting of F, Cl, Br, I, OH, $CF_3$, nitro, cyano, amino, methyl, ethyl, methoxy, ethoxy, cyclopropyl or phenyl, and the heterocyclic group contains 1 to 3 heteroatoms selected from N, O or S;

each of $R^{1g}$, $R^{1h}$, $R^{1i}$, $R^{1j}$ is independently selected from H or $C_{1-4}$ alkyl;

alternatively, $R^{1g}$, $R^{1h}$ form a 4 to 6 membered heterocyclic ring with the nitrogen atom to which they are attached, and the ring is optionally further substituted with substituents selected from the group consisting of F, Cl, Br, I, OH, $CF_3$, cyano, nitro, methyl, ethyl, methoxy, ethoxy or —S(=O)$_p$—$C_{1-4}$ alkyl, the heterocyclic group contains 1 to 3 heteroatoms selected from N, O or S;

p is 2;

q is 0 or 1;

a is 3;

$R^4$ is selected from propanoyl or isopropyl;

each of $R^2$, $R^3$, $R^7$, $R^8$ is independently selected from H, $C_{1-4}$ alkyl, —C(=O)O—$C_{1-4}$ alkyl or —C(=O)O-benzyl;

b is 0;

c is 0.

3. The compound or a stereoisomer, or pharmaceutically acceptable salt thereof according to claim 2, wherein the compound has formula (II):

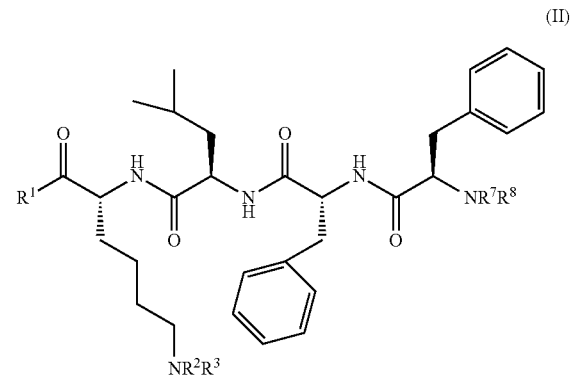

(II)

$R^1$ is

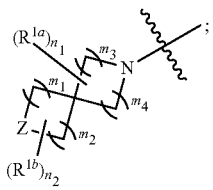

each of $m_1$, $m_2$, $m_3$, $m_4$ is independently selected from 1 or 2;

each of $n_1$, $n_2$ is independently selected from 0 or 2;

$R^{1a}$, $R^{1b}$ are F;

Z is selected from $CR^{z1}R^{z2}$ or $NR^{z3}$;

each of $R^{z1}$, $R^{z2}$ is independently selected from H, carboxyl,

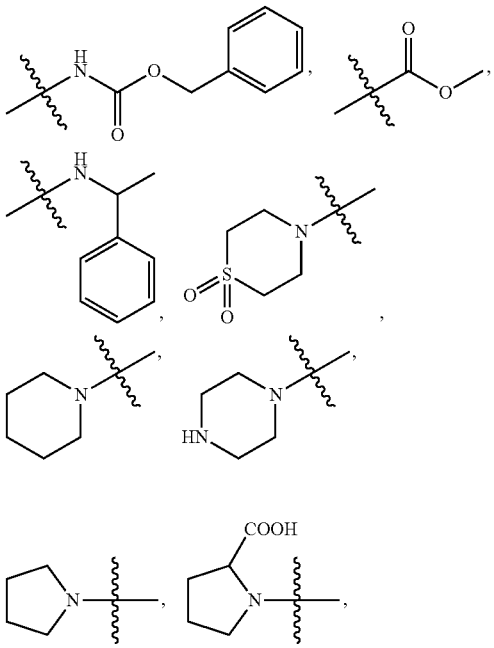

amino, —CH$_2$NH$_2$ or

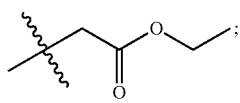 [SMILES: *CC(=O)OCC]

alternatively, R$^{z1}$ and R$^{z2}$ optionally form a lactam with the carbon atom to which they are attached

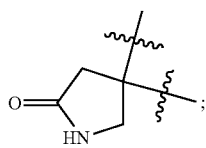 [SMILES: *C1(*)CNC(=O)C1]

R$^{z3}$ each is independently selected from H, —C(=O)—C$_{1-4}$ alkyl, —C(=O)—C$_{3-6}$ carbocyclic group, —C(=O)O—C$_{1-4}$ alkyl, —S(=O)$_p$—C$_{1-4}$ alkyl, —S(=O)$_p$—C$_{3-6}$ carbocyclic group, —C(=O)NR$^{1g}$R$^{1h}$, —S(=O)$_p$—NR$^{1i}$R$^{1j}$ or a 3 to 6 membered heterocyclic group, wherein the alkyl, carbocyclic or heterocyclic group is optionally further substituted with 0 to 3 substituents selected from the group consisting of F, Cl, Br, I, OH, CF$_3$, nitro, cyano, amino, methyl, ethyl, methoxy, ethoxy, cyclopropyl or phenyl, the heterocyclic group contains 1 to 3 heteroatoms selected from N, O or S;

each of R$^{1g}$, R$^{1h}$, R$^{1i}$, R$^{1j}$ independently selected from H or C$_{1-4}$ alkyl;

alternatively, R$^{1g}$, R$^{1h}$ form a 4 to 6 membered heterocyclic ring with the nitrogen atom to which they are attached, and the ring is optionally further substituted with substituents selected from the group consisting of F, CF$_3$, methyl, methoxy or —S(=O)$_p$—C$_{1-4}$ alkyl, the heterocyclic group contains 1 to 3 heteroatoms selected from N, O or S;

p is 2;

each of R$^2$, R$^3$, R$^7$, R$^8$ is independently selected from H, methyl or —C(=O)O-tert-butyl.

4. The compound or a stereoisomer, or pharmaceutically acceptable salt thereof according to claim 3, wherein the compound has formula (II): and R$^{z3}$ is each independently selected from H,

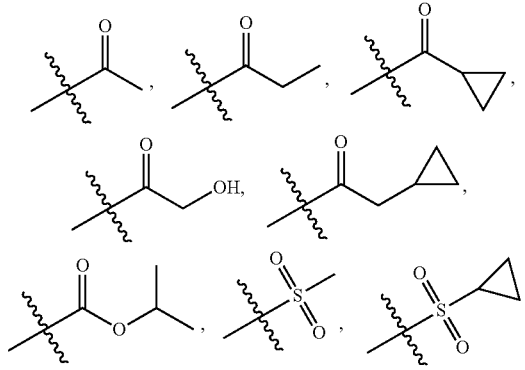

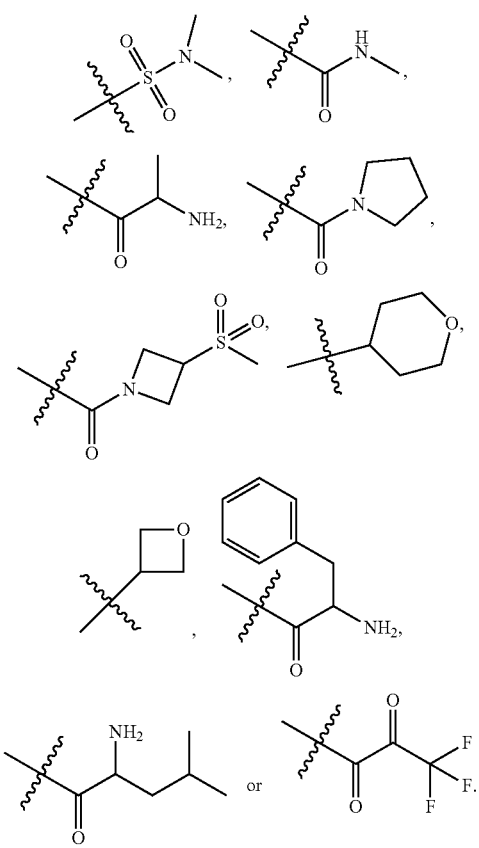

5. The compound or a stereoisomer, or pharmaceutically acceptable salt thereof according to claim 4, wherein R$^1$ is selected from

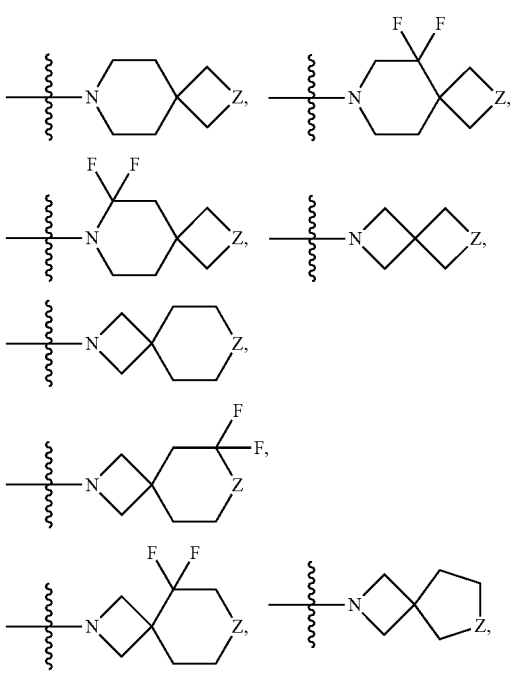

-continued
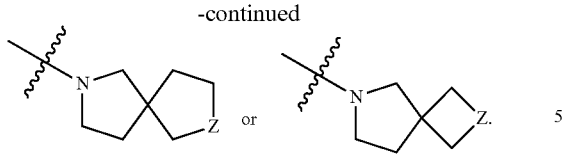 or 5
6. The compound or a stereoisomer, or pharmaceutically acceptable salt thereof according to claim 5, wherein the compound is selected from:
Compound 2
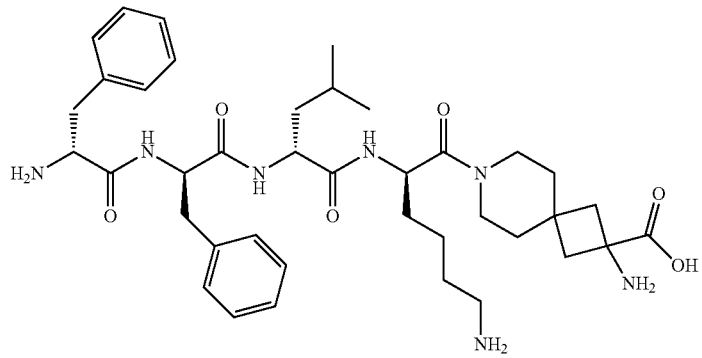
Compound 3
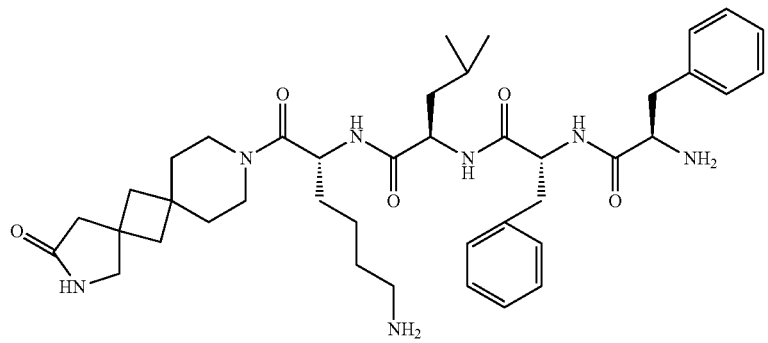
Compound 4
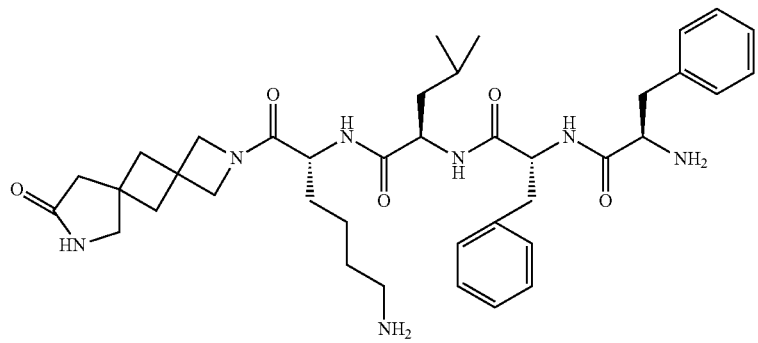

Compound 6
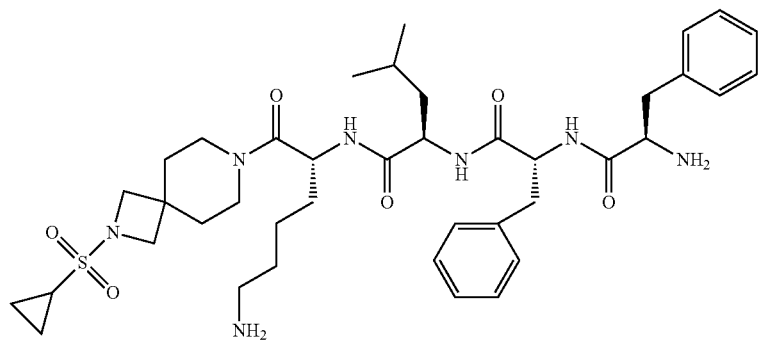
Compound 7
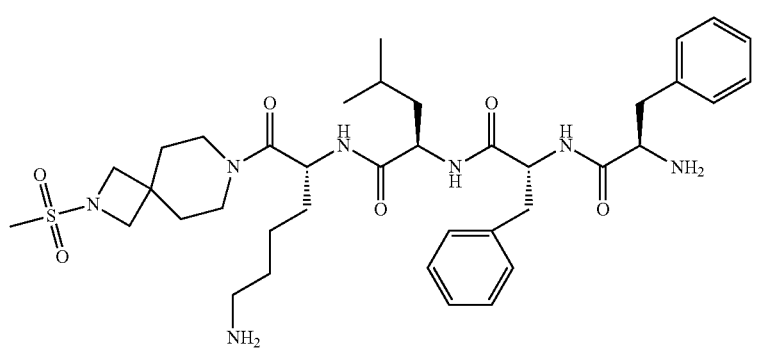
Compound 8
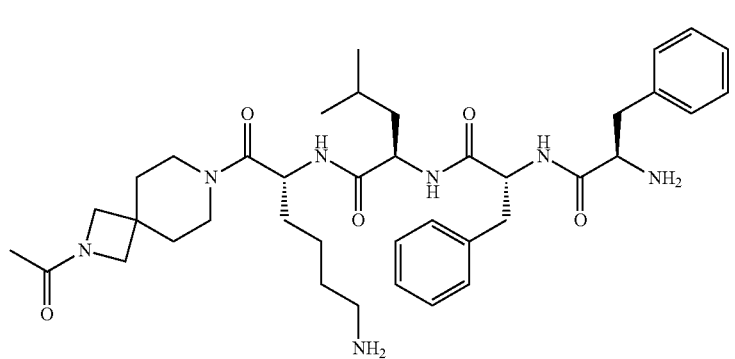
Compound 9
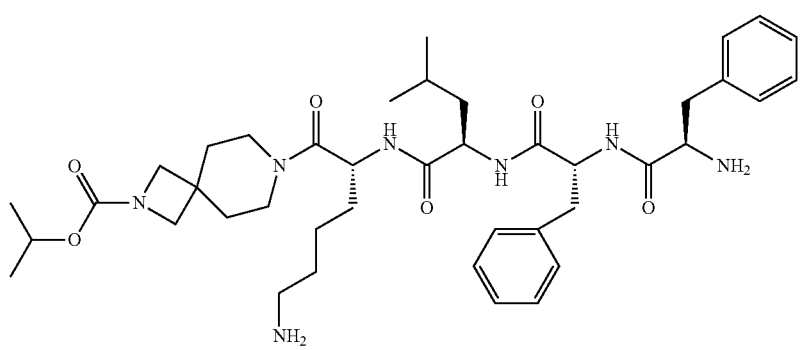

-continued
Compound 10
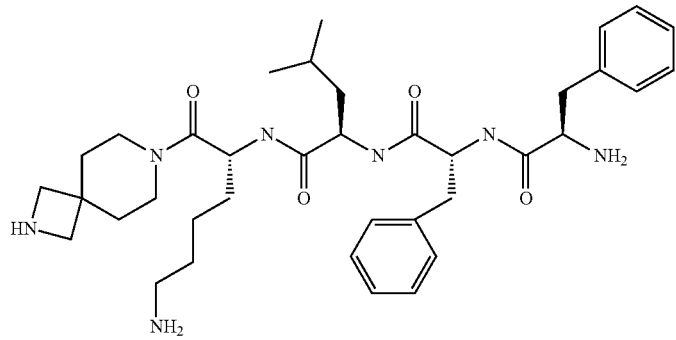
Compound 11
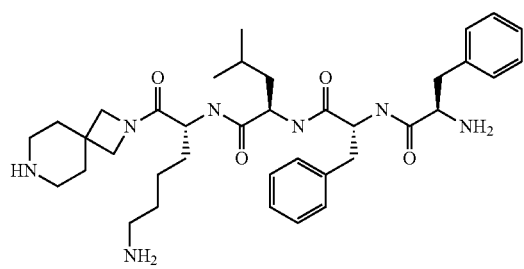
Compound 12
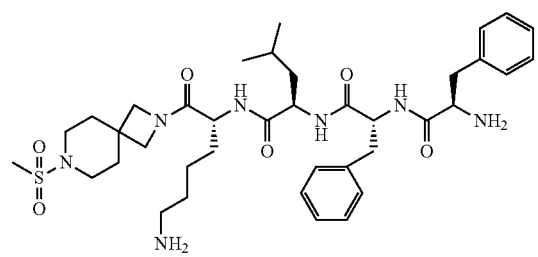
Compound 13
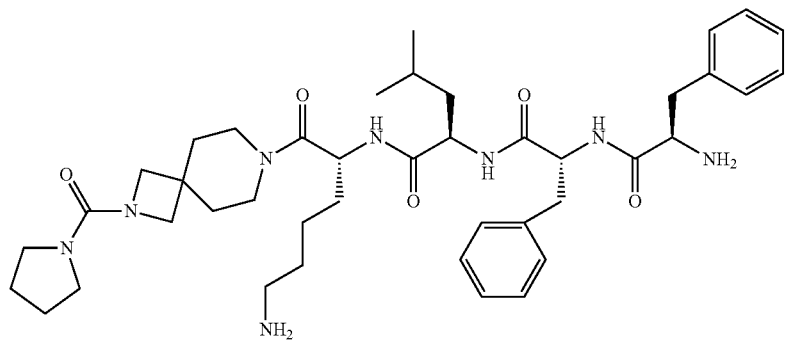
Compound 14
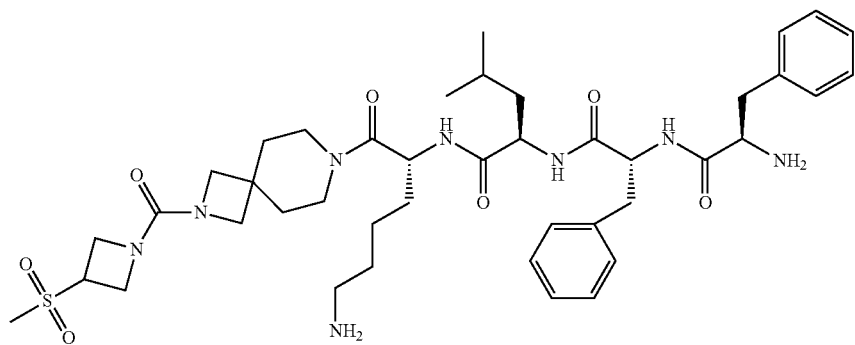

-continued
Compound 15
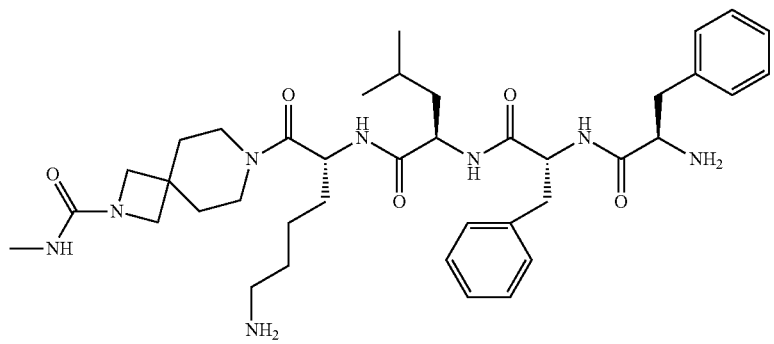
Compound 16
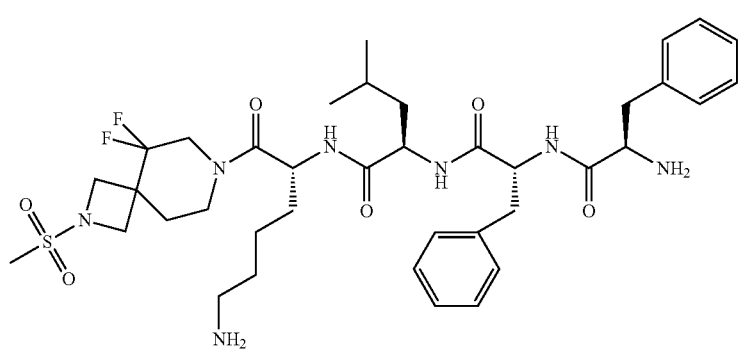
Compound 17
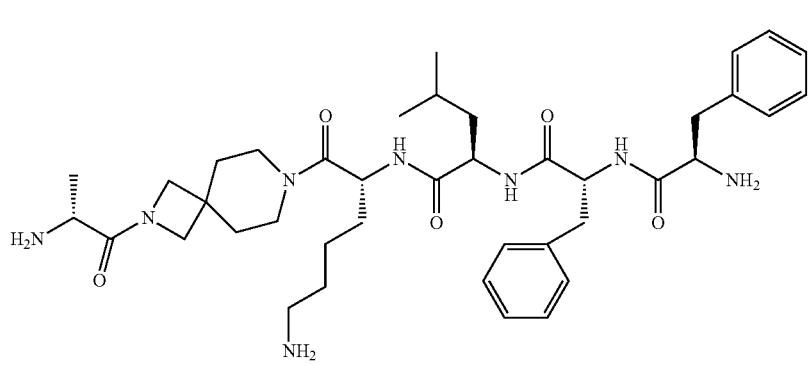
Compound 18
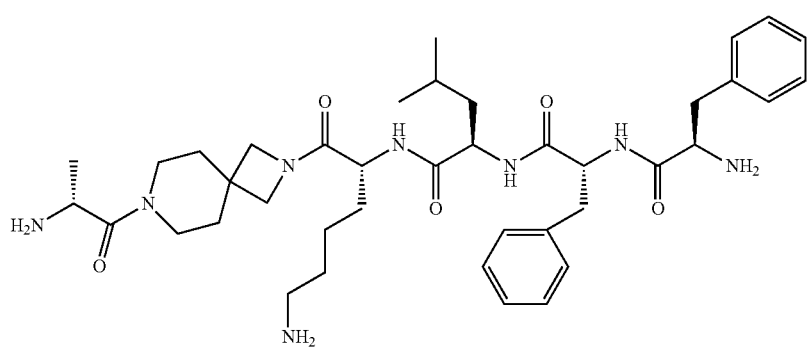

Compound 19
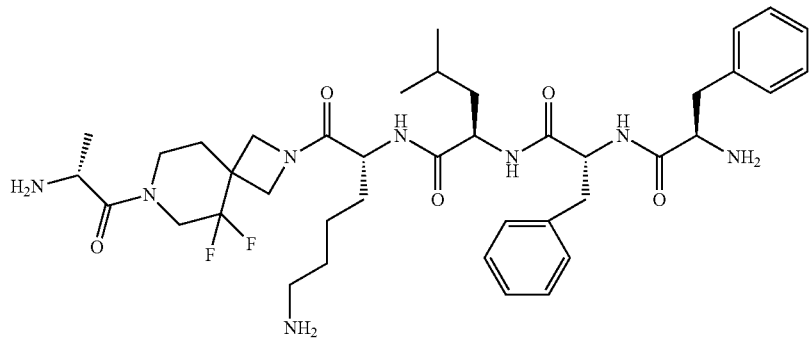
Compound 20
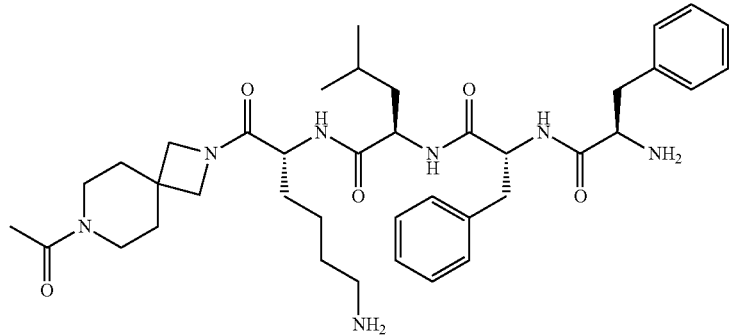
Compound 21
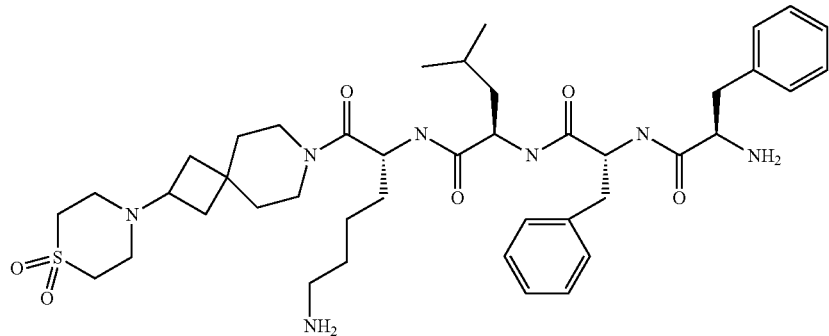
Compound 22
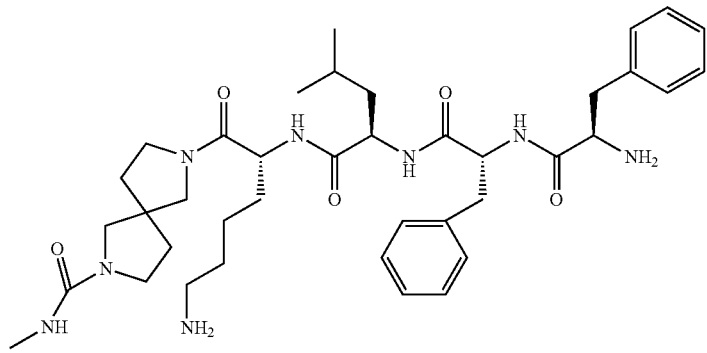

Compound 23
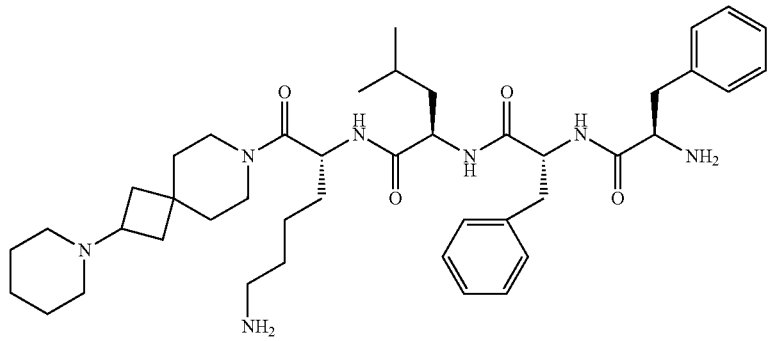
Compound 24
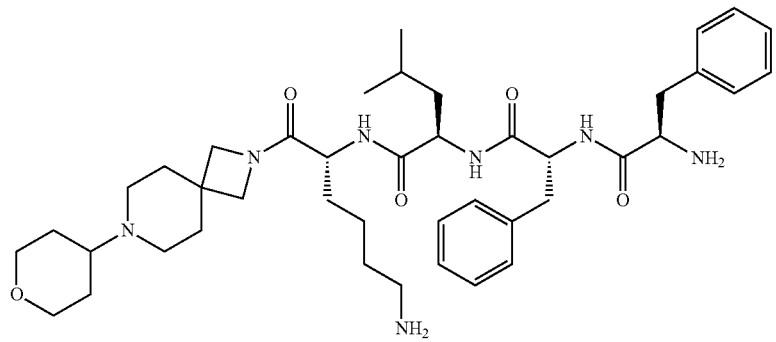
Compound 25
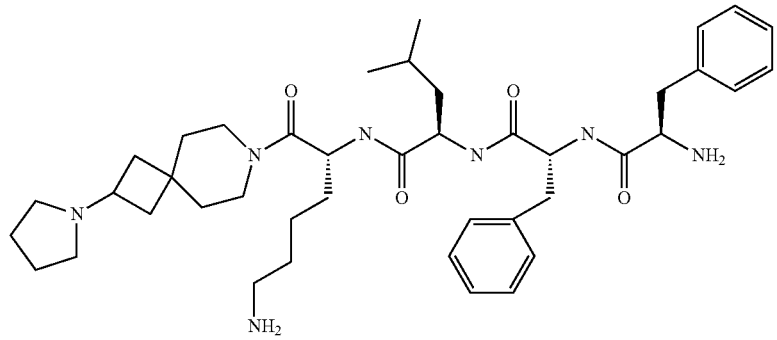
Compound 26
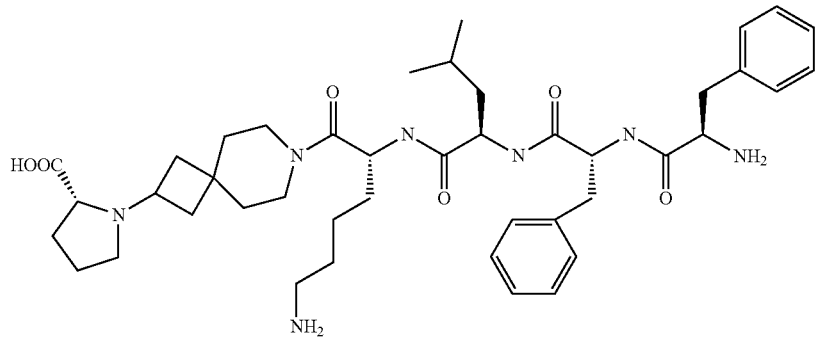

-continued
Compound 27
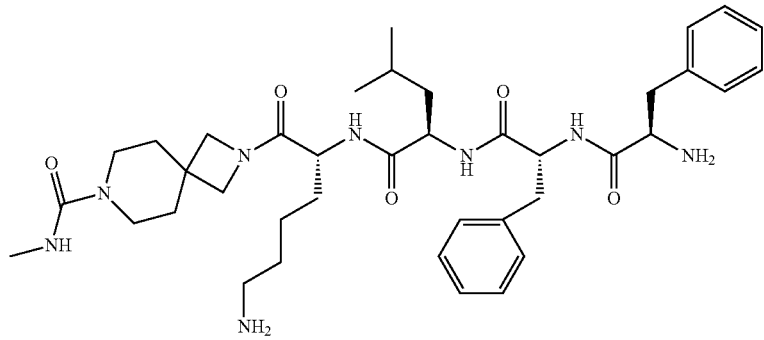
Compound 28
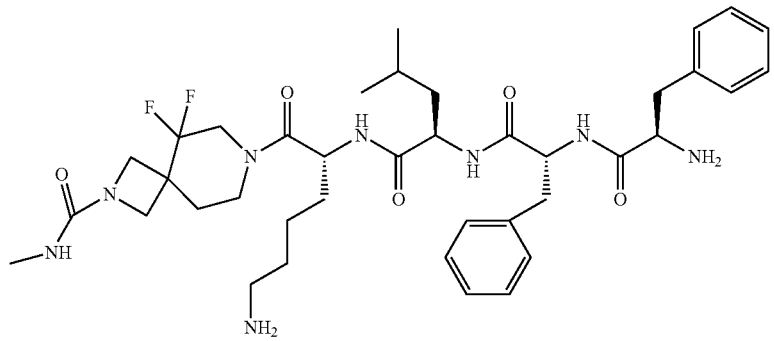
Compound 29
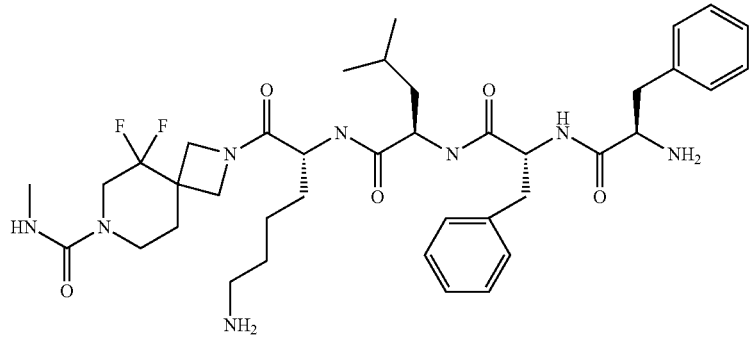
Compound 30
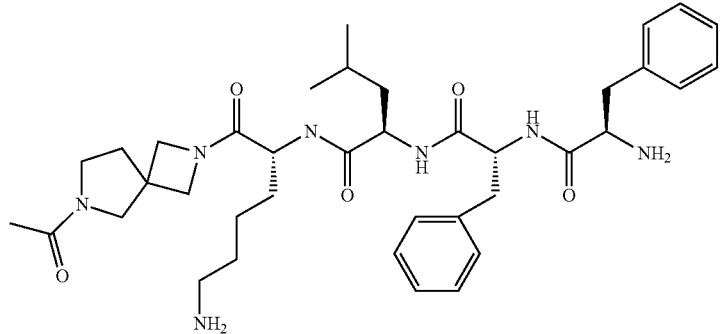

-continued
Compound 31
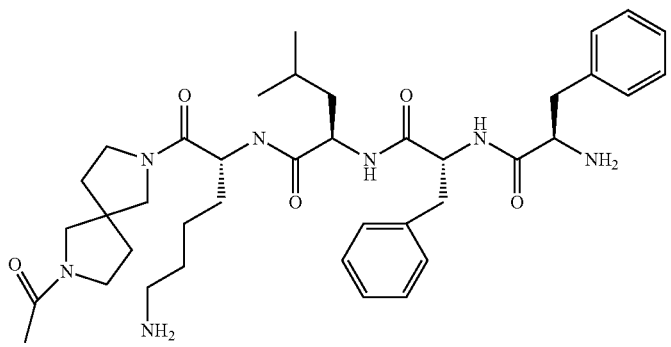
Compound 32
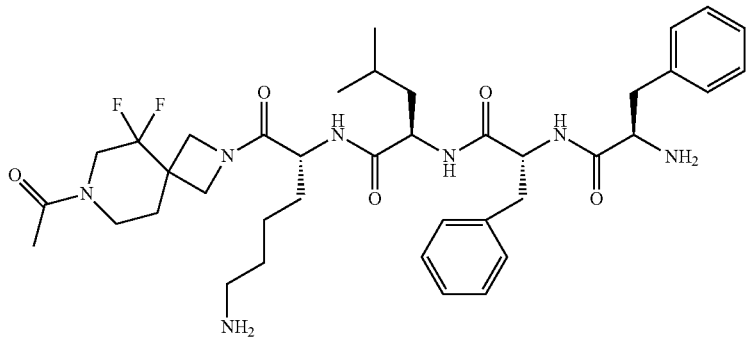
Compound 33
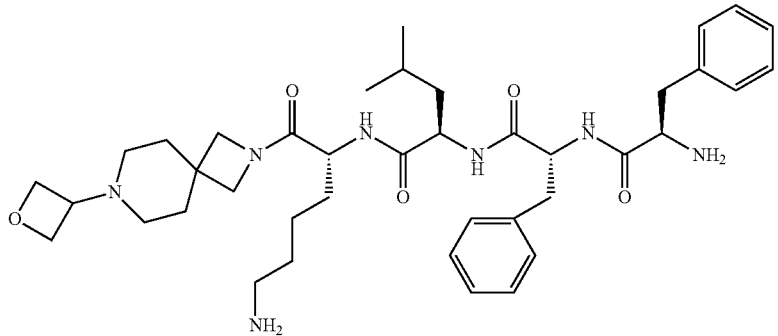
Compound 34
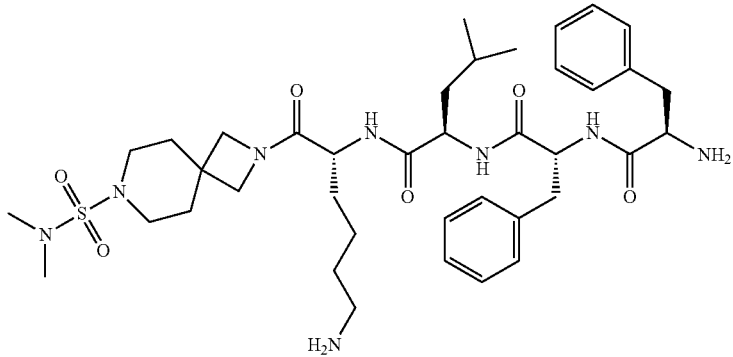

Compound 35
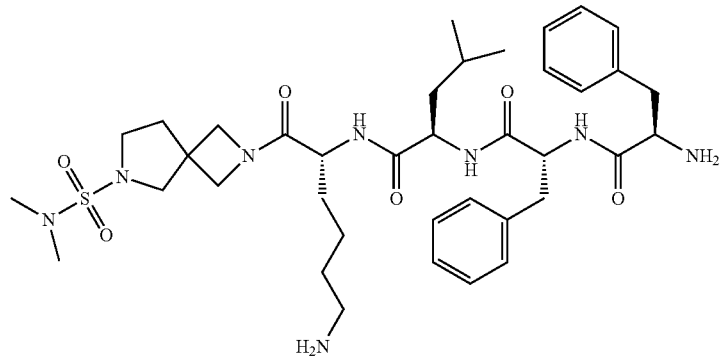
Compound 36
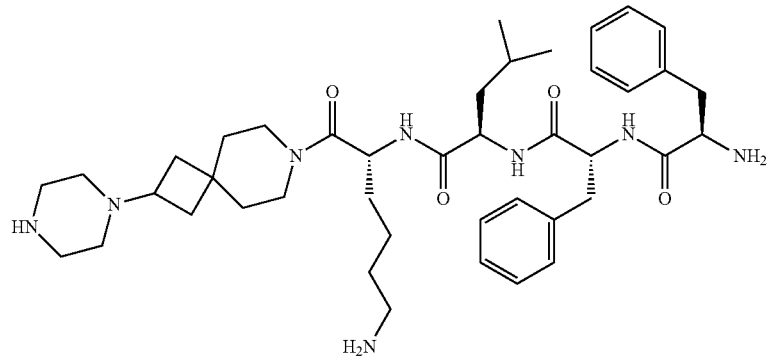
Compound 37
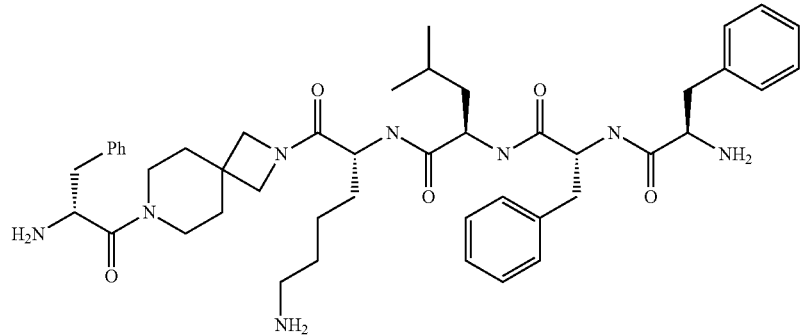
Compound 38
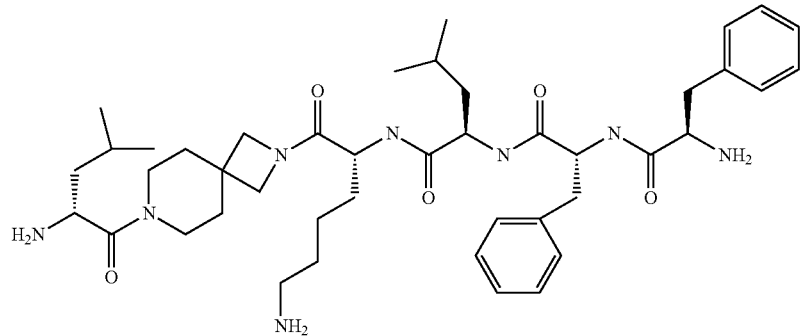

Compound 39
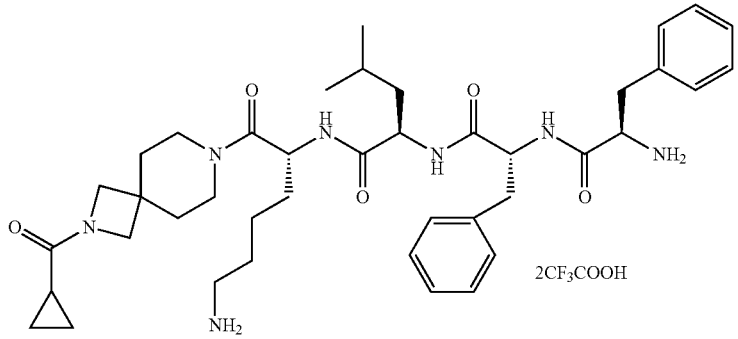
Compound 40
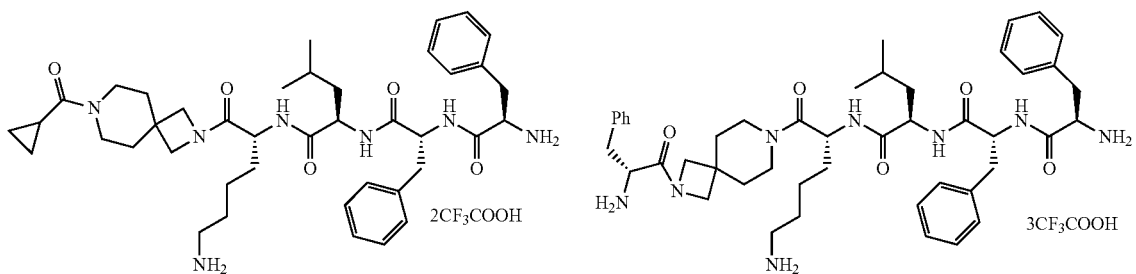
Compound 41
Compound 42
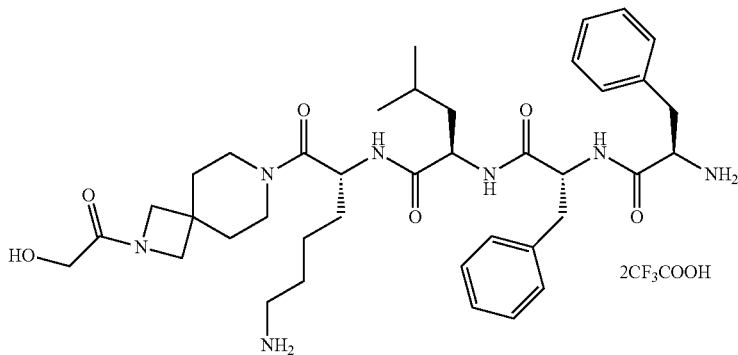
Compound 43
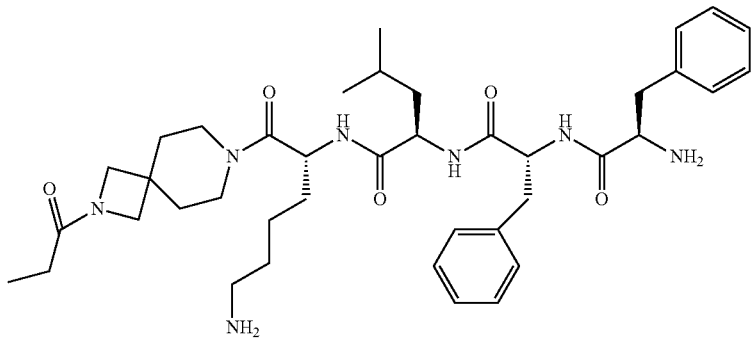

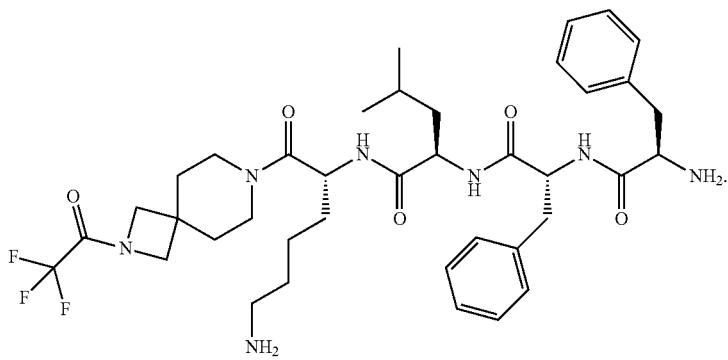

Compound 44

7. The compound or a stereoisomer, or pharmaceutically acceptable salt thereof according to claim 1, wherein the pharmaceutically acceptable salts are selected from trifluoroacetates.

8. A pharmaceutical composition comprising the compound or stereoisomer, or pharmaceutically acceptable salt thereof according to claim 1, and one or more pharmaceutically acceptable carriers and/or excipients.

9. A method for treating or reducing a κ-opioid receptor-associated disease or condition in a mammal, the method comprising administering a compound or a stereoisomer, or pharmaceutically acceptable salt thereof according to claim 1;
wherein the κ opioid receptor-associated disease or condition is selected from the group consisting of pain, inflammation, itching, edema, hyponatremia, hypokalemia, ileus, cough and glaucoma.

10. The method according to claim 9, wherein the κ opioid receptor-associated disease or condition is pain.

11. The method according to claim 10, wherein the pain is selected from the group consisting of neuropathic pain, somatic pain, visceral pain and dermatalgia.

12. The method according to claim 10, wherein the pain is selected from the group consisting of arthritis pain, kidney stone pain, hysterospasm, dysmenorrhea, endometriosis, dyspepsia, post-surgical pain, post-medical treatment pain, eye pain, otitis pain, fulminant cancer pain and gastrointestinal disorders-associated pain.

13. A method for treating or reducing a κ-opioid receptor-associated disease or condition in a mammal, wherein the method comprises administering the pharmaceutical composition of claim 8; wherein the κ opioid receptor-associated disease or condition is selected from the group consisting of pain, inflammation, itching, edema, hyponatremia, hypokalemia, ileus, cough and glaucoma.

* * * * *